US008309600B2

(12) United States Patent
Shi et al.

(10) Patent No.: US 8,309,600 B2
(45) Date of Patent: Nov. 13, 2012

(54) GPR120 RECEPTOR AGONISTS AND USES THEREOF

(75) Inventors: Dong Fang Shi, Fremont, CA (US); Jiangao Song, Sunnyvale, CA (US); Jingyuan Ma, Sunnyvale, CA (US); Aaron Novack, San Jose, CA (US); Phuongly Pham, Hayward, CA (US); Imad Fayek Nashashibi, San Jose, CA (US); Christopher J. Rabbat, Agoura Hills, CA (US); Xin Chen, San Ramon, CA (US)

(73) Assignee: Metabolex Inc., Hayward, CA (US)

( * ) Notice: Subject to any disclaimer, the term of this patent is extended or adjusted under 35 U.S.C. 154(b) by 339 days.

(21) Appl. No.: 12/641,263

(22) Filed: Dec. 17, 2009

(65) Prior Publication Data

US 2010/0190831 A1 Jul. 29, 2010

Related U.S. Application Data

(60) Provisional application No. 61/138,923, filed on Dec. 18, 2008.

(51) Int. Cl.
A61K 31/343 (2006.01)
C07D 307/83 (2006.01)

(52) U.S. Cl. ........................ 514/468; 549/462
(58) Field of Classification Search .................. 514/468; 549/462
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,013,556 | A | 5/1991 | Woodle et al. |
| 5,032,577 | A | 7/1991 | Fung et al. |
| 6,921,767 | B2 | 7/2005 | Srinivasan et al. |
| 2004/0092538 | A1 | 5/2004 | Nagarajan et al. |
| 2010/0144806 | A1 | 6/2010 | Yasuma et al. |
| 2010/0216827 | A1 | 8/2010 | Ma et al. |

FOREIGN PATENT DOCUMENTS

| EP | 0224816 A1 | 6/1987 |
| EP | 0234872 B1 | 11/1991 |
| EP | 1829863 A1 | 9/2007 |
| EP | 1067109 B1 | 12/2009 |
| EP | 2151236 | 2/2010 |
| EP | 2 298 750 A1 | 3/2011 |
| MX | 2009008921 A | 8/2009 |
| WO | WO 98/07715 A1 | 2/1998 |
| WO | WO00/74666 | 12/2000 |
| WO | WO-03/099793 A1 | 12/2003 |
| WO | WO 2004/011445 A1 | 2/2004 |
| WO | WO 2004/031162 A1 | 4/2004 |
| WO | WO-2005/051890 | 6/2005 |
| WO | WO2005/080340 | 9/2005 |
| WO | WO-2005/086661 | 9/2005 |
| WO | WO2006/102375 | 9/2006 |
| WO | WO2006/102426 | 9/2006 |
| WO | WO 2007/007919 A2 | 1/2007 |
| WO | WO-2007/013689 | 2/2007 |
| WO | WO 2007/030061 A1 | 3/2007 |
| WO | WO-2007/049050 | 5/2007 |
| WO | WO-2008/001931 | 1/2008 |
| WO | WO 2008/030618 A1 | 3/2008 |
| WO | WO-2009/048527 | 4/2008 |
| WO | WO-2008/054675 | 5/2008 |
| WO | WO 2008/073825 A1 | 6/2008 |
| WO | WO-2008/103500 A1 | 8/2008 |
| WO | WO 2008/103501 A1 | 8/2008 |
| WO | WO-2008/130514 | 10/2008 |
| WO | WO 2008/139987 A1 | 11/2008 |
| WO | WO 2008/151211 A1 | 12/2008 |
| WO | WO2009/046371 | 4/2009 |
| WO | WO2010/048207 | 4/2010 |
| WO | WO2010/080537 | 7/2010 |

OTHER PUBLICATIONS

King, Med. Chem., (1994) pp. 206-208.*
"Report of the Expert Committee on the Diagnosis and Classification of Diabetes Mellitus." *Diabetes Care*, (1999) vol. 2 (Suppl 1):S5-19.
Barrett-Conner, "Epidemiology, obesity, and non-insulin-dependent diabetes mellitus." *Epidemol Rev* (1989) 11: 172-181.
Bell et al., "Diabetes mellitus and genetically programmed defects in β-cell function." *Nature* (2001) 414: 788-791.
Briscoe et al., "Pharmacological regulation of insulin secretion in MIN6 cells through the fatty acid receptor GPR40: identification of agonist and antagonist small molecules." *British Journal of Pharmacology* (2006) 148, 619-628.
Bromidge et al. "1-[2-C(Heteroarylmethoxy)aryl] carbamoyl] indolines are selective and orally active 5-HT2C receptor inverse agonists." *Bioorganic & Medicinal Chemistry Letters, Pergamon, Elsevier Science*, GB, (2000) 10(16), pp. 1867-1870, XP004216018.
Brubaker, "The Glucagon-Like Peptides Pleiotropic Regulators of Nutrient Homeostatsis." *Ann N Y Acad Sci* (2006) 1070: 10-26.
Cavaghan et al., "Interactions between insulin resistance and insulin secretion in the development of glucose intolerance." *J Clin Invest* (2000) 106(3): 329-333. Chiasson et al., "The Efficacy of Acarbose in the Treatment of Patients with Non-Insulin-dependent Diabetes Mellitus: A Multicenter Controlled Clinical Trial." *Ann Intern Med* (1994) 121(12): 928-935.
Coniff et al., "Acarbose: A Review of US Clinical Experience." *Clin Ther* (1997) 19(1): 16-26.
Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus." *Am J Med* (1995) 98: 443-451.
Defronzo et al. (eds.), *Diabetes Reviews* (1997) vol. 5 No. 4.
Drucker, "The role of gut hormones in glucose homeostasis." *J Clin Invest* (2007) 117(1): 24-32.
Elahi et al., "The insulinotropic actions of glucose-dependent insulinotropic polypeptide (GIP) and glucagon-like peptide-1 (7-37) in normal and diabetic subjects." *Regul Pept* (1994) 51: 63-74.
Farilla et al., "Glucagon-Like Peptide 1 Inhibits Cell Apoptosis and Improves glucose Responsiveness of Freshly Isolated Human Islets." *Endocrinology* (2003) 144(12): 5149-5158.

(Continued)

Primary Examiner — Taofiq A Solola
(74) Attorney, Agent, or Firm — Foley & Lardner LLP

(57) ABSTRACT

GPR120 agonists are provided. These compounds are useful for the treatment of metabolic diseases, including Type II diabetes and diseases associated with poor glycemic control.

15 Claims, No Drawings

OTHER PUBLICATIONS

Farilla et al., "Glucagon-Like Peptide-1 Promotes Islet Cell Growth and Inhibits Apoptosis in Zucher Diabetic Rats." *Endocrinology* (2002) 143(11): 4397-4408.

Filipsson et al., "The Neuropeptide Pituitary Adenylate Cyclase-Activating Polypeptide and Islet Function." *Diabetes* (2001) 50(9): 1959-1969.

Flier, "Insulin Receptors and Insulin Resistance." *Ann Rev Med* (1983) 34: 145-160.

Friedrichsen et al., "Stimulation of pancreatic β-cell replication by incretins involves transcriptional induction of cyclin D1 via multiple signalling pathways." *J Endocrinol* (2006) 188(3): 481-492.

Gilon et al., "Mechanisms and Physiological Significance of the Cholinergic Control of Pancreatic β-Cell Function." *Endocr Rev* (2001) 22(5): 565-604.

Gloyn et al., "Insights into the Structure and Regulation of Glucokinase from a Novel Mutation (V62M), Which Causes Maturity-onset Diabetes of the Young." *J Biol Chem* (2005) 280(14): 14105-14113.

González et al., "Investigational treatments for type 2 diabetes mellitus: exenatide and liraglutide." *Expert Opin Investig Drugs* (2006) 15(8): 887-895.

Gotoh et al., *Biochem. Biophys. Res. Commun.* Mar. 2007; 354(2): 591-597.

Green et al. "Dipeptidyl peptidase IV (DPP IV) inhibitors: a newly emerging drug class for the treatment of type 2 diabetes." *Diabetes Vasc. Dis. Res.* (2006), 3:159-165.

Guertin et al., "Small Molecule Glucokinase Activators as Glucose Lowering Agents: A New Paradigm for Diabetes Therapy." *Curr Med Chem* (2006) 13(15): 1839-1843.

Haffner, "Management of Dyslipidemia in Adults With Diabetes." *Diabetes Care* (1998) 21(1): 160-178.

Hansotia et al., "Extrapancreatic incretin receptors modulate glucose homeostasis, body weight, and energy expenditure." *J Clin Invest* (2007) 117(1): 143-152, Epub Dec. 21, 2006.

Hill et al. "Synthesis of Some New 2-Aryloxy and 2-Alkyloxy Pyridines." *Journal of Organic Chemistry*, American Chemical Society, Easton.; US, (1948) 14:783-789, XP001109578.

Hirasawa, et al., *Nature Medicine* Jan. 2005; 11: 90-94.

Hussain et al., "Increased Pancreatic β-Cell Proliferation Mediated by CREB Binding Protein Gene Activation." *Mol Cell Biol* (2006) 26(20): 7747-7759.

Iakoubov, et al., *Endocrinology* Mar. 2007; 148(3): 1089-1098.

Iwamoto et al., "Effect of Combination Therapy of Troglitazone and Sulphonylureas in Patients with Type 2 Diabetes Who Were Poorly Controlled by Sulphonylurea Therapy Alone." *Diabet Med* (1996) 13: 365-370.

Jimenez et al. "Practical and Efficient Synthesis of Alkyl, Alkenyl and Aryl-alkyl α,α-Difluoro Esters as Precursors of Potential Inhibitors of the Pheromone Catabolism in Insects." *Synthesis* 2000, 13, 1917-1924.

Kahn, "The Importance of β-Cell Failure in the Development and Progression of Type 2 Diabetes." *J Clin Endicrinol Metab* (2001) 86:4047-4058.

Kahn, "The Importance of the β-Cell in the Pathogenesis of Type 2 Diabetes Mellitus." *Am J Med* (2000) 108 Suppl 6a, 2S-8S.

Kahn, "Type 2 Diabetes: When Insulin Secretion Fails to Compensate for Insulin Resistance." *Cell* (1998) 92: 593-596.

Kaplan et al., "Cardiovascular diseases" in Health and Human Behavior, *McGraw-Hill*, New York (1993) pp. 206-242.

Katsuma et al. "Free Fatty Acids Inhibit Serum Deprivation-induced Apoptosis through GPR120 in a Murine Enteroendocrine Cell Line STC-1*" *J. Biol. Chem.* May 2005; 280:19507-19515.

Kim et al., "Exendin-4 induction of cyclin D1 expression in INS-1 β-cells: involvement of cAMP-responsive element." *J Endocrinol* (2006) 188(3): 623-633.

Knowler et al., "Obesity in the Pima Indians: its magnitude and relationship with diabetes[1,2]." *Am J Clin Nutr* (1991) 53: 1543S-1551S.

Kwiterovich, "State-of-the-Art Update and Review: Clinical Trials of Lipid-Lowering Agents." *Am J Cardiol* (1998) 82(12A): 3U-17U.

Langer, "New Methods of Drug Delivery." *Science* (1990) 249: 1527-1533.

Levy et al., "Beta-cell Deterioration Determines the Onset and Rate of Progression of Secondary Dietary Failure in Type 2 Diabetes Mellitus: the 10-year Follow-up of the Belfast Diet Study." *Diabetes Med* (1998) 15: 290-296.

Li et al., "Glucagon-like Peptide-1 Receptor Signaling Modulates β Cell Apoptosis." *J Biol Chem* (2003) 278(1): 471-478.

Mahler et al., "Clinical Review 102 Type 2 Diabetes Mellitus: Update on Diagnosis, Pathophysiology, and Treatment." *J Clin Endocrinol Metab* (1999) 84(4): 1165-1171.

Matschinsky et al., "Perspectives in Diabetes the Network of Glucokinase-Expressing Cells in Glucose Homeostasis and the Potential of Glucokinase Activators for Diabetes Therapy." *Diabetes* (2006) 55(1): 1-12.

Matschinsky, "Glucokinase, Glucose Homeostasis, and Diabetes Mellitus." *Curr Diab Rep* (2005) 5(3): 171-176.

Matsumura, et al., *Biomed. Res.* Feb. 2007; 28(1) 49-55.

Meneilly et al., "The Effect of Glyburide on β-Cell Sensitivity to Glucose-Dependent Insulinotropic Polypeptide." *Diabetes Care* (1993) 16(1): 110-114.

Nauck et al., "Preserved Incretin Activity of Glucagon-like Peptide 1 [7-36 Amide] but Not of Synthetic Human Gastric Inhibitory Polypeptide in Patients with type-2 Diabetes Mellitus." *J Clin Invest* (1993) 91: 301-307.

Prentki et al., "Islet β cell Failure in type 2 dieabetes." *J Clin Invest* (2006) 116(7): 1802-1812.

Qader et al., "Expression of islet inducible nitric oxide synthase and inhibition of glucose-stimulated insulin release after long-term lipid infusion in the rat is counteracted by PACAP27." *Am J Physiol Endocrinol Metab* (2007) 292(5): E1447-E1455.

Rayasam, et al., *Expert Opin. Ther. Targets* May 2007; 11(5): 661-671.

Reaven, "Insulin Resistance and Human Disease: A Short History." *J Basic & Clin Phys & Pharm* (1998) 9: 387-406.

Reimann et al., "Signaling Mechanisms Underlying the Release of Glucagon-Like Peptide 1." *Diabetes* (2006) 55(Suppl 2): S78-S85.

Saltiel, "New Perspectives into the Molecular Pathogenesis and Treatment of Type 2 Diabetes." *Cell* (2001) 104: 517-529.

Steinthorsdottir et al., "A variant in *CDKAL1* influences insulin response and risk of type 2 diabetes." *Nature Genetics* (2007) 39(6):770-775.

Tanaka et al., "Cloning and characterization of the rat free fatty acid receptor GPR120: in vivo effect of the natural ligand on GLP-1 secretion and proliferation of pancreatic β cells." *Naunyn Schmiedeberg Arch Pharmacol* (2008); 377(4-6):515-22.

Thorens, "GLUT2 in pancreatic and extra-pancreatic gluco-detection." *Mol Membr Biol* (2001) 18(4): 265-273.

Turner et al. "Glycemic Control With Diet, Sulfonylurea, Metformin, or Insulin in Patients With Type 2 Diabetes Mellitus: Progressive Requirement for Multiple Therapies (UKPDS 49)." *JAMA* 281:2005-2012, 1999.

Turner et al., "Insulin resistance, impaired glucose tolerance and non-insulin-dependent diabetes, pathologic mechanisms and treatment: Current status and therapeutic possibilities." *Prog Drug Res* (1998) 51: 33-94.

United Kingdom Prospective Diabetes Study Group: "UKPDS 28: A Randomized Trial of Efficacy of Early Addition of Metformin in Sulfonylurea-Treated Type 2 Diabetes." *Diabetes Care* (1998) 21(1): 87-92.

Vilsbøll et al., "Reduced Postprandial Concentrations of Intact Biologically Active Glucagon-Like Peptide 1 in Type 2 Diabetic Patients." *Diabetes* (2001) 50: 609-613.

XP002573727, Database Registry [Online] Chemical Abstracts Service, Columbus, Ohio, US; Sep. 26, 2008.

XP002573728, Database Registry [Online] Chemical Abstracts Service, Columbus, Ohio, US; Sep. 25, 2008.

Yamada et al., "Cytosolic $Ca^{2+}$ responses to sub-picomolar and nanomolar PACAP in pancreatic β-cells are mediated by VPAC2 and PAC1 receptors." *Regul Pept* (2004) 123(1-3): 147-153.

Zhou et al., "Overexpression of Repressive cAMP Response Element Modulators in High Glucose and Fatty Acid-treated Rat Islets." *J Biol Chem* (2003) 278(51): 51316-51323.

Allen et al., "Halofenate is a selective peroxisome proliferator-activated receptor gamma modulator with antidiabetic activity", Diabetes, 2006, 55(9):2523-2533.

U.S. Appl. No. 12/817,116, filed Jun. 16, 2010, Dong Fang et al.

Aronow et al., "Halofenate: An effective Hypolipemia- and hypouricemia-inducing drug", Current Therapuetic Research, 1973, 15(12):902-906.

Mandel, "Studies on the mechanism of action of halofenate", LIPIDS, 1977, 12(1):34-43.

Saxena et al., "Genome-Wide Association Analysis Identifies Loci for Type 2 Diabetes and Triglyceride Levels", Science, 2007, 316(5829):1331-1336.

King et al. Bioisosteres, Conformational Restriction, and Prodrugs—Case History: An Example of a Conformational Restriction Approach. Med. Chem. (1994) pp. 206-208.

* cited by examiner

GPR120 RECEPTOR AGONISTS AND USES THEREOF

CROSS-REFERENCE TO RELATED APPLICATION

This application claims the benefit under 35 U.S.C. 119(e) of U.S. Provisional Application No. 61/138,923, filed Dec. 18, 2008, which is incorporated by reference in its entirety into this application.

BACKGROUND OF THE INVENTION

Diabetes mellitus can be divided into two clinical syndromes, Type I and Type II diabetes mellitus. Type I diabetes, or insulin-dependent diabetes mellitus, is a chronic autoimmune disease characterized by the extensive loss of beta cells in the pancreatic islets of Langerhans (hereinafter referred to as "pancreatic islet cells" or "islet cells"), which produce insulin. As these cells are progressively destroyed, the amount of secreted insulin decreases, eventually leading to hyperglycemia (abnormally high level of glucose in the blood) when the amount secreted drops below the level required for euglycemia (normal blood glucose level). Although the exact trigger for this immune response is not known, patients with Type I diabetes have high levels of antibodies against pancreatic beta cells (hereinafter "beta cells"). However, not all patients with high levels of these antibodies develop Type I diabetes.

Type II diabetes, or non-insulin-dependent diabetes mellitus, develops when muscle, fat and liver cells fail to respond normally to insulin. This failure to respond (called insulin resistance) may be due to reduced numbers of insulin receptors on these cells, or a dysfunction of signaling pathways within the cells, or both. The beta cells initially compensate for this insulin resistance by increasing their insulin output. Over time, these cells become unable to produce enough insulin to maintain normal glucose levels, indicating progression to Type II diabetes (Kahn S E, *Am J Med* (2000) 108 Suppl 6a, 2S-8S).

The fasting hyperglycemia that characterizes Type II diabetes occurs as a consequence of the combined lesions of insulin resistance and beta cell dysfunction. The beta cell defect has two components: the first component, an elevation of basal insulin release (occurring in the presence of low, non-stimulatory glucose concentrations), is observed in obese, insulin-resistant pre-diabetic stages as well as in Type II diabetes. The second component is a failure to increase insulin release above the already elevated basal output in response to a hyperglycemic challenge. This lesion is absent in prediabetes and appears to define the transition from normo-glycemic insulin-resistant states to frank diabetes. There is currently no cure for diabetes. Conventional treatments for diabetes are very limited, and focus on attempting to control blood glucose levels in order to minimize or delay complications. Current treatments target either insulin resistance (metformin, thiazolidinediones ("TZDs")), or insulin release from the beta cell (sulphonylureas, exenatide). Sulphonylureas, and other compounds that act by depolarizing the beta cell, have the side effect of hypoglycemia since they cause insulin secretion independent of circulating glucose levels. One approve drug, Byetta (exenatide) stimulates insulin secretion only in the presence of high glucose, but is not orally available and must be injected. Januvia (sitagliptin) is another recently approved drug that increases blood levels of incretin hormones, which can increase insulin secretion, reduce glucagon secretion and have other less well characterized effects. HoweverJanuvia and other dipeptidyl peptidases IV inhibitors may also influence the tissue levels of other hormones and peptides, and the long-term consequences of this broader effect have not been fully investigated. There is an unmet need for oral drugs that stimulate insulin secretion in a glucose dependent manner.

Progressive insulin resistance and loss of insulin secreting pancreatic beta cells are primary characteristics of Type II diabetes. Normally, a decline in the insulin sensitivity of muscle and fat is compensated for by increases in insulin secretion from the beta cell. However, loss of beta cell function and mass results in insulin insufficiency and diabetes (Kahn B B, *Cell* 92:593-596, 1998; Cavaghan M K, et al., *J Clin Invest* 106:329-333, 2000; Saltiel A R, *Cell* 104:517-529, 2001; Prentki M and Nolan C J, *J Clin Invest* 116:1802-1812 (2006); and Kahn S E, *J Clin Endocrinol Metab* 86:4047-4058, 2001). Hyperglycemia further accelerates the decline in beta cell function (UKPDS Group, *JAMA* 281: 2005-2012, 1999; Levy J, et al., *Diabetes Med* 15:290-296, 1998; and Zhou Y P, et al., *J Biol Chem* 278:51316-23, 2003). Several of the genes in which allelic variation is associated with an increased risk of Type II diabetes are expressed selectively in the beta cell (Bell G I and Polonsky K S, *Nature* 414:788-791 (2001); Saxena R, et al., *Science* (2007) Apr. 26; and Valgerdur Steinthorsdottir, et al., *Nature Genetics* (2007) Apr. 26).

Insulin secretion from the beta cells of pancreatic islets is elicited by increased levels of blood glucose. Glucose is taken up into the beta cell primarily by the beta cell and liver selective transporter GLUT2 (Thorens B, *Mol Membr Biol* 2001 October-December; 18(4):265-73). Once inside the cell, glucose is phosphorylated by glucokinase, which is the primary glucose sensor in the beta cell since it catalyzes the irreversible rate limiting step for glucose metabolism (Matschinsky F M, *Curr Diab Rep* 2005 June; 5(3):171-6). The rate of glucose-6-phosphate production by glucokinase is dependent on the concentration of glucose around the beta cell, and therefore this enzyme allows for a direct relationship between level of glucose in the blood and the overall rate of glucose oxidation by the cell. Mutations in glucokinase produce abnormalities in glucose dependent insulin secretion in humans giving further evidence that this hexokinase family member plays a key role in the islet response to glucose (Gloyn A L, et al., *J Biol Chem* 2005 Apr. 8; 280(14):14105-13, Epub 2005 Jan. 25). Small molecule activators of glucokinase enhance insulin secretion and may provide a route for therapeutic exploitation of the role of this enzyme (Guertin K R and Grimsby J, *Curr Med Chem* 2006; 13(15):1839-43; and Matschinsky F M, et al., *Diabetes* 2006 January; 55(1):1-12) in diabetes. Glucose metabolism via glycolysis and mitochondrial oxidative phosphorylation ultimately results in ATP production, and the amount of ATP produced in a beta cell is directly related to the concentration of glucose to which the beta cell is exposed.

Glucose dependent insulin secretion from the beta cell is dependent on numerous neurotransmitters and blood-borne hormones, as well as local, intra-islet factors. CNS activation of the vagal innervation of the islet can lead to the release of small molecules such as acetylcholine and peptides such as vasoactive intestinal polypeptide (VIP), gastrin releasing peptide (GRP) and Pituitary Adenylate Cyclase Activating Peptide (PACAP). Acetylcholine activation of phospholipase C through the $G_{\alpha q}$-coupled GPCR M3 muscarinic receptor leads to release of $Ca^{2+}$ from intracellular stores (Gilon P and Henquin J C, *Endocr Rev* 2001 October; 22(5):565-604). Cholinergic agonists also lead to a subtle $Na^+$-dependent plasma membrane depolarization that can work in concert with glucose-initiated depolarization to enhance insulin release (Gilon P and Henquin J C, *Endocr Rev* 2001 October; 22(5):565-604). VIP and PACAP each bind to an overlapping set of G$_\alpha$-coupled GPCRs (PAC1, VIPR1, and VIPR2) on the beta cell that lead to stimulation of adenylate cyclase and an increase in intracellular cAMP (Filipsson K, et al., *Diabetes* 2001 September; 50(9):1959-69; Yamada H, et al., *Regul Pept* 2004 Dec. 15; 123(1-3):147-53; and Qader S S, et al., *Am J Physiol Endocrinol Metab* 2007 May; 292(5):E1447-55).

Incretin hormones such as Glucagon-Like Peptide 1 (GLP-1) and Glucose-dependent Insulinotropic Polypeptide (GIP, also known as Gastric Inhibitory Polypeptide) also bind to specific Galpha$_s$-coupled GPCRs receptors on the surface of islet cells, including beta cells, and raise intracellular cAMP (Drucker D J, *J Clin Invest* 2007 January; 117(1):24-32). Although the receptors for these hormones are present in other cells and tissues, the overall sum of effects of these peptides appear to be beneficial to control of glucose metabolism in the organism (Hansotia T, et al., *J Clin Invest* 2007 January; 117(1):143-52, Epub 2006 Dec. 21). GIP and GLP-1 are produced and secreted from intestinal K and L cells, respectively, and these peptide hormones are released in response to meals by both direct action of nutrients in the gut lumen and neural stimulation resulting from food ingestion. GIP and GLP-1 have short half-lives in human circulation due to the action of the protease dipeptidyl-peptidase IV (DP-PIV), and inhibitors of this protease can lower blood glucose due to their ability to raise the levels of active forms of the incretin peptides. The glucose lowering that can be obtained with DPPIV inhibitors, however, is somewhat limited since these drugs are dependent on the endogenous release of the incretin hormones. Peptides (e.g., exanatide (Byetta)) and peptide-conjugates that bind to the GIP or GLP-1 receptors but are resistant to serum protease cleavage can also lower blood glucose substantially (Gonzalez C, et al., *Expert Opin Investig Drugs* 2006 August; 15(8):887-95), but these incretin mimetics must be injected and tend to induce a high rate of nausea and therefore are not ideal therapies for general use in the Type II diabetic population. The clinical success of DPPIV inhibitors and incretin mimetics, though far from ideal, do point to the potential utility of compounds that increase incretin activity in the blood. Some studies have indicated that beta cell responsiveness to GIP is diminished in Type II diabetes (Nauck M A, et al., *J Clin Invest* 91:301-307 (1993); and Elahi D, et al., *Regul Pept* 51:63-74 (1994)). Restoration of this responsiveness (Meneilly G S, et al., *Diabetes Care* 1993 January; 16(1):110-4) may be a promising way to improve beta cell function in vivo.

Since increased incretin activity has a positive effect on glucose dependent insulin secretion and perhaps other mechanisms that lead to lower blood glucose, it is also of interest to explore therapeutic approaches to increasing incretin release from intestinal K and L cells. GLP-1 secretion appears to be attenuated in Type II diabetes (Vilsboll T, et al., *Diabetes* 50:609-613), so improving incretin release may ameliorate this component of metabolic dysregulation. Nutrients such as glucose and fat in the gut lumen prompt incretin secretion by interaction with apical receptors (Vilsboll T, et al., *Diabetes* 50:609-613). GLP-1 and GIP release can also result from neural stimulation; acetylcholine and GRP can enhance incretin release in a manner perhaps analogous to the effects of these neurotransmitters on the beta cell in regard to insulin secretion (Brubaker P, *Ann N Y Acad Sci* 2006 July; 1070:10-26; and Reimann F, et al., *Diabetes* 2006 December; 55(Suppl 2):S78-S85). Somatostatin, leptin and free fatty acids also appear to modulate incretin secretion (Brubaker P, *Ann N Y Acad Sci* 2006 July; 1070:10-26; and Reimann F, et al., *Diabetes* 2006 December; 55(Suppl 2):S78-S85). To date, however, there does not appear to be a way to selectively impact these pathways to promote incretin secretion for therapeutic benefit. There is a need for oral drugs that stimulate incretin secretion in the treatment of diabetes.

Incretins can also increase the rate of beta cell proliferation and decrease the apoptotic rates of beta cells in animal models (Farilla L, et al., *Endocrinology* 2002 November; 143(11): 4397-408) and human islets in vitro (Farilla L, et al., *Endocrinology* 2003 December; 144(12):5149-58). The net result of these changes is an increase in beta cell number and islet mass, and this should provide for increased insulin secretory capacity, which is another desired aim of anti-diabetic therapies. GLP-1 has also been shown to protect islets from the destructive effects of agents such as streptozotocin by blocking apoptosis (Li Y, et al., *J Biol Chem* 2003 Jan. 3; 278(1): 471-8). Cyclin D1, a key regulator of progression through the cell cycle, is up-regulated by GLP-1, and other agents that increase cAMP and PKA activity also have a similar effect (Friedrichsen B N, et al., *J Endocrinol* 2006 March; 188(3): 481-92; and Kim M J, et al., *J Endocrinol* 2006 March; 188(3):623-33). Increased transcription of the cyclin D1 gene occurs in response to PKA phosphorylation of CREB (cAMP-response element binding) transcription factors (Hussain M A, et al., *Mol Cell Biol* 2006 October; 26(20): 7747-59). There is a need for oral drugs that increase beta cell number and islet mass in the treatment of diabetes.

G protein-coupled receptors (GPCRs) are cell-surface receptors that play an important physiological role by transducing and amplifying extra-cellular signals such as hormones, growth factors, neurotransmitters and physiologically active substances. GPCRs are associated with changes in intracellular $Ca^{2+}$ concentration as well as increases in intracellular inositol 1,4,5-triphosphate (IP3) concentration. These second messengers serve to focus the signal transduction events and stimulate other pathways. Hence, GPCRs are therapeutically important target classes in the pharmaceutical industry.

GPR120 is a GPCR for unsaturated long-chain free fatty acids (FFA) and is highly expressed in lung, intestine, adipocytes and taste cells as well as in the enteroendocrine cell lines such as STC-1 and GLUTag (Hirasawa et al., *Nature Medicine* 2005 January; 11: 90-94; and Iakoubov et al., *Endocrinology* 2007 March; 148(3): 1089-1098; and Katsuma et al., *J. Biol. Chem.* 2005 May; 280:19507-19515; Matsumura et al., *Biomed. Res.* 2007 February; 28(1) 49-55). The stimulation of GPR120 by FFAs increases the release of $Ca^{2+}$ from intracellular stores indicating that GPR120 is a G$\alpha$q-coupled receptor. GPR120 mediates the effect of unsaturated long-chain free fatty acids in stimulating GLP-1 and cholecystokinin (CCK) secretion, increases plasma insulin, activation of the extracellular signal-regulated kinase (ERK) cascade, proliferation of pancreatic $\beta$ cells, inhibition of serum deprivation-induced apoptosis and adipogenesis (Katsuma et al., *J. Biol. Chem.* 2005 May; 280:19507-19515; and Rayasam et al., *Expert Opin. Ther. Targets* 2007 May; 11(5): 661-671; and Tanaka et al., *Naunyn Schmiedeberg Arch Pharmacol* 2008 June; 377(4-6):515-522; and Gotoh et al., *Biochem. Biophys. Res. Commun.* 2007 March; 354(2): 591-597).

Free fatty acids have been demonstrated as ligands for recently identified orphan GPCRs (Rayasam et al., *Expert Opin Ther Targets* 2007 May; 11(5):661-671). GPR120 shares ligand specificity with other fatty acid receptors and there is a need for the development of small molecule agents that are specific modulators for GPR120 function. In particular, GPR120 is a promising target for the treatment of diabetes, obesity and the metabolic syndrome considering the significant role of GLP-1 and CCK in insulin secretion, gastric emptying and appetite feeding control.

BRIEF SUMMARY OF THE INVENTION

Novel GPR120 compound agonists, methods for their preparation, and related synthetic intermediates and compositions are provided. The novel GPR120 agonists are useful in the treatment of diabetes and other related diseases including metabolic syndrome, dyslipidemia, insulin resistance, and complications of diabetes.

Further provided are methods for treating diseases such as Type II diabetes and other diseases and conditions using one or more of these compounds or compositions, as described in further detail below. The invention also provides methods of raising intracellular levels of $Ca^{2+}$ by using one or more of the compounds described herein. Further, the compounds may be used to stimulate insulin production and stimulate secretion of insulin, glucagon-like peptide 1 (GLP1), and glucose dependent insulinotropic polypeptide (GIP) in a mammal, in particular a human. Additionally, the compounds described herein are useful in lowering blood glucose when administered to a mammal in need of treatment to lower blood glucose.

DETAILED DESCRIPTION OF THE INVENTION

The abbreviations used herein are conventional, unless otherwise defined: AcOH: acetic acid; nBuLi: n-butyllithium; $Cs_2CO_3$: cesium carbonate; $CH_2Cl_2$ or DCM: dichloromethane; $CH_3MgI$: methyl magnesium iodide; $CuCl_2$: copper chloride; DAST: (diethylamino)sulfur trifluoride; DEAD: diethyl azodicarboxylate; DIBAL: diisobutylaluminum hydride; DIPEA: diisopropylethylamine; DMF: dimethylformamide; DMSO: dimethyl sulfoxide; $Et_3N$: triethylamine; EtOAc: ethyl acetate; EtOH: ethanol; g: gram(s); h: hour; $H_2$: hydrogen; HBr: hydrogen bromide; HCl: hydrogen chloride; $H_2O$: water; $H_2O_2$: hydrogen peroxide; HPLC: high performance liquid chromatography; KCN: potassium cyanide; LHMDS: lithium hexamethyldisilazide; $LiAlH_4$: lithium aluminum hydride; LiOH: lithium hydroxide; M: molar; MeCN: acetonitrile; MeI: methyl iodide; MeOH: methanol; $MgSO_4$: magnesium sulfate; $MgCO_3$: magnesium carbonate; mg: milligram; MsCl: mesyl chloride; mmol: millimoles; mL: milliliter; sodium hydrogen sulfite; $NaHSO_3$; mCPBA: meta-chloroperoxybenzoic acid; N: normality; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium bisulfate; $Na_2SO_4$: sodium sulfate; NBS: N-bromosuccinimide; $NH_4Cl$: ammonium chloride; $NH_4OAc$: ammonium acetate; NMR: nuclear magnetic resonance; Pd/C: palladium on carbon; $PPh_3$: triphenyl phosphine; iPrOH: isopropyl alcohol; $SOCl_2$: thionyl chloride; THF: tetrahydrofuran; TLC: thin layer chromatography; µL: microliter.

Unless otherwise stated, the following terms used in the specification and claims have the meanings given below.

"Alkyl" refers to monovalent saturated aliphatic hydrocarbyl groups having from 1 to 10 carbon atoms and, in some embodiments, from 1 to 6 carbon atoms. "$C_{u-v}$alkyl" refers to alkyl groups having from u to v carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Substituted alkyl" and "substituted $C_{u-v}$alkyl" refers to an alkyl group having from 1 to 5 and, in some embodiments, 1 to 3 or 1 to 2 substituents selected from the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, $SO_3H$, substituted sulfonyl, sulfonyloxy, thioacyl, thiocyanate, thiol, alkylthio, and substituted alkylthio, wherein said substituents are as defined herein.

"Alkenyl" refers to a linear or branched hydrocarbyl group having from 2 to 10 carbon atoms and, in some embodiments, from 2 to 6 carbon atoms or 2 to 4 carbon atoms and having at least one site of vinyl unsaturation (>C=C<). "$C_{u-v}$alkenyl" refers to alkenyl groups having from u to v carbon atoms and is meant to include for example, ethenyl, propenyl, 1,3-butadienyl, and the like.

"Substituted alkenyl" and "substituted $C_{u-v}$alkenyl" refers to alkenyl groups having from 1 to 3 substituents and, in some embodiments, 1 to 2 substituents, selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined as herein and with the proviso that any hydroxy or thiol substitution is not attached to an acetylenic carbon atom.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. "$C_{u-v}$alkynyl" refers to alkynyl groups having from u to v carbon atoms and is meant to include ethynyl, propynyl, and the like.

"Substituted alkynyl" and "substituted $C_{u-v}$alkynyl" refers to alkynyl groups having from 1 to 3 substituents and, in some embodiments, from 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy. "$C_{u-v}$alkoxy" refers to alkoxy groups having from u to v carbon atoms "Substituted alkoxy" and "substituted $C_{u-v}$alkoxy" refers to the group —O-(substituted alkyl) wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, substituted hydrazino, heteroaryl, substituted heteroaryl, heterocyclic and substituted heterocyclic are as defined herein. Acyl includes the "acetyl" group $CH_3C(O)$—.

"Acylamino" refers to the groups —$NR^{20}$C(O)H, —$NR^{20}$C(O)alkyl, —$NR^{20}$C(O) substituted alkyl, —$NR^{20}$C(O)cycloalkyl, —$NR^{20}$C(O) substituted cycloalkyl, —$NR^{20}$C(O) alkenyl, —$NR^{20}$C(O) substituted alkenyl, —$NR^{20}$C(O) alkynyl, —$NR^{20}$C(O) substituted alkynyl, —$NR^{20}$C(O) aryl, —$NR^{20}$C(O) substituted aryl, —$NR^{20}$C(O)heteroaryl, —$NR^{20}$C(O) substituted heteroaryl, —$NR^{20}$C(O)heterocyclic, and —$NR^{20}$C(O) substituted heterocyclic wherein $R^{20}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{21}R^{22}$ where $R^{21}$ and $R^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —$S(O)_2$-alkyl, —$S(O)_2$-substituted alkyl, —$S(O)_2$-alkenyl, —$S(O)_2$-substituted alkenyl, —$S(O)_2$-cycloalkyl, —$S(O)_2$-substituted cylcoalkyl, —$S(O)_2$-aryl, —$S(O)_2$-substituted aryl, —$S(O)_2$-heteroaryl, —$S(O)_2$-substituted heteroaryl, —$S(O)_2$-heterocyclyl, and —$S(O)_2$-substituted heterocyclyl and wherein $R^{21}$ and $R^{22}$ are optionally joined together with the nitrogen bound thereto to form a heterocyclyl or substituted heterocyclyl group, provided that $R^{21}$ and $R^{22}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{21}$ is hydrogen and $R^{22}$ is alkyl, the substituted amino group is sometimes referred to herein as alkylamino. When $R^{21}$ and $R^{22}$ are alkyl, the substituted amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, hydroxy, alkoxy, and substituted alkoxy, and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, hydroxy, alkoxy, and substituted alkoxy are as defined herein.

"Aminothiocarbonyl" refers to the group —$C(S)NR^{23}R^{24}$ where $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{20}C(O)NR^{23}R^{24}$ where $R^{20}$ is hydrogen or alkyl and $R^{23}$ and $R^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where $R^{23}$ and $R^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{20}$C(S)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —S(O)$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—S(O)$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{20}$—S(O)$_2$NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{25}$)NR$^{23}$R$^{24}$ where R$^{25}$, R$^{23}$, and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8-tetrahydronaphthalene-2-yl is an aryl group as its point of attachment is at the 2-position of the aromatic phenyl ring).

"Substituted aryl" refers to aryl groups which are substituted with 1 to 8 and, in some embodiments, 1 to 5, 1 to 3 or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are defined herein.

"Arylalkyl" or "Aryl(C$_1$-C$_z$)alkyl" refers to the radical —R$^u$R$^v$ where R$^u$ is an alkylene group (having 8 or fewer main chain carbon atoms) and R$^v$ is an aryl group as defined herein. Thus, "arylalkyl" refers to groups such as, for example, benzyl, and phenylethyl, and the like. Similarly, "Arylalkenyl" means a radical —R$^u$R$^v$ where R$^u$ is an alkenylene group (an alkylene group having 1 or 2 double bonds) and R$^v$ is an aryl group as defined herein, e.g., styrenyl, 3-phenyl-2-propenyl, and the like.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azido" refers to the group —N$_3$.

"Hydrazino" refers to the group —NHNH$_2$.

"Substituted hydrazino" refers to the group —NR$^{26}$NR$^{27}$NR$^{28}$ where R$^{26}$, R$^{27}$, and R$^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, and substituted sulfonyl and wherein R$^{27}$ and R$^{28}$ are optionally joined, together with the nitrogen bound thereto to form a heterocyclic or substituted heterocyclic group, provided that R$^{27}$ and R$^{28}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, substituted heterocyclic and substituted sulfonyl are as defined herein.

"Cyano" or "carbonitrile" refers to the group —CN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{20}$—C(O)O-alkyl, —NR$^{20}$—C(O)O-substituted alkyl, —NR$^{20}$—C(O)O-alkenyl, —NR$^{20}$—C(O)O-substituted alkenyl, —NR$^{20}$—C(O)O-alkynyl, —NR$^{20}$—C(O)O-substituted alkynyl, —NR$^{20}$—C(O)O-aryl, —NR$^{20}$—C(O)O-substituted aryl, —NR$^{20}$—C(O)β-cycloalkyl, —NR$^{20}$—C(O)O-substituted cycloalkyl, —NR$^{20}$—C(O)O-heteroaryl, —NR$^{20}$—C(O)O-substituted heteroaryl, —NR$^{20}$—C(O)O-heterocyclic, and —NR$^{20}$—C(O)O-substituted heterocyclic wherein R$^{20}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl. "C$_{u-v}$cycloalkyl" refers to cycloalkyl groups having u to v carbon atoms as ring members. "C$_{u-v}$cycloalkenyl" refers to cycloalkenyl groups having u to v carbon atoms as ring members.

"Cycloalkenyl" refers to a partially saturated cycloalkyl ring having at least one site of >C=C< ring unsaturation.

"Substituted cycloalkyl" refers to a cycloalkyl group, as defined herein, having from 1 to 8, or 1 to 5, or, in some embodiments, 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiocyanate, thiol, alkylthio, and substituted alkylthio, wherein said substituents are as defined herein. The term "substituted cycloalkyl" includes substituted cycloalkenyl groups.

"Cycloalkyloxy" refers to —O-cycloalkyl wherein cycloalkyl is as defined herein.

"Substituted cycloalkyloxy" refers to —O-(substituted cycloalkyl) wherein substituted cycloalkyl is as defined herein.

"Cycloalkylthio" refers to —S-cycloalkyl wherein substituted cycloalkyl is as defined herein.

"Substituted cycloalkylthio" refers to —S-(substituted cycloalkyl) wherein substituted cycloalkyl is as defined herein.

"Guanidino" refers to the group —NHC(=NH)NH$_2$.

"Substituted guanidino" refers to —NR$^{29}$C(=NR$^{29}$)N(R$^{29}$)$_2$ where each R$^{29}$ is independently selected from the group consisting of hydrogen, alkyl, substituted alkyl, aryl, substituted aryl, heteroaryl, substituted heteroaryl, heterocyclyl, and substituted heterocyclyl and two R$^{29}$ groups attached to a common guanidino nitrogen atom are optionally joined together with the nitrogen bound thereto to form a heterocyclic or substituted heterocyclic group, provided that at least one R$^{29}$ is not hydrogen, and wherein said substituents are as defined herein.

"Halo" or "halogen" refers to fluoro, chloro, bromo and iodo.

"Haloalkyl" refers to substitution of alkyl groups with 1 to 5 or, in some embodiments, 1 to 3 halo groups, e.g., —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Haloalkoxy" refers to substitution of alkoxy groups with 1 to 5 or, in some embodiments, 1 to 3 halo groups, e.g., —OCH$_2$Cl, —OCH$_2$F, —OCH$_2$CH$_2$Br, —OCH$_2$CH$_2$Cl, —OCF$_3$, and the like.

"Hydroxy" or "hydroxyl" refers to the group —OH.

"Heteroalkyl" means an alkyl radical as defined herein with 1, 2 or 3 substituents independently selected from cyano, —OR$^w$, —NR$^x$R$^y$, —SR$^z$, —S(O)R$^z$, and —S(O)$_2$R$^z$ (where n is 0, 1, or 2), with the understanding that the point of attachment of the heteroalkyl radical is through a carbon atom of the heteroalkyl radical. R$^w$ is hydrogen, alkyl, cycloalkyl, cycloalkyl-alkyl, aryl, arylalkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or arylalkyl. R$^y$ is hydrogen, alkyl, cycloalkyl, cycloalkyl-alkyl, aryl, arylalkyl, alkoxycarbonyl, aryloxycarbonyl, carboxamido, mono- or di-alkylcarbamoyl or alkylsulfonyl. R$^z$ is hydrogen, alkyl, cycloalkyl, cycloalkyl-alkyl, aryl, arylalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^w$, R$^x$, R$^y$, and R$^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —OR$^w$, —NR$^x$R$^y$, —SR$^z$, —S(O)R$^z$, or —S(O)$_2$R$^z$ portions.

"Heteroaryl" refers to an aromatic group of from 1 to 14 carbon atoms and 1 to 6 heteroatoms selected from the group consisting of oxygen, nitrogen, and sulfur and includes a 5- to 18-member ring or ring system that includes a single ring (e.g., imidazolyl) or multiple rings (e.g., benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g., 1,2,3,4-tetrahydroquinolin-6-yl and 5,6,7,8-tetrahydroquinolin-3-yl). In one embodiment, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, tetrazolyl, triazolyl, imidazolyl, isoxazolyl, pyrrolyl, pyrazolyl, pyridazinyl, pyrimidinyl, benzofuranyl, tetrahydro benzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

"N-linked" refers to nitrogen containing groups in which the point of attachment is to the nitrogen atom of the nitrogen containing group. For example, "N-linked tetrazolyl" is a group in which the point of attachment is to a nitrogen atom of the tetrazolyl group. Similarly, N-linked triazolyl, N-linked imidazolyl, N-linked pyrazolyl and N-linked pyrrolyl are groups in which the point of attachment is to a nitrogen atom of the triazole, imidazole, pyrazole, and pyrrol group, respectively. Similarly, "N-linked imidazolyl" refers to an imidazole in which the point of attachment is to the nitrogen atom.

"Substituted heteroaryl" refers to heteroaryl groups that are substituted with from 1 to 8, or, in some embodiments, 1 to 5, or 1 to 3, or 1 to 2 substituents selected from the group consisting of the substituents defined for substituted aryl.

"Heteroaryloxy" refers to —O-heteroaryl wherein heteroaryl is as defined herein.

"Substituted heteroaryloxy" refers to the group —O-(substituted heteroaryl) wherein heteroaryl is as defined herein.

"Heteroarylthio" refers to the group —S-heteroaryl wherein heteroaryl is as defined herein.

"Substituted heteroarylthio" refers to the group —S-(substituted heteroaryl) wherein heteroaryl is as defined herein.

"Heterocycle" or "heterocyclic" or "heterocyclo" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the term "heterocyclic", "heterocycle", "heterocyclo", "heterocycloalkyl" or "heterocyclyl" applies when there is at least one ring heteroatom and the point of attachment is at an atom of a non-aromatic ring (e.g., 1,2,3,4-tetrahydroquinoline-3-yl, 5,6,7,8-tetrahydroquinoline-6-yl, and decahydroquinolin-6-yl). In one embodiment, the nitrogen and/or sulfur atom(s) of the heterocyclic group are optionally oxidized to provide for the N-oxide, sulfinyl, and sulfonyl moieties. More specifically the heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

"Substituted heterocycle" or "substituted heterocyclic" or "substituted heterocyclo" or "substituted heterocycloalkyl" or "substituted heterocyclyl" refers to heterocyclic groups, as defined herein, that are substituted with from 1 to 5 or, in some embodiments, 1 to 3 of the substituents as defined for substituted cycloalkyl.

"Heterocyclyloxy" refers to the group —O-heterocyclyl wherein heterocyclyl is as defined herein.

"Substituted heterocyclyloxy" refers to the group —O-(substituted heterocyclyl) wherein heterocyclyl is as defined herein.

"Heterocyclylthio" refers to the group —S-heterocyclyl wherein heterocyclyl is as defined herein.

"Substituted heterocyclylthio" refers to the group —S-(substituted heterocycyl) wherein heterocyclyl is as defined herein.

Examples of heterocycle and heteroaryl groups include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (═O).

"Oxide" refers to products resulting from the oxidation of one or more heteroatoms. Examples include N-oxides, sulfoxides, and sulfones.

"Spirocycloalkyl" refers to a 3- to 10-member cyclic substituent formed by replacement of two hydrogen atoms at a common carbon atom with an alkylene group having 2 to 9 carbon atoms, as exemplified by the following structure wherein the methylene group shown below attached to bonds marked with wavy lines is substituted with a spirocycloalkyl group:

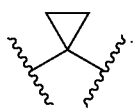

"Sulfonyl" refers to the divalent group —S(O)$_2$—.

"Substituted sulfonyl" refers to the group —S(O)$_2$-alkyl, —S(O)$_2$-substituted alkyl, —S(O)$_2$-alkenyl, —S(O)$_2$-substituted alkenyl, —S(O)$_2$-alkynyl, —S(O)$_2$-substituted alkynyl, —S(O)$_2$-cycloalkyl, —S(O)$_2$-substituted cylcoalkyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-S(O)$_2$—, phenyl-S(O)$_2$—, and 4-methylphenyl-S(O)$_2$—.

"Sulfonyloxy" refers to the group —OS(O)$_2$-alkyl, —OS(O)$_2$-substituted alkyl, —OS(O)$_2$-alkenyl, —OS(O)$_2$-substituted alkenyl, —OS(O)$_2$-cycloalkyl, —OS(O)$_2$-substituted cylcoalkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the atom (=S).

"Thiocyanate" refers to the group —SCN.

"Compound" and "compounds" as used herein refers to a compound encompassed by the generic formulae disclosed herein, any subgenus of those generic formulae, and any forms of the compounds specified by the generic and subgeneric formulae, such as a pharmaceutically acceptable salt. Unless specified otherwise, the term further includes the isotopes, racemates, stereoisomers, and tautomers of the compound or compounds.

"Isotopes" refer to pharmaceutically acceptable isotopically-labeled compounds wherein one or more atoms are replaced by atoms having the same atomic number, but an atomic mass different from the atomic mass usually found in nature. Suitable isotopes include isotopes of hydrogen, such as $^2$H and $^3$H. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

"Racemates" refers to a mixture of enantiomers.

"Solvate" or "solvates" of a compound refer to those compounds, where compounds are as defined herein, that are bound to a stoichiometric or non-stoichiometric amount of a solvent. Solvates of a compound includes solvates of all forms of the compound such as the oxide, ester, prodrug, or pharmaceutically acceptable salt of the disclosed generic and subgeneric formulae. Preferred solvents are volatile, non-toxic, and/or acceptable for administration to humans. The present invention provides solvates of the compounds disclosed herein.

"Stereoisomer" or "stereoisomers" refer to compounds that differ in the chirality of one or more stereocenters. Stereoisomers include enantiomers and diastereomers. The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of *Advanced Organic Chemistry*, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a patient. Prodrugs of a compound of the present invention are prepared by modifying functional groups present in the compound in such a way that the modifications may be cleaved in vivo to release the parent compound, or an active metabolite. For example, prodrugs include compounds wherein a hydroxy, amino, or sulfhydryl group in a compound is bonded to any group that may be cleaved in vivo to regenerate the free hydroxyl, amino, or sulfhydryl group, respectively. Particularly favored derivatives and prodrugs are those that increase the bioavailability of the compounds of the embodiments when such compounds are administered to a patient (e.g., by allowing an orally administered compound to be more readily absorbed into the blood) or which enhance delivery of the parent compound to a biological compartment (e.g., the brain or lymphatic system) relative to the parent species. Prodrugs include ester, amide, and carbamate (e.g., N,N-dimethylaminocarbonyl) forms of hydroxy functional groups of compounds of the invention. Examples of ester prodrugs include formate, acetate, propionate, butyrate, acrylate, and ethylsuccinate derivatives. An general overview of prodrugs is provided in T Higuchi and V Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and includes, by way of example only, sodium, potassium, calcium, magnesium, ammonium, and tetraalkylammonium. When the molecule contains a basic functionality, acid addition salts of organic or inorganic acids, such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2- naphthalenesulfonic acid, oxalic acid, 4-toluenesulfonic acid, camphorsulfonic acid, methanesulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Salts can also be formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like. Pharmaceutically acceptable salts are suitable for administration in a patient and possess desirable pharmacological properties. Suitable salts further include those described in P. Heinrich Stahl, Camille G. Wermuth (Eds.), *Handbook of Pharmaceutical Salts Properties, Selection, and Use;* 2002.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The terms "optional" or "optionally" as used throughout the specification means that the subsequently described event or circumstance may but need not occur, and that the description includes instances where the event or circumstance occurs and instances in which it does not. For example, "heterocyclyl group optionally mono- or di-substituted with an alkyl group" means that the alkyl may but need not be present, and the description includes situations where the heterocyclyl group is mono- or disubstituted with an alkyl group and situations where the heterocyclyl group is not substituted with the alkyl group.

Turning next to the compositions of the invention, the term "pharmaceutically acceptable carrier or excipient" means a carrier or excipient that is useful in preparing a pharmaceutical composition that is generally safe, and possesses acceptable toxicities. Acceptable carriers or excipients include those that are acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes inhibiting the disease, i.e., arresting or reducing the development of the disease or its clinical symptoms, or relieving the disease, i.e., causing regression of the disease or its clinical symptoms.

A preferred embodiment of the invention is treatment of a disease that consists of relieving the disease.

The term "diagnosing" refers to determining the presence or absence of a particular disease or condition. Additionally, the term refers to determining the level or severity of a particular disease or condition, as well as monitoring of the disease or condition to determine its response to a particular therapeutic regimen.

The term "1,3-dioxolane" refer to the cyclic acetal:

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "mammal" includes, without limitation, humans, domestic animals (e.g., dogs or cats), farm animals (cows, horses, or pigs), and laboratory animals (mice, rats, hamsters, guinea pigs, pigs, rabbits, dogs, or monkeys).

The term "insulin resistance" can be defined generally as a disorder of glucose metabolism. More specifically, insulin resistance can be defined as the diminished ability of insulin to exert its biological action across a broad range of concentrations producing less than the expected biologic effect (see, e.g., Reaven G M, *J. Basic & Clin. Phys. & Pharm*. (1998) 9:387-406 and Flie J, *Ann. Rev. Med*. (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, metabolic syndrome, hypertension, obesity, atherosclerosis and a variety of other disorders. Eventually, the insulin resistant individuals can progress to a point where a diabetic state is reached.

The term "diabetes mellitus" or "diabetes" means a disease or condition that is generally characterized by metabolic defects in production and utilization of glucose that result in the failure to maintain appropriate blood sugar levels in the body. The result of these defects is elevated blood glucose, referred to as "hyperglycemia." Two major forms of diabetes are Type I diabetes and Type II diabetes. As described above, Type I diabetes is generally the result of an absolute deficiency of insulin, the hormone that regulates glucose utilization. Type II diabetes often occurs in the face of normal, or even elevated levels of insulin and can result from the inability of tissues to respond appropriately to insulin. Most Type II diabetic patients are insulin resistant and have a relative deficiency of insulin, in that insulin secretion can not compensate for the resistance of peripheral tissues to respond to insulin. In addition, many Type II diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in women with no previous history of Type I or Type II diabetes.

The term "metabolic syndrome" refers to a cluster of metabolic abnormalities including abdominal obesity, insulin resistance, glucose intolerance, diabetes, hypertension and dyslipidemia. These abnormalities are known to be associated with an increased risk of vascular events.

The term "abdominal obesity" is defined by a cutoff point of waist circumference $\geq 102$ cm in men and $\geq 80$ cm in women, as recommended by the third report of the national cholesterol education program expert panel on detection, evaluation, and treatment of high blood cholesterol in adults (NCEP/ATP Panel III).

The guidelines for diagnosis of Type II diabetes, impaired glucose tolerance, and gestational diabetes have been outlined by the American Diabetes Association (see, e.g., The Expert Committee on the Diagnosis and Classification of Diabetes Mellitus, *Diabetes Care*, (1999) Vol. 2 (Suppl 1):S5-19).

The term "secretagogue" means a substance or compound that stimulates secretion. For example, an insulin secretagogue is a substance or compound that stimulates secretion of insulin.

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications that generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications that generally result from large blood vessel damage. These complications include, e.g., cardiovascular disease and peripheral vascular disease. Cardiovascular disease refers to diseases of blood vessels of the heart. See, e.g., Kaplan R M, et al., "Cardiovascular diseases" in *Health and Human Behavior*, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels.

The term "modulate" or "modulating" refers to the treating, prevention, suppression, enhancement, or induction of a function or condition. For example, compounds can modulate Type II diabetes by increasing insulin in a human, thereby suppressing hyperglycemia. Compounds can also modulate GPR120 by acting as GPR120 agonists.

The term "triglyceride(s)" ("TGs"), as used herein, incorporates its common usage. TGs consist of three fatty acid molecules esterified to a glycerol molecule. TGs serve to store fatty acids that are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL and/or VLDL, and depressed levels of HDL).

The term "hyperlipidemia" includes, but is not limited to, the following:
(1) Familial Hyperchylomicronemia, a rare genetic disorder that causes a deficiency in an enzyme, LP lipase, that breaks down fat molecules. The LP lipase deficiency can cause the accumulation of large quantities of fat or lipoproteins in the blood;
(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;
(3) Familial Combined Hyperlipidemia, also known as multiple lipoprotein-type hyperlipidemia is an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine, which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated TG levels (and usually not cholesterol levels) and can often be associated with low plasma HDL levels.

Risk factors for hyperlipidemia include, but are not limited to, the following: (1) disease risk factors, such as a history of Type I diabetes, Type II diabetes, Cushing's syndrome, hypothyroidism and certain types of renal failure; (2) drug risk factors, which include, birth control pills; hormones, such as estrogen, and corticosteroids; certain diuretics; and various β-blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index ("BMI") greater than 27.8 kg/m² for men and 27.3 kg/m² for women (BMI equals weight (kg)/height (m²)). Obesity is linked to a variety of medical conditions including diabetes and hyperlipidemia. Obesity is also a known risk factor for the development of Type II diabetes (see, e.g., Barrett-Conner E, *Epidemol. Rev.* (1989) 11:172-181; and Knowler, et al., *Am. J. Clin. Nutr.* (1991) 53:1543-1551).

The term "pancreas" refers to a gland organ in the digestive and endocrine system of vertebrates, including mammals. The pancreas secretes both digestive enzymes and hormones such as insulin, GLP-1 and GIP, as well as other hormones.

The term "islet" or "islet of Langerhans" refers to endocrine cells of the pancreas that are grouped together in islets and secrete insulin and other hormones.

The term "beta cell" refers to cells found in the islet of Langerhans that secrete insulin, amylin, and other hormones.

The term "endocrine cell" refers to cells that secrete hormones into the blood stream. Endocrine cells are found various glands and organ systems of the body including the pancreas, intestines, and other organs.

The term "L cell" refers to gut endocrine cells that produce GLP-1.

The term "K cell" refers to gut endocrine cells that produce GIP.

The term "incretin" refers to a group of hormones that increases insulin secretion in response to food intake. Incretins include GLP-1 and GIP.

The term "insulin" refers to a polypeptide hormone that regulates glucose metabolism. Insulin binds to insulin receptors in insulin sensitive cells and mediates glucose uptake. Insulin is used to treat Type I diabetes and may be used to treat Type II diabetes.

The term "GLP-1" or "glucagon-like peptide" is a peptide hormone primarily produced by L cells. GLP-1 increases insulin secretion, decreases glucagon secretion, increases beta cell mass and insulin gene expression, inhibits acid secretion and gastric emptying in the stomach, and decreases food intake by increasing satiety.

The term "GIP" or "gastric inhibitory peptide" or "glucose dependent insulinotropic polypeptide" refers to a peptide hormone produced primarily by K cells. GIP stimulates insulin secretion. GIP also has significant effects on lipid metabolism.

The term "cAMP" or "cyclic AMP" or "cyclic adenosine monophosphate" refers to an intracellular signaling molecule involved in many biological processes, including glucose and lipid metabolism.

The term "agonist" refers to a compound that binds to a receptor and triggers a response in a cell. An agonist mimics the effect of an endogenous ligand, a hormone for example, and produces a physiological response similar to that produced by the endogenous ligand.

The term "partial agonist" refers to a compound that binds to a receptor and triggers a partial response in a cell. A partial agonist produces only a partial physiological response of the endogenous ligand.

Accordingly, in one embodiment, provided is a compound of Formula (I)

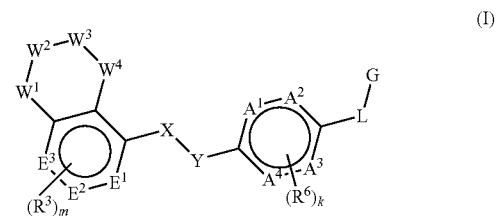

or a pharmaceutically acceptable salt thereof, wherein:

$A^1$, $A^2$, $A^3$, and $A^4$ are independently selected from the group consisting of N and C, with the proviso that only 0, 1, or 2 of $A^1$, $A^2$, $A^3$, and $A^4$ is N;

one of X and Y is a bond or —CH$_2$—, —C$_2$H$_4$— and the other of X and Y is selected from the group consisting of —CH$_2$—, —C(O)—, —C(O)NR$^a$, —NR$^a$—, —O—, —S—, —S(O)—, and —S(O)$_2$—;

$E^1$, $E^2$, and $E^3$ are independently selected from the group consisting of C and N;

one of $W^1$, $W^2$, $W^3$, and $W^4$ is independently selected from the group consisting of a bond, NR$^a$, CR$^1$R$^2$, O, S, S(O), and S(O)$_2$, and the remaining $W^1$, $W^2$, $W^3$, and $W^4$ are all CR$^1$R$^2$;

L is —(CR$^4$R$^5$)$_q$— wherein optionally one —(CR$^4$R$^5$)— is replaced with —O— or —S—;

the subscript k is 0, 1, 2, or 3;

the subscript m is 0, 1, 2, or 3;

the subscript q is 0, 1, 2, 3, or 4;

G is selected from the group consisting of

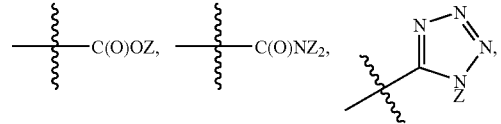

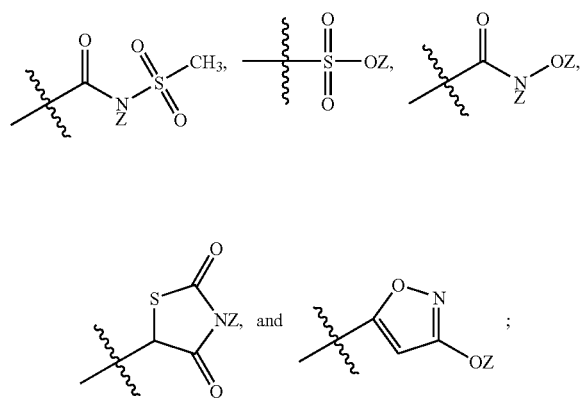

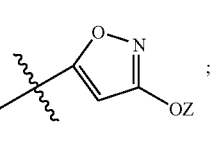

each Z is independently selected from the group consisting of H, alkyl, and substituted alkyl;

each $R^1$ and $R^2$ is independently selected from the group consisting of H, halo, alkyl, substituted alkyl, cycloalkyl, substituted cycloalkyl, alkenyl, substituted alkenyl, alkynyl, substituted alkynyl, oxo, CN, —$OR^a$, —$NR^aR^b$, —$C(O)R^a$, —$C(O)OR^a$, —$C(O)NR^aR^b$, —$NR^aC(O)R^b$, —$SR^a$, —$S(O)R^a$, and —$S(O)_2R^a$, and optionally $R^1$ and $R^2$ can cyclize to form a 3- 4-, 5-, or 6-membered heterocyclyl or cycloalkyl ring;

each $R^3$ is independently selected from the group consisting of H, halo, alkyl, substituted alkyl, alkoxy, substituted alkoxy, amino, substituted amino, aryloxy, and —CN;

each $R^4$ and $R^5$ is independently selected from the group consisting H, fluoro, alkyl, substituted alkyl, and alkoxy, and optionally $R^4$ and $R^5$ can cyclize to form a 3-, 4-, 5-, or 6-membered heterocyclyl or cycloalkyl ring;

each $R^6$ is independently selected from the group consisting of H, halo, alkyl, substituted alkyl, cycloalkyl, substituted cycloalkyl, alkenyl, substituted alkenyl, alkynyl, substituted alkynyl, CN, —$OR^a$, —$NR^aR^b$, —$C(O)R^a$, —$C(O)OR^a$, —$C(O)NR^aR^b$, —$NR^aC(O)R^b$, —$SR^a$, —$S(O)R^a$, and —$S(O)_2R^a$;

each of $R^a$ and $R^b$ is independently selected from the group consisting of H, alkyl, substituted alkyl, cycloalkyl, heterocyclyl, substituted heterocyclyl, alkenyl, alkynyl, aryl, substituted aryl, heteroaryl, and substituted heteroaryl.

In some aspects, $W^4$ is O, $W^3$ is a bond, and $W^1$ and $W^2$ are both $CR^1R^2$. In further aspects, $W^1$ is O, $W^2$ is a bond, and $W^3$ and $W^4$ are both $CR^1R^2$.

In one embodiment, provided is a compound of Formula (II) or Formula (III)

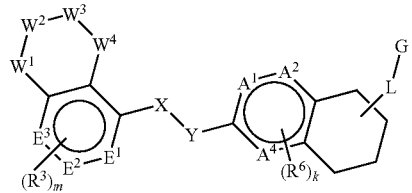

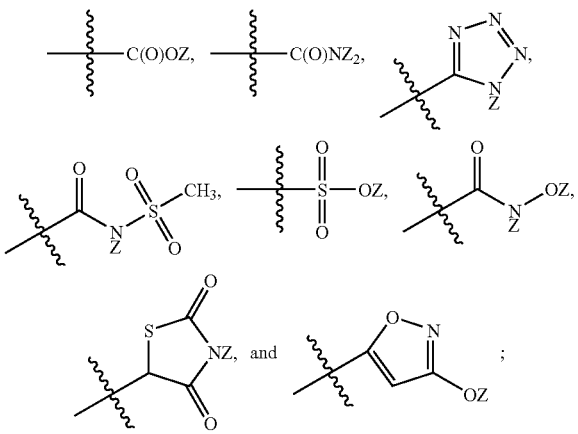

or a pharmaceutically acceptable salt thereof, wherein:
$A^1$, $A^2$, and $A^4$ are independently selected from the group consisting of N and C, with the proviso that only 0, 1, or 2 of $A^1$, $A^2$, and $A^4$ is N;

one of X and Y is a bond or —$CH_2$—, —$C_2H_4$— and the other of X and Y is selected from the group consisting of —$CH_2$—, —C(O)—, —$C(O)NR^a$, —$NR^a$—, —O—, —S—, —S(O)—, and —$S(O)_2$—;

$E^1$, $E^2$, and $E^3$ are independently selected from the group consisting of C and N;

one of $W^1$, $W^2$, $W^3$, and $W^4$ is independently selected from the group consisting of a bond, $NR^a$, $CR^1R^2$, O, S, S(O), and $S(O)_2$, and the remaining $W^1$, $W^2$, $W^3$, and $W^4$ are all $CR^1R^2$;

L is —$(CR^4R^5)_q$— wherein optionally one —$(CR^4R^5)$— is replaced with —O— or —S—;
the subscript k is 0, 1, 2, or 3;
the subscript m is 0, 1, 2, or 3;
the subscript q is 0, 1, 2, or 3;
G is selected from the group consisting of

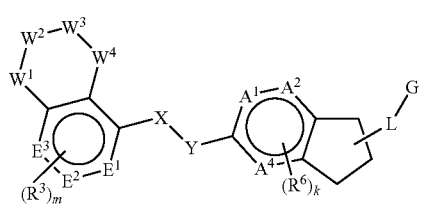

each Z is independently selected from the group consisting of H, alkyl, and substituted alkyl;

each $R^1$ and $R^2$ is independently selected from the group consisting of H, halo, alkyl, substituted alkyl, cycloalkyl, substituted cycloalkyl, alkenyl, substituted alkenyl, alkynyl, substituted alkynyl, oxo, CN, —$OR^a$, —$NR^aR^b$, —$C(O)R^a$, —$C(O)OR^a$, —$C(O)NR^aR^b$, —$NR^aC(O)R^b$, —$SR^a$, —$S(O)R^a$, and —$S(O)_2R^a$, and optionally $R^1$ and $R^2$ can cyclize to form a 3- 4-, 5-, or 6-membered heterocyclyl or cycloalkyl ring;

each $R^3$ is independently selected from the group consisting of H, halo, alkyl, substituted alkyl, alkoxy, substituted alkoxy, amino, substituted amino, aryloxy, and —CN;

each $R^4$ and $R^5$ is independently selected from the group consisting H, fluoro, alkyl, substituted alkyl, and alkoxy, and optionally $R^4$ and $R^5$ can cyclize to form a 3-, 4-, 5-, or 6-membered heterocyclyl or cycloalkyl ring;

each $R^6$ is independently selected from the group consisting of H, halo, alkyl, substituted alkyl, cycloalkyl, substituted cycloalkyl, alkenyl, substituted alkenyl, alkynyl, substituted alkynyl, CN, —$OR^a$, —$NR^aR^b$, —$C(O)R^a$, —$C(O)OR^a$, —$C(O)NR^aR^b$, —$NR^aC(O)R^b$, —$SR^a$, —$S(O)R^a$, and —$S(O)_2R^a$;

each of $R^a$ and $R^b$ is independently selected from the group consisting of H, alkyl, substituted alkyl, cycloalkyl, heterocyclyl, substituted heterocyclyl, alkenyl, alkynyl, aryl, substituted aryl, heteroaryl, and substituted heteroaryl.

In some embodiments, $W^4$ is O, $W^3$ is a bond, and $W^1$ and $W^2$ are both $CR^1R^2$. In some aspects, G is —C(O)OZ. In some such aspects, Z is H.

In some embodiments, $W^1$ is O, $W^2$ is a bond, and $W^3$ and $W^4$ are both $CR^1R^2$. In some aspects, G is —C(O)OZ. In some such aspects, Z is H.

In some embodiments, each $R^1$ and $R^2$ is independently selected from the group consisting of H, fluoro, —$CH_3$, and —$CF_3$.

In some embodiments, $R^1$ and $R^2$ cyclize to form a 3- to 6-membered heterocyclyl or cycloalkyl ring.

In some embodiments, $E^1$, $E^2$, and $E^3$ are all C.

In some embodiments, $A^1$, $A^2$, $A^3$, and $A^4$ are all C.

In some embodiments, $A^1$, $A^2$, and $A^4$ are all C.

In yet another aspect, $W^4$ is O; $W^3$ is a bond; and $W^1$ and $W^2$ are both $CR^1R^2$; $E^1$, $E^2$, and $E^3$ are all C; and $A^1$, $A^2$, $A^3$, and $A^4$ are all C.

In some embodiments, X and Y are selected from the group consisting of C and O. In some aspects, X is —$CH_2$— and Y is O.

In some embodiments, $R^3$ is independently selected from the group consisting of fluoro, chloro, —$CH_3$, and —$CF_3$. In some aspects, m is 1.

In some embodiments, $R^6$ is independently selected from the group consisting of fluoro, chloro, —$CH_3$, and —$CF_3$. In some aspects, k is 0, 1, or 2.

In some embodiments, the subscript q is 1 or 2.

In some embodiments, $R^4$ and $R^5$ are independently selected from the group consisting of H and $CH_3$.

In some embodiments, $R^4$ and $R^5$ cyclize to form a cyclopropyl ring.

In one embodiment, provided are esters of the compounds of Formula (I), (II) and (III). In some embodiments, the esters are compounds wherein the carboxylic acid group is derivatized to be an ester, such as when Z in the formulae is alkyl or substituted alkyl.

In some aspects of the compounds of Formula (I), $W^4$ is O; $W^3$ is a bond; and $W^1$ and $W^2$ are both $CR^1R^2$; $E^1$, $E^2$, and $E^3$ are all C; $A^1$, $A^2$, $A^3$ and $A^4$ are all C; X is —$CH_2$—; Y is —O—; the subscript q is 2; and G is —C(O)OZ.

In some aspects of the compounds of Formula (II) and (III), $W^4$ is O; $W^3$ is a bond; and $W^1$ and $W^2$ are both $CR^1R^2$; $E^1$, $E^2$, and $E^3$ are all C; $A^1$, $A^2$, and $A^4$ are all C; X is —$CH_2$—; Y is —O—; the subscript q is 1; and G is —C(O)OZ.

In one embodiment, provided is a compound of Formula (A)

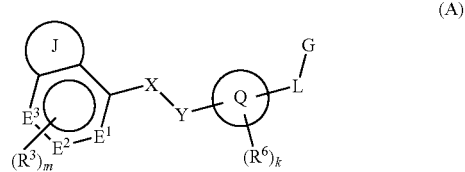

(A)

or a pharmaceutically acceptable salt thereof, wherein:
the group J is absent or selected from the group consisting

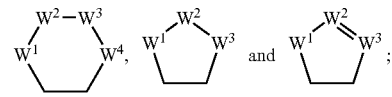

the ring Q is selected from the group consisting of aryl, heteroaryl,

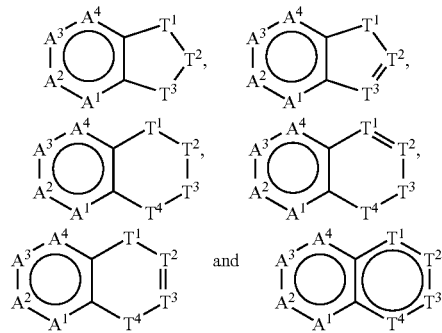

wherein Q is optionally substituted with $(R^6)_k$;
$A^1$, $A^2$, $A^3$ and $A^4$ are independently selected from the group consisting of N and C, with the proviso that only 0, 1 or 2 of $A^1$, $A^2$, $A^3$ and $A^4$ is N;
$T^1$, $T^2$, $T^3$ and $T^4$ are independently selected from the group consisting of N, O, $CR^1$ and $CR^1R^2$, with the proviso that only 0, 1 or 2 of $T^1$, $T^2$, $T^3$ and $T^4$ is selected from N and O;
$W^1$, $W^2$, $W^3$ and $W^4$ are independently selected from the group consisting of N, $NR^a$, $CR^1$, $CR^1R^2$, O, S, S(O) and $S(O)_2$, with the proviso that ring J is not 1,3-dioxolane;
$E^1$, $E^2$ and $E^3$ are independently selected from the group consisting of C and N;
one of X and Y is a bond, —$CH_2$—, —CHD-, or —$CD_2$-, and the other of X and Y is selected from the group consisting of —$CH_2$—, —CHD-, —$CD_2$-, —C(O), —C(O)$NR^a$, —$NR^a$—, —O—, —S—, —S(O)— and —$S(O)_2$—;
L is —$(CR^4R^5)_q$— wherein optionally one —$(CR^4R^5)$— is replaced with —N—, —O—, —S—, —$CR^4$=$CR^5$—, or -phenyl-;
G is selected from the group consisting of —C(O)OZ and —C(O)$NZ_2$;
each Z is independently selected from the group consisting of H, alkyl and substituted alkyl;
each $R^1$ and $R^2$ is independently selected from the group consisting of H, deuterium, halo, alkyl, substituted alkyl, cycloalkyl, substituted cycloalkyl, alkenyl, substituted alkenyl, alkynyl, substituted alkynyl, oxo, alkoxy, substituted alkoxy, CN, —NR$^a$R$^b$, —C(O)R$^a$, —C(O)OR$^a$, —C(O)NR$^a$R$^b$, —NR$^a$C(O)R$^b$, —SR$^a$, —S(O)R$^a$ and —S(O)$_2$R$^a$, and optionally R$^1$ and R$^2$ can cyclize to form a C$_{3-7}$heterocyclyl, substituted C$_{3-7}$heterocyclyl, spiro C$_{3-7}$heterocyclyl, substituted spiro C$_{3-7}$heterocyclyl, C$_{3-7}$cycloalkyl, substituted C$_{3-7}$cycloalkyl, spiroC$_{3-7}$cycloalkyl or spiro substituted C$_{3-7}$cycloalkyl;

each R$^3$ is independently selected from the group consisting of H, halo, alkyl, substituted alkyl, alkoxy, substituted alkoxy, —C(O)NR$^a$R$^b$, —NR$^a$C(O)R$^b$, —NR$^a$R$^b$, aryl, substituted aryl, heteroaryl, substituted heteroaryl, aryloxy, substituted aryloxy and —CN;

each R$^4$ and R$^5$ is independently selected from the group consisting H, deuterium, fluoro, alkyl, substituted alkyl, alkoxy and substituted alkoxy, and optionally R$^4$ and R$^5$ can cyclize to form a C$_{3-7}$heterocyclyl, substituted C$_{3-7}$heterocyclyl, spiro C$_{3-7}$heterocyclyl, substituted spiro C$_{3-7}$heterocyclyl, C$_{3-7}$cycloalkyl, substituted C$_{3-7}$cycloalkyl, spiroC$_{3-7}$cycloalkyl or spiro substituted C$_{3-7}$cycloalkyl;

each R$^6$ is independently selected from the group consisting of H, halo, alkyl, substituted alkyl, aryl, substituted aryl, heteroaryl, substituted heteroaryl, cycloalkyl, substituted cycloalkyl, alkenyl, substituted alkenyl, alkynyl, substituted alkynyl, CN, —OR$^a$, —NR$^a$R$^b$, —C(O)R$^a$, —C(O)OR$^a$, —C(O)NR$^a$R$^b$, —NR$^a$C(O)R$^b$, —SR$^a$, —S(O)R$^a$ and —S(O)$_2$R$^a$;

each of R$^a$ and R$^b$ is independently selected from the group consisting of H, alkyl, substituted alkyl, cycloalkyl, heterocyclyl, substituted heterocyclyl, alkenyl, alkynyl, aryl, substituted aryl, heteroaryl and substituted heteroaryl.

the subscript k is 0, 1, 2 or 3;

the subscript m is 0, 1, 2 or 3; and the subscript q is 0, 1, 2, 3 or 4.

In another embodiment, provided is a compound of Formula (B)

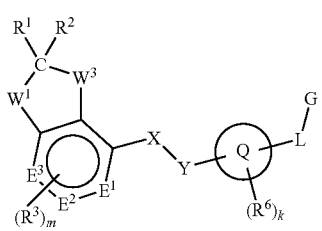

(B)

or a pharmaceutically acceptable salt thereof wherein R$^1$, R$^2$, R$^3$, R$^6$, W$^1$, W$^3$, E$^1$, E$^2$, E$^3$, X Y, Q, L, G, m and k are as defined in Formula (A) provided that W$^1$ and W$^3$ are not both O.

In some embodiments of the compound of Formula (B), W$^1$ and W$^3$ are independently selected from the group consisting of CR$^1$R$^2$ and O.

In some embodiments, provided is a compound of Formula (C):

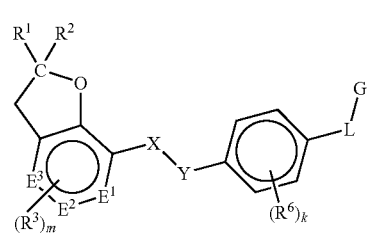

(C)

or a pharmaceutically acceptable salt thereof wherein R$^1$, R$^2$, R$^3$, R$^6$, E$^1$, R$^2$, E$^3$, X, Y, L, G, m and k are as defined.

In some embodiments, provided is a compound of Formula (C) wherein E$^1$, E$^2$ and E$^3$ are all C.

In some aspects, X is selected from the group consisting of —CH$_2$—, —CHD- and —CD$_2$-, and Y is O.

In a further aspect, in L the subscript q is 2 or 3. In some aspects, the subscript q is 2.

In a further aspect, G is —C(O)OZ. In some aspects, Z is alkyl or H.

In a further aspect, the subscript m is 1 or 2, and each R$^3$ is independently selected from the group consisting of halo, alkyl, substituted alkyl, alkoxy and substituted alkoxy. In some aspects, each R$^3$ is independently selected from the group consisting of F, Cl, —CH$_3$, —CF$_3$ and —OCH$_3$.

In a further aspect, R$^1$ and R$^2$ are independently selected from the group consisting of C$_{1-3}$alkyl and —CF$_3$. In some aspects, R$^1$ and R$^2$ are both —CH$_3$.

In a further aspect, the subscript k is 0, 1 or 2.

In a further aspect, each R$^6$ is independently selected from the group consisting of fluoro, chloro, —CH$_3$, —C$_2$H$_5$ and —CF$_3$.

In one embodiment of the compound of Formula (A), Q is

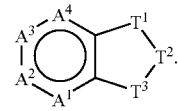

In some aspects, the ring J is absent and each R$^3$ is independently selected from the group consisting of alkoxy, substituted alkoxy and halo.

In another embodiment, provided is a synthetic intermediate or a compound or a pharmaceutically acceptable salt thereof as described in the Examples.

In other embodiments provided are compound agonists or a pharmaceutically acceptable salt thereof or synthetic intermediates thereof as exemplified in Chemical Examples section below.

In some embodiments, the compounds of Formula (I)-(III) and (A)-(C) and pharmaceutically acceptable salts thereof have an EC$_{50}$ against human GPR120 of 10 μM or less. In other aspects, the compounds have an EC$_{50}$ of greater than 1 μM and less than or equal to 10 μM. In other aspects the compounds have an EC$_{50}$ of 1 μM or less.

Preparation Of Compounds Of The Invention

The compounds of the present invention can be prepared in a number of ways familiar to one skilled in the art of organic chemistry synthesis. The synthetic route of compounds in the present invention is not limited to the methods outlined herein or as provided in the Examples. Individual compounds may require manipulation of the conditions in order to accommodate various functional groups and may require appropriate use of protecting groups. Purification, if necessary, can be accomplished on a silica gel column eluted with the appropriate organic solvent system. Also, reverse phase HPLC or recrystallization may be employed.

Compositions And Methods Of Treatment

In accordance with the present invention methods of treating a disease or condition selected from the group consisting of Type I diabetes, Type II diabetes and metabolic syndrome are provided. The method comprises administering to a subject in need of such treatment a therapeutically effective amount of a compound of the present invention.

In another aspect, methods of raising intracellular levels of $Ca^{2+}$ in a cell expressing GPR120 are provided. The method comprises exposing a cell that expresses GPR120 to a compound of the invention. $Ca^{2+}$ levels are determined by the methods disclosed in the Example sections herein.

In one embodiment, the cell that expresses GPR120 is a pancreatic cell, an islet cell, or a beta cell, an intestinal endocrine cell, an L cell or a K cell.

Another aspect of the invention provides a method of stimulating insulin production in a mammal, in particular a human. The method comprises administering a therapeutically effective amount of a compound of the invention to the mammal. In response to administration of a compound to the subject, insulin is produced by the beta cells. Biological Example 3 provides detailed methods by which a skilled artisan can measure insulin secretion in laboratory animals in response to administration of a compound of the invention.

In another aspect, the invention provides a method of stimulating insulin secretion in a mammal, in particular a human. The method comprises administering a therapeutically effective amount of a compound of the invention to the mammal. In response to administration of a compound to the subject, insulin is secreted into the blood stream by the beta cells.

A further aspect of the invention provides a method of stimulating glucose-dependent insulin secretion in a mammal, in particular a human. The method comprises administering a therapeutically effective amount of a compound of the invention to the mammal. After administration to the subject, insulin is secreted into the blood stream by the beta cells in a glucose-dependent manner. Biological Example 4 provides methods that show the blood glucose lowering effects of the compounds of the invention.

In another embodiment, the invention provides methods of lowering blood glucose in a mammal, preferably a human. The method comprises administering a therapeutically effective amount of a compound of the invention to the mammal. In response to administration of a compound to the subject, blood glucose levels are lowered. The method further comprises steps to measure blood glucose levels before and after administration of a compound of the invention. Blood glucose levels are easily measured by numerous commercially available glucose monitoring devices that measure blood glucose from samples of blood or urine. Blood glucose can also be measured by commercially available glucometers that do not require blood or urine samples. Biological Examples 3 and 4 provide methods that teach how to measure improvements in diabetes parameters, including blood glucose monitoring.

Another aspect of the invention provides a method of stimulating incretin production in a mammal, in particular a human. The method comprises administering a therapeutically effective amount of a compound of the invention to the mammal. In response to administration of a compound to the subject, glucagon-like peptide 1 and glucose-dependent insulinotropic polypeptide is produced by the intestinal endocrine cells. Biological Example 5 provides detailed methods by which a skilled artisan can measure incretin production in laboratory animals in response to administration of a compound of the invention.

Combination Therapy

As noted above, the compounds of the present invention will, in some instances, be used in combination with other therapeutic agents to bring about a desired effect. Selection of additional agents will, in large part, depend on the desired target therapy (see, e.g., Turner N, et al., *Prog. Drug Res.* (1998) 51:33-94; Haffner S, *Diabetes Care* (1998) 21:160-178; and DeFronzo R, et al. (eds.), *Diabetes Reviews* (1997) Vol. 5 No. 4). A number of studies have investigated the benefits of combination therapies with oral agents (see, e.g., Mahler R, *J. Clin. Endocrinol. Metab.* (1999) 84:1165-71; United Kingdom Prospective Diabetes Study Group: UKPDS 28, *Diabetes Care* (1998) 21:87-92; Bardin C W (ed.), *Current Therapy in Endocrinology and Metabolism*, 6th Ed. (Mosby-Year Book, Inc., St. Louis, Mo. 1997); Chiasson J, et al., *Ann. Intern. Med.* (1994) 121:928-935; Coniff R, et al., *Clin. Ther.* (1997) 19:16-26; Coniff R, et al., *Am. J. Med.* (1995) 98:443-451; and Iwamoto Y, et al., *Diabet. Med.* (1996) 13:365-370; Kwiterovich P, *Am. J. Cardiol* (1998) 82(12A):3U-17U). These studies indicate that diabetes modulation can be further improved by the addition of a second agent to the therapeutic regimen. Combination therapy includes administration of a single pharmaceutical dosage formulation that contains a compound as provided herein and one or more additional active agents, as well as administration of a compound as provided herein and each active agent in its own separate pharmaceutical dosage formulation. For example, a compound as provided herein and a DPP4 inhibitor can be administered to the human subject together in a single oral dosage composition, such as a tablet or capsule, or each agent can be administered in separate oral dosage formulations. Where separate dosage formulations are used, a compound as provided herein and one or more additional active agents can be administered at essentially the same time (i.e., concurrently), or at separately staggered times (i.e., sequentially). Combination therapy is understood to include all these regimens.

An example of combination therapy can be seen in modulating (preventing the onset of the symptoms or complications associated with) diabetes (or treating, preventing or reducing the risk of developing diabetes and its related symptoms, complications, and disorders), wherein a compound as provided herein can be effectively used in combination with, for example, biguanides (such as metformin); thiazolidinediones (such as ciglitazone, pioglitazone, troglitazone, and rosiglitazone); dipeptidyl-peptidase-4 ("DPP4") inhibitors (such as vildagliptin and sitagliptin); glucagonlike peptide-1 ("GLP-1") receptor agonists (such as exanatide) (or GLP-1 mimetics); PPAR gamma agonists or partial agonists; dual PPAR alpha, PPAR gamma agonists or partial agonists; dual PPAR delta, PPAR gamma agonists or partial agonists; pan PPAR agonists or partial agonists; dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose); sulfonylureas (such as chlorpropamide, tolbutamide, acetohexamide, tolazamide, glyburide, gliclazide, glynase, glimepiride, and glipizide); pramlintide (a synthetic analog of the human hormone amylin); other insulin secretogogues (such as repaglinide, gliquidone, and nateglinide); insulin (or insulin mimetics); glucagon receptor antagonists; gastric inhibitory peptide ("GIP"); or GIP mimetics; as well as the active agents discussed below for treating obesity, hyperlipidemia, atherosclerosis and/or metabolic syndrome.

Another example of combination therapy can be seen in treating obesity or obesity-related disorders, wherein a compound as provided herein can be effectively used in combination with, for example, phenyl propanolamine, phenteramine; diethylpropion; mazindol; fenfluramine; dexfenfluramine; phentiramine, β-3 adrenoceptor agonist agents; sibutramine; gastro intestinal lipase inhibitors (such as orlistat); and leptins. Other agents used in treating obesity or obesity-related disorders wherein a compound as provided herein can be effectively used in combination with, for example, cannabinoid-1 ("CB-1") receptor antagonists (such as rimonabant); PPAR delta agonists or partial agonists; dual PPAR alpha, PPAR delta agonists or partial agonists; dual PPAR delta, PPAR gamma agonists or partial agonists; pan PPAR agonists or partial agonists; neuropeptide Y; enterostatin; cholecytokinin; bombesin; amylin; histamine $H_3$ receptors; dopamine $D_2$ receptors; melanocyte stimulating hormone; corticotrophin releasing factor; galanin; and gamma amino butyric acid (GABA).

Still another example of combination therapy can be seen in modulating hyperlipidemia (treating hyperlipidemia and its related complications), wherein a compound as provided herein can be effectively used in combination with, for example, statins (such as atorvastatin, fluvastatin, lovastatin, pravastatin, and simvastatin), CETP inhibitors (such as torcetrapib); a cholesterol absorption inhibitor (such as ezetimibe); PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; fenofibric acid derivatives (such as gemfibrozil, clofibrate, fenofibrate, and bezafibrate); bile acid-binding resins (such as colestipol or cholestyramine); nicotinic acid; probucol; betacarotene; vitamin E; or vitamin C.

A further example of combination therapy can be seen in modulating atherosclerosis, wherein a compound as provided herein is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin); an HMG-CoA synthase inhibitor; a squalene epoxidase inhibitor; or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide); anti-oxidant vitamins, such as vitamin C and E and beta carotene; a β-blocker; an angiotensin II antagonist; an angiotensin converting enzyme inhibitor; PPAR alpha agonists or partial agonists; PPAR delta agonists or partial agonists; PPAR gamma agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; and a platelet aggregation inhibitor, such as fibrinogen receptor antagonists (i.e., glycoprotein IIb/IIIa fibrinogen receptor antagonists) and aspirin. As noted above, a compound as provided herein can be administered in combination with more than one additional active agent, for example, a combination of a compound as provided herein with an HMG-CoA reductase inhibitor (e.g., atorvastatin, fluvastatin, lovastatin, pravastatin, and simvastatin) and aspirin, or a compound as provided herein with an HMG-CoA reductase inhibitor and a β-blocker.

Additionally, a therapeutically effective amount of a compound as provided herein and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor; an HMG-CoA synthase inhibitor; a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; CETP inhibitors such as torcetrapib; a cholesterol absorption inhibitor such as ezetimibe; PPAR alpha agonists or partial agonists; PPAR delta agonists or partial agonists; dual PPAR alpha, PPAR delta agonists or partial agonists; dual PPAR alpha, PPAR gamma agonists or partial agonists; dual PPAR delta, PPAR gamma agonists or partial agonists; pan PPAR agonists or partial agonists; niacinamide; a cholesterol absorption inhibitor; a bile acid sequestrant anion exchange resin; a LDL receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, β-3 adrenergic receptor agonists; sulfonylureas, biguanides, α-glucosidase inhibitors, other insulin secretogogues, and insulin can be used together for the preparation of a pharmaceutical composition useful for the above-described treatments.

An additional example of combination therapy can be seen in modulating metabolic syndrome (or treating metabolic syndrome and its related symptoms, complications and disorders), wherein a compound as provided herein can be effectively used in combination with, for example, the active agents discussed above for modulating or treating diabetes, obesity, hyperlipidemia, atherosclerosis, and/or their respective related symptoms, complications and disorders.

In a further embodiment, a compound of the present invention can be administered in combination with halofenic acid, an ester of halofenic acid, or another prodrug of halofenic acid, preferably with (−)-(4-chlorophenyl)-(3-trifluoromethylphenoxy)-acetic acid 2-acetylaminoethyl ester.

In particular, this invention provides methods of treating a mammal, in particular a human by administering a compound as provided herein and a DPP4 inhibitor.

The DPP4 inhibitors useful in the present invention are sitagliptin (Merck), vildagliptin (Novartis), BMS-477118 (saxagliptin) (Bristol-Myers Squibb), R1438 (aminomethylpyridine) (Roche), NVP DPP728 (Novartis), PSN9301 (Prosidion), P32/98 (isoleucine thiozolidide) (Probiodrug), GSK823093C (Denagliptin) (Glaxo Smithkline), SYR-322 (Alogliptin) (Takeda), N,N-7201 (NovoNordisk), ALS2-0426 (Alantos). (Green B D, Flatt P R, Bailey C J, Dipeptidyl peptidase IB (DPP4) inhibitors: a newly emerging drug class for the treatment of Type II diabetes, *Diabetes Vasc. Dis. Res.* 2006, 3:159-165). Preferred DPP4 inhibitors are sitagliptin, vildagliptin, Denagliptin, saxagliptin, and alogliptin). Even more preferred CPP4 inhibitors are sitagliptin and vildagliptin.

A compound as provided herein and DPP4 inhibitor are administered in a single dosage or in separate dosages. The single dosage is administered once a day or multiple times a day. When a compound as provided herein and DPP4 inhibitor are administered is separate dosages, the dosages can be administered once a day or multiple times a day.

A compound as provided herein and DPP4 inhibitor can be dosed at the same time, within several minutes, or separated by hours. By way of example, a compound as provided herein and DPP4 inhibitor can be dosed together in the morning, with no further dosing for the remainder of the day. Alternatively, in the morning, a compound as provided herein and a DPP4 inhibitor is dosed followed with a second dose of a compound as provided herein and/or a DPP4 inhibitor in the evening or after a meal.

It can be necessary to administer dosages of a compound as provided herein and/or DPP4 inhibitor once a day or more than once a day, or before or after a meal, as will be apparent to those skilled in the art. Further, it is noted that the clinician or treating physician will know how and when to start, interrupt, adjust, or terminate therapy in conjunction with individual patient response.

In one embodiment, when the compound as provided herein and the DPP4 inhibitor are administered in a single dosage, the compound and DPP4 inhibitor are formulated into a single pill, single table, or a single capsule. When the compound and DPP4 inhibitor are administered in separate dosages, the compound is formulated into a pill, tablet or capsule and the DPP4 inhibitor is formulated into a separate pill or capsule.

When a compound as provided herein and DPP4 inhibitor are administered in separate dosages, the compound can be administered first and the DPP4 inhibitor can be administered next, following administration of the compound. Alternatively, the DPP4 inhibitor can be administered first and the compound can be administered next. The time between the first administration and the second administration can be varied by a skilled practitioner. In one embodiment, the first administration (a compound as provided herein or a DPP4 inhibitor), is followed immediately by the second administration (a compound as provided herein or a DPP4 inhibitor). In another embodiment, the second administration is within 2 minutes, 5 minutes, 10 minutes, 15 minutes, 30 minutes, or 60 minutes, 1 hour, 2 hours, 3 hours, 4 hours, 5 hours, 6 hours, 7 hours, 8 hours, 9 hours, 10 hours, 11 hours, or 12 hours following the first administration. Yet another embodiment provides for the administration of a compound as provided herein and/or DPP4 inhibitor in the morning followed by the administration of a compound as provided herein and/or DPP4 inhibitor in the evening.

In addition, the present invention provides for kits with unit doses of a compound as provided herein and/or DPP4 inhibitor, either in oral or injectable doses. In addition to the containers containing the unit doses will be an informational package insert describing the use and attendant benefits of the drugs in treating Type II diabetes, obesity, hyperlipidemia, atherosclerosis and metabolic syndrome, and/or their respective related symptoms, complications and disorders. Preferred compounds and unit doses are those described herein above.

Another aspect of this invention provides methods of lowering blood levels of glucose in a subject by administering a compound as provided herein and a DPP4 inhibitor. The method comprises administering a therapeutically effective amount of the compound and DPP4 inhibitor to the mammal. The method further comprises steps to measure blood glucose levels before and after administration of a compound as provided herein and DPP4 inhibitor. Blood glucose levels are easily measured by numerous commercially available glucose monitoring devices that measure blood glucose from samples of blood or urine, or as taught herein. Blood glucose can also be measured by commercially available glucometers that do not require blood or urine samples.

Another aspect of this invention provides methods of lowering blood levels of insulin in a subject by administering a compound as provided herein and a DPP4 inhibitor. The method comprises administering a therapeutically effective amount of the compound and DPP4 inhibitor to the mammal. The method further comprises steps to measure blood insulin levels before and after administration of the compound and a DPP4 inhibitor. Blood insulin levels are easily measured by well-known insulin monitoring assays that measure insulin from samples of blood or urine, or as taught herein.

In another aspect, this invention provides methods of increasing blood levels of incretins in a subject by administering a compound of this invention and a DPP4 inhibitor. The incretins are GLP-1 and GIP. The method comprises administering a therapeutically effective amount of a compound as provided herein and DPP4 inhibitor to the mammal. The method further comprises steps to measure blood incretin levels before and after administration of a compound as provided herein and a DPP4 inhibitor. Blood incretin levels are easily measured by well-known incretin monitoring assays, or as taught herein.

Yet another aspect of this invention provides methods of lowering blood triglyceride levels in a subject by administering a compound as provided herein and a DPP4 inhibitor. The method comprises administering a therapeutically effective amount of the compound and DPP4 inhibitor to the mammal. The method further comprises steps to measure blood triglycerides levels before and after administration of the compound and DPP4 inhibitor. Blood triglyceride levels are easily measured by numerous commercially available devices that measure blood triglyceride levels from samples of blood.

A further aspect of this invention provides methods of lowering gastric emptying in a subject by administering a compound of the invention and a DPP4 inhibitor. The method comprises administering a therapeutically effective amount of a compound as provided herein and DPP4 inhibitor to the mammal.

Another aspect of this invention provides methods of increasing insulin production in the islet cells of a subject by administering a compound as provided herein and a DPP4 inhibitor. The method comprises administering a therapeutically effective amount of a compound as provided herein and DPP4 inhibitor to the mammal. The method further comprises steps to measure insulin production in islet cells or the beta cells of the pancreas before and after administration of the compound and a DPP4 inhibitor. The insulin production of islets and beta cells are easily measured by well-known assays, or as taught herein.

In yet another aspect, this invention provides methods of preserving islet function in a subject by administering a compound as provided herein and a DPP4 inhibitor. The method comprises administering a therapeutically effective amount of a compound as provided herein and DPP4 inhibitor to the mammal. The method further comprises steps to measure the function of islets or beta cell's ability to produce insulin before and after administration of the compound and a DPP4 inhibitor. The insulin production of islets and beta cells are easily measured by well-known assays, or as taught herein.

The compounds that are used in the methods of the present invention can be incorporated into a variety of formulations and medicaments for therapeutic administration. More particularly, a compound as provided herein can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, and/or intratracheal administration. Moreover, the compound can be administered in a local rather than systemic manner, in a depot or sustained release formulation. In addition, the compounds can be administered in a liposome.

The compounds can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. The compounds can be administered alone, in combination with each other, or they can be used in combination with other known compounds.

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compound and optionally a DPP4 inhibitor can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compound and optionally DPP4 inhibitors can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide ("DMSO") also can be employed. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays, animal models, or microdosing of human subjects.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds that exhibit high therapeutic indices are preferred. The data obtained from these cell culture assays and animal studies can be used in formulating a dosage range that is not toxic for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition (see, e.g., Fingl, et al., 1975 In: *The Pharmacological Basis of Therapeutics*, Ch. 1).

The amount of a compound as provided herein that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg, between 1 mg to about 500 mg, and between 1 mg to about 300 mg of the active compound. In another example, the unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

CHEMICAL EXAMPLES

General Methods. All operations involving moisture and/or oxygen sensitive materials were conducted under an atmosphere of dry nitrogen in pre-dried glassware. Unless noted otherwise, materials were obtained from commercially available sources and used without further purification.

Flash chromatography was performed on an Isco Combiflash Companion using RediSep Rf silica gel cartridges by Teledyne Isco. Thin layer chromatography was performed using precoated plates purchased from E. Merck (silica gel 60 $PF_{254}$, 0.25 mm) and spots were visualized with long-wave ultraviolet light followed by an appropriate staining reagent.

Nuclear magnetic resonance ("NMR") spectra were recorded on a Varian Inova-400 resonance spectrometer. $^1H$ NMR chemical shifts are given in parts per million (δ) down-field from tetramethylsilane ("TMS") using TMS or the residual solvent signal ($CHCl_3$=δ 7.24, DMSO=δ 2.50) as internal standard. $^1H$ NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 11.0.

LCMS analysis was performed using a PE SCIEX API 2000 mass spectrometer with a Phenomenex Luna 5 micron $C_{18}$ column.

Preparatory HPLC was performed on a Gilson HPLC 215 liquid handler with a Phenomenex column (Gemini 10µ, $C_{18}$, 110A) and a UV/VIS 156 detector.

Microwave reactions were performed in a Biotage Intiator EXP US.

When production of starting materials is not particularly described, the compounds are known or may be prepared analogously to methods known in the art or as disclosed in the preparation of intermediates or examples. One of skill in the art will appreciate that synthetic methodologies described herein are only representative of methods for preparation of the compounds of the present invention, and that other well known methods may similarly be used. The present invention is further exemplified, but not limited, by the following examples that illustrate the preparation of the compounds of the invention.

Preparation of Intermediates

Intermediate 1

5-chloro-7-(chloromethyl)-2,2-dimethyl-2,3-dihydrobenzofuran (5)

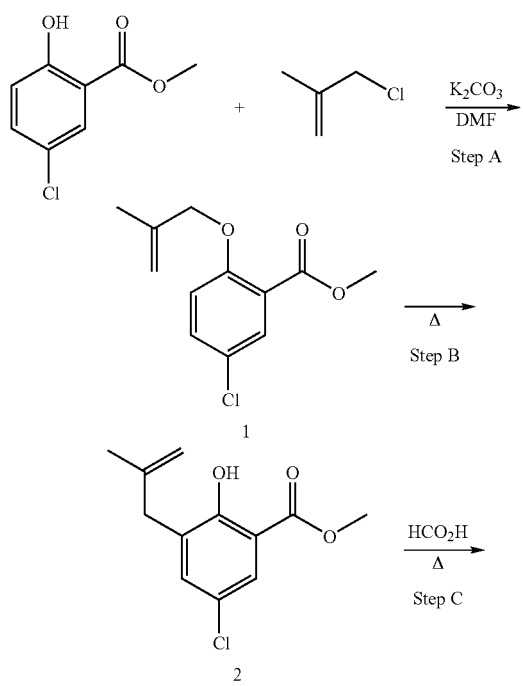

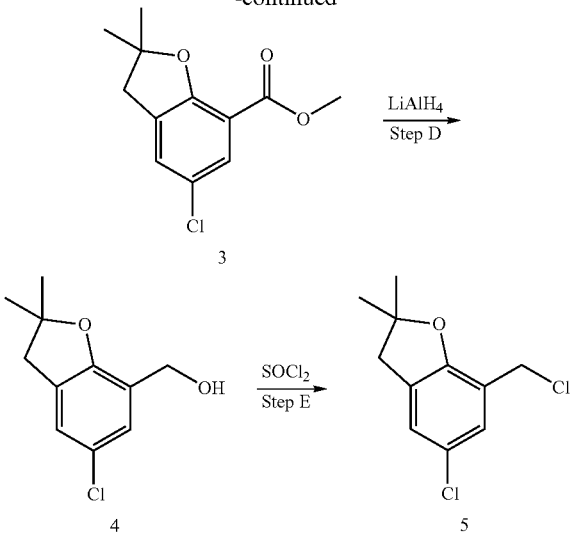

Step A: To a solution of methyl 5-chloro-2-hydroxybenzoate (2.5 g, 13.4 mmol) in dimethylformamide (25 mL) was added potassium carbonate (2.22 g, 16.1 mmol) and 3-chloro-2-methylprop-1-ene (1.46 g, 16.1 mmol). The suspension was heated at 70° C. for 18 h, cooled to room temperature, diluted with water (50 mL), and extracted with ethyl acetate (2×25 mL). The organic layers were combined, dried over sodium sulfate, filtered and concentrated in vacuo. The residue was purified by chromatography (0-20% EtOAc in hexanes) to provide the desired ester (1).

Step B: To a 20 mL microwave tube was added compound (1) (2.00 g, 8.31 mmol) and N-methylpyrrolidinone (15 mL). The tube was sealed and heated in the microwave at 200° C. for 8 h. The solution was cooled to room temperature, diluted with water (50 mL), and extracted with ethyl acetate (2×25 mL). The organic layers were combined, dried over sodium sulfate, filtered and concentrated. The residue was purified by chromatography (0-30% EtOAc in hexanes) to provide the desired ester (2).

Step C: Compound (2) (2.00 g, 8.31 mmol) was dissolved in formic acid (10 mL) and water (1 mL) and refluxed for 18 h. The solution was cooled to room temperature, diluted with water (50 mL), and extracted with ethyl acetate (2×25 mL). The organic layers were combined, dried over sodium sulfate, filtered and concentrated in vacuo. The residue was purified by chromatography (0-30% EtOAc in hexanes) to provide the desired ester (3).

Step D: Compound (3) (2.00 g, 8.31 mmol) was dissolved in anhydrous tetrahydrofuran (15 mL) and cooled to 0° C. under nitrogen. Lithium aluminum hydride in tetrahydrofuran (1.0 M, 8.31 mL, 8.31 mmol) was added over a ten minute period. After the addition was complete, the solution was allowed to warm to room temperature and stirred for an additional sixty minutes. The solution was cooled to 0° C. and quenched by the addition of ethyl acetate (10 mL) followed by a saturated sodium sulfate aqueous solution (10 mL). The mixture was diluted with ethyl acetate and filtered through a pad of celite. The combined filtrates were dried over sodium sulfate and concentrated in vacuo. The residue was purified by silica gel chromatography (0-100% EtOAc in hexanes) to provide the desired alcohol (4).

Step E: To a solution of compound (4) (1.00 g, 4.70 mmol) in acetonitrile (20 mL) was added thionyl chloride (0.682 mL, 9.4 mmol). The solution was stirred for 4 h and then concentrated in vacuo. The residue was dissolved in ethyl acetate, washed with water and brine. The organic layer was separated, dried over sodium sulfate, filtered and concentrated in vacuo. The residue was purified by chromatography (0-30% EtOAc in hexanes) to provide compound (5).

Intermediate 2 ethyl 3-(3,5-difluoro-4-hydroxyphenyl)-2-methyl-propanoate (9)

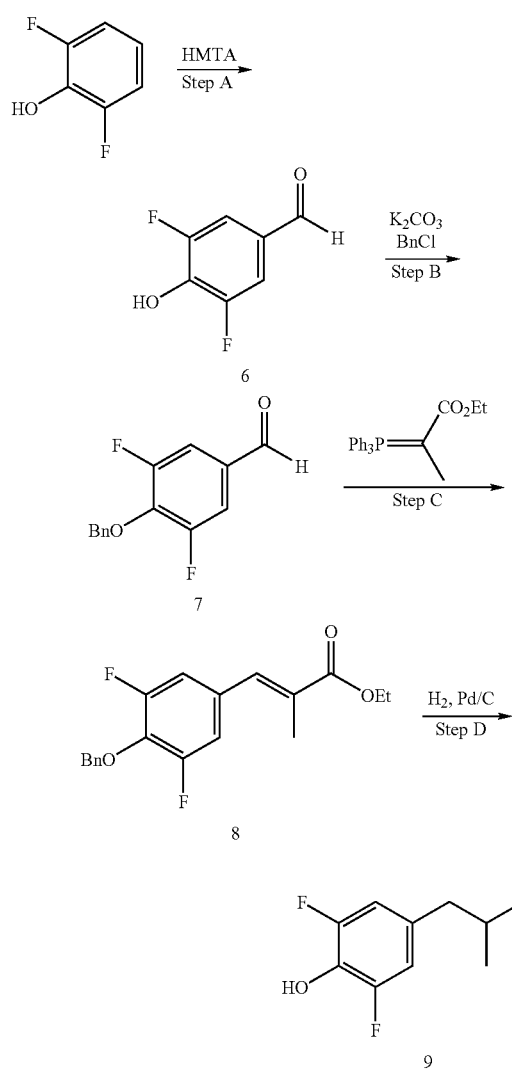

Step A: A solution of 2,6-difluorophenol (25 g, 192 mmol), hexamethylenetetramine (26 g, 192 mmol) and trifluoroacetic acid (190 mmol) was refluxed overnight. The reaction was cooled and diluted with water (200 mL) and extracted with dichloromethane (3×100 mL). The organic layer was washed with 10% aqueous potassium carbonate (2×100 mL). The aqueous layer was acidified with concentrated hydrochloric acid and extracted with ethyl acetate. The organic layer was dried over sodium sulfate, filtered, and concentrated in vacuo to yield 3,5-difluoro-4-hydroxybenzaldehyde as a white solid. Upon sitting the desired product began to precipitate from the original aqueous layer that was extracted with dichloromethane. The layer was filtered to provide the product (6) as long white crystals.

Step B: To a mixture of 3,5-difluoro-4-hydroxybenzaldehyde (6) (8.26 g, 52.2 mmol), and potassium carbonate (14.4 g, 104.4 mmol) in dimethylformamide (100 mL) was added benzyl chloride (7.2 mL, 62.7 mmol) and stirred overnight at 50° C. The reaction was diluted with water and extracted with ethyl acetate (3×75 mL). The organic layer was dried over sodium sulfate, filtered, and concentrated in vacuo. The residue was purified by flash column chromatography on silica gel (0-100% EtOAc in hexanes) to afford 4-(benzyloxy)-3,5-difluorobenzaldehyde (7).

Step C: A solution of 4-(benzyloxy)-3,5-difluorobenzaldehyde (7) (1.32 g, 5.34 mmol) and (1-ethoxycarbonylethylidene)triphenyl phosphorane (2.32 g, 6.41 mmol) in tetrahydrofuran (53 mL) was refluxed for 2 hours. The reaction was concentrated in vacuo and was purified by flash column chromatography (0-100% EtOAc in hexanes) to give (E)-ethyl 3-(4-(benzyloxy)-3,5-difluorophenyl)-2-methylacrylate (8).

Step D: To a solution (E)-ethyl 3-(4-(benzyloxy)-3,5-difluorophenyl)-2-methylacrylate (8) (1.4 g, 4.21 mmol) in ethanol (25 mL) was added Pd/C (140 mg, 10% Degussa type). A balloon of hydrogen gas was added and the reaction was evacuated and back-filled with hydrogen three times. The reaction was stirred under a hydrogen balloon overnight at room temperature, filtered through a pad of celite and concentrated in vacuo to give ethyl 3-(3,5-difluoro-4-hydroxyphenyl)-2-methylpropanoate (9).

Intermediate 3 ethyl 3-(3,5-difluoro-4-hydroxyphenyl)propanoate (11)

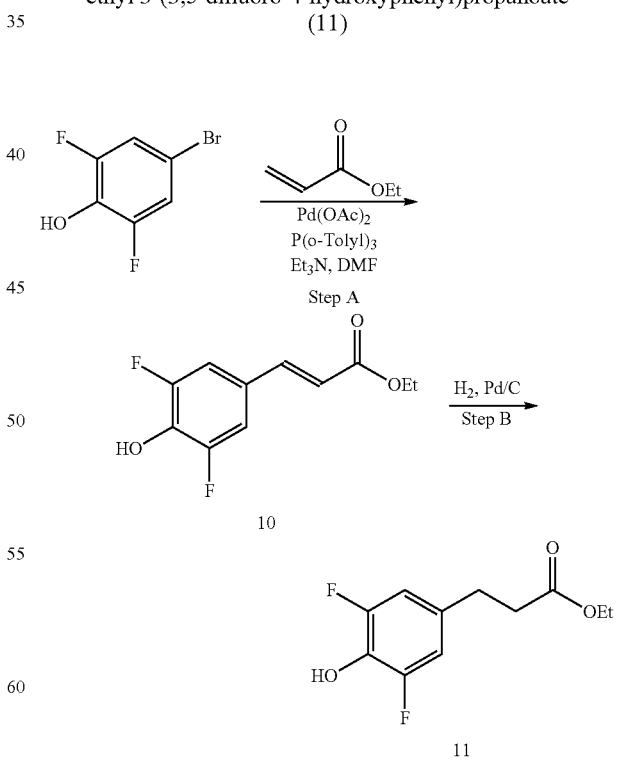

Step A: In a 350-mL pressure-glass was added 4-bromo-2,6-difluorophenol (23.82 g, 0.11 mol), triethylamine (55 mL, 0.39 mol), ethyl acrylate (34.27 g, 0.34 mol), DMF (50 mL), palladium (II) acetate (1.29 g, 5.75 mmol), and followed by tri-o-tolyphosphine (2.34 g, 7.6 mmol) under $N_2$. The mixture in the sealed glass was stirred at 110° C. overnight (21 hours), cooled to room temperature and added EtOAc (150 mL) and stirred for 30 minutes, filtered through celite and rinsed with EtOAc (3×100 mL). The filtrate was acidified with 2N HCl to pH ~2. The organic layer was separated, and the aqueous layer was extracted with EtOAc (2×50 mL). The organic layers were combined and washed with water (2×100 mL), brine (100 mL) and dried over sodium sulfate. After filtration, heptane (200 mL) was added and the solution was concentrated in vacuo. The resulting precipitate was filtered, washed with heptane (2×50 mL) and dried to afford the desired product as a light-yellow solid. The mother liquor was concentrated in vacuo to obtain additional desired product (10) as a pale-yellow solid. $^1$H NMR (400 MHz, CDCl$_3$) δ: 7.50 (d, J=15.9 Hz, 1H), 7.09 (d, J=8.3 Hz, 2H), 6.29 (d, J=15.9 Hz, 1H), 5.54 (br, 1H), 4.26 (q, J=7.1 Hz, 2H), 1.33 (t, J=7.1 Hz, 3H).

Step B: To a solution of (E)-ethyl 3-(3,5-difluoro-4-hydroxyphenyl)acrylate (10) (0.751 g, 3.29 mmol) in ethanol (20 mL) was added Pd/C (81 mg, 10% Degussa type). A balloon of hydrogen gas was added and the reaction was evacuated and back-filled with hydrogen three times. The reaction was stirred under a hydrogen balloon overnight at room temperature, filtered through a pad of celite and concentrated in vacuo to give ethyl 3-(3,5-difluoro-4-hydroxyphenyl)propanoate (11).

palladium (II) acetate (1.29 g, 5.75 mmol), and tri-o-tolyphosphine (2.34 g, 7.6 mmol) under $N_2$. The mixture was sealed in the glass tube and was stirred at 110° C. overnight (21 hours). The reaction was cooled to room temperature and EtOAc (150 mL) was added. The mixture was stirred for 30 minutes, filtered through celite and rinsed with EtOAc (3×100 mL). The filtrate was acidified with 2N HCl to pH ~2. The organic layer was separated, and the aqueous layer was extracted with EtOAc (2×50 mL). The organic layers were combined and washed with water (2×100 mL), brine (100 mL) and dried over sodium sulfate. After filtration, heptane (200 mL) was added and the solution was concentrated in vacuo. The resulting precipitate was filtered, washed with heptane (50 mL×2) and dried to afford the desired product as a light-yellow solid. The mother liquor was concentrated in vacuo to obtain additional desired product (10) as a pale-yellow solid. $^1$H NMR (400 MHz, CDCl$_3$) δ: 7.50 (d, J=15.9 Hz, 1H), 7.09 (d, J=8.3 Hz, 2H), 6.29 (d, J=15.9 Hz, 1H), 5.54 (br, 1H), 4.26 (q, J=7.1 Hz, 2H), 1.33 (t, J=7.1 Hz, 3H).

Step B: To a mixture of N-methyl-N'-nitro-N-nitrosoguanidine (TCI-America catalogue #M0527, 10 g on a dry weight basis, 0.068 mol) in ether (150 mL) at 0° C. was added a cold solution of potassium hydroxide (12.60 g) in water (21 mL). After stirring for 2 minutes, a portion of the yellow ethereal solution of the resulting diazomethane was added to a solution of ethyl 3-(3,5-difluoro-4-hydroxyphenyl)acrylate (10) (2.28 g, 0.010 mol) in ether (100 mL) at 0° C. A portion of palladium (II) acetate (0.372 g, 1.66 mmol) was added followed by an additional portion of diazomethane solution. This process was continued until all the diazomethane solution and palladium (II) acetate was added. The resulting dark mixture was stirred at 0-5° C. for 4 hours and acetic acid (6 drops) was added to quench any excess reagent. After removal of solvent in vacuo, the residue was purified by chromatography on silica gel (0-30% EtOAc in hexanes) to afford the desired product (12) as a white solid. $^1$H NMR (400 MHz, CDCl$_3$) δ: 6.67 (d, J=8.4 Hz, 2H), 5.05 (br, 1H), 4.20 (q, J=7.1 Hz, 2H), 2.45-2.40 (m, 1H), 1.87-1.74 (m, 1H), 1.39-1.14 (m, 5H).

Intermediate 4 ethyl 2-(3,5-difluoro-4-hydroxyphenyl)cyclopropanecarboxylate (12)

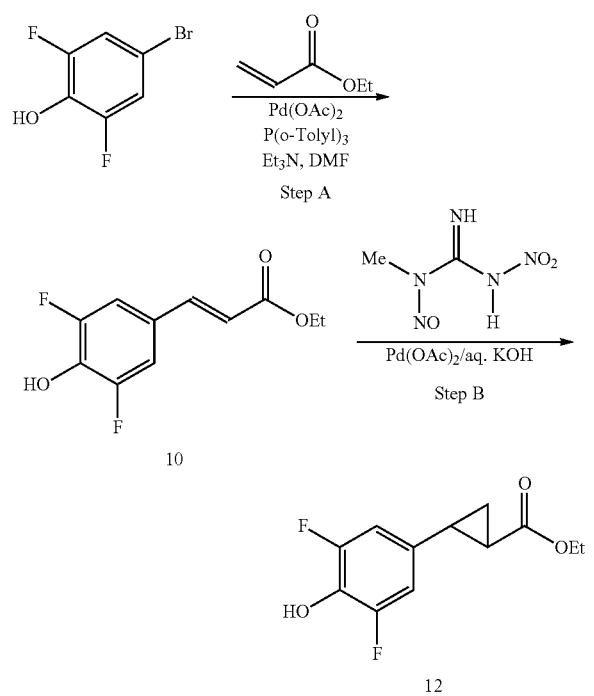

Step A: In a 350-mL pressure-tube was added 4-bromo-2,6-difluorophenol (23.82 g, 0.11 mol), triethylamine (55 mL, 0.39 mol), ethyl acrylate (34.27 g, 0.34 mol), DMF (50 mL), Intermediate 5

(2,2-dimethylchroman-8-yl)methanol (16)

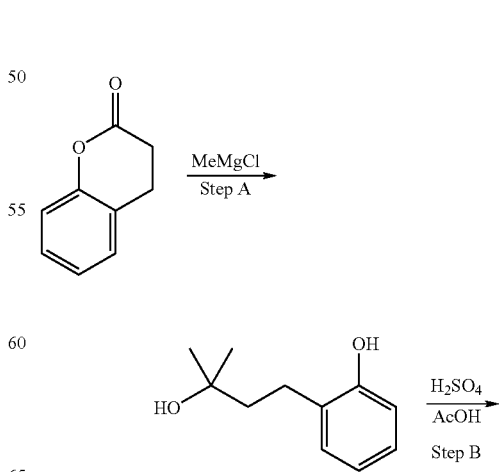

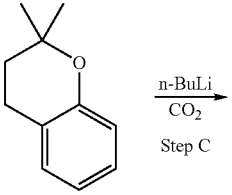

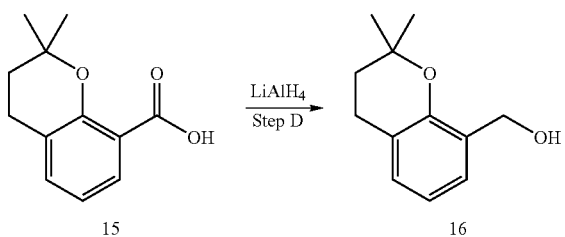

Step A: To a solution of methyl magnesium chloride (3M in tetrahydrofuran, 60 mL, 180 mmol) was added a solution of coumarin (11.4 mL, 90 mmol) in tetrahydrofuran (20 mL) drop wise over forty minutes. The reaction was stirred for 18 h. The solution was quenched with ice cold water (20 mL) and extracted with ethyl acetate (2×25 mL). The organic extracts were combined, dried over sodium sulfate, filtered and concentrated in vacuo to obtain the expected compound (13) as a white powder.

Step B: Alcohol (13) (7.6 g, 42.2 mmol) was dissolved in acetic acid (45 mL) and 20% sulfuric acid was added (17 mL). The solution was heated at 100° C. for 45 minutes. After allowing the solution to cool to room temperature, ice (20 g) was added. The mixture was extrated with ethyl acetate (2×25 mL), the organic extracts were combined, dried over sodium sulfate, filtered and concentrated in vacuo. The residue was purified by vacuum distillation (85° C. oil bath, 5 mmHg) to provide (14).

Step C: To a solution of n-butyllithium (26 mL, 2.5 M in hexanes) was added anhydrous diethyl ether (30 mL). A solution of compound (14) (4.2 g, 26 mmol) in 30 mL of anhydrous diethyl ether was added drop wise. After the addition was complete, the reaction was refluxed for 90 minutes. The solution was cooled to room temperature and poured into a flask containing a slurry of dry ice in anhydrous diethyl ether. Water was added (50 mL) and the solution was extracted with ethyl acetate (2×50 mL). The organic extracts were combined, dried over sodium sulfate, filtered and concentrated in vacuo to obtain the expected compound (15).

Step D: Compound (15) (0.230 g, 1.12 mmol) was dissolved in anhydrous tetrahydrofuran (5 mL) and cooled to 0° C. under nitrogen. Lithium aluminum hydride in tetrahydrofuran (1.0 M, 1.2 mL, 1.2 mmol) was added over a ten minute period. After the addition was complete, the solution was allowed to warm to room temperature and stirred for an additional sixty minutes. The solution was cooled to 0° C. and quenched by the addition of ethyl acetate (10 mL) followed by a saturated sodium sulfate aqueous solution (10 mL). The mixture was diluted with ethyl acetate and filtered through a pad of celite. The combined filtrates were dried over sodium sulfate and concentrated in vacuo. The residue was purified by flash column chromatography (0-100% EtOAc in hexanes) to provide the desired alcohol (16).

Intermediate 6 ethyl 2-(6-fluoro-5-hydroxy-2,3-dihydro-1H-inden-1-yl)acetate (22)

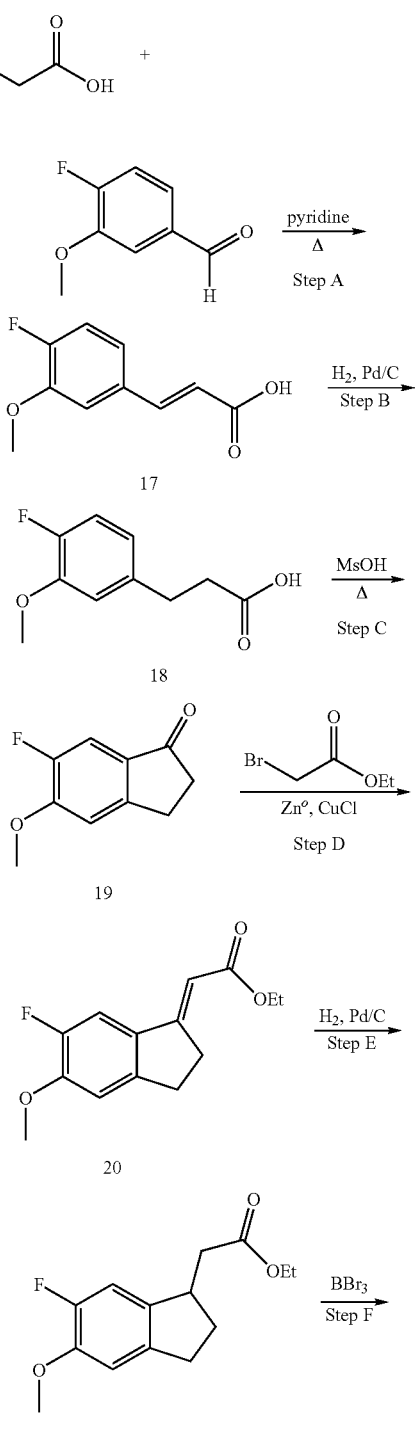

-continued

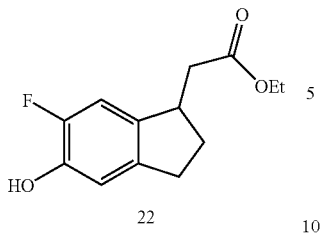

Step A: To a solution of malonic acid (21.5 g, 207 mmol) in pyridine (50 mL) was added 4-fluoro-3-methoxybenzaldehyde (16 g, 104 mmol) and piperidine (1.5 mL). The reaction was refluxed for 13 h. Water was added (25 mL) followed by concentrated HCl (40 mL). The precipitated product (17) was collected by filtration and washed with water.

Step B: To a solution of (17) (25 g, 127 mmol) in ethanol (40 mL) was added Pd/C (2 g, 10% Degussa type). A balloon of hydrogen gas was added and the reaction was evacuated and back-filled with hydrogen three times. The reaction was stirred under a hydrogen balloon overnight at room temperature, filtered through a pad of celite and concentrated in vacuo to provide compound (18).

Step C: To a 20 mL microwave tube was added compound (18) (2.00 g, 10.1 mmol) and methylsulfonic acid (15 mL). The tube was sealed and heated at 90° C. for 10 minutes. The resulting solution was poured into an ice bath, neutralized to pH 7 with aqueous NaOH. The resulting precipitate was collected by filtration and washed with water to provide compound (19).

Step D: To a solution of ketone (19) (3.56 g, 19.8 mmol) in toluene/tetrahydrofuran (50:1, 40 mL) was added Zn° dust (2.6 g, 39.6 mmol) and copper (I) chloride (0.4 g, 3.96 mmol). The suspension was heated at 90° C. for 30 minutes. After cooling to room temperature, ethylbromoacetate (3.4 mL. 31.6 mmol) was added. The suspension was heated at 100° C. for 4 hours. After cooling to room temperature, an aqueous solution of HCl (50 mL. 2N) was added and the solution was extrated with ethyl acetate (2×50 mL). The organic extracts were combined, dried over sodium sulfate, filtered and concentrated in vacuo. The residue was purified by flash column chromatography (0-50% EtOAc in hexanes) to provide the desired ester (20) as a mixture of isomers.

Step E: To a solution of (20) (0.79 g, 3.2 mmol) in ethanol (10 mL) was added Pd/C (0.08 g, 10% Degussa type). A balloon of hydrogen gas was added and the reaction was evacuated and back-filled with hydrogen three times. The reaction was stirred under a hydrogen balloon overnight at room temperature, filtered through a pad of celite and concentrated in vacuo to provide compound (21).

Step F: To a solution of ester (21) (1.06 g, 4.2 mmol) in dichloromethane (40 mL) at 0° C. was added boron tribromide (3.96 mL, 41.9 mmol). The solution was stirred for 2 hours and quenched with ethanol (5 mL) followed by a saturated solution of sodium bicarbonate (5 mL). The organic layer was separated, dried over sodium sulfate, filtered and concentrated in vacuo to obtain the expected product (22).

Intermediate 7 ethyl 2-(2-(3,5-difluoro-4-hydroxyphenyl)cyclopropyl)acetate (506)

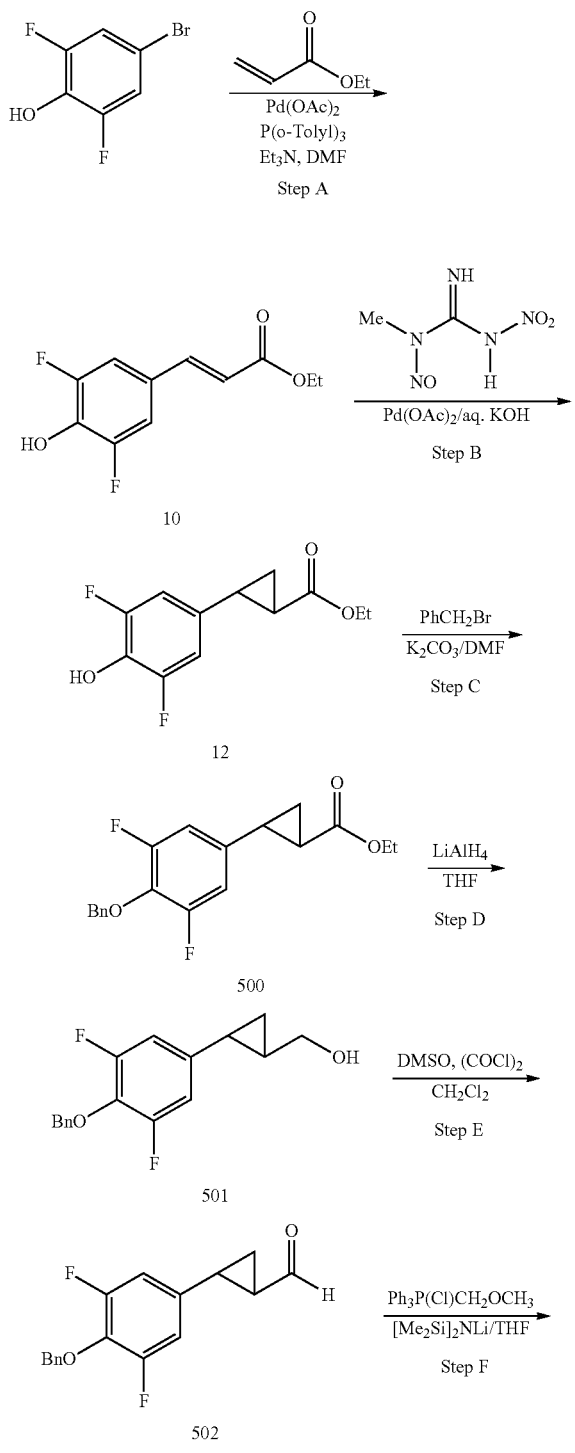

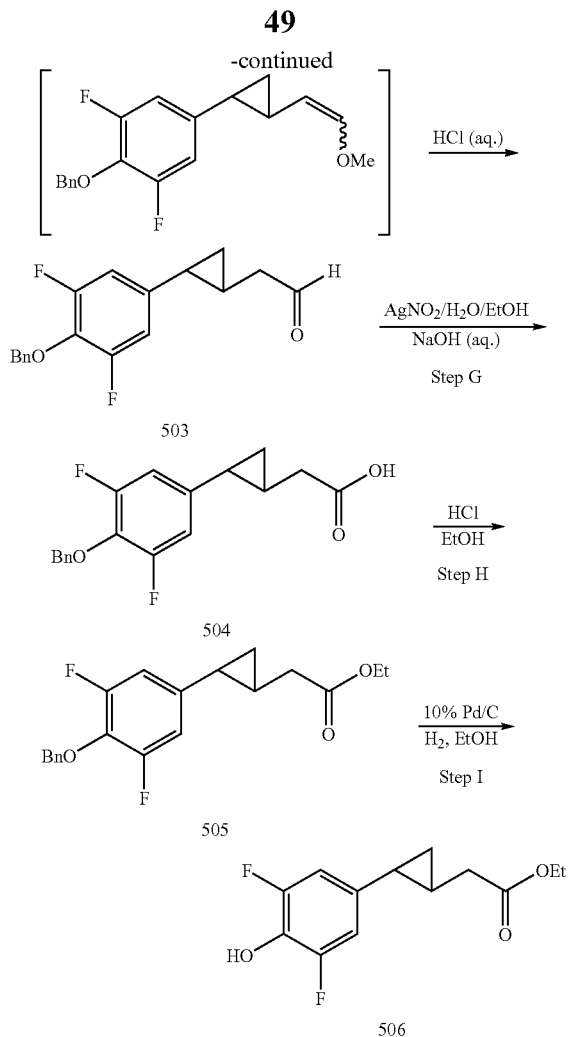

Step A: In a 350-mL pressure-tube was added 4-bromo-2,6-difluorophenol (23.82 g, 0.11 mol), triethylamine (55 mL, 0.39 mol), ethyl acrylate (34.27 g, 0.34 mol), DMF (50 mL), palladium (II) acetate (1.29 g, 5.75 mmol), and tri-o-tolyphosphine (2.34 g, 7.6 mmol) under $N_2$. The mixture was sealed in the glass tube and was stirred at 110° C. overnight (21 hours). The reaction was cooled to room temperature and EtOAc (150 mL) was added. The mixture was stirred for 30 minutes, filtered through celite and rinsed with EtOAc (100 mL×3). The filtrate was acidified with 2N HCl to pH ~2. The organic layer was separated, and the aqueous layer was extracted with EtOAc (50 mL×2). The organic layers were combined and washed with water ((100 mL×2), brine (100 mL) and dried over sodium sulfate. After filtration, heptane (200 mL) was added and the solution was concentrated in vacuo. The resulting precipitate was filtered, washed with heptane (50 mL×2) and dried to afford the desired product (10) (17.09 g) as a light-yellow solid. The mother liquor was concentrated to obtain additional desired product (4.29 g) as a pale-yellow solid. $^1$H NMR (400 MHz, CDCl$_3$) δ: 7.50 (d, J=15.9 Hz, 1H), 7.09 (d, J=8.3 Hz, 2H), 6.29 (d, J=15.9 Hz, 1H), 5.54 (br, 1H), 4.26 (q, J=7.1 Hz, 2H), 1.33 (t, J=7.1 Hz, 3H).

Step B: To a mixture of N-methyl-N'-nitro-N-nitrosoguanidine (TCI-America catalogue #M0527, 10 g on a dry weight basis, 0.068 mol) in ether (150 mL) at 0° C. was added a cold solution of KOH (12.60 g) in water (21 mL). After stirring for 2 minutes, a portion of the yellow ethereal solution of the resulting diazomethane was added to a solution of ethyl 3-(3,5-difluoro-4-hydroxyphenyl)acrylate (10) (2.28 g, 0.010 mol) in ether (100 mL) at 0° C. A portion of palladium (II) acetate (0.372 g, 1.66 mmol) was added followed by an additional portion of diazomethane solution. This process was continued until all the diazomethane solution and palladium (II) acetate was added. The resulting dark mixture was stirred at 0-5° C. for 4 hours and acetic acid (6 drops) was added to quench any excess reagent. After removal of solvent, the residue was purified by chromatography on silica gel (0-30% EtOAc in hexanes) to afford 2.04 g of the desired product as a white solid (12). $^1$H NMR (400 MHz, CDCl$_3$) δ: 6.67 (d, J=8.4 Hz, 2H), 5.05 (br, 1H), 4.20 (q, J=7.1 Hz, 2H), 2.45-2.40 (m, 1H), 1.87-1.74 (m, 1H), 1.39-1.14 (m, 5H).

Step C: To a mixture of ethyl 2-(3,5-difluoro-4-hydroxyphenyl)cyclopropanecarboxylate (12) (2.04 g, 8.4 mmol) and potassium carbonate (1.69 g, 12.2 mmol) in DMF (15 mL) was added benzyl bromide (1.88 g, 11 mmol). The mixture was stirred at rt overnight and partitioned between ethyl acetate and water. The organic extract was washed with water and brine, dried over sodium sulfate and concentrated in vacuo. Purification by flash chromatography on silica gel (0-20% EtOAc in hexanes) gave 2.76 g of desired product (500) as a white solid. $^1$H NMR (400 MHz, CDCl$_3$) δ: 7.50-7.43 (m, 2H), 7.38-7.32 (m, 3H), 6.62 (d, J=9.0 Hz, 2H), 5.12 (s, 2H), 4.19-4.11 (m, 2H), 2.43-2.38 (m, 1H), 1.89-1.76 (m, 1H), 1.65-1.58 (m, 1H), 1.29-1.15 (m, 4H).

Step D: To a solution of ethyl 2-(4-(benzyloxy)-3,5-difluorophenyl)cyclo propanecarboxylate (500) (2.74 g, 8.24 mmol) in tetrahydrofuran (10 mL) at 0° C. was added a solution of LiAlH$_4$ (1N in ether, 12.5 mL). After stirring at room temperature for 2 hours, 8 mL of EtOAc was added and the solution was stirred for 10 minutes. Water (10 mL) was added and the mixture was stirred for an additional 10 minutes, filtered through celite and rinsed with EtOAc. The filtration was partitioned between EtOAc and water/brine, washed with water/brine, dried over sodium sulfate and concentrated in vacuo to afford 2.25 g of desired product (501) as a colorless liquid. The product was sufficiently pure to be used directly in subsequent Swern oxidation. 1H NMR (400 MHz, CDCl$_3$) δ: 7.49-7.39 (m, 2H), 7.39-7.33 (m, 3H), 6.59 (d, J=9.2 Hz, 2H), 5.10 (s, 2H), 3.68-3.51 (m, 2H), 1.81-1.68 (m, 1H), 1.47-1.20 (m, 1H), 1.02-0.83 (m, 2H).

Step E: DMSO (2.5 mL) was added to a solution of oxalyl chloride (2.12 g, 16.7 mmol) in anhydrous dichloromethane (15 mL) at −78° C., and then a solution of (2-(4-(benzyloxy)-3,5-difluorophenyl)-cyclopropyl)methanol (501) (2.25 g, 7.75 mmol) in dichloromethane (5 mL) was added, followed by Et$_3$N (5.6 mL). Purification by flash chromatography on silica gel (0-30%) gave 2.07 g of desired product (502) as a colorless liquid. $^1$H NMR (400 MHz, CDCl$_3$) δ: 9.37 (s, 1H), 7.47-7.41 (m, 2H), 7.40-7.29 (m, 3H), 6.65 (d, J=7.1 Hz, 2H), 5.13 (s, 2H), 2.59-2.45 (m, 1H), 2.19-2.10 (m, 1H), 1.78-1.65 (m, 1H), 1.51-1.36 (m, 1H).

Steps F, G and H: These reactions were conducted according to the protocol described in US patent (US 2004/0092538, pp 40-41).

Step I: To a solution of ethyl 2-(2-(4-(benzyloxy)-3,5-difluorophenyl)cyclopropyl)acetate (505) (0.782 g, 2.25 mmol) in EtOAc/EtOH (5 mL/10 mL) was added 159 mg of 10% Pd/C, and the mixture was stirred under a hydrogen balloon overnight. After filtration through celite and washing with EtOH, the filtrate was concentrated in vacuo to afford 0.508 g of desired product (506) as a pale-yellow liquid. The product was sufficiently pure to be used directly in subsequent couplings. ¹H NMR (400 MHz, CDCl₃) δ: 6.67 (d, J=8.4 Hz, 2H), 4.96 (br, 1H), 4.23-4.05 (m, 2H), 2.50-2.26 (m, 2H), 1.70-1.66 (m, 1H), 1.33-1.19 (m, 4H), 0.97-0.79 (m, 2H).

Intermediate 8 ethyl 2-(4-hydroxyphenylthio)acetate (507)

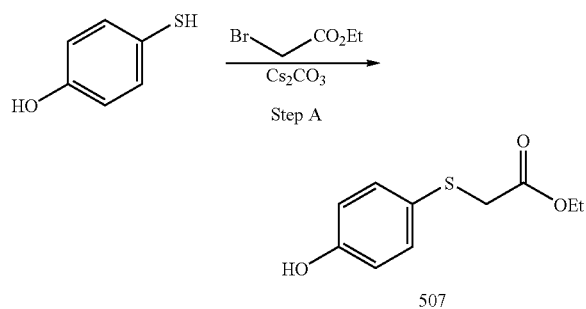

Step A: To a solution of 4-mercaptophenol (49.7 mg, 0.39 mmol) in tetrahydrofuran (2 mL) was added cesium carbonate (128 mg, 0.39 mmol) and ethyl bromoacetate (44 μL, 0.39 mmol) and the reaction was stirred at 50° C. overnight. The reaction was quenched with water and extracted with ethyl acetate (3×10 mL). The organic layer was dried over sodium sulfate, filtered, and concentrated in vacuo. The residue was purified by flash column chromatography on silica gel with hexanes and EtOAc to afford ethyl 2-(4-hydroxyphenylthio)acetate (507).

Intermediate 9

7-(chloromethyl)-2-methylbenzo[b]thiophene (511)

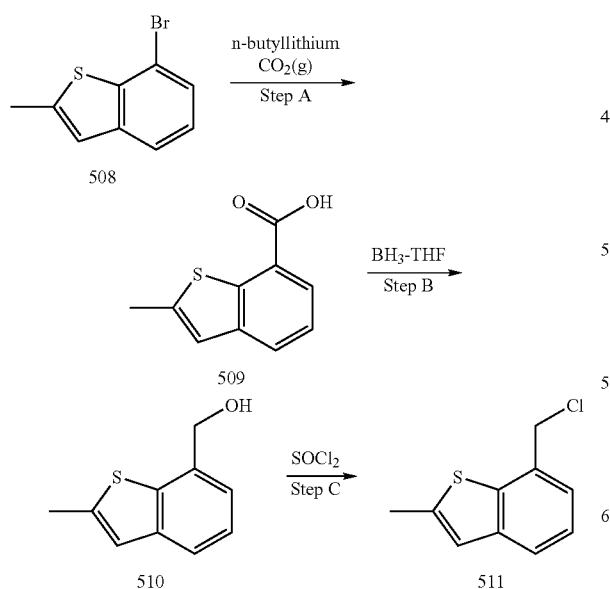

Step A: The solution of 7-bromo-2-methylbenzo[b]thiophene (508) (0.908 g, 4.0 mmol) in tetrahydrofuran (16 mL) was cooled to −78° C. under nitrogen. n-butyllithium (2.40 mL, 6.0 mmol, 1.0M in Hexanes) was added dropwise. After the addition was complete, the reaction mixture was stirred at −78° C. for 1 h, then poured on to the mixture of dry ice in ethyl ether (30 mL). The reaction was stirred to reach room temperature for 5 hours, followed by washing with 1N HCl, brine and dried over sodium sulfate, filtered, and concentrated in vacuo. The obtained white solid was washed with hexanes to provide 2-methylbenzo[b]thiophene-7-carboxylic acid (509) (0.240 g, 31.2%). LC-MS ESI m/z: found 191.0 [M−H]⁻.

Step B: The carboxylic acid (509) (0.240 g, 1.25 mmol) was dissolved in anhydrous tetrahydrofuran (12 mL) and cooled to 0° C. under nitrogen. BH₃-tetrahydrofuran complex (3.12 mL, 3.12 mmol, 1.0 M in tetrahydrofuran) was added slowly. After the addition was complete, the solution was allowed to warm to room temperature and stirred for an additional 1 hour. The solution was cooled to 0° C. and quenched by the addition of methanol (5 mL) followed by a saturated sodium sulfate aqueous solution (5 mL). The mixture was diluted with ethyl acetate and washed with brine and dried over sodium sulfate, filtered, and concentrated in vacuo to provide (2-methylbenzo[b]thiophen-7-yl)methanol (510) (0.203 g, 91.2%) as a colorless oil.

Step C: Thionyl chloride (0.415 mL, 5.69 mmol) was added slowly to an ice cold solution of the alcohol (510) (0.203 g, 1.14 mmol) in dichloromethane (6.0 mL). The reaction mixture was stirred and warmed to room temperature for 1 h. The resulting solution was quenched slowly with saturated sodium bicarbonate (10 mL) and extracted with dichloromethane, the organic layer was dried over sodium sulfate, filtered, and concentrated in vacuo to provide the intermediate 7-(chloromethyl)-2-methylbenzo[b]thiophene (511) (0.150 g, 67.0%) as a yellow oil.

Intermediate 10 ethyl 2-(6-hydroxy-1,2,3,4-tetrahydronaphthalen-1-yl)acetate (514)

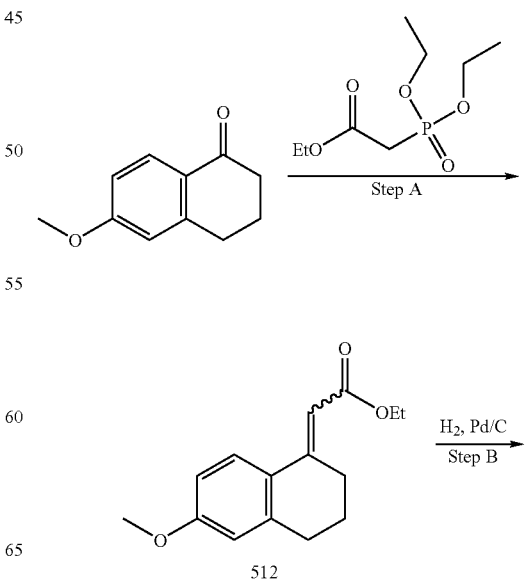

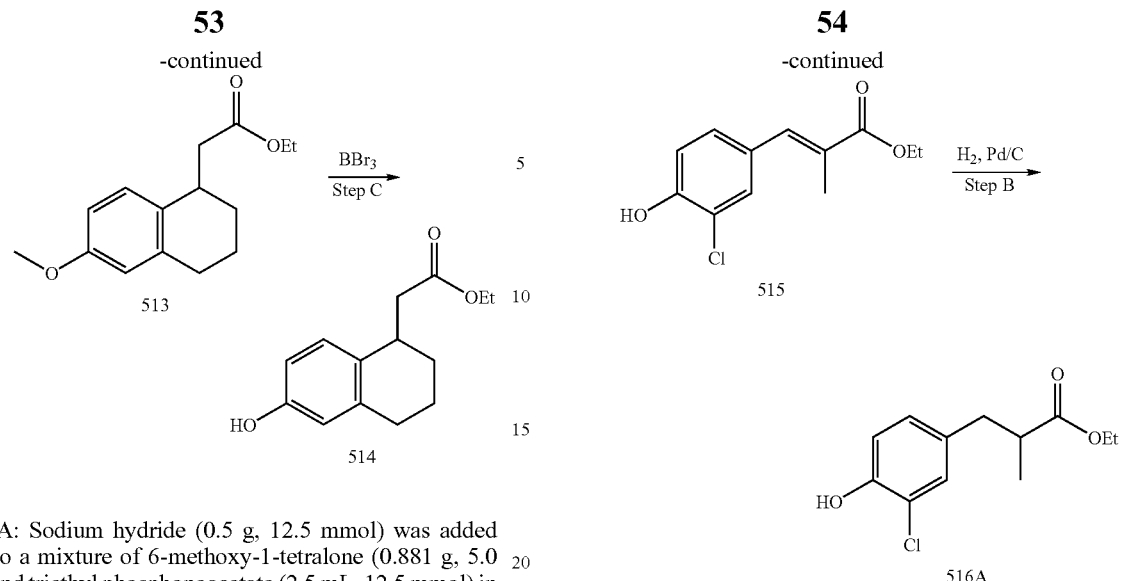

Step A: Sodium hydride (0.5 g, 12.5 mmol) was added slowly to a mixture of 6-methoxy-1-tetralone (0.881 g, 5.0 mmol) and triethyl phosphonoacetate (2.5 mL, 12.5 mmol) in anhydrous tetrahydrofuran (25 mL) at 0° C. The reaction was warmed to room temperature and refluxed under nitrogen for 48 hours. The reaction mixture was quenched with water and extracted with ethyl acetate. The organic phase was washed with water, brine, dried with sodium sulfate and concentrated under reduced pressure. The residue was purified by flash chromatography on silica gel (40% EtOAc in hexanes) to provide ethyl 2-(6-methoxy-3,4-dihydronaphthalen-1(2H)-ylidene)acetate (512) (0.792 g, 64.3%) as a yellow oil.

Step B: To a solution of the alkene (512) (0.792 g, 3.22 mmol) in ethanol (53 mL) was added Pd/C (100 mg, 10% Degussa type). A balloon of hydrogen gas was added and the reaction was evacuated and back-filled with hydrogen three times. The reaction was stirred under a hydrogen balloon overnight at room temperature, then filtered through a pad of celite and concentrated in vacuo to give ethyl 2-(6-methoxy-1,2,3,4-tetrahydronaphthalen-1-yl)acetate (513) (0.708 g, 88.7%) as a colorless oil.

Step C: To a solution of ethyl 2-(6-methoxy-1,2,3,4-tetrahydronaphthalen-1-yl)acetate (513) (0.708 g, 2.85 mmol) in dichloromethane (28 mL) at 0° C. was added boron tribromide (0.809 mL, 8.56 mmol). The solution was stirred for 2 hours and quenched with ethanol (5 mL) followed by a saturated solution of sodium bicarbonate (5 mL). The organic layer was separated, dried over sodium sulfate, filtered and concentrated in vacuo to obtain the intermediate ethyl 2-(6-hydroxy-1,2,3,4-tetrahydronaphthalen-1-yl)acetate (514) (0.600 g, 90.0%) as an oil residue.

Intermediate 11 ethyl 3-(3-chloro-4-hydroxyphenyl)-2-methylpropanoate (516A)

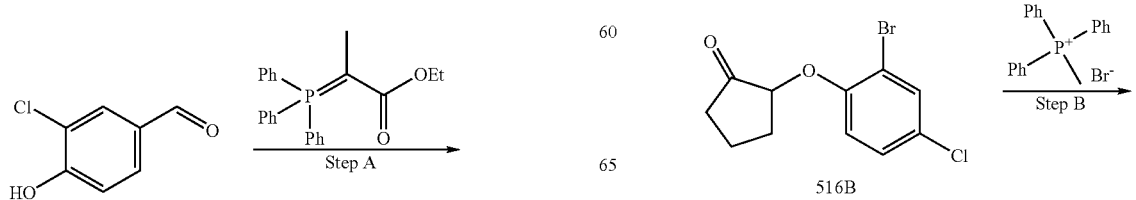

Step A: The mixture of 3-chloro-4-hydroxybenzaldehyde (0.783 g, 5 mmol) and ethyl 2-(triphenylphosphoranylidene) propionate (2.72 g, 7.5 mmol) in anhydrous tetrahydrofuran (25 mL) was heated at 60° C. under nitrogen for 4 hours. The solvent was removed in vacuo and purified by silica gel chromatography (40% EtOAc in hexanes) to provide ethyl 3-(3-chloro-4-hydroxyphenyl)-2-methylacrylate (515) (1.11 g, 95.2%) as a white solid.

Step B: To a solution of the alkene (515) (0.481 g, 2.0 mmol) in ethyl acetate (20 mL) was added Pd/C (48 mg, 10% Degussa type). A balloon of hydrogen gas was added and the reaction was evacuated and back-filled with hydrogen three times. The reaction was stirred overnight under a hydrogen balloon at room temperature, then filtered through a pad of celite and concentrated in vacuo to provide the intermediate ethyl 3-(3-chloro-4-hydroxyphenyl)-2-methylpropanoate (516A) (0.470 g, 96.9%) as a white solid. LC-MS ESI m/z: found 243.2 [M+H]$^+$.

Intermediate 12

5-chloro-7-(chloromethyl)-3H-spiro[benzofuran-2,1'-cyclopentane] (522)

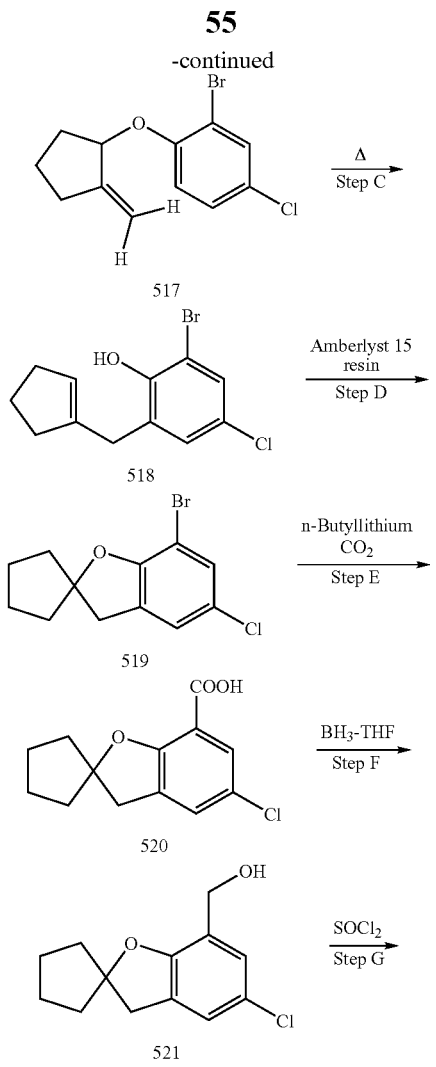

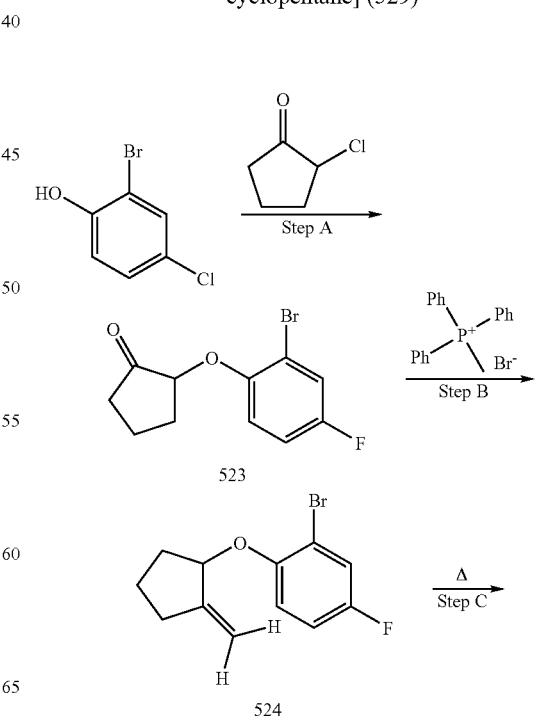

Step A: To a solution of ethyl 2-bromo-4-chlorophenol (10.9 g, 52.5 mmol) in acetone (105 mL) was added potassium carbonate (14.5 g, 105 mmol), followed by 2-chlorocyclopentanone (6.3 mL, 63 mmol). The mixture was refluxed at 100° C. overnight, then filtered through celite, concentrated in vacuo and purified by flash chromatography on silica gel (20% EtOAc in hexanes) to provide 2-(2-bromo-4-chlorophenoxy)cyclopentanone (516B) (10.8 g, 71.0%) as a yellow oil.

Step B: To the mixture of methyl triphenylphosphonium bromide (16.0 g, 44.8 mmol) in anhydrous tetrahydrofuran (125 mL) at 0° C. under nitrogen was added portion wise the potassium tert-butoxide (5.0 g, 44.8 mmol). After stirring at 0° C. for 30 minutes, the mixture of 2-(2-bromo-4-chlorophenoxy)cyclopentanone (516B) (10.8 g, 37.3 mmol) in tetrahydrofuran (40 mL) was added slowly. The resulting mixture was stirred at room temperature under nitrogen for 3 hours. The reaction mixture was quenched with water and extracted with ethyl acetate. The organic phase was washed with water, brine, dried with sodium sulfate and concentrated under reduced pressure. The residue was purified by flash chromatography on silica gel (5-10% EtOAc in hexanes) to provide 2-bromo-4-chloro-1-(2-methylenecyclopentyloxy)benzene (517) (6.2 g, 58.2%) as a colorless oil.

Step C: 2-Bromo-4-chloro-1-(2-methylenecyclopentyloxy)benzene (517) (6.2 g, 21.7 mmol) was heated at 150° C. for 6 hours. The residue was purified by flash chromatography on silica gel (5-10% EtOAc in hexanes) to provide 2-bromo-4-chloro-6-(cyclopentenylmethyl)phenol (518) (5.7 g, 53.0%) as a yellow oil.

Step D: The mixture of 2-bromo-4-chloro-6-(cyclopentenylmethyl)phenol (518) (5.7 g, 19.8 mmol) and Amberlyst® 15 ion-exchange resin (5.2 g) in toluene (100 mL) was heated at 80° C. for 3 hours. Subsequently, the Amberlyst 15 resin was filtered off and the filtrate was concentrated in vacuo to give 7-bromo-5-chloro-3H-spiro[benzofuran-2,1'-cyclopentane] (519) (5.4 g, 94.9%) as a yellow oil.

Step E: Similar manner described for the synthesis of (509) was used to synthesize the 5-chloro-3H-spiro[benzofuran-2,1'-cyclopentane]-7-carboxylic acid (520) (1.0 g, 44.5%) as an off-white solid.

Step F: Similar manner described for the synthesis of (510) was used to synthesize (5-chloro-3H-spiro[benzofuran-2,1'-cyclopentane]-7-yl)methanol (521) (0.640 g, 67.8%) as a colorless oil.

Step G: Similar manner described for the synthesis of (511) was used to synthesize the intermediate 5-chloro-7-(chloromethyl)-3H-spiro[benzofuran-2,1'-cyclopentane] (522) (0.630 g, 91.4%) as a yellow oil.

Intermediate 13

7-(chloromethyl)-5-fluoro-3H-spiro[benzofuran-2,1'-cyclopentane] (529)

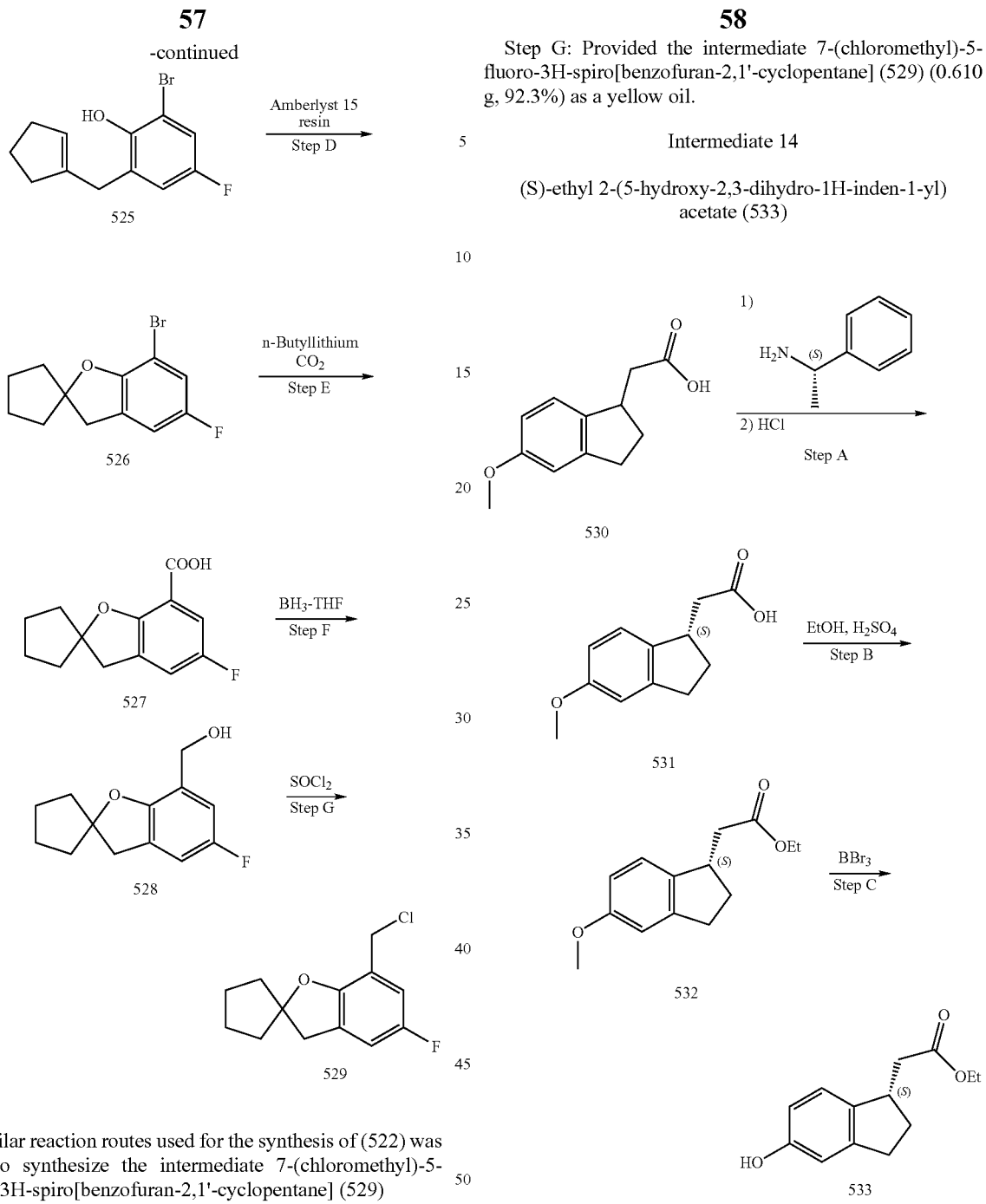

Step G: Provided the intermediate 7-(chloromethyl)-5-fluoro-3H-spiro[benzofuran-2,1'-cyclopentane] (529) (0.610 g, 92.3%) as a yellow oil.

Intermediate 14

(S)-ethyl 2-(5-hydroxy-2,3-dihydro-1H-inden-1-yl)acetate (533)

Similar reaction routes used for the synthesis of (522) was used to synthesize the intermediate 7-(chloromethyl)-5-fluoro-3H-spiro[benzofuran-2,1'-cyclopentane] (529)

Step A: Provided 2-(2-bromo-4-fluorophenoxy)cyclopentanone (523) (13.3 g, 92.7%), as a yellow oil.

Step B: Provided 2-bromo-4-fluoro-1-(2-methylenecyclopentyloxy)benzene (524) (9.7 g, 73.4%) as a colorless oil.

Step C: Provided 2-bromo-6-(cyclopentenylmethyl)-4-fluorophenol (525) (8.2 g, 62.2%) as a yellow oil.

Step D: Provided 7-bromo-5-fluoro-3H-spiro[benzofuran-2,1'-cyclopentane] (526) (8.2 g, 100%), yellow oil.

Step E: Provided 5-fluoro-3H-spiro[benzofuran-2,1'-cyclopentane]-7-carboxylic acid (527) (1.75 g, 86.6%) as an off-white solid.

Step F: Provided (5-fluoro-3H-spiro[benzofuran-2,1'-cyclopentane]-7-yl)methanol (528) (0.610 g, 37.0%) as a colorless oil.

Step A: The chiral base (S)-1-phenylethanamine (4.6 mL, 35.7 mmol) was added slowly into the stirring mixture of 2-(5-methoxy-2,3-dihydro-1H-inden-1-yl)acetic acid (530) (7.0 g, 34.0 mmol) in acetone (170 mL). After the addition was complete, an additional portion of acetone (10 mL) was added and stirring was continued for 1 hour. The precipitate was collected by filtration, washed with acetone and dried under vacuum. The solids were re-suspended in acetone (100 mL) and warmed to reflux until all the solids dissolved. The resulting reaction mixture was slowly cooled down to room temperature overnight, during which time the precipitates formed. The suspension was cooled to 0° C. and the white solid was collected and washed with cold acetone by filtration. The solids were dissolved in 1N HCl and extracted with EtOAc. The organic phase was washed with water, brine, dried with sodium sulfate and concentrated in vacuo to provide (S)-2-(5-methoxy-2,3-dihydro-1H-inden-1-yl)acetic (531) (1.65 g, 23.5%, 99.9% ee) as an oil residue.

Step B: The mixture of (S)-2-(5-methoxy-2,3-dihydro-1H-inden-1-yl)acetic (531) (1.65 g, 8.0 mmol) and $H_2SO_4$ (0.111 mL, 4.0 mmol) in ethanol (5 mL) was refluxed at 100° C. for 2 hours. The solvent was removed in vacuo. The residue was dissolved in ethyl acetate and washed with water. The organic layer was separated, dried over sodium sulfate, filtered and concentrated in vacuo to provide (S)-ethyl 2-(5-methoxy-2,3-dihydro-1H-inden-1-yl)acetate (532) (1.8 g, 96.0%) as an oil Step C: Similar manner described for the synthesis of (514) was used to synthesize (S)-ethyl 2-(5-hydroxy-2,3-dihydro-1H-inden-1-yl)acetate (533) (1.6 g, 94.5%) as an oil residue.

Intermediate 15

(S)-ethyl 2-(5-hydroxy-2,3-dihydro-1H-inden-1-yl) acetate (536)

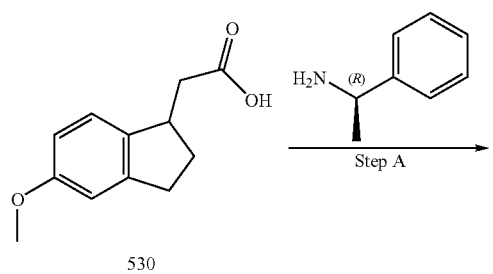

Similar reaction routes used for the synthesis of (533) was used to synthesize the intermediate (S)-ethyl 2-(5-hydroxy-2,3-dihydro-1H-inden-1-yl)acetate (536)

Step A: Provided (R)-2-(5-methoxy-2,3-dihydro-1H-inden-1-yl)acetic acid (534) (2.67 g, 38.1%, 92.0% ee pure) as an oil residue.

Step B: Provided (R)-ethyl 2-(5-methoxy-2,3-dihydro-1H-inden-1-yl)acetate (535) (2.9 g, 96.9%) as an oil residue.

Step C: Provided the intermediate (R)-ethyl 2-(5-hydroxy-2,3-dihydro-1H-inden-1-yl)acetate (536) (1.7 g, 61.1%) as an oil residue.

Intermediate 16 ethyl 2-(3-fluoro-4-hydroxyphenyl)cyclopropanecarboxylate (539)

Step A: The mixture of 3-fluoro-4-methoxybenzaldehyde (5.1 g, 33.0 mmol) and (carbethoxymethylene)triphenylphosphorane (17.2 g, 49.5 mmol) in anhydrous toluene (165 mL) was refluxed at 120° C. under nitrogen for 4 hours. The solvent was removed in vacuo and purified by silica gel chromatography (10-20% EtOAc in hexanes) to provide (E)-ethyl 3-(3-fluoro-4-methoxyphenyl)acrylate (537) (6.5 g, 87.6%) as a white solid.

Step B: To a mixture of N-methyl-N'-nitro-N-nitrosoguanidine (TCI-America catalogue #M0527, 3.7 g on a dry weight basis, 25.0 mmol) in ether (50 mL) at 0° C. was added a cold solution of 25% aqueous KOH (20 mL). After stifling for 2 minutes, a portion of the yellow ethereal solution of the resulting diazomethane was added to a solution of the alkene (537) (1.1 g, 5.0 mmol) in ether (25 mL) at 0° C. A portion of palladium (II) acetate (0.112 g, 0.50 mmol) was added followed by an additional portion of diazomethane solution. This process was continued until all the diazomethane solution and palladium (II) acetate was added. The resulting mixture was stirred at 0-5° C. for 4 hours and acetic acid (6 drops) was added to quench any excess reagent. The resulting mixture was concentrated in vacuo to provide ethyl 2-(3-fluoro-4-methoxyphenyl)cyclopropane carboxylate (538) (0.990 g, 83.0%) as a yellow oil.

Step C: Similar manner described for the synthesis of (514) was used to synthesize the intermediate ethyl 2-(3-fluoro-4-hydroxyphenyl)cyclopropanecarboxylate (539) (0.850 g, 91.1%) as a colorless oil.

Intermediate 17 ethyl 4-(4-hydroxyphenyl)-3-methylbutanoate (542)

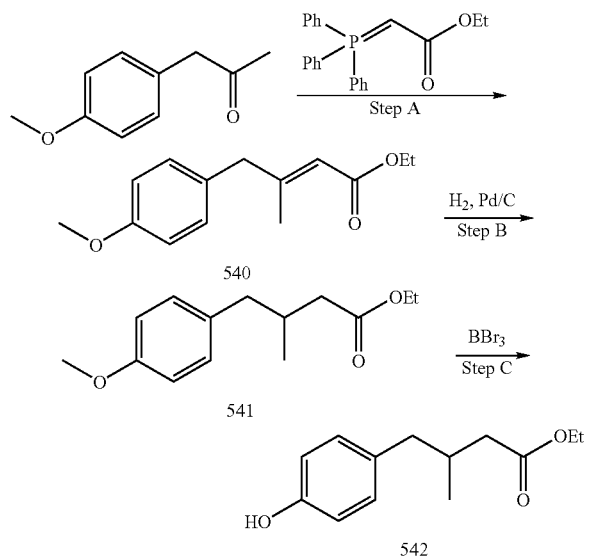

Step A: Similar manner described for the synthesis of (537) was used to synthesize ethyl 4-(4-methoxyphenyl)-3-methylbut-2-enoate (540) (4.5 g, 64.3%) as a colorless oil.

Step B: Similar manner described for the synthesis of (513) was used to synthesize ethyl 4-(4-methoxyphenyl)-3-methylbutanoate (541) (2.0 g, 98.4%) as a colorless oil.

Step C: Similar manner described for the synthesis of (514) was used to synthesize the intermediate ethyl 4-(4-hydroxyphenyl)-3-methylbutanoate (542) (0.80 g, 42.5%) as a colorless oil.

Intermediate 18

7-(chloromethyl)-2,2-dimethyl-5-phenyl-2,3-dihydrobenzofuran (547)

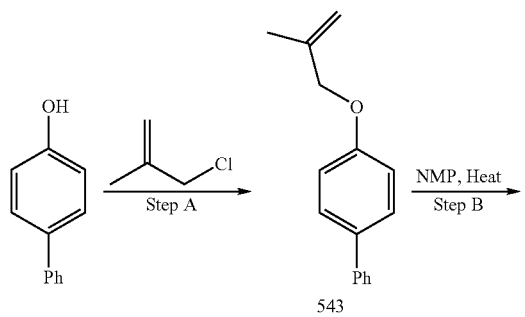

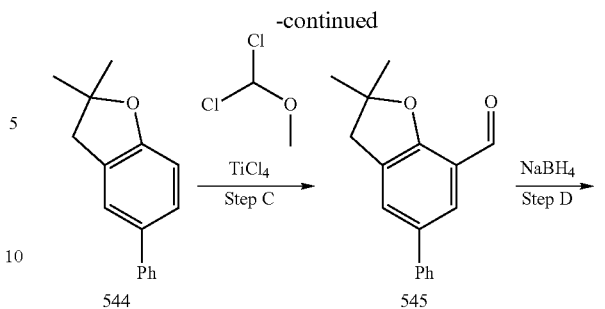

Step A: Similar manner described for the synthesis of (516B) was used to synthesize 4-(2-methylallyloxy)biphenyl (543) (5.9 g, 89.5%) as a white solid.

Step B: The mixture of 4-(2-methylallyloxy)biphenyl (543) (5.9 g, 26.4 mmol) in N-methyl-2-pyrrolidone was microwaved at 210° C. for 8 hours. The residue was dissolved in ethyl acetate and washed with water. The organic layer was separated, dried over sodium sulfate, filtered and concentrated in vacuo. The residue was purified by flash chromatography on silica gel (5-10% EtOAc in hexanes) to provide 2,2-dimethyl-5-phenyl-2,3-dihydrobenzofuran (544) (3.6 g, 60.8%) as a white solid.

Step C: To an ice cold solution of 2,2-dimethyl-5-phenyl-2,3-dihydrobenzofuran (544) (2.24 g, 10.0 mmol) in dichloromethane (15 mL) was added slowly titanium tetrachloride (2 mL, 18 mmol). After stirring of 5 minutes, dichloro(methoxy)methane (1 mL, 11 mol) was added slowly. The resulting mixture was stirred at 0° C. for 3 hours, quenched slowly with ice water. The product was extracted with dichloromethane. The organic layer was separated, dried over sodium sulfate, filtered and concentrated in vacuo. The residue was purified by flash chromatography on silica gel (5-10% EtOAc in hexanes) to provide 2,2-dimethyl-5-phenyl-2,3-dihydrobenzofuran-7-carbaldehyde (545).

Step D: To an ice cold solution of 2,2-dimethyl-5-phenyl-2,3-dihydrobenzofuran-7-carbaldehyde (545) (1 g, 3.96 mmol) in methanol (20 mL) was added portion wise sodium borohydride (179.9 mg, 4.76 mmol). The resulting mixture was stirred at 0° C. for 3 hours, quenched slowly with water. The product was extracted with dichloromethane. The organic layer was separated, dried over sodium sulfate, filtered and concentrated in vacuo. The residue was purified by flash chromatography on silica gel (20% EtOAc in hexanes) to provide (2,2-dimethyl-5-phenyl-2,3-dihydrobenzofuran-7-yl)methanol (546).

Step E: Similar manner described for the synthesis of (511) was used to synthesize the intermediate 7-(chloromethyl)-2,2-dimethyl-5-phenyl-2,3-dihydrobenzofuran (547).

Intermediate 19

6-chloro-4-(chloromethyl)-2,2-dimethyl-2,3-dihydrobenzofuran (552)

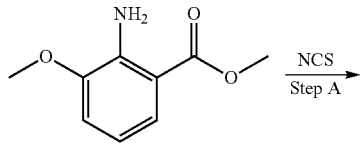

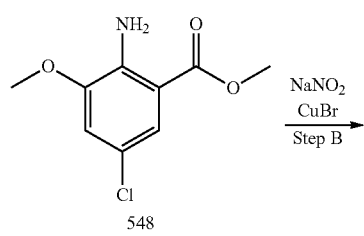

548

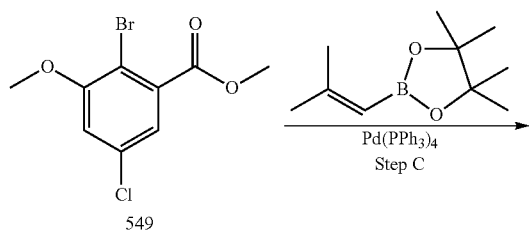

549

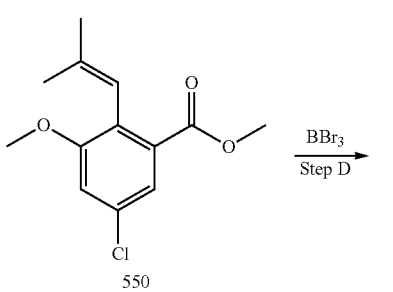

550

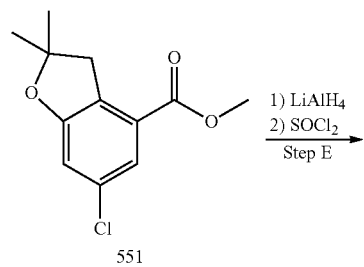

551

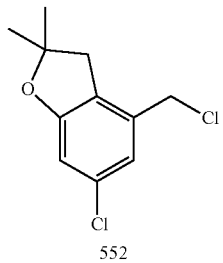

552

Step A: To a mixture of methyl 2-amino-3-methoxybenzoate (10 g, 55 mmol) in DMF (200 mL) was added N-chlorosuccinimide (8.08 g, 60.5 mmol) at room temperature, and the resulting mixture was stirred at 50° C. for 2 hours. The reaction was cooled to room temperature, diluted with water (300 mL), and extracted with ethyl acetate (2×100 mL). The organic layers were combined and washed with water (2×100 mL), brine (100 mL) and dried over sodium sulfate, filtered and concentrated in vacuo. The residue was purified by chromatography to provide the desired product (548).

Step B: To a mixture of methyl 2-amino-5-chloro-3-methoxybenzoate (548) (5.2 g, 24 mmol) in water (25 mL) and concentrated sulfuric acid (2.7 mL) was added the solution of sodium nitrite (1.7 g, 24 mmol) in water (25 mL) at room temperature. The mixture was stirred at room temperature for 30 minutes and added to the mixture of copper bromide (5.2 g, 36 mmol) in concentrated hydrogen bromide (10 mL) and water (20 mL) at room temperature. The mixture was stirred at room temperature overnight, was filtered through a pad of celite and rinsed with EtOAc (3×100 mL). The organic layer was separated, and the aqueous layer was extracted with EtOAc (2×50 mL). The organic layers were combined and washed with water (2×100 mL), brine (100 mL) and dried over $Na_2SO_4$, filtered and concentrated in vacuo. The residue was purified by chromatography to provide the desired product (549).

Step C: A mixture of methyl 2-bromo-5-chloro-3-methoxybenzoate (549) (1.1 g, 4 mmol), 4,4,5,5-tetramethyl-2-(2-methylprop-1-en-1-yl)-1,3,2-dioxaborolane (0.72 g, 4 mmol), $Pd(PPh_3)_4$ (138 mg, 0.12 mmol), 2N aqueous sodium carbonate (8 mL), methanol (10 mL), and toluene (6.0 mL) was heated in a pressure tube at 120° C. overnight. Ethyl acetate and water was added and the layers separated. The aqueous phase was extracted with ethyl acetate and the combined organic layers were dried over sodium sulfate, filtered and concentrated in vacuo. The crude compound was purified by flash column chromatography on silica gel with hexanes and EtOAc to afford the desired product (550).

Step D: To solution of methyl 5-chloro-3-methoxy-2-(2-methylprop-1-en-1-yl)benzoate (550) (0.6 g, 2.3 mmol) in dichloromethane (20 mL) at −78° C. was added boron tribromide (0.67 mL, 6.9 mmol). The solution was allowed to warm to room temperature and stirred overnight. The reaction was quenched with methanol (5 mL) followed by a saturated solution of sodium bicarbonate (5 mL). The organic layer was separated, dried over sodium sulfate, filtered and concentrated in vacuo. The crude compound was purified by flash column chromatography on silica gel with hexanes and EtOAc to afford the desired product (551).

Step E: Compound (552) was prepared in a similar manner as that described for the synthesis of (4) and (5)

Intermediate 20 ethyl 2-(4-hydroxybenzyl)cyclopropanecarboxylate (556)

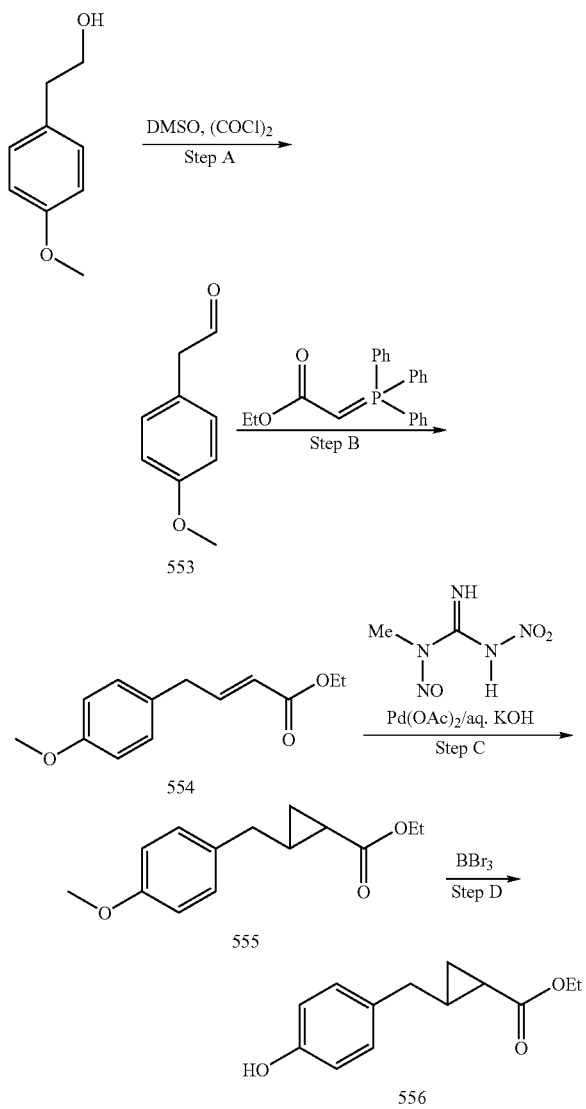

Step A: DMSO (5.2 mL, 72.6 mmol) in dichloromethane (14.5 mL) was added to a solution of oxalyl chloride (3.1 mL, 36.3 mmol) in dichloromethane (83 mL) at −70° C. under nitrogen. After stirring for 5 minutes, 2-(4-methoxyphenyl)ethanol (5.0 g, 33.0 mmol) dissolved in dichloromethane (33 mL) was added drop wise (20 min). Stirring was continued for an additional 20 min. and triethyl amine (9.7 mL, 69.3 mmol) was added, and the reaction mixture was stirred and warmed slowly to room temperature for 1 hour. The reaction mixture was diluted with water. The organic layer was separated, dried over sodium sulfate, filtered and concentrated in vacuo to provide 2-(4-methoxyphenyl)acetaldehyde (553) (2.2 g, 44.4%) as an oil residue.

Step B: Similar manner described for the synthesis of (537) was used to synthesize (E)-ethyl 4-(4-methoxyphenyl)but-2-enoate (554) (1.1 g, 38.2%) as a colorless oil.

Step C: Similar manner described for the synthesis of (538) was used to synthesize ethyl 2-(4-methoxybenzyl)cyclopropanecarboxylate (555) (1.2 g, 99.0%) as a colorless oil.

Step D: Similar manner described for the synthesis of (514) was used to synthesize the intermediate ethyl 2-(4-hydroxybenzyl)cyclopropanecarboxylate (556) (0.945 g, 80.1%) as a colorless oil.

Intermediate 21 ethyl 2-(2-(4-hydroxyphenyl)cyclopropyl)acetate (562)

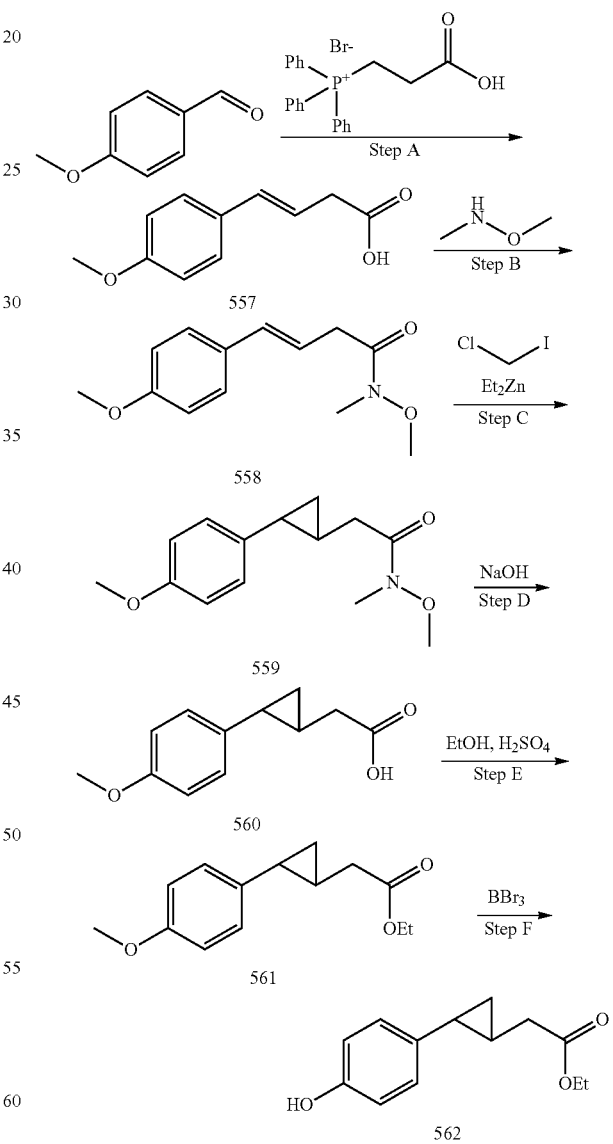

Step A: The mixture of (2-carboxyethyl)triphenylphosphonium bromide (20.0 g, 54.0 mmol) and 4-methoxybenzaldehyde (6.5 g, 53.5 mmol) in anhydrous DMSO (64 mL) was added slowly to the suspension of 60% NaH in mineral oil (4.3 g, 107 mmol) in anhydrous tetrahydrofuran (32 mL). The reaction mixture was stirred at 0° C. for 30 minutes then warmed to room temperature over 4 hours. The reaction mixture was quenched with 1N HCl (150 mL) and extracted with ethyl acetate. The organic phase was washed with water, brine, dried with sodium sulfate and concentrated under reduced pressure. The residue was purified by flash chromatography on silica gel (50% EtOAc in hexanes) to provide (E)-4-(4-methoxyphenyl)but-3-enoic acid (557) (5.7 g, 55.0%) as a yellow solid.

Step B: To the mixture of carboxylic acid (557) (5.7 g, 29.5 mmol) in DMF (150 mL) was added 0-(Benzotriazol-1-yl)-N,N,N',N'-tetramethyluronium tetrafluoroborate (9.5 g, 29.5 mol). After stifling for 5 minutes, N,O-dimethylhydroxylamine. HCl (2.9 g, 29.5 mmol) was added, followed by Et$_3$N (8.2 mL, 58.9 mmol). The reaction mixture was stirred at room temperature for 3 hours, diluted with water and extracted with ethyl acetate. The organic phase was washed with water, brine, dried over sodium sulfate and concentrated in vacuo. The residue was purified by flash chromatography on silica gel (40% EtOAc in hexanes) to provide (E)-N-methoxy-4-(4-methoxyphenyl)-N-methylbut-3-enamide (558) (2.1 g, 29.6%) as a yellow solid.

Step C: The solution of diethyl zinc in hexanes (1M, 17.4 mL, 17.4 mmol) was added slowly to the mixture of iodomethane (2.5 mL, 34.9 mmol), dimethoxy ethane (1.82 mL) in dichloromethane (25 mL) at −15° C. After stifling for 20 minutes, the solution of (E)-N-methoxy-4-(4-methoxyphenyl)-N-methylbut-3-enamide (558) (2.0 g, 8.7 mmol) in dichloromethane (10 mL) was added to the reaction mixture. The resulting mixture was allowed to warm to room temperature over 24 hours. The reaction mixture was diluted with water and extracted with dichloromethane. The organic phase was washed with water, brine, dried over sodium sulfate and concentrated in vacuo. The residue was purified by flash chromatography on silica gel (30% EtOAc in hexanes) to provide N-methoxy-2-(2-(4-methoxyphenyl)cyclopropyl)-N-methylacetamide (559) (1.8 g, 85.2%) as a yellow oil.

Step D: The mixture of N-methoxy-2-(2-(4-methoxyphenyl)cyclopropyl)-N-methylacetamide (559) (1.8 g, 7.4 mmol), 2.5N NaOH (15 mL) and EtOH (15 mL) was stirred at 60° C. for 24 hours. The reaction mixture was acidified with HCl and extracted with EtOAc. The organic phase was washed with water, brine, dried over sodium sulfate and concentrated in vacuo to provide 2-(2-(4-methoxyphenyl)cyclopropyl)acetic acid (560) (1.5 g, 96.1%) as a yellow solid.

Step E: Similar manner described for the synthesis of (532) was used to synthesize ethyl 2-(2-(4-methoxyphenyl)cyclopropyl)acetate (561) (1.2 g, 71.3%) as a colorless oil.

Step F: Similar manner described for the synthesis of (514) was used to synthesize the intermediate ethyl 2-(2-(4-hydroxyphenyl)cyclopropyl)acetate (562) (0.488 g, 43.6%) as a colorless oil.

Intermediate 22 ethyl 3-(4-hydroxy-2,6-dimethylphenyl)propanoate (564)

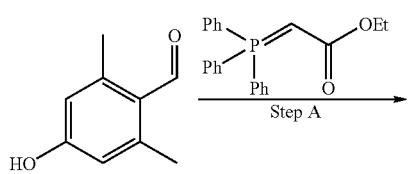

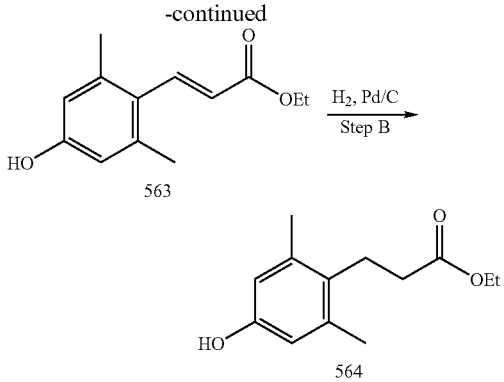

Step A: Similar manner described for the synthesis of (537) was used to synthesize (E)-ethyl 3-(4-hydroxy-2,6-dimethylphenyl)acrylate (563) (3.4 g, 100%) as a white solid.

Step B: Similar manner described for the synthesis of (513) was used to synthesize the intermediate ethyl 3-(4-hydroxy-2,6-dimethylphenyl)propanoate (564) (1.0 g, 97.8%) as a colorless oil.

Intermediate 23 ethyl 3-(4-hydroxy-2,5-dimethylphenyl)propanoate (567)

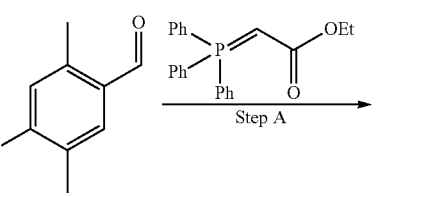

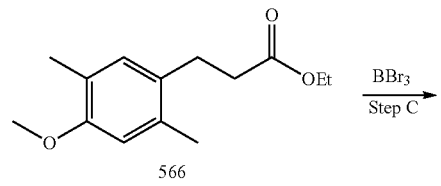

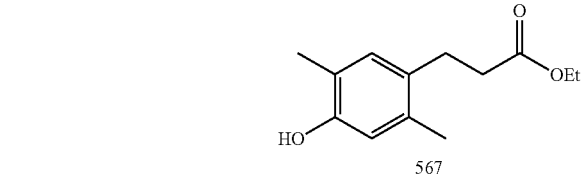

Step A: Similar manner described for the synthesis of (537) was used to synthesize (E)-ethyl 3-(4-methoxy-2,5-dimethylphenyl)acrylate (565) (3.2 g, 91.0%) as a white solid.

Step B: Similar manner described for the synthesis of (513) was used to synthesize ethyl 3-(4-methoxy-2,5-dimethylphenyl)propanoate (566) (1.1 g, 72.7%) as a colorless oil.

Step C: Similar manner described for the synthesis of (514) was used to synthesize the intermediate ethyl 3-(4-hydroxy-2,5-dimethylphenyl)propanoate (567) (0.970 g, 89.1%) as a colorless oil.

Intermediate 24 ethyl 3-(4-hydroxy-2,6-dimethylphenyl)propanoate (570)

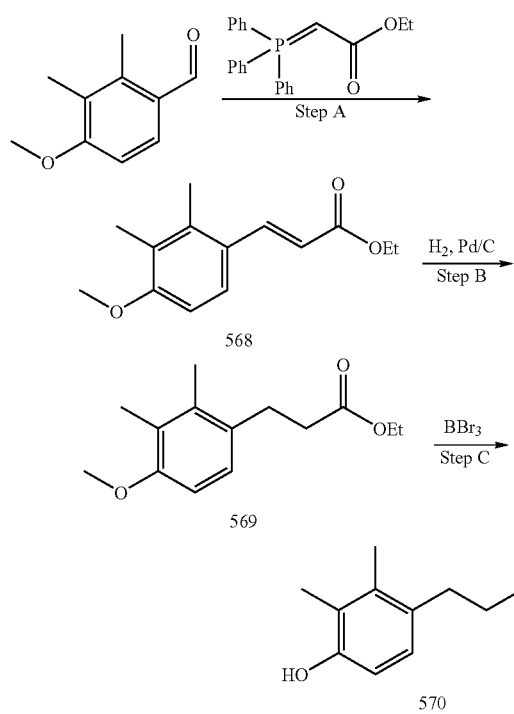

Step A: Similar reaction routes used for the synthesis of (537) was used to synthesize (E)-ethyl 3-(4-methoxy-2,3-dimethylphenyl)acrylate (568) (3.2 g, 90.7%) as a white solid.

Step B: Similar reaction routes used for the synthesis of (513) was used to synthesize ethyl 3-(4-methoxy-2,3-dimethylphenyl)propanoate (569) (1.3 g, 86.0%) as a white solid.

Step C: Similar reaction routes used for the synthesis of (514) was used to synthesize the intermediate ethyl 3-(4-hydroxy-2,3-dimethylphenyl)propanoate (570) (1.2 g, 89.3%) as a white solid.

Intermediate 25 ethyl 2-(2-(2-fluoro-4-hydroxyphenyl)cyclopropyl)acetate (576)

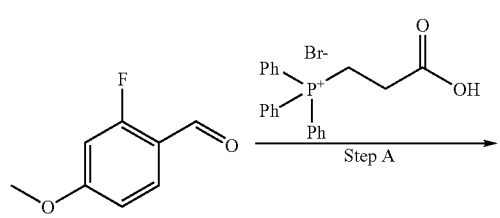

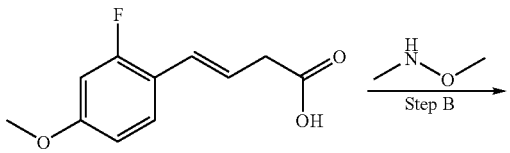

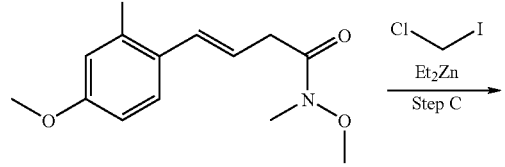

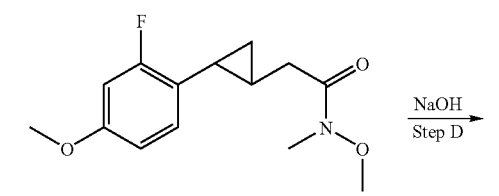

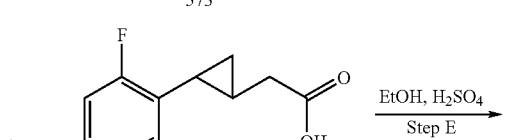

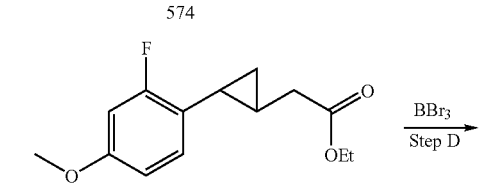

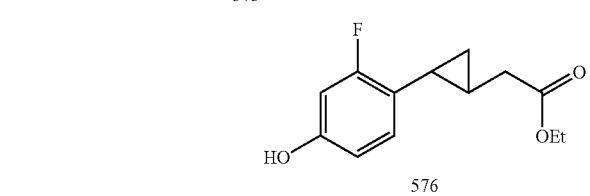

Similar reaction routes used for the synthesis of (562) was used to synthesize the intermediate ethyl 2-(2-(2-fluoro-4-hydroxyphenyl)cyclopropyl)acetate (576)

Step A: Provided (E)-4-(2-fluoro-4-methoxyphenyl)but-3-enoic acid (571) (5.0 g, 47.4%) as a yellow oil.

Step B: Provided (E)-4-(2-fluoro-4-methoxyphenyl)-N-methoxy-N-methylbut-3-enamide (572) (3.4 g, 56.7%) as a yellow oil.

Step C: Provided 2-(2-(2-fluoro-4-methoxyphenyl)cyclopropyl)-N-methoxy-N-methyl acetamide (573) (3.5 g, 96.7%) as a yellow oil.

Step D: Provided 2-(2-(2-fluoro-4-methoxyphenyl)cyclopropyl)acetic acid (574) (2.7 g, 92.4%) as a yellow oil.

Step E: Provided ethyl 2-(2-(2-fluoro-4-methoxyphenyl)cyclopropyl)acetate (575) (1.9 g, 62.8%), yellow oil.

Step F: Provided the intermediate ethyl 2-(2-(2-fluoro-4-hydroxyphenyl)cyclopropyl)acetate (576) (1.4 g, 78.6%), colorless oil.

Intermediate 26 ethyl 3-(5-fluoro-4-hydroxy-2-methylphenyl)propanoate (579)

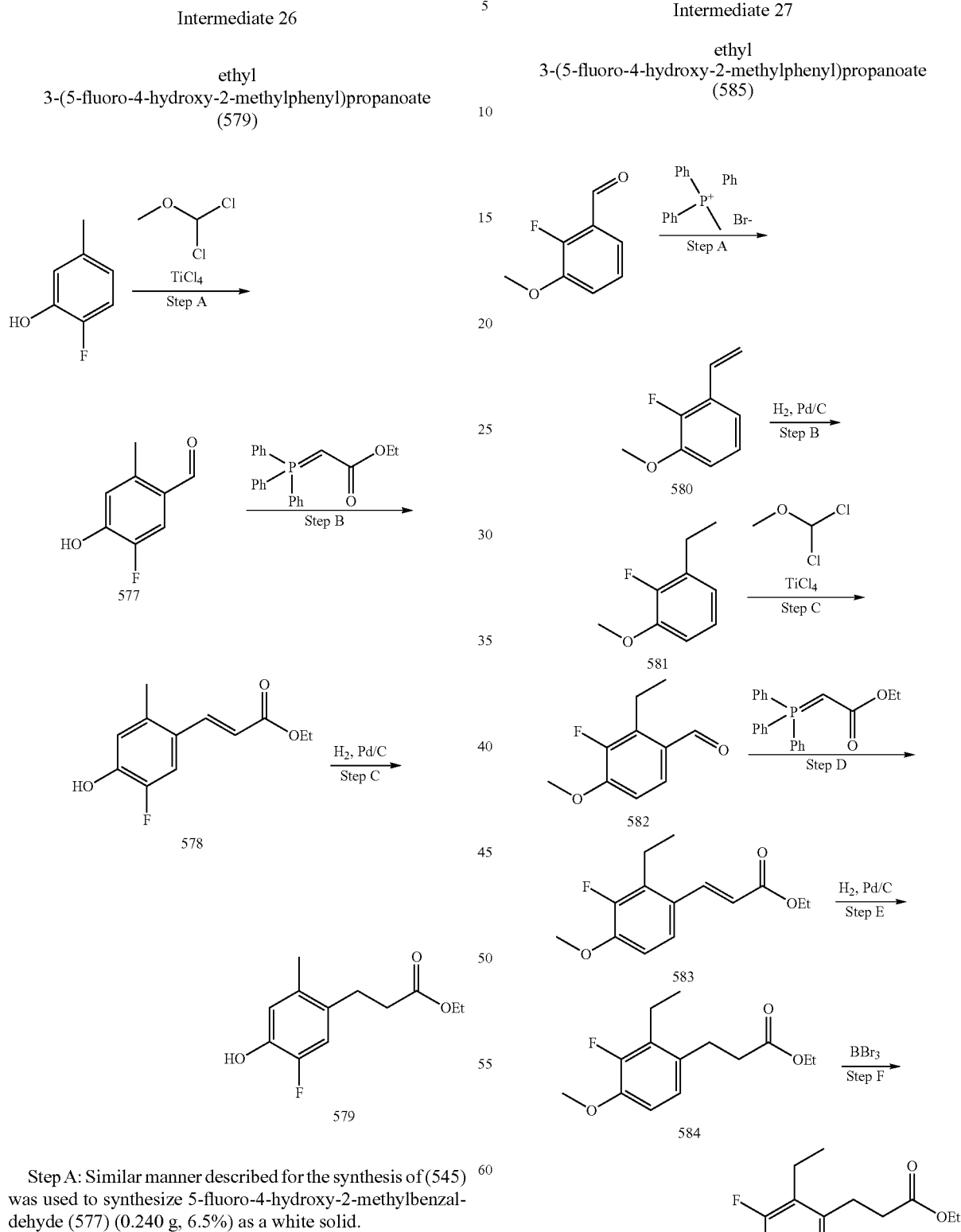

Step A: Similar manner described for the synthesis of (545) was used to synthesize 5-fluoro-4-hydroxy-2-methylbenzaldehyde (577) (0.240 g, 6.5%) as a white solid.

Step B: Similar manner described for the synthesis of (537) was used to synthesize (E)-ethyl 3-(5-fluoro-4-hydroxy-2-methylphenyl)acrylate (578) (0.330 g, 94.5%) as a white solid.

Step C: Similar manner described for the synthesis of (513) was used to synthesize ethyl 3-(5-fluoro-4-hydroxy-2-methylphenyl)propanoate (579) (0.325 g, 97.6%) as a colorless oil.

Intermediate 27 ethyl 3-(5-fluoro-4-hydroxy-2-methylphenyl)propanoate (585)

Step A: Similar manner described for the synthesis of (517) was used to synthesize 2-fluoro-1-methoxy-3-vinylbenzene (580) (3.5 g, 88.5%) as a colorless oil.

Step B: Similar manner described for the synthesis of (513) was used to synthesize 1-ethyl-2-fluoro-3-methoxybenzene (581) (3.2 g, 89.7%) as a colorless oil.

Step C: Similar manner described for the synthesis of (545) was used to synthesize 2-ethyl-3-fluoro-4-methoxybenzaldehyde (582) (2.7 g, 73.2%) as a colorless oil.

Step D: Similar manner described for the synthesis of (537) was used to synthesize (E)-ethyl 3-(2-ethyl-3-fluoro-4-methoxyphenyl)acrylate (583) (1.3 g, 89.4%) as a white solid.

Step E: Similar manner described for the synthesis of (513) was used to synthesize ethyl 3-(2-ethyl-3-fluoro-4-methoxyphenyl)propanoate (584) (1.3 g, 98.5%) as a colorless oil.

Step F: Similar manner described for the synthesis of (514) was used to synthesize the intermediate ethyl 3-(5-fluoro-4-hydroxy-2-methylphenyl)propanoate (585) (1.2 g, 98.2%) as a colorless oil.

Intermediate 28 ethyl 3-(5-fluoro-4-hydroxy-2-methylphenyl)propanoate (588)

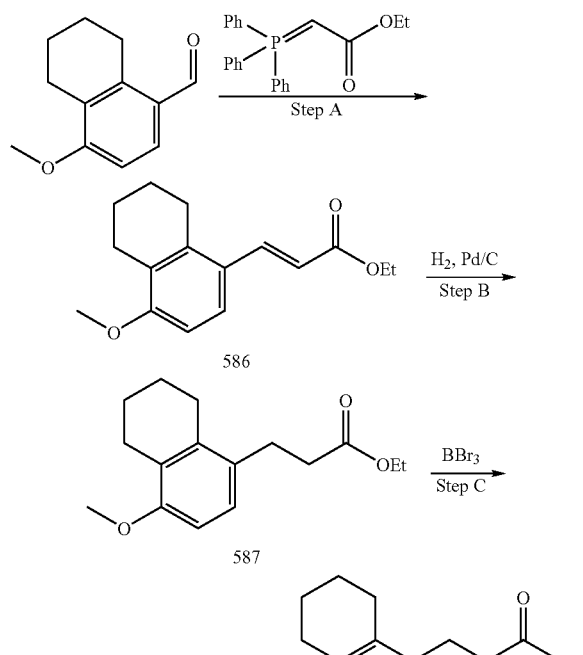

Similar reaction routes used for the synthesis of (567) was used to synthesize the intermediate ethyl 3-(5-fluoro-4-hydroxy-2-methylphenyl)propanoate (588)

Step A: Provided (E)-ethyl 3-(4-methoxy-5,6,7,8-tetrahydronaphthalen-1-yl)acrylate (586) (0.540 g, 78.3%) as a white solid.

Step B: Provided ethyl 3-(4-methoxy-5,6,7,8-tetrahydronaphthalen-1-yl)propanoate (587) (0.510 g, 93.7%), as an oil residue.

Step C: Provided the intermediate ethyl 3-(4-hydroxy-5,6,7,8-tetrahydronaphthalen-1-yl)propanoate (588) (0.243 g, 50.3%) as an oil residue.

Intermediate 2 ethyl 3-(2-ethyl-5-fluoro-4-hydroxyphenyl)propanoate (594)

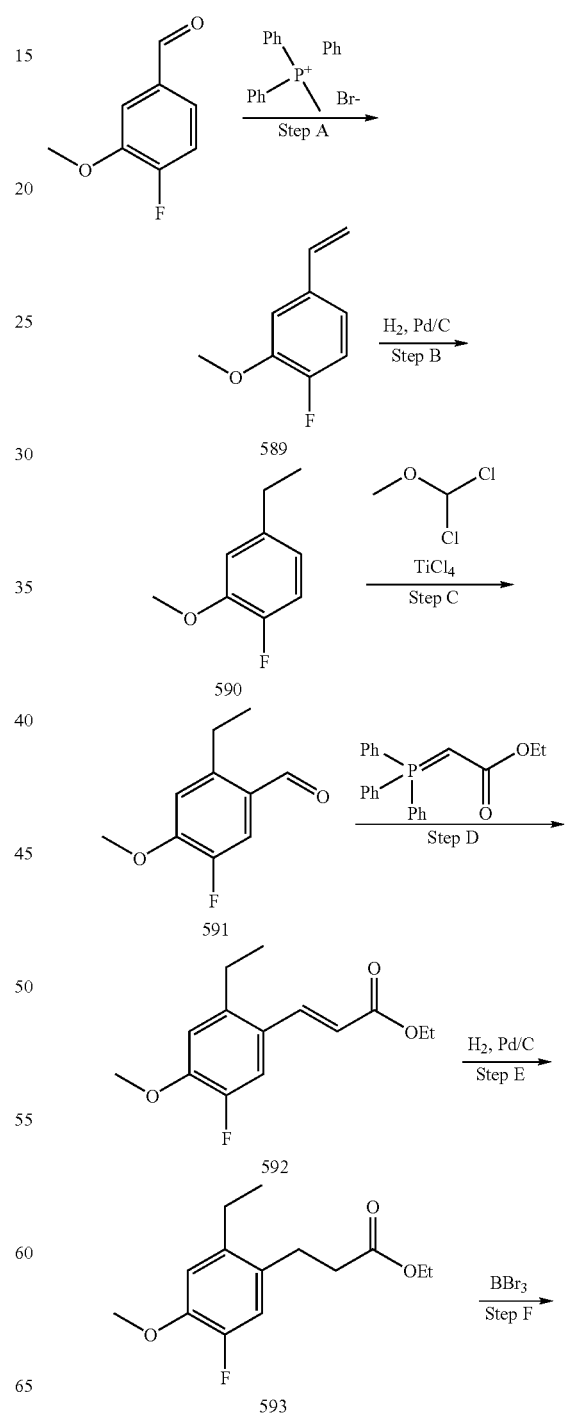

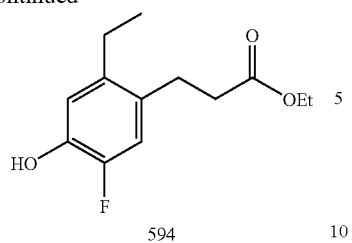

594

Similar reaction routes used for the synthesis of (585) was used to synthesize the intermediate ethyl 3-(2-ethyl-5-fluoro-4-hydroxyphenyl)propanoate (594)

Step A: Provided 1-fluoro-2-methoxy-4-vinylbenzene (589) (1.5 g, 30.3%) as a colorless oil.

Step B: Provided 4-ethyl-1-fluoro-2-methoxybenzene (590) (1.1 g, 71.7%) as a colorless oil.

Step C: Provided 2-ethyl-5-fluoro-4-methoxybenzaldehyde (591) (0.980 g, 76.1%) as a colorless oil.

Step D: Provided (E)-ethyl 3-(2-ethyl-5-fluoro-4-methoxyphenyl)acrylate (592) (1.3 g, 96.5%) as a colorless oil.

Step E: Provided ethyl 3-(2-ethyl-5-fluoro-4-methoxyphenyl)propanoate (593) (1.3 g, 96.2%) as a colorless oil.

Step F: Provided the intermediate ethyl 3-(2-ethyl-5-fluoro-4-hydroxyphenyl) propanoate (594) (0.617 g, 51.4%) as a colorless oil.

Intermediate 30 ethyl 3-(3-fluoro-4-hydroxy-2-propylphenyl)propanoate (600)

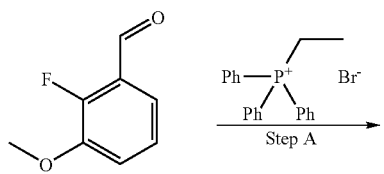

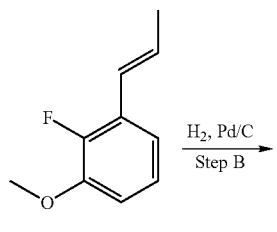

595

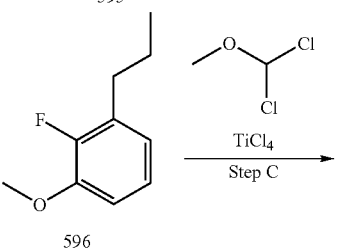

596

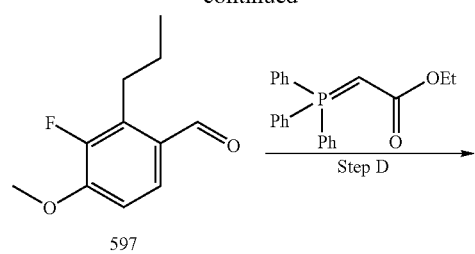

597

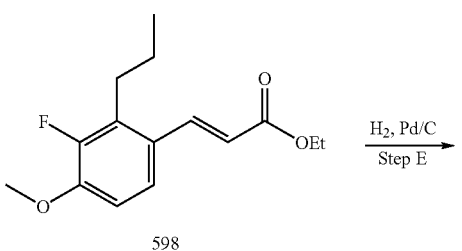

598

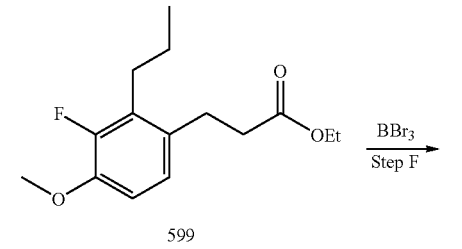

599

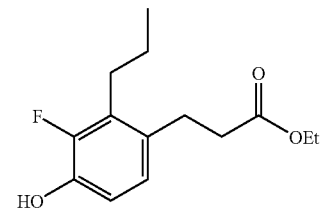

600

Similar reaction routes used for the synthesis of (585) was used to synthesize the intermediate ethyl 3-(3-fluoro-4-hydroxy-2-propylphenyl)propanoate (600)

Step A: Provided (E)-2-fluoro-1-methoxy-3-(prop-1-enyl)benzene (595) (1.4 g, 32.5%) as a colorless oil.

Step B: Provided 2-fluoro-1-methoxy-3-propylbenzene (596) (1.2 g, 83.0%) as a colorless oil.

Step C: Provided 3-fluoro-4-methoxy-2-propylbenzaldehyde (597) (1.0 g, 73.4%) as a colorless oil.

Step D: Provided (E)-ethyl 3-(3-fluoro-4-methoxy-2-propylphenyl)acrylate (598) (1.2 g, 86.8%) as a colorless oil.

Step E: Provided ethyl 3-(3-fluoro-4-methoxy-2-propylphenyl)propanoate (599) (1.2 g, 95.9%) as a colorless oil.

Step F: Provided the intermediate ethyl 3-(3-fluoro-4-hydroxy-2-propylphenyl) propanoate (600) (1.1 g, 98.2%) as a colorless oil.

Intermediate 31 ethyl 3-(3-fluoro-4-hydroxy-2-pentylphenyl)propanoate (606)

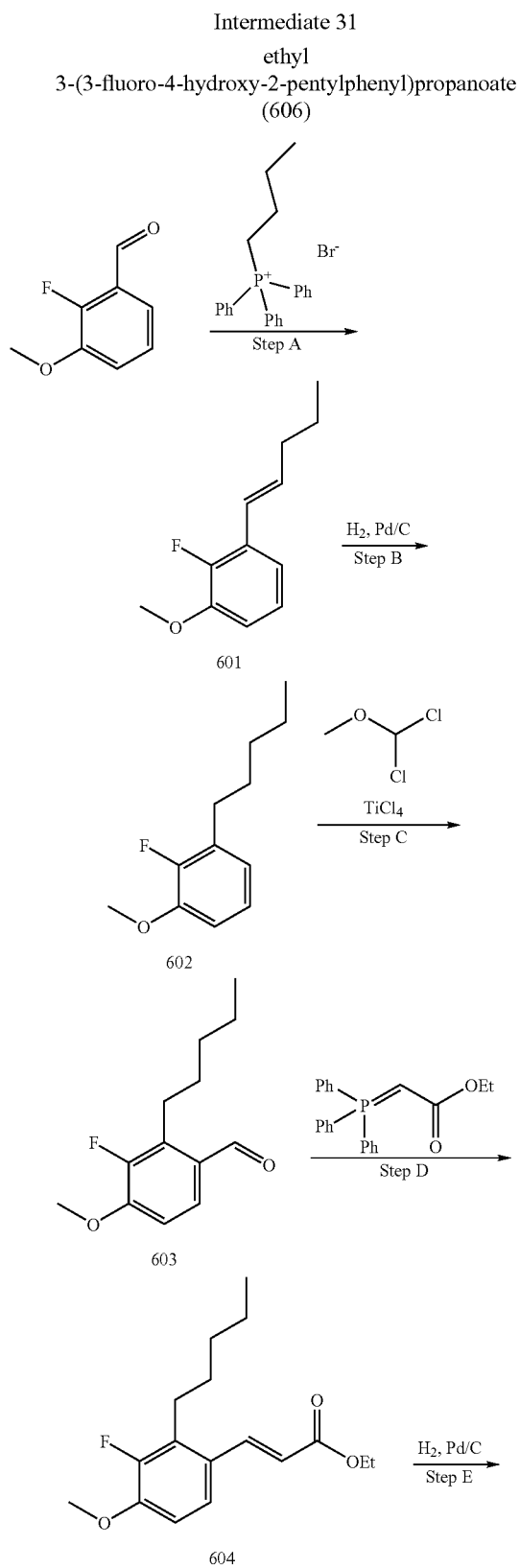

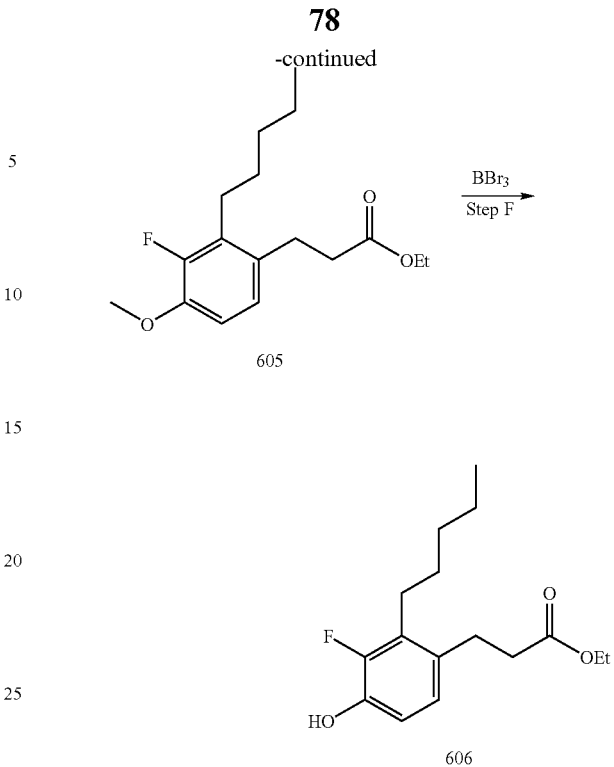

Similar reaction routes used for the synthesis of (585) was used to synthesize the intermediate ethyl 3-(3-fluoro-4-hydroxy-2-pentylphenyl)propanoate (606)

Step A: Provided (E)-2-fluoro-1-methoxy-3-(pent-1-enyl) benzene (601) (3.5 g, 69.3%) as a colorless oil.

Step B: Provided 2-fluoro-1-methoxy-3-pentylbenzene (602) (3.1 g, 88.2%) as a colorless oil.

Step C: Provided 3-fluoro-4-methoxy-2-pentylbenzaldehyde (603) (2.4 g, 67.9%) as a colorless oil.

Step D: Provided (E)-ethyl 3-(3-fluoro-4-methoxy-2-pentylphenyl)acrylate (604) (2.9 g, 89.7%) as a white solid.

Step E: Provided ethyl 3-(3-fluoro-4-methoxy-2-pentylphenyl)propanoate (605) (2.7 g, 94.4%) as a colorless oil.

Step F: Provided the intermediate ethyl 3-(3-fluoro-4-hydroxy-2-pentylphenyl) propanoate (606) (2.5 g, 98.7%) as a colorless oil.

Intermediate 32 ethyl 3-(2-ethyl-3-fluoro-4-hydroxyphenyl)-2-methylpropanoate (609)

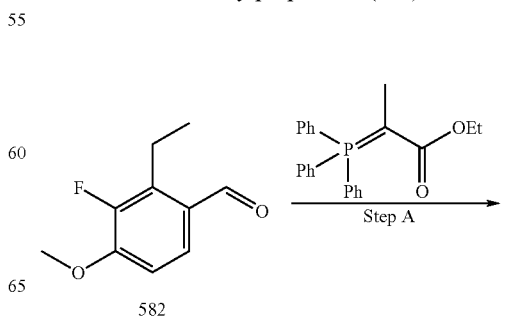

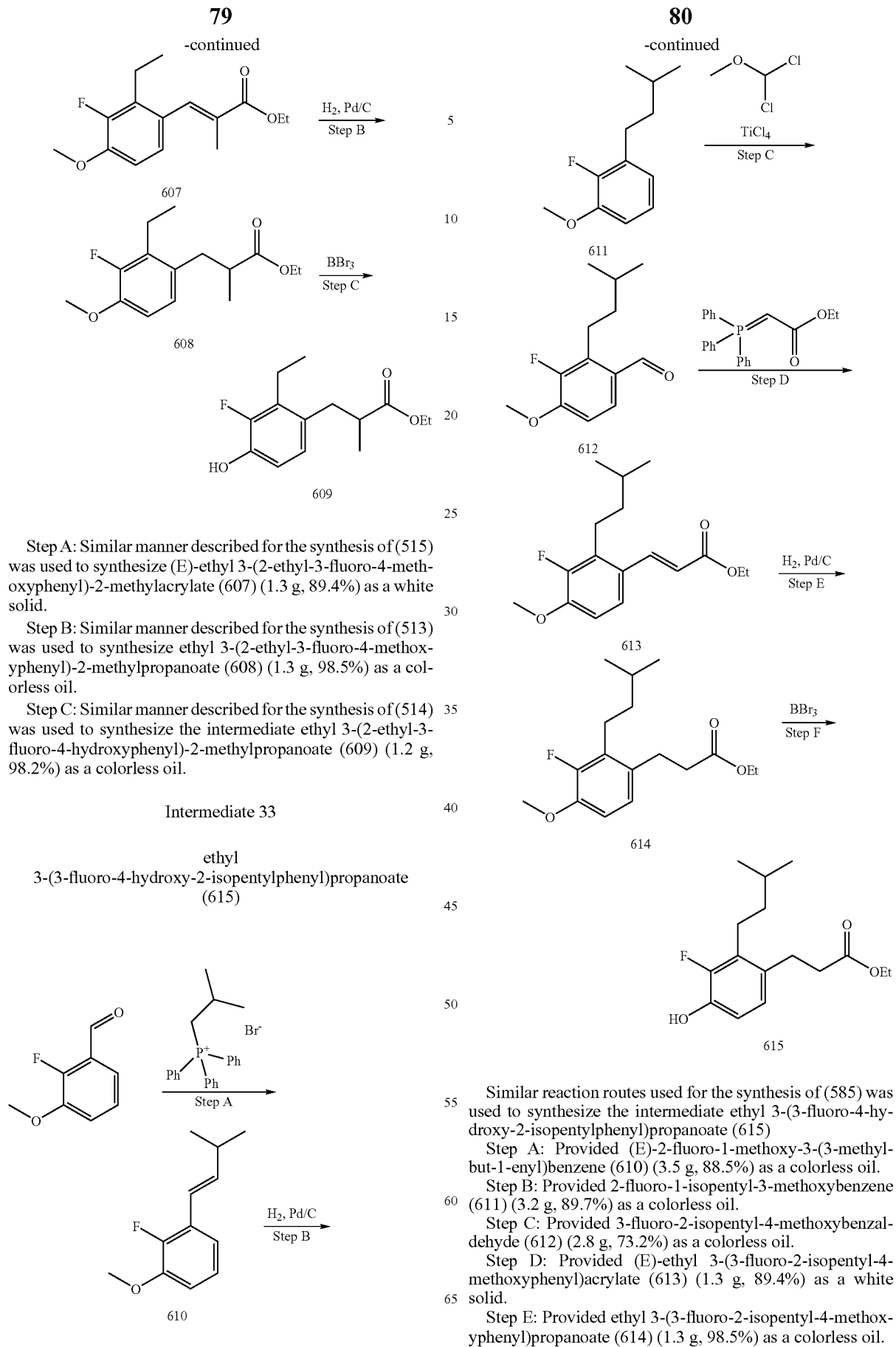

Step A: Similar manner described for the synthesis of (515) was used to synthesize (E)-ethyl 3-(2-ethyl-3-fluoro-4-methoxyphenyl)-2-methylacrylate (607) (1.3 g, 89.4%) as a white solid.

Step B: Similar manner described for the synthesis of (513) was used to synthesize ethyl 3-(2-ethyl-3-fluoro-4-methoxyphenyl)-2-methylpropanoate (608) (1.3 g, 98.5%) as a colorless oil.

Step C: Similar manner described for the synthesis of (514) was used to synthesize the intermediate ethyl 3-(2-ethyl-3-fluoro-4-hydroxyphenyl)-2-methylpropanoate (609) (1.2 g, 98.2%) as a colorless oil.

Intermediate 33 ethyl 3-(3-fluoro-4-hydroxy-2-isopentylphenyl)propanoate (615)

Similar reaction routes used for the synthesis of (585) was used to synthesize the intermediate ethyl 3-(3-fluoro-4-hydroxy-2-isopentylphenyl)propanoate (615)

Step A: Provided (E)-2-fluoro-1-methoxy-3-(3-methylbut-1-enyl)benzene (610) (3.5 g, 88.5%) as a colorless oil.

Step B: Provided 2-fluoro-1-isopentyl-3-methoxybenzene (611) (3.2 g, 89.7%) as a colorless oil.

Step C: Provided 3-fluoro-2-isopentyl-4-methoxybenzaldehyde (612) (2.8 g, 73.2%) as a colorless oil.

Step D: Provided (E)-ethyl 3-(3-fluoro-2-isopentyl-4-methoxyphenyl)acrylate (613) (1.3 g, 89.4%) as a white solid.

Step E: Provided ethyl 3-(3-fluoro-2-isopentyl-4-methoxyphenyl)propanoate (614) (1.3 g, 98.5%) as a colorless oil.

Step F: Provided the intermediate ethyl 3-(3-fluoro-4-hydroxy-2-isopentylphenyl) propanoate (615) (1.2 g, 98.2%) as a colorless oil.

Intermediate 34 ethyl 3-(2-butyl-3-fluoro-4-hydroxyphenyl)propanoate (621)

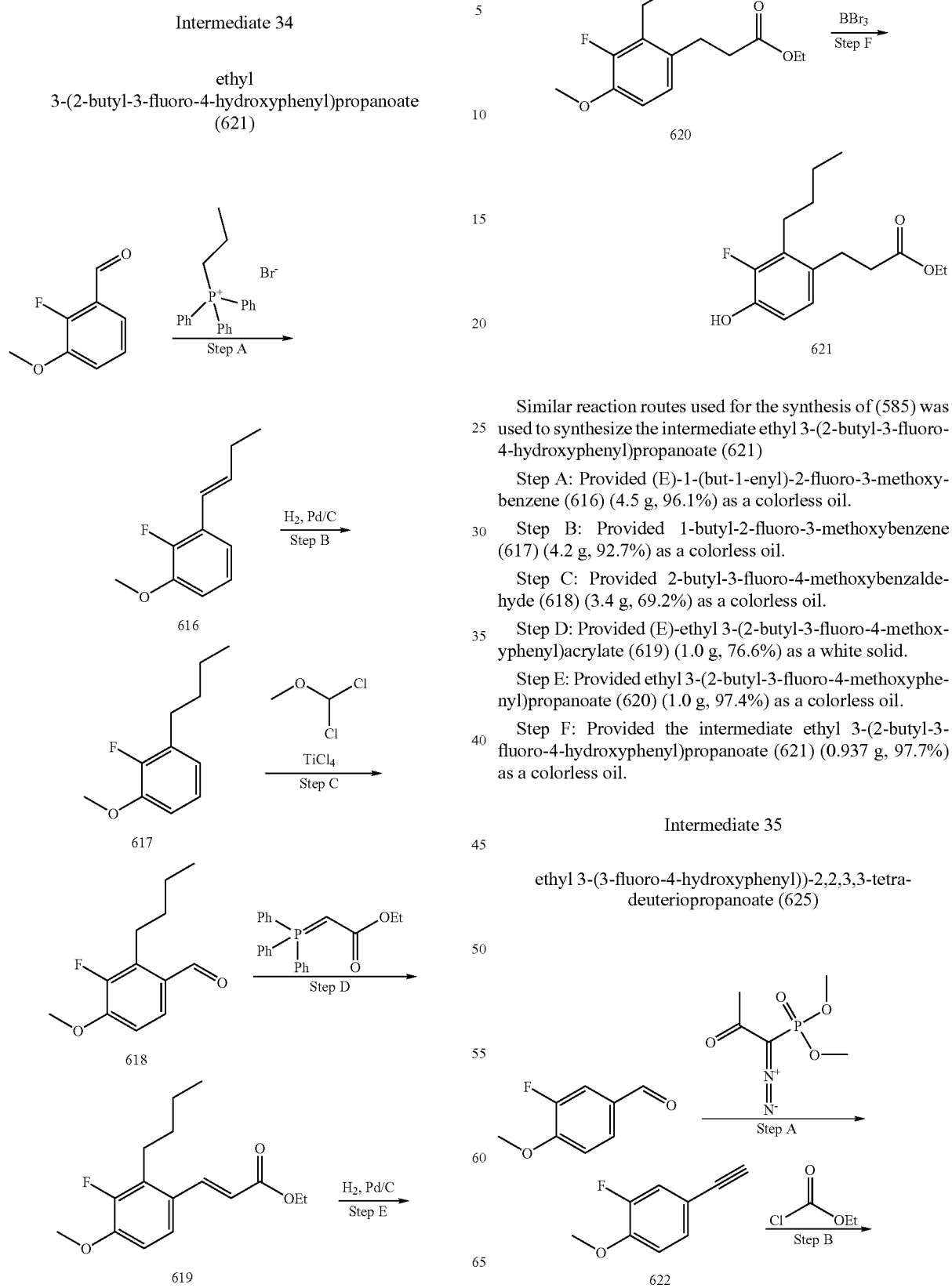

Similar reaction routes used for the synthesis of (585) was used to synthesize the intermediate ethyl 3-(2-butyl-3-fluoro-4-hydroxyphenyl)propanoate (621)

Step A: Provided (E)-1-(but-1-enyl)-2-fluoro-3-methoxybenzene (616) (4.5 g, 96.1%) as a colorless oil.

Step B: Provided 1-butyl-2-fluoro-3-methoxybenzene (617) (4.2 g, 92.7%) as a colorless oil.

Step C: Provided 2-butyl-3-fluoro-4-methoxybenzaldehyde (618) (3.4 g, 69.2%) as a colorless oil.

Step D: Provided (E)-ethyl 3-(2-butyl-3-fluoro-4-methoxyphenyl)acrylate (619) (1.0 g, 76.6%) as a white solid.

Step E: Provided ethyl 3-(2-butyl-3-fluoro-4-methoxyphenyl)propanoate (620) (1.0 g, 97.4%) as a colorless oil.

Step F: Provided the intermediate ethyl 3-(2-butyl-3-fluoro-4-hydroxyphenyl)propanoate (621) (0.937 g, 97.7%) as a colorless oil.

Intermediate 35 ethyl 3-(3-fluoro-4-hydroxyphenyl))-2,2,3,3-tetra-deuteriopropanoate (625)

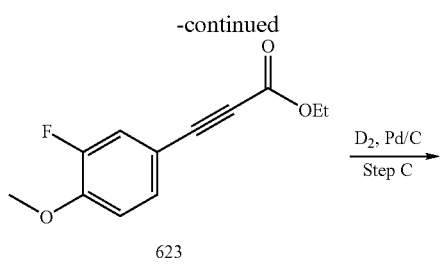

623

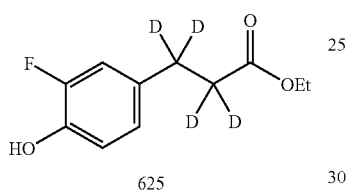

624

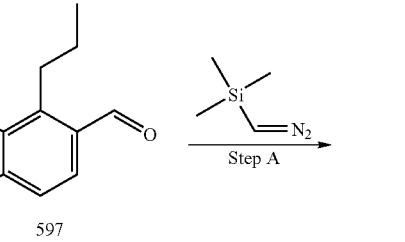

625

Step A: To the mixture of 3-fluoro-4-methoxybenzaldehyde (0.589 g, 3.0 mmol), potassium carbonate (1.8 g, 13.0 mmol) in methanol (65 mL) at room temperature was added slowly dimethyl 1-diazo-2-oxopropylphosphonate (1.4 g, 7.2 mmol). The resulting mixture was stirred at room temperature for 2 hours, quenched with saturated sodium bicarbonate and extracted with ethyl acetate. The organic phase was washed with water, brine, dried over sodium sulfate and concentrated under reduced pressure. The residue was purified by flash chromatography on silica gel (10% EtOAc in hexanes) to provide 4-ethynyl-2-fluoro-1-methoxybenzene (622) (0.750 g, 76.9%) as a colorless oil.

Step B: To the mixture of diisopropylamine (0.262 mL, 1.87 mmol) in tetrahydrofuran (5 mL) at −78° C. under nitrogen was added slowly the solution of n-butyllithium (1.17 mL, 1.87 mmol, 1.6M in hexanes). After stifling for 30 minutes, the solution of 4-ethynyl-2-fluoro-1-methoxybenzene (622) (0.180 g, 0.94 mmol) in tetrahydrofuran (1 mL) was added slowly into the reaction mixture. The mixture was allowed to reach 0° C. over 1 hour and ethyl chloroformate (0.134 mL, 1.4 mmol) was added. The resulting mixture was stirred to room temperature for 12 hours, quenched with saturated ammonium chloride and extracted with ethyl ether. The organic phase was washed with water, brine, dried over sodium sulfate and concentrated under reduced pressure. The residue was purified by flash chromatography on silica gel (5-10% EtOAc in hexanes) to provide ethyl 3-(3-fluoro-4-methoxyphenyl)propiolate (623) (0.070 g, 6.3%) as a colorless oil.

Step C: Similar manner described for the synthesis of (513), (except $D_2$ balloon used), was used to synthesize deuterated ethyl 3-(3-fluoro-4-methoxyphenyl)propanoate (624) (0.050 g, 68.9%) as a colorless oil.

Step D: Similar manner described for the synthesis of (514) was used to synthesize the intermediate deuterated ethyl 3-(3-fluoro-4-hydroxyphenyl)propanoate (625) (0.043 g, 92.1%) as a colorless oil.

Intermediate 36 ethyl 3-(3-fluoro-4-hydroxy-2-propylphenyl))-2,2,3,3-tetradeuteriopropanoate (629)

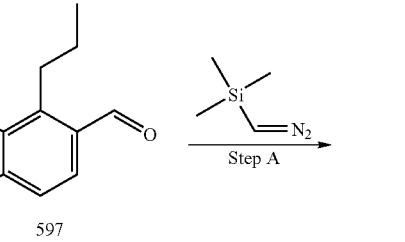

597

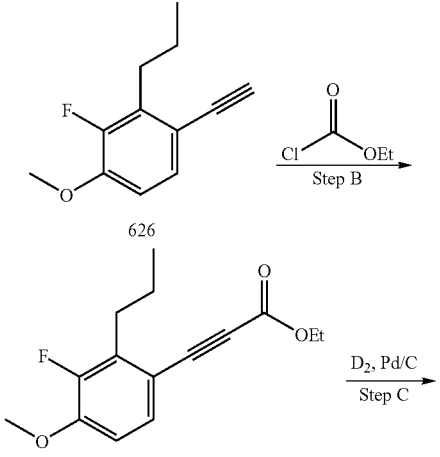

626

627

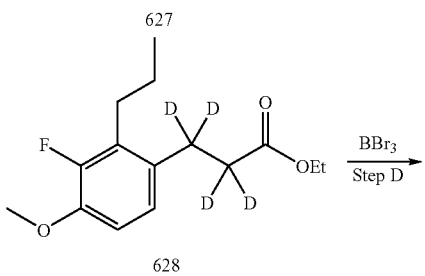

628

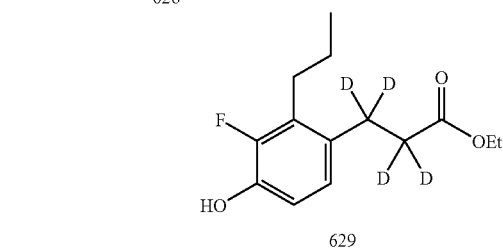

629

Step A: To a solution of diisopropylamine (0.841 mL, 6.0 mmol) in tetrahydrofuran (15 mL) at −78° C. under nitrogen was added slowly the solution of n-butyllithium (3.75 mL, 6.0 mmol, 1.6M in hexanes). After stifling for 30 minutes, the solution of TMS-diazomethane (3.0 mL, 6.0 mmol, 2M in hexanes) was added slowly into the reaction mixture. The mixture was stirred for 30 minutes then was added the solution of 3-fluoro-4-methoxy-2-propylbenzaldehyde (597) (0.589 g, 3.0 mmol) in tetrahydrofuran (3 mL). The resulting mixture was stirred at room temperature for 12 hours, quenched with saturated ammonium chloride and extracted with ethyl ether. The organic phase was washed with water, brine, dried over sodium sulfate and concentrated under reduced pressure. The residue was purified by flash chromatography on silica gel (10% EtOAc in hexanes) to provide 1-ethynyl-3-fluoro-4-methoxy-2-propylbenzene (626) (0.180 g, 31.2%) as a colorless oil.

Step B: Similar manner described for the synthesis of (623) was used to synthesize ethyl 3-(3-fluoro-4-methoxy-2-propylphenyl)propiolate (627) (0.140 g, 56.6%) as a colorless oil.

Step C: Similar manner described for the synthesis of (513), (except $D_2$ balloon was used), was used to synthesize deuterated ethyl 3-(3-fluoro-4-methoxy-2-propylphenyl)propanoate (628) (0.085 g, 58.9%) as a colorless oil.

Step D: Similar manner described for the synthesis of (514) was used to synthesize the intermediate deuterated ethyl 3-(3-fluoro-4-hydroxy-2-propylphenyl)propanoate (629) (0.078 g, 96.6%) as a colorless oil.

Intermediate 37 ethyl 3-(2-ethyl-3-fluoro-4-hydroxyphenyl))-2,2,3,3-tetradeuteriopropanoate (633)

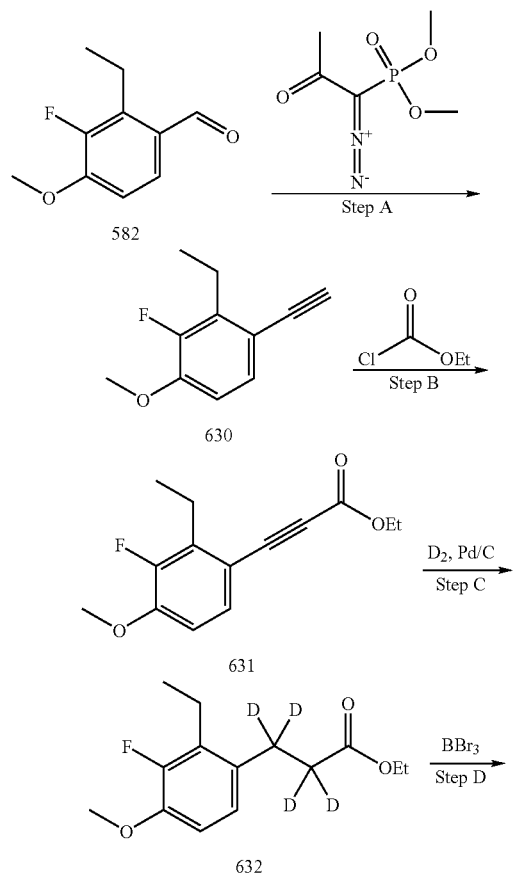

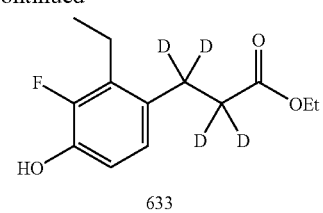

Similar reaction routes used for the synthesis of (625) was used to synthesize the intermediate (633)

Step A: Similar manner described for the synthesis of (622) was used to synthesize 2-ethyl-1-ethynyl-3-fluoro-4-methoxybenzene (630) (0.390 g, 72.9%) as a colorless oil.

Step B: Provided ethyl 3-(2-ethyl-3-fluoro-4-methoxyphenyl)propiolate (631) (0.100 g, 18.3%) as a colorless oil.

Step C: Provided deuterated ethyl 3-(2-ethyl-3-fluoro-4-methoxyphenyl)propanoate (632) (0.080 g, 77.5%) as a colorless oil.

Step D: Provided the intermediate deuterated ethyl 3-(2-ethyl-3-fluoro-4-hydroxyphenyl) propanoate (633) (0.062 g, 82.0%) as a colorless oil.

Intermediate 38 ethyl 3-(3-fluoro-4-hydroxy-2-methylphenyl)propanoate (637)

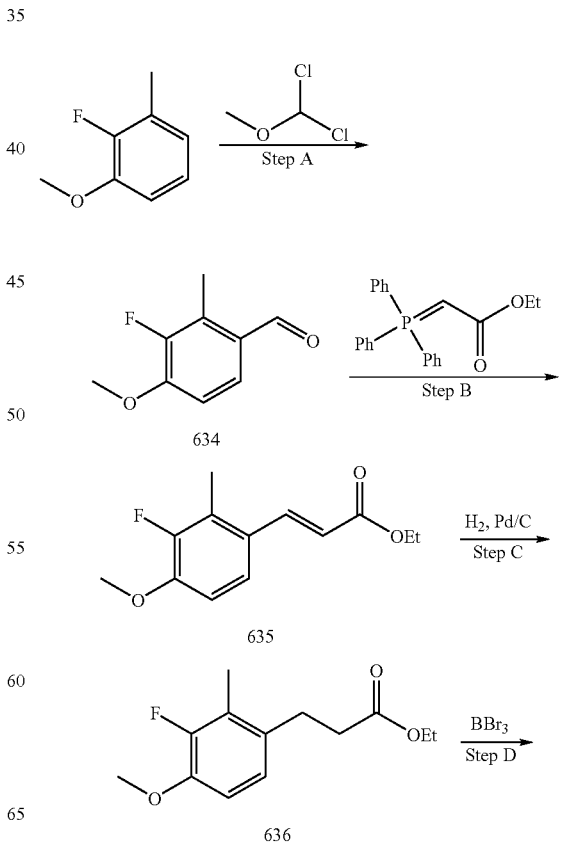

-continued

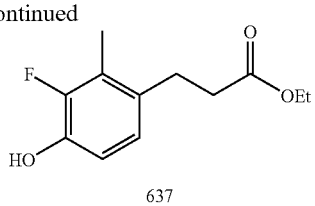

637

Step A: Similar manner described for the synthesis of (545) was used to synthesize 3-fluoro-4-methoxy-2-methylbenzaldehyde (634) (0.910 g, 73.1%) as a white powder.

Step B: Similar manner described for the synthesis of (537) was used to synthesize (E)-ethyl 3-(3-fluoro-4-methoxy-2-methylphenyl)acrylate (635) (1.2 g, 90.8%) as a white powder.

Step C: Similar manner described for the synthesis of (513) was used to synthesize ethyl 3-(3-fluoro-4-methoxy-2-methylphenyl)propanoate (636) (1.2 g, 97.5%) as a colorless oil.

Step D: Similar manner described for the synthesis of (514) was used to synthesize the intermediate ethyl 3-(3-fluoro-4-hydroxy-2-methylphenyl)propanoate (637) (1.0 g, 95.1%) as a colorless oil.

Intermediate 39 ethyl 3-(3-ethyl-4-hydroxyphenyl)propanoate (641)

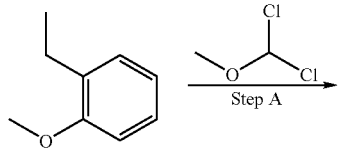

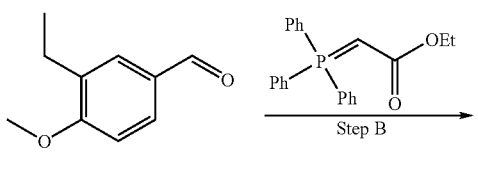

638

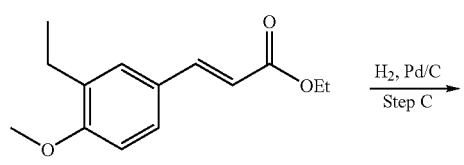

639

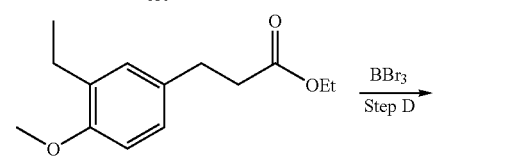

640

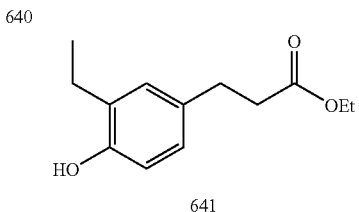

641

Step A: Similar reaction routes used for the synthesis of (545) was used to synthesize 3-ethyl-4-methoxybenzaldehyde (638) (0.690 g, 89.4%) as a yellow oil.

Step B: Similar reaction routes used for the synthesis of (537) was used to synthesize (E)-ethyl 3-(3-ethyl-4-methoxyphenyl)acrylate (639) (0.440 g, 100%) as a colorless oil.

Step C: Similar reaction routes used for the synthesis of (513) was used to synthesize ethyl 3-(3-ethyl-4-methoxyphenyl)propanoate (640) (0.360 g, 91.1%) as a colorless oil.

Step D: Similar reaction routes used for the synthesis of (514) was used to synthesize the intermediate ethyl 3-(3-ethyl-4-hydroxyphenyl)propanoate (641) (0.316 g, 93.6%) as a colorless oil.

Intermediate 40 ethyl 3-(3-ethyl-4-hydroxyphenyl)-2-methylpropanoate (644)

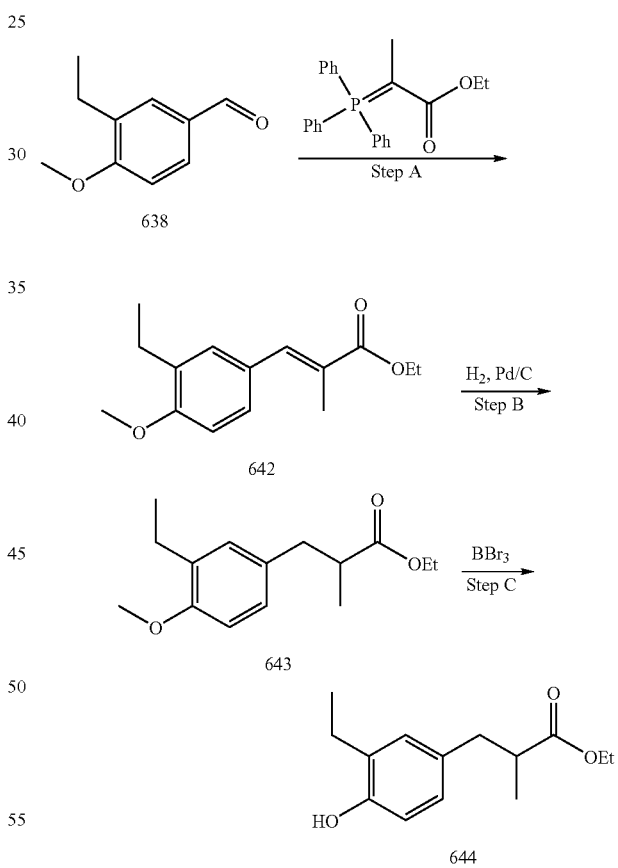

Step A: Similar reaction routes used for the synthesis of (515) was used to synthesize (E)-ethyl 3-(3-ethyl-4-methoxyphenyl)-2-methylacrylate (642) (0.460 g, 99.0%) as a white powder.

Step B: Similar reaction routes used for the synthesis of (513) was used to synthesize ethyl 3-(3-ethyl-4-methoxyphenyl)-2-methylpropanoate (643) (0.400 g, 86.3%) as a colorless oil.

Step C: Similar reaction routes used for the synthesis of (514) was used to synthesize the intermediate ethyl 3-(3-ethyl-4-hydroxyphenyl)-2-methyl propanoate (644) (0.343 g, 90.7%) as a colorless oil.

Intermediate 41 ethyl 3-(4-aminophenyl)-2-methylpropanoate (646)

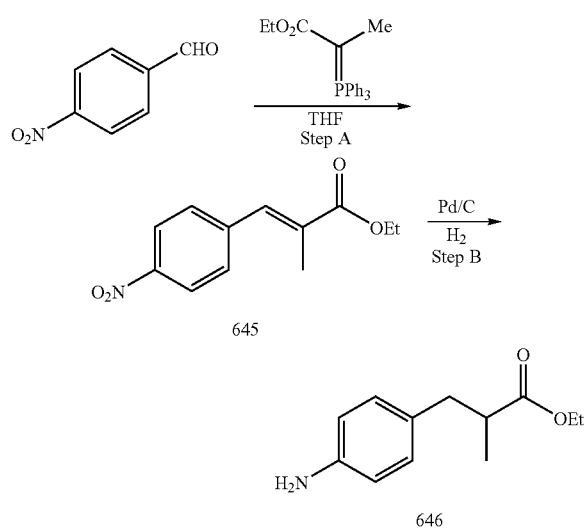

Step A: A solution of 4-nitrobenzaldehyde (2 g, 13.2 mmol) and (1-ethoxy carbonylethylidene)triphenyl phosphorane (4.80 g, 13.2 mmol) in tetrahydrofuran (130 mL) was refluxed for 24 hours. The reaction was concentrated in vacuo and was purified by flash column chromatography on silica gel with hexanes and EtOAc to give (E)-ethyl 2-methyl-3-(4-nitrophenyl)acrylate (645).

Step B: To a solution of (E)-ethyl 2-methyl-3-(4-nitrophenyl)acrylate (645) (2.49 g, 10.6 mmol) in ethanol (100 mL) was added Pd/C (250 mg, 10% Degussa type). A balloon of hydrogen gas was added and the reaction was evacuated and back-filled with hydrogen three times. The reaction was stirred overnight at room temperature, was filtered through a pad of celite and concentrated in vacuo to give ethyl 3-(4-aminophenyl)-2-methylpropanoate (646).

Intermediate 42

4-(2-(5-fluoro-2,2-dimethyl-2,3-dihydrobenzofuran-7-yl)ethyl)phenol (650)

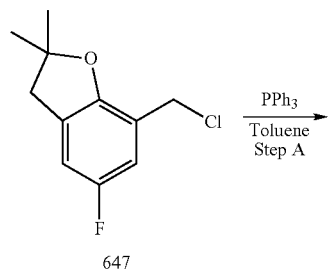

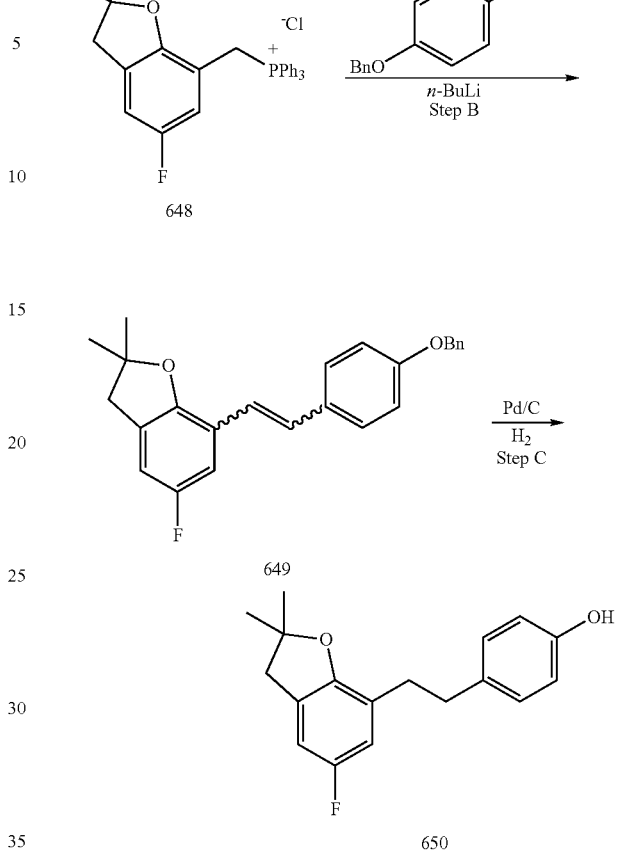

Step A: 7-(chloromethyl)-5-fluoro-2,2-dimethyl-2,3-dihydrobenzofuran (647) (1 g, 4.66 mmol), triphenyl phosphine (1.22 g, 4.66 mmol) and toluene (46 mL) were heated at reflux for 48 hours. The reaction was filtered and the solid was washed with diethyl ether to provide ((5-fluoro-2,2-dimethyl-2,3-dihydrobenzofuran-7-yl)methyl)triphenyl phosphonium chloride (648).

Step B: To a solution of ((5-fluoro-2,2-dimethyl-2,3-dihydrobenzofuran-7-yl)methyl) triphenyl phosphonium chloride (648) (500 mg, 1.09 mmol) in anhydrous tetrahydrofuran at room temperature (10 mL) was added n-butyllithium (0.67 mL, 1.31 mmol, 2 M in hexane). After stirring for 10 min 4-(benzyloxy)benzaldehyde (231 mg, 1.09 mmol) was added and stirred for an additional 3 hours. The reaction was quenched with water and extracted with ethyl acetate. The combined organic phase was dried over sodium sulfate, filtered and concentrated in vacuo. The crude compound was purified by flash column chromatography on silica gel with hexanes and EtOAc (20%) to give 7-(4-(benzyloxy)styryl)-5-fluoro-2,2-dimethyl-2,3-dihydrobenzofuran as a cis/trans mixture (649).

Step C: To a solution 7-(4-(benzyloxy)styryl)-5-fluoro-2,2-dimethyl-2,3-dihydrobenzofuran (649) (207.7 mg, 0.583 mmol) in ethanol (6 mL) was added Pd/C (20 mg, 10% Degussa type). A balloon of hydrogen gas was added and the reaction was evacuated and back-filled with hydrogen three times. The reaction was stirred overnight at room temperature, was filtered through a pad of celite and concentrated in vacuo to give 4-(2-(5-fluoro-2,2-dimethyl-2,3-dihydrobenzofuran-7-yl)ethyl)phenol (650).

Intermediate 43 ethyl 3-(5-hydroxy-[1,1'-biphenyl]-2-yl)propanoate (653)

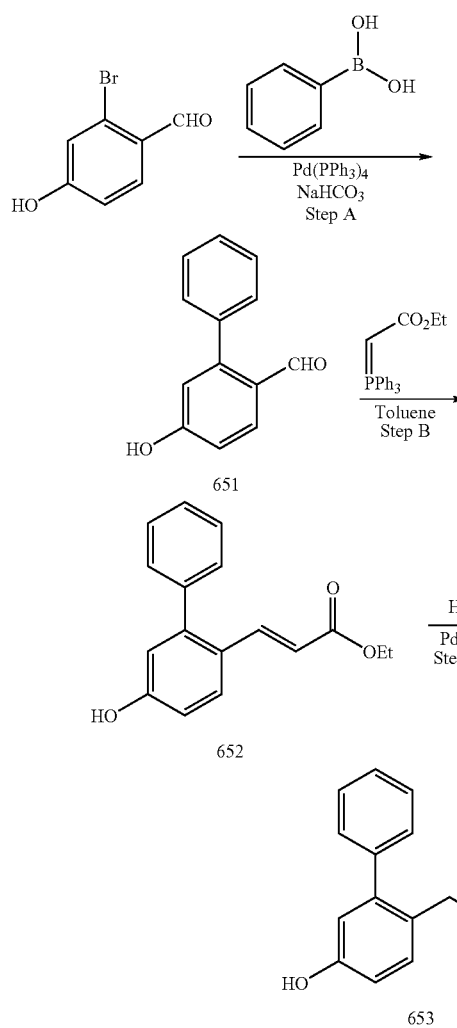

Step A: A mixture of 2-bromo-4-hydroxybenzaldehyde (350 mg, 1.74 mmol), phenyl boronic acid (233.5 mg, 1.92 mmol), Pd(PPh₃)₄ (60 mg, 0.052 mmol), saturated sodium bicarbonate (6.0 mL), methanol (15 mL), and toluene (6.0 mL) was heated in a pressure tube at 120° C. overnight. Ethyl acetate and water were added and the layers separated. The aqueous phase was extracted with ethyl acetate and the combined organic layers were dried over sodium sulfate, filtered and concentrated in vacuo. The crude compound was purified by flash column chromatography on silica gel with hexanes and EtOAc (30%) to afford 5-hydroxy-[1,1'-biphenyl]-2-carbaldehyde (651).

Step B: A solution of 5-hydroxy-[1,1'-biphenyl]-2-carbaldehyde (651) (292 mg, 1.47 mmol) and (carboxymethylene)-triphenylphosphorane (564.5 mg, 1.62 mmol) in toluene (15 mL) was refluxed for 24 hours. The reaction was concentrated in vacuo and was purified by flash column chromatography on silica gel with hexanes and EtOAc (30%) to give (E)-ethyl 3-(5-hydroxy-[1,1'-biphenyl]-2-yl)acrylate (652).

Step C: To a solution (E)-ethyl 3-(5-hydroxy-[1,1'-biphenyl]-2-yl)acrylate (652) (420 mg, 1.57 mmol) in ethanol (6 mL) was added Pd/C (42 mg, 10% Degussa type). A balloon of hydrogen gas was added and the reaction was evacuated and back-filled with hydrogen three times. The reaction was stirred overnight at room temperature, was filtered through a pad of celite and concentrated in vacuo to give ethyl 3-(5-hydroxy-[1,1'-biphenyl]-2-yl)propanoate (653).

Intermediate 44

5-chloro-7-(chloromethyl)-2,2-dimethylbenzofuran-3(2H)-one (657)

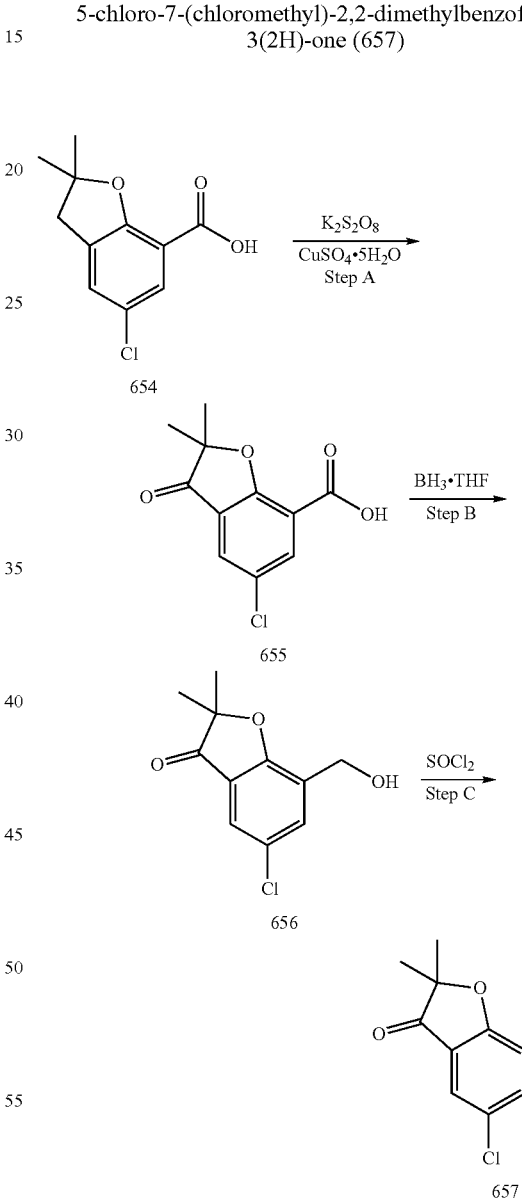

Step A: A solution of 5-chloro-2,2-dimethyl-2,3-dihydrobenzofuran-7-carboxylic acid (654) (2.39 g, 10.5 mmol), potassium persulfate (8.55 g, 31.6 mmol), cupric sulfate pentahydrate (2.62 g, 10.5 mmol) and acetonitrile/water (1:1) (90 mL) were heated at reflux for 1 hour. Ethyl acetate and water were added and the layers separated. The aqueous phase was extracted with ethyl acetate and the combined organic layers were dried over sodium sulfate, filtered and concentrated in vacuo to provide 5-chloro-2,2-dimethyl-3-oxo-2,3-dihydrobenzofuran-7-carboxylic acid (655) as a yellow solid.

Step B: To a solution of 5-chloro-2,2-dimethyl-3-oxo-2,3-dihydrobenzofuran-7-carboxylic acid (655) (2.67 g, 11.1 mmol) in tetrahydrofuran (56 mL) was added BH₃.tetrahydrofuran (11.1 mL, 11.1 mmol) drop wise and stirred overnight. The reaction was quenched with water and methanol and then extracted with ethyl acetate. The organic layer was washed with saturated sodium bicarbonate and then dried over sodium sulfate, filtered and concentrated in vacuo. The crude compound was purified by flash column chromatography on silica gel with hexanes and EtOAc (50%) to afford 5-chloro-7-(hydroxymethyl)-2,2-dimethylbenzofuran-3(2H)-one (656) (278 mg). The saturated sodium bicarbonate layer was acidified to recover the starting acid (655) (1.68 g).

Step C: A solution of 5-chloro-7-(hydroxymethyl)-2,2-dimethylbenzofuran-3(2H)-one (656) (278 mg, 1.23 mmol) in neat thionyl chloride (5 mL) was stirred at room temperature for 48 hours. The reaction was concentrated to obtain 5-chloro-7-(chloromethyl)-2,2-dimethylbenzofuran-3(2H)-one (657) as a brown/grey solid.

Intermediate 45

7-(bromomethyl)-5-fluoro-2,2-dimethylbenzofuran-3(2H)-one (660)

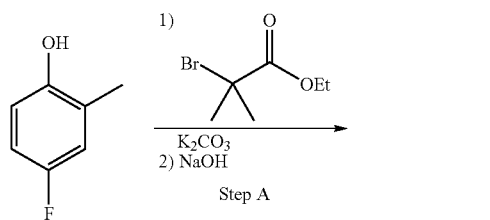

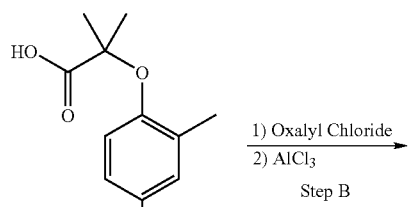

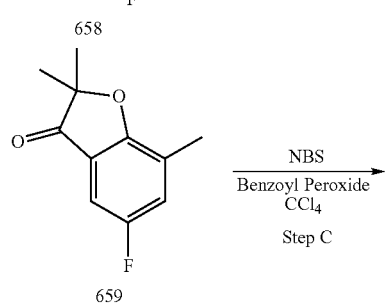

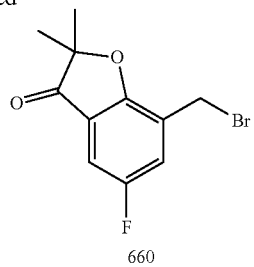

Step A: A solution of 4-fluoro-2-methylphenol (10 g, 79.28 mmol), ethyl 2-bromoisobutyrate (23.2 mL, 158.6 mmol), potassium carbonate (21.9 g, 158.6 mmol), and DMSO (80 mL) was stirred at room temperature for 72 hours. Water and ethyl acetate were added and the layers were separated. The aqueous phase was extracted with ethyl acetate (3×50 mL) and the combined organic layers were washed with brine, dried over sodium sulfate, filtered and concentrated in vacuo. The crude compound was purified by flash column chromatography on silica gel with hexanes and EtOAc (20%) to afford ethyl 2-(4-fluoro-2-methylphenoxy)-2-methylpropanoate. To a solution of ethyl 2-(4-fluoro-2-methylphenoxy)-2-methylpropanoate (13.3 g, 55.44 mmol) in tetrahydrofuran (40 mL) and methanol (10 mL) was added NaOH (6.66 g, 166.32 mmol) in water (14 mL) and stirred overnight. The volatiles were removed in vacuo and acidified with concentrated HCl. The milky white solution was extracted with ethyl acetate, dried over sodium sulfate, filtered and concentrated in vacuo to give 2-(4-fluoro-2-methylphenoxy)-2-methylpropanoic acid (658) as a yellow solid.

Step B: To a solution of 2-(4-fluoro-2-methylphenoxy)-2-methylpropanoic acid (658) (5 g, 23.6 mmol) in tetrahydrofuran (50 mL) at 0° C. was added cat. DMF and oxayl chloride (2.5 mL, 28.3 mmol). The reaction was warmed to room temperature, stirred for 1 hour, and concentrated in vacuo. The oil was dissolved in dichloromethane (50 mL), cooled to −78° C. and AlCl₃ (7.6 g, 56.6 mmol) was added. The reaction was allowed to warm to room temperature overnight. Ice water was added and the dichloromethane was removed in vacuo. The aqueous phase was extracted with ethyl acetate (3×50 mL) and washed with saturated sodium bicarbonate dried over sodium sulfate, filtered and concentrated in vacuo. The crude compound was purified by flash column chromatography on silica gel with hexanes and EtOAc (20%) to provide 5-fluoro-2,2,7-trimethylbenzofuran-3(2H)-one (659).

Step C: A solution of provide 5-fluoro-2,2,7-trimethylbenzofuran-3(2H)-one (659) (100 mg, 0.515 mmol), N-Bromosuccinimide (100.8 mg, 0.567 mmol), benzoyl chloride (1.2 mg, 0.005 mmol) and carbon tetrachloride (2 mL) was heated at reflux overnight. Saturated sodium bicarbonate was added and extracted with ethyl acetate, dried over sodium sulfate, filtered and concentrated in vacuo. The crude compound was purified by flash column chromatography on silica gel with hexanes and EtOAc (5%) to give 7-(bromomethyl)-5-fluoro-2,2-dimethylbenzofuran-3(2H)-one (660).

Intermediate 46 ethyl 3-(5-fluoro-4-hydroxy-2-propylphenyl)propanoate (666)

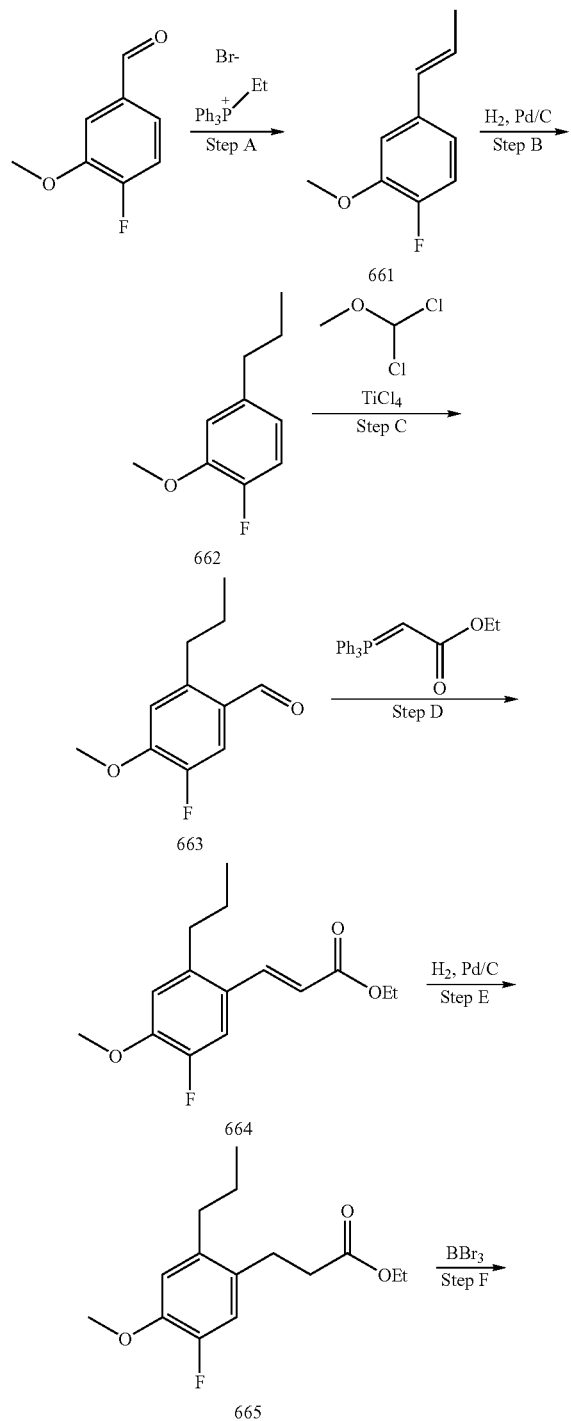

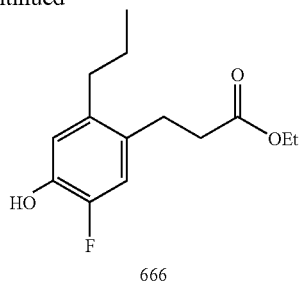

Step A-F: Compound (666) was prepared in a similar manner as that described for the synthesis of (585).

Intermediate 47

5-bromo-7-(chloromethyl)-2,2-dimethyl-2,3-dihydrobenzofuran (670)

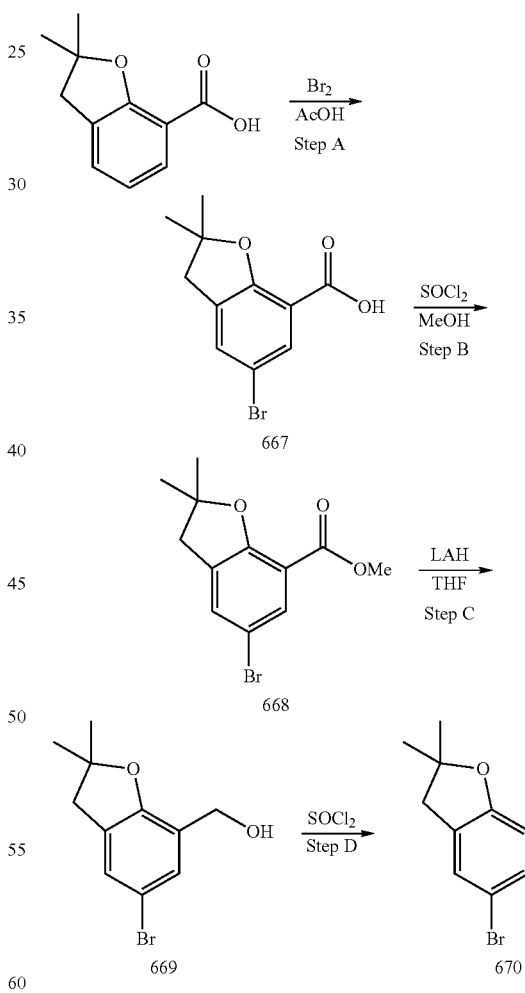

Step A: Using a dropping funnel, bromine (0.8 mL, 15.6 mmol) in acetic acid (6 mL) was added to a solution of 2,2-dimethyl-2,3-dihydrobenzofuran-7-carboxylic acid (1 g, 5.20 mmol) in acetic acid at 0° C. The reaction was allowed to warm to room temperature and stirred overnight. A 2M solution of sodium sulfite was added until all of the red color disappeared. The volatiles were removed in vacuo and dichloromethane was added and the layers separated. The organic phase was washed with water and brine, dried over sodium sulfate, filtered and concentrated in vacuo to yield 5-bromo-2,2-dimethyl-2,3-dihydrobenzofuran-7-carboxylic acid (667).

Step B: Thionyl chloride (0.6 mL, 8.12 mmol) was added slowly to a solution of 5-bromo-2,2-dimethyl-2,3-dihydrobenzofuran-7-carboxylic acid (667) (1.1 g, 4.06 mmol) in methanol (41 mL). After refluxing for 3 hours the solvent was removed in vacuo to obtain methyl 5-bromo-2,2-dimethyl-2,3-dihydrobenzofuran-7-carboxylate (668).

Step C: To a solution of methyl 5-bromo-2,2-dimethyl-2,3-dihydrobenzofuran-7-carboxylate (668) (466 mg, 1.63 mmol) in tetrahydrofuran (16 mL) at 0° C. was added LAH (1 mL, 1.96 mmol). The reaction was stirred at 0° C. for 1 hour and quenched with 0.2 mL of water, 0.2 mL of 15% NaOH and 0.6 mL of water. The reaction was warmed to room temperature and diluted with diethyl ether. Magnesium sulfate was added and the solution was filtered, washed with diethyl ether, and the solvent removed in vacuo to provide (5-bromo-2,2-dimethyl-2,3-dihydrobenzofuran-7-yl)methanol (669).

Step D: To a solution of (5-bromo-2,2-dimethyl-2,3-dihydrobenzofuran-7-yl)methanol (669) (390 mg, 1.51 mmol) in dichloromethane (15 mL) was added thionyl chloride (0.56 mL, 7.58 mmol). The reaction was stirred at room temperature for 2 hours and then concentrated to afford 5-bromo-7-(chloromethyl)-2,2-dimethyl-2,3-dihydrobenzofuran (670).

Intermediate 48 ethyl 3-(3-((dimethylamino)methyl)-4-hydroxyphenyl)-2-methylpropanoate (673)

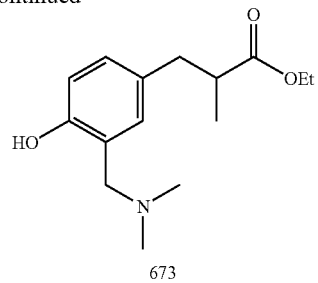

Step A: Compound (671) was prepared in a similar manner as that described for the synthesis of (515)

Step B: Compound (672) was prepared in a similar manner as that described for the synthesis of (513)

Step C: To a solution of ethyl 3-(4-hydroxyphenyl)-2-methylpropanoate (672) (150 mg, 0.72 mmol), potassium carbonate (149.3 mg, 1.08 mmol) in toluene (7 mL) was added N,N-dimethylmethylideneammonium iodide (173.2 mg, 0.94 mmol) and stirred for 72 hours. Water was added and the reaction was extracted with ethyl acetate and the combined organic layers dried over sodium sulfate, filtered and concentrated in vacuo. The crude compound was purified by flash column chromatography on silica gel with hexanes and EtOAc (50%) to give ethyl 3-(3-((dimethylamino)methyl)-4-hydroxyphenyl)-2-methylpropanoate (673).

Intermediate 49

(2,2-dimethyl-5-(1H-tetrazol-1-yl)-2,3-dihydrobenzofuran-7-yl)methanol (678)

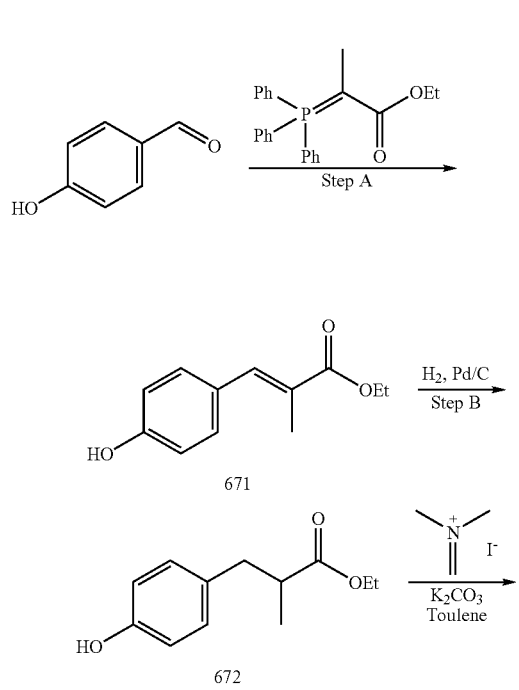

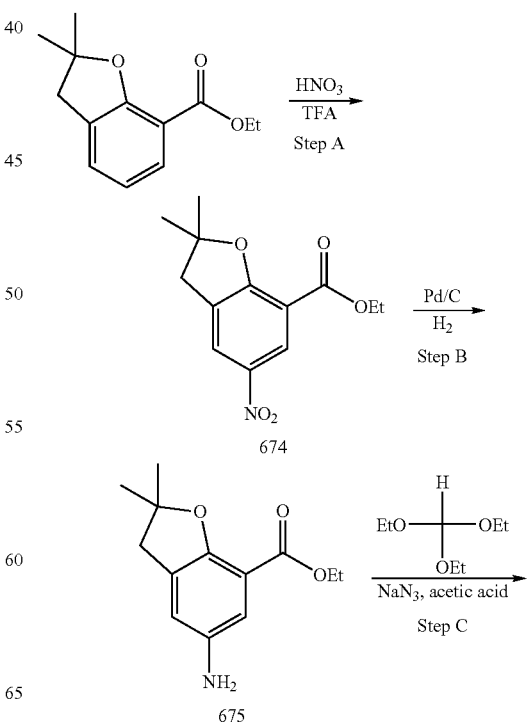

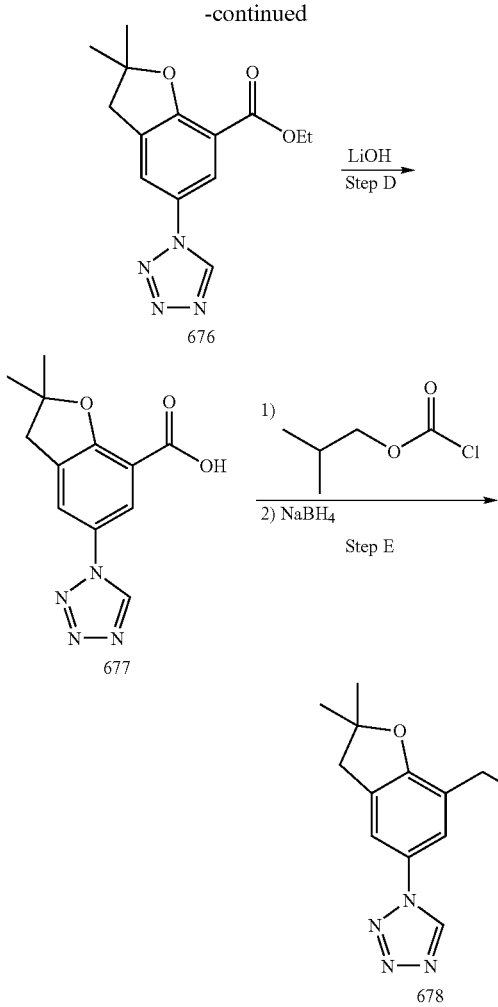

The crude compound was purified by flash column chromatography on silica gel with hexanes and EtOAc (50%) to afford ethyl 2,2-dimethyl-5-(1H-tetrazol-1-yl)-2,3-dihydrobenzofuran-7-carboxylate (676) (184 mg, 50%).

Step D: A solution of ethyl 2,2-dimethyl-5-(1H-tetrazol-1-yl)-2,3-dihydrobenzofuran-7-carboxylate (676) (182 mg, 0.631 mmol), lithium hydroxide (106 mg, 2.53 mmol), methanol (1 mL), tetrahydrofuran (1 mL), and water (4 mL) was heated at 50° C. for 1 hour. The volatiles were removed in vacuo and 2N HCl was added. The white solid was collected by filtration washing with water to provide 2,2-dimethyl-5-(1H-tetrazol-1-yl)-2,3-dihydrobenzofuran-7-carboxylic acid (677) (136 mg, 83%).

Step E: A solution of 2,2-dimethyl-5-(1H-tetrazol-1-yl)-2,3-dihydrobenzofuran-7-carboxylic acid (677) (135 mg, 0.519 mmol), N-methylmorpholine (57 μL, 0.519 mmol), and tetrahydrofuran (10 mL) at 0° C. was added isobutylchloroformate (68 μL, 0.519 mmol) and stirred for 2 hours. Sodium borohydride (58.9 mg, 1.56 mmol) in water (3 mL) was added and stirred for 1 hour and at room temperature for an additional 1 hour. The reaction was concentrated in vacuo and water was added. The aqueous phase was extracted with ethyl acetate and the combined organic layers dried over sodium sulfate, filtered and concentrated in vacuo. The crude compound was purified by flash column chromatography on silica gel with hexanes and EtOAc (60%) to afford (2,2-dimethyl-5-(1H-tetrazol-1-yl)-2,3-dihydrobenzofuran-7-yl)methanol (678) (77.8 mg, 61%).

Intermediate 50

Ethyl 3-(3,5-difluoro-4-hydroxyphenyl)-2-ethoxypropanoate (681)

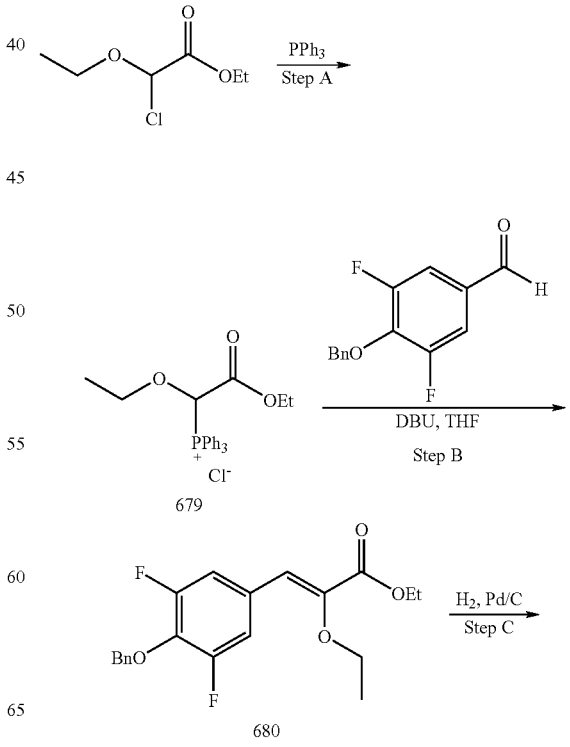

Step A: To a solution of ethyl 2,2-dimethyl-2,3-dihydrobenzofuran-7-carboxylate (1 g, 4.54 mmol) in trifluoroacetic acid (7 mL) at 0° C. was slowly added nitric acid (1.36 mL). The reaction was stirred at 0° C. for one hour and then at room temperature for 30 minutes. The reaction was added to ice and the resultant solid was collected by filtration, and washed with water to provide ethyl 2,2-dimethyl-5-nitro-2,3-dihydrobenzofuran-7-carboxylate (674) as a yellow solid (1.02 g, 83%).

Step B: To a solution ethyl 2,2-dimethyl-5-nitro-2,3-dihydrobenzofuran-7-carboxylate (674) (1.02 g, 3.84 mmol) in ethanol (40 mL) was added Pd/C (100 mg, 10% Degussa type). A balloon of hydrogen gas was added and the reaction was evacuated and back-filled with hydrogen three times. The reaction was stirred overnight at room temperature, filtered through a pad of celite and concentrated in vacuo to give ethyl 5-amino-2,2-dimethyl-2,3-dihydrobenzofuran-7-carboxylate (675) (899 mg, 99%)

Step C: A solution of ethyl 5-amino-2,2-dimethyl-2,3-dihydrobenzofuran-7-carboxylate (675) (300 mg, 1.28 mmol), triethyl orthoformate (0.42 mL, 2.55 mmol), sodium azide (124.8 mg, 1.92 mmol), and acetic acid (12 mL) was heated at 100° C. for 2 hours. The reaction was cooled to room temperature and water was added. The aqueous phase was extracted with ethyl acetate and the combined organic layers dried over sodium sulfate, filtered and concentrated in vacuo.

-continued

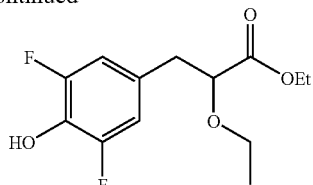

Step A: To a solution of 2-chloro-2-ethoxyacetic acid ethyl ester (10 g, 60 mmol) in chloroform (30 mL) was added triphenylphosphine (15.7 g, 60 mmol) and stirred overnight at room temperature. The solvent was removed in vacuo, and diethyl ether was added. The solvent was again removed and dried on high vacuum to give (1,2-diethoxy-2-oxoethyl)triphenylphosphonium chloride (21 g, 82% yield) (679) as a foamy solid.

Step B: To a solution of (1,2-diethoxy-2-oxoethyl)triphenylphosphonium chloride (679) (1.61 g, 3.76 mmol) in tetrahydrofuran (56 mL) was added DBU (0.67 ml, 4.51 mmol) and the reaction was stirred for 10 minutes at room temperature. 4-(benzyloxy)-3,5-difluorobenzaldehyde (1.40 g, 5.64 mmol) was added in one portion and the reaction was stirred at room temperature for 18 hours. The solvent was removed in vacuo, diethyl ether was added and the solids filtered. The filtrate was concentrated in vacuo and the residue oil was purified by flash column chromatography (0-30% EtOAc in hexanes) to provide (Z)-ethyl 3-(4-(benzyloxy)-3,5-difluorophenyl)-2-ethoxyacrylate (680).

Step C: To a solution (Z)-ethyl 3-(4-(benzyloxy)-3,5-difluorophenyl)-2-ethoxyacrylate (680) (1.3 g, 3.59 mmol) in ethanol (25 mL) was added Pd/C (140 mg, 10% Degussa type). A balloon of hydrogen gas was added and the reaction was evacuated and back-filled with hydrogen three times. The reaction was stirred overnight at room temperature, was filtered through a pad of celite and concentrated in vacuo to give ethyl 3-(3,5-difluoro-4-hydroxyphenyl)-2-ethoxypropanoate (0.81 g) (681).

Intermediate 51 ethyl 2-(4-hydroxy-3-methylphenoxy)acetate (682)

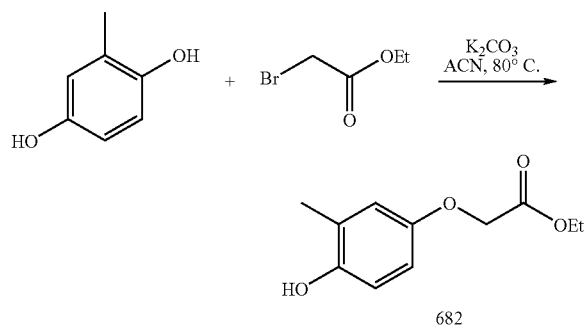

A mixture of 2-methylbenzene-1,4-diol (5 g, 40.2 mmol), ethyl 2-bromoacetate (1.1 eq.), and potassium carbonate (2 eq.) in acetonitrile (50 mL) was heated at 80° C. for 18 hours. The reaction was cooled to room temperature, and the acetonitrile was removed in vacuo. Water was added and the crude residue was extracted with ethyl acetate. The organic layer was washed with brine, dried over sodium sulfate, filtered and concentrated in vacuo. The residue was purified by silica gel chromatography (0-100% EtOAc in hexanes) to provide ethyl 2-(4-hydroxy-3-methylphenoxy)acetate (682) as a pink solid.

Intermediate 52 ethyl 2-(4-hydroxy-2-methylphenoxy)acetate (685)

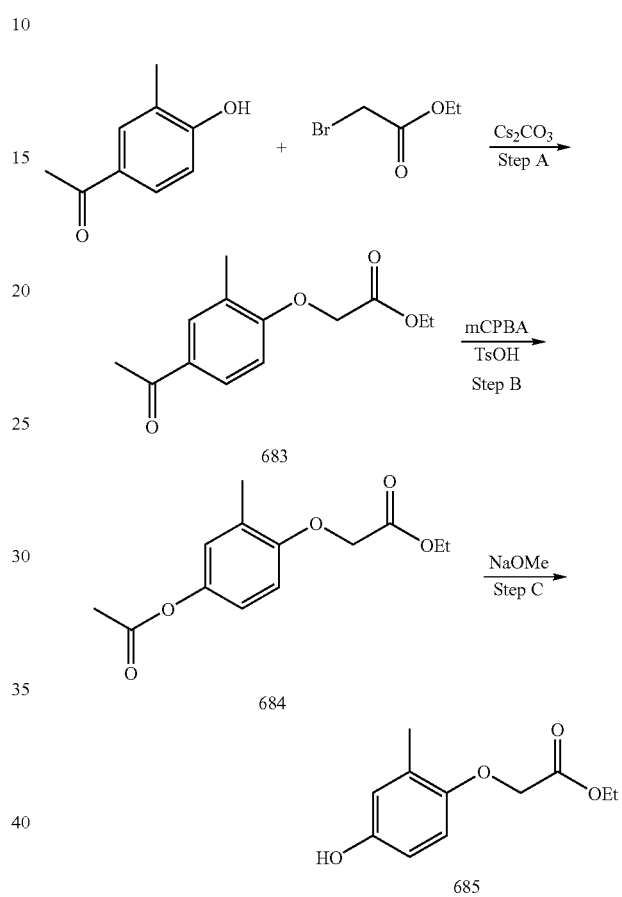

Step A: A mixture of 1-(4-hydroxy-3-methylphenyl)ethanone (5 g, 33.3 mmol), ethyl 2-bromoacetate (1.1 eq.), and cesium carbonate (2 eq.) in acetonitrile (200 mL) was stirred at room temperature overnight. The acetonitrile was removed in vacuo, and the crude oil was dissolved in ethyl acetate (50 mL) and washed with 1M HCl (2×50 mL), water (2×50 mL), and brine (50 mL). The organic layer was dried over sodium sulfate, filtered and concentrated in vacuo to obtain ethyl 2-(4-acetyl-2-methylphenoxy)acetate (683).

Step B: A solution of ethyl 2-(4-acetyl-2-methylphenoxy)acetate (683) (8.78 g, 37 mmol), mCPBA (2.eq.), and p-TsOH monohydrate (0.15 eq.) in dichloromethane (160 mL) was heated at 40° C. overnight. The reaction was cooled to room temperature and washed with 1M KI (2×200 mL), 5% NaHSO$_3$ (2×150 mL), and water (200 mL). The organic layer was dried over sodium sulfate, filtered and concentrated in vacuo. The crude material was purified by silica gel chromatography (0-100% EtOAc in hexanes) to provide ethyl 2-(4-acetoxy-2-methylphenoxy)acetate (684) (72%).

Step C: To a solution of ethyl 2-(4-acetoxy-2-methylphenoxy)acetate (684) (6.79 g, 27 mmol) in dry methanol (150 mL) was added sodium methoxide (1.1 eq.) and the reaction was stirred at room temperature under N$_2$ for 3 hours. The reaction was quenched with 1M HCl and the volatiles were removed in vacuo. The oil was dissolved in ethyl acetate (100 mL) and washed with water (2×100 mL), and brine (100 mL). The organic layer was dried over sodium sulfate, filtered and concentrated in vacuo to afforded ethyl 2-(4-hydroxy-2-methylphenoxy)acetate (685) as a white solid (77%).

Intermediate 53 ethyl 2-(4-hydroxyphenoxy)acetate (688)

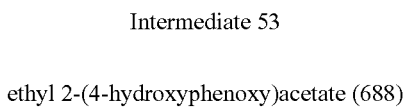

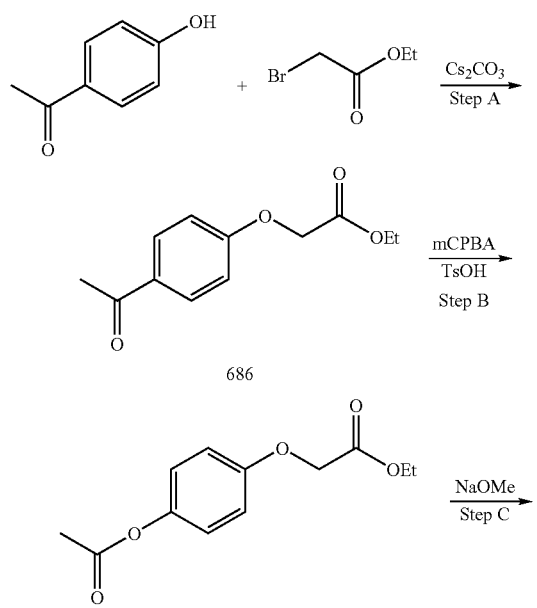

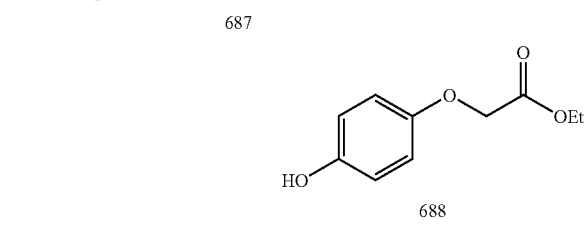

Step A-C: Compound (688) was prepared in a similar manner as that described for the synthesis of (685).

Intermediate 54

5-chloro-7-(chloromethyl)-2,3,3-trimethyl-2,3-dihydrobenzofuran (693)

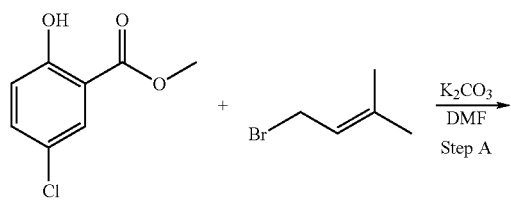

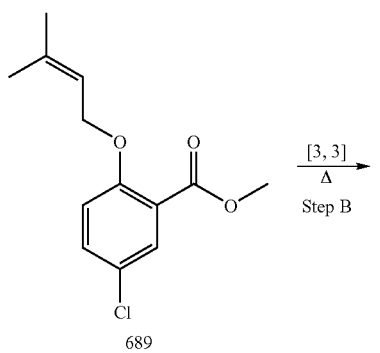

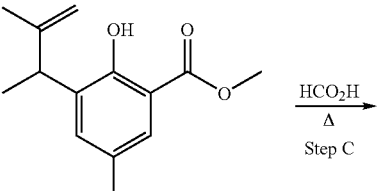

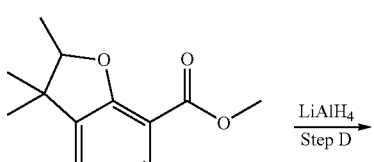

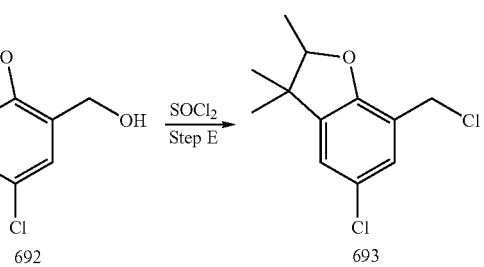

Step A-E: Compound (693) was prepared in a similar manner as that described for the synthesis of (5).

Intermediate 55 methyl 3-(4-hydroxyphenyl)-4-methylpentanoate (695)

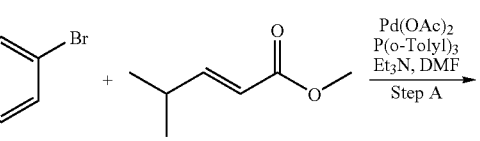

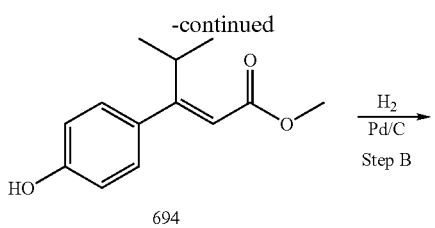

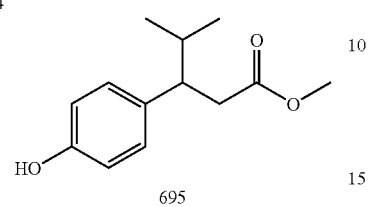

Step A-B: Compound (695) was prepared in a similar manner as that described for the synthesis of (11).

Intermediate 56 methyl 5-hydroxy-2,3-dihydro-1H-indene-2-carboxylate (697)

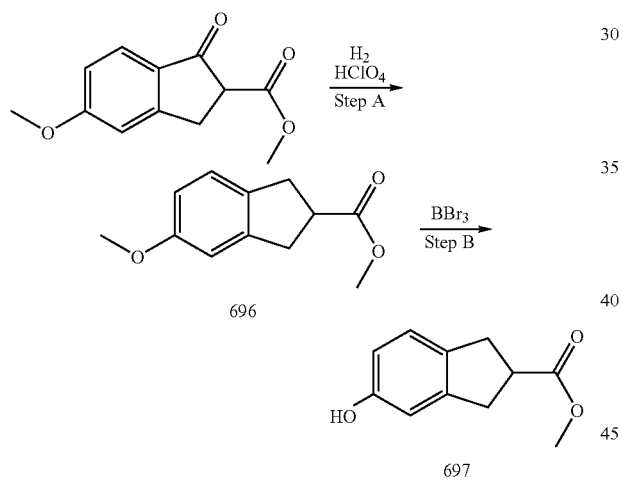

Step A: A mixture of methyl 5-methoxy-1-oxo-2,3-dihydro-1H-indene-2-carboxylate (5.5 g, 25 mmol) in acetic acid (0.64 M) and perchloric acid (14.9 M) was suspended in a pressure vessel and was shook under a hydrogen atmosphere (30 psi) for 4 hours. The mixture was filtered through a pad of celite and washed with chloroform. The organic phase was washed with water (5×) until the pH was neutral, followed with a wash with brine. The organic layer was dried over sodium sulfate, filtered and concentrated in vacuo. The crude material was purified by silica gel chromatography (0-100% EtOAc in hexanes) to provide methyl 5-methoxy-2,3-dihydro-1h-indene-2-carboxylate (696) (46%).

Step B: To a solution of methyl 5-methoxy-2,3-dihydro-1h-indene-2-carboxylate (696) (2.35 g, 11.4 mmol) in anhydrous dichloromethane (40 mL) cooled to −78° C. was added boron tribromide (1.5 eq.). The reaction was allowed to stir at −78° C. for 30 minutes, 0° C. for 2 hours, and at room temperature overnight. The reaction mixture was cooled to 0° C. and quenched slowly with methanol. After stifling for 15 minutes a saturated sodium bicarbonate solution was added slowly to the mixture and allowed to stir at 0° C. for 30 minutes. Ethyl acetate was added and the layers were separated. The aqueous layer was extracted with ethyl acetate and the combined organic layers were dried over sodium sulfate, filtered and concentrated in vacuo to afford methyl 5-hydroxy-2,3-dihydro-1H-indene-2-carboxylate (697).

Intermediate 57 ethyl 3-(4-hydroxy-2-isopropoxyphenyl)propanoate (700)

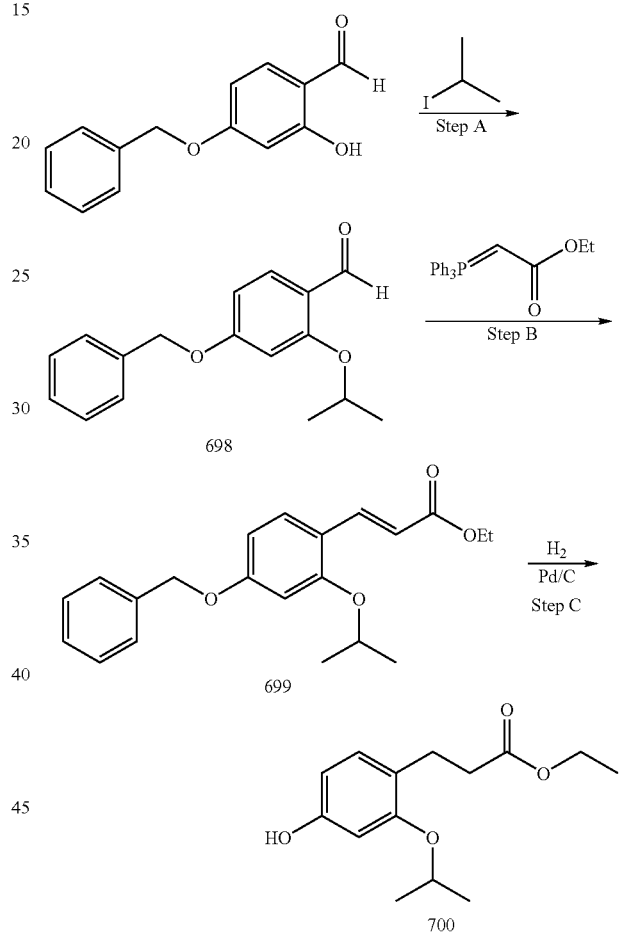

Step A: A mixture of 4-(benzyloxy)-2-hydroxybenzaldehyde (1 g, 4.38 mol), 2-iodopropane (1.2 eq.) and potassium carbonate (2.5 eq.) in acetone (40 mL) was refluxed overnight. The reaction was cooled to room temperature and filtered through a celite plug, and concentrated to dryness. The crude material was purified by flash column chromatography with ethyl acetate and hexanes to provide 4-(benzyloxy)-2-isopropoxybenzaldehyde (698).

Step B: A solution of 4-(benzyloxy)-2-isopropoxybenzaldehyde (698) (480 mg, 1.776 mmol) and (carbethoxymethylene)triphenylphosphorane (1.1 eq.) in toluene was heated at 100° C. overnight. The reaction was cooled to room temperature and concentrated in vacuo. The crude material was purified by silica gel chromatography (0-50% EtOAc in hexanes) to afford (E)-ethyl 3-(4-(benzyloxy)-2-isopropoxyphenyl)acrylate (699)

Step C: To (E)-ethyl 3-(4-(benzyloxy)-2-isopropoxyphenyl)acrylate (699) (530 mg, 1.56 mmol) in ethanol (12 mL) was added Pd/C (0.5 eq, 10% Degussa type). A balloon of hydrogen gas was added and the reaction was evacuated and back-filled with hydrogen three times. The reaction was stirred overnight at room temperature, filtered through a pad of celite and concentrated in vacuo to give ethyl 3-(4-hydroxy-2 isopropoxyphenyl)propanoate (700).

Intermediate 58

5-chloro-7-(chloromethyl)-2-methylbenzofuran (705)

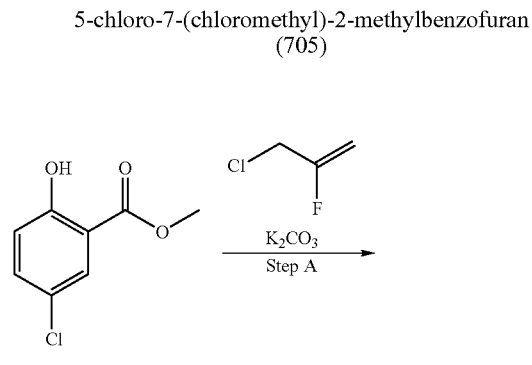

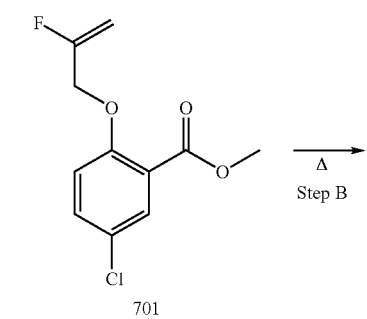

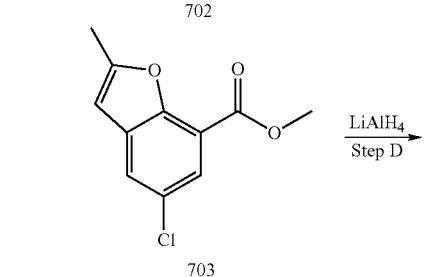

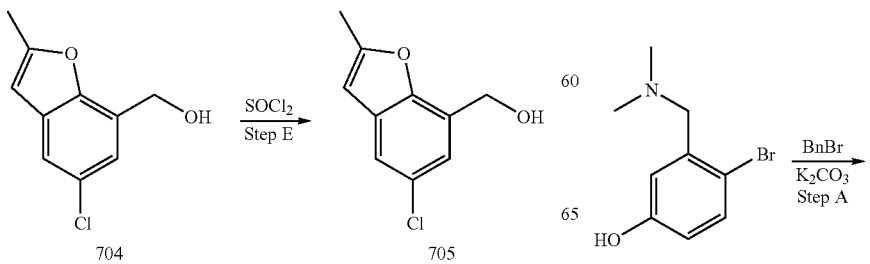

Step A-E: Compound (705) was prepared in a similar manner as that described for the synthesis of (5).

Intermediate 59 ethyl 3-(4-hydroxynaphthalen-1-yl)propanoate (708)

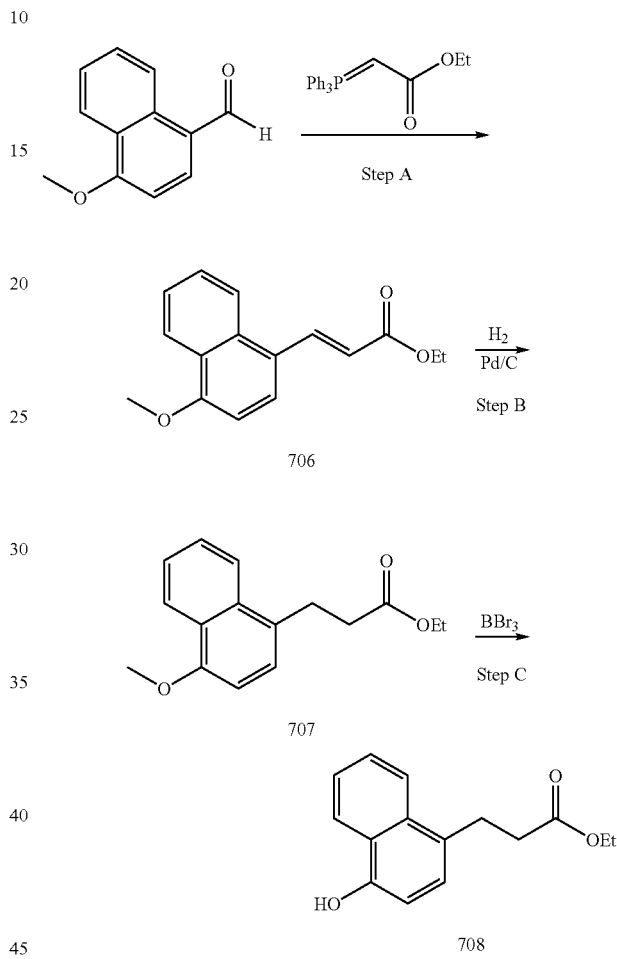

Step A-C: Compound (708) was prepared in a similar manner as that described for the synthesis of (542).

Intermediate 60 ethyl 3-(2-((dimethylamino)methyl)-4-hydroxyphenyl)propanoate (711)

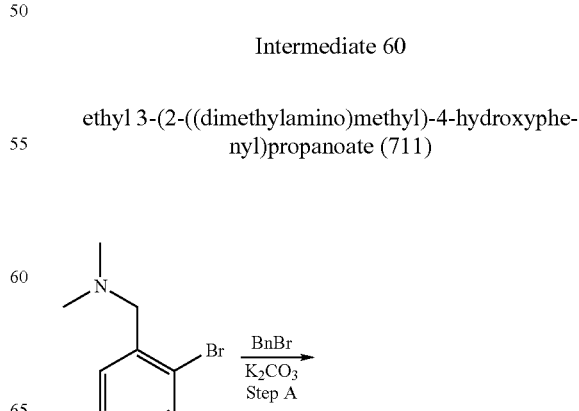

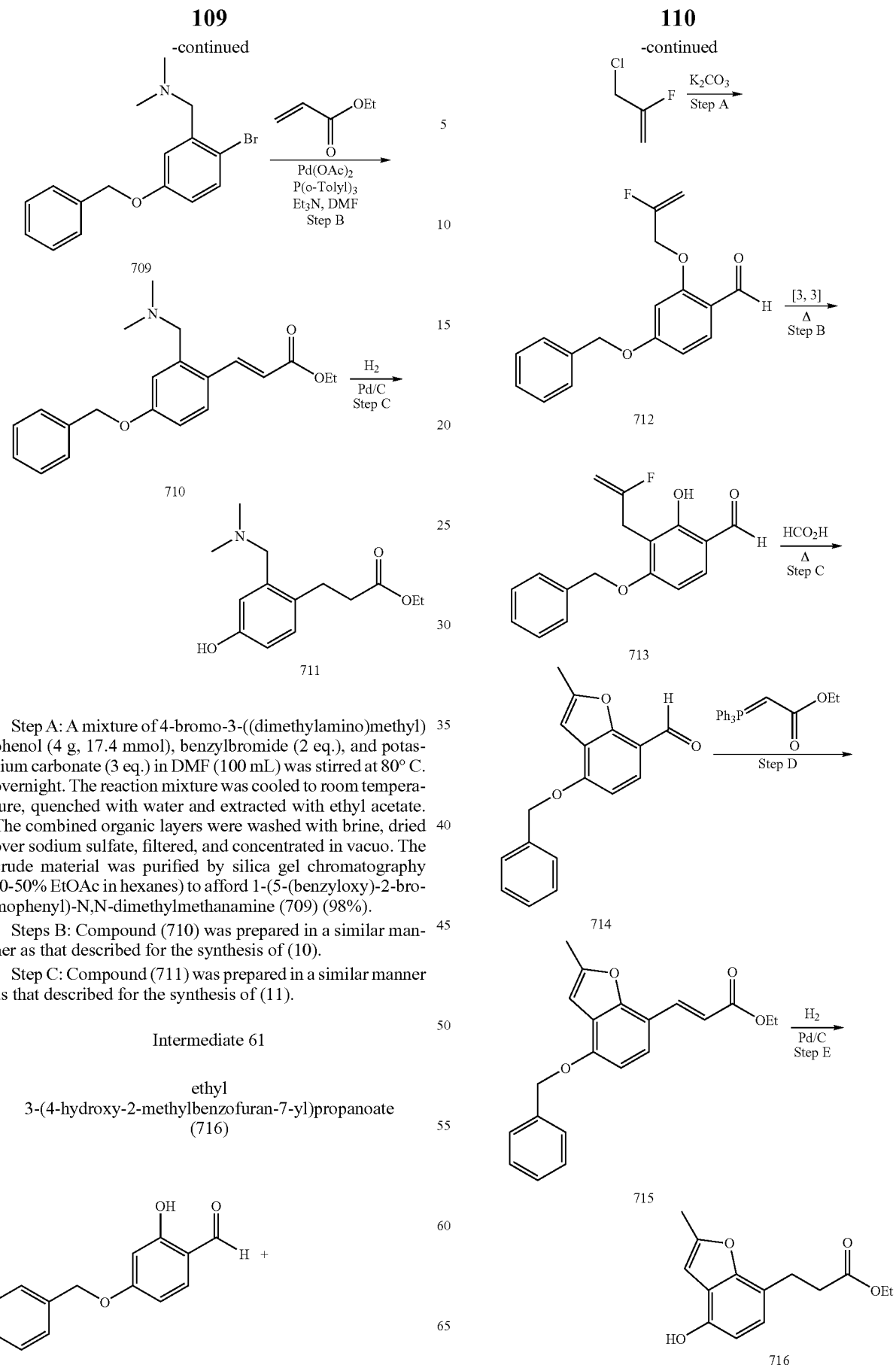

Step A: A mixture of 4-bromo-3-((dimethylamino)methyl) phenol (4 g, 17.4 mmol), benzylbromide (2 eq.), and potassium carbonate (3 eq.) in DMF (100 mL) was stirred at 80° C. overnight. The reaction mixture was cooled to room temperature, quenched with water and extracted with ethyl acetate. The combined organic layers were washed with brine, dried over sodium sulfate, filtered, and concentrated in vacuo. The crude material was purified by silica gel chromatography (0-50% EtOAc in hexanes) to afford 1-(5-(benzyloxy)-2-bromophenyl)-N,N-dimethylmethanamine (709) (98%).

Steps B: Compound (710) was prepared in a similar manner as that described for the synthesis of (10).

Step C: Compound (711) was prepared in a similar manner as that described for the synthesis of (11).

Intermediate 61 ethyl 3-(4-hydroxy-2-methylbenzofuran-7-yl)propanoate (716)

Step A-C: Compound (714) was prepared in a similar manner as that described for the synthesis of (3).

Step D: Compound (715) was prepared in a similar manner as that described for the synthesis of (537)

Step E: Compound (716) was prepared in a similar manner as that described for the synthesis of (513)

Intermediate 62

5-chloro-7-(chloromethyl)-3,3-dimethyl-2,3-dihydrobenzofuran (725)

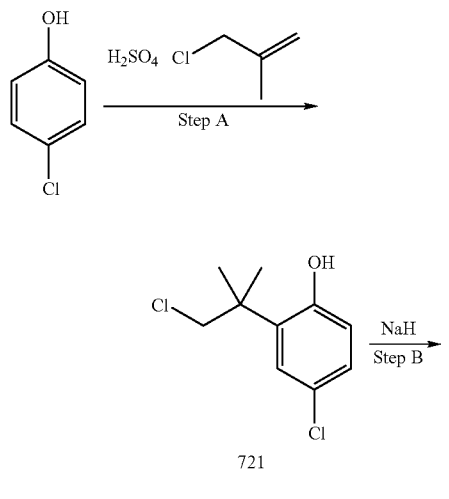

Step A: To a solution of 4-chlorophenol (12.6 g, 0.1 mol) and 3-chloro-2-methyl-propene (10.8 g, 0.12 mol) was added concentrated sulfuric acid (5 g, 0.05 mol) and stirred at 0° C. for 1 hour. The mixture was diluted with cold water and extracted with ether. The ethereal extract was washed with brine, dried over anhydrous sodium sulfate, filtered, and evaporated under reduced pressure. The residue was purified by flash chromatography on silica gel to afford 4-chloro-2-(1-chloro-2-methylpropan-2-yl)phenol (721).

Step B: To a suspension of NaH (1.44 g, 36 mmol) in anhydrous tetrahydrofuran was added 4-chloro-2-(1-chloro-2-methylpropan-2-yl)phenol (721) (6.6 g, 30.0 mmol) at 0° C. The reaction mixture was stirred at 0° C. for 1 hour. The reaction was quenched with methanol, diluted with water, and extracted with ether. The ethereal extract was washed with brine, dried over anhydrous sodium sulfate, filtered and evaporated in vacuo. The residue was purified by flash chromatography on silica gel to give 5-chloro-3,3-dimethyl-2,3-dihydrobenzofuran (722).

Step C: Compound (723) was prepared in a similar manner as that described for the synthesis of (545).

Step D: Compound (724) was prepared in a similar manner as that described for the synthesis of (546).

Step E: Compound (725) was prepared in a similar manner as that described for the synthesis of (511).

Intermediate 63

3,3-dideuterio-5-chloro-7-(chloromethyl)-2,2-dimethyl-2,3-dihydrobenzofuran (730)

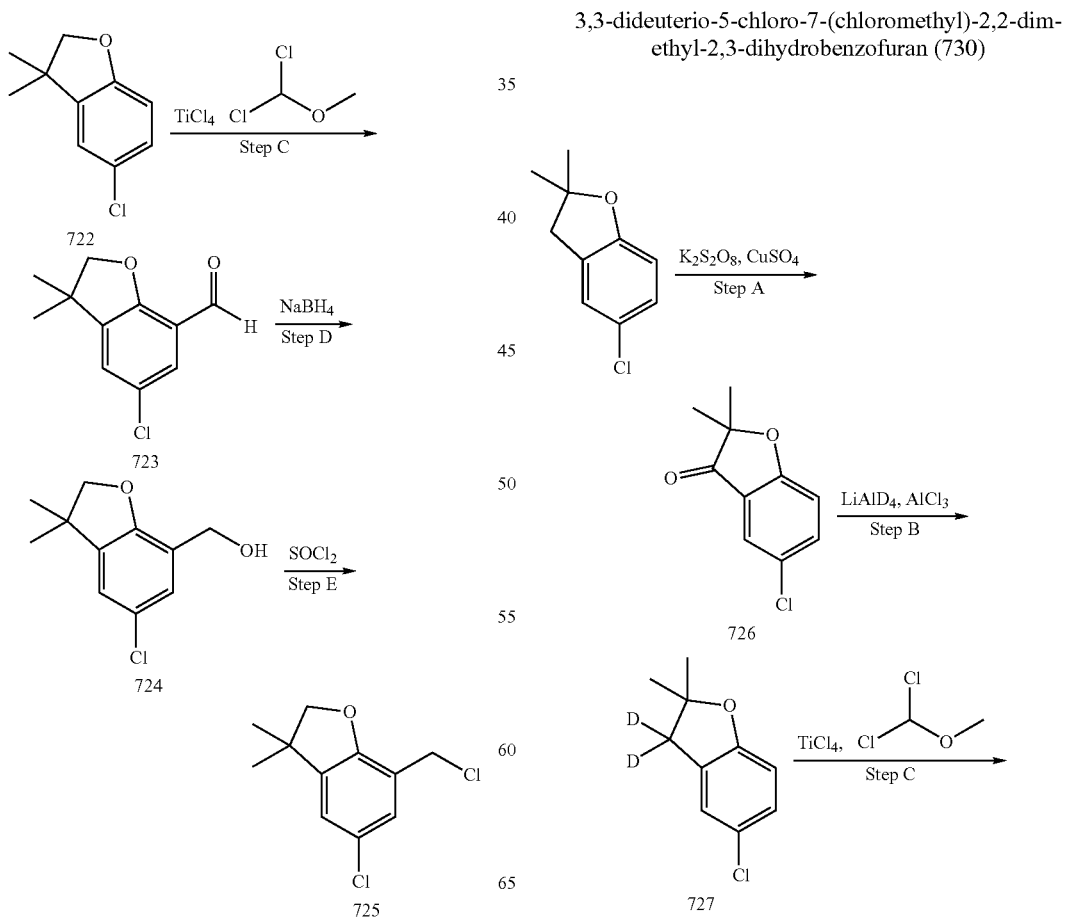

113
-continued

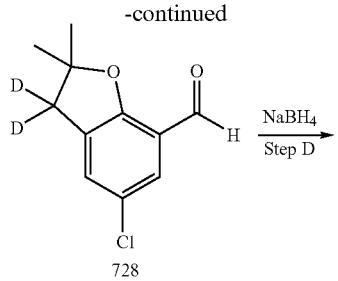
728

729

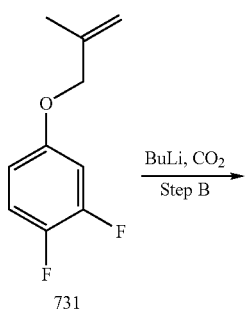
730

Step A: Compound (726) was prepared in a similar manner as that described for the synthesis of (655).

Step B: Lithium aluminum deuteride (0.21 g, 5.0 mmol) in dry ether (10 mL) was stirred for 15 min under nitrogen and aluminum chloride (0.7 g, 5.5 mmol) in dry ether (10 mL) was slowly added. Five minutes after the addition, a mixture of 5-chloro-2,2-dimethylbenzofuran-3(2H)-one (726) (1 g, 5 mmol) and aluminum chloride (0.7 g, 5.5 mmol) in dry ether (20 mL) was added to the solution of mixed metal hydride. The reaction mixture was vigorously stirred for 45 min under nitrogen, and the reaction was quenched with D₂O (5 mL) followed by 6 N sulfuric acid (6 mL). The reaction mixture was further diluted with water (25 mL), and the aqueous layer was extracted with four portions of ether (4×30 mL). The combined organic layers were washed with water, 10% sodium bicarbonate solution, and water and dried over sodium sulfate. The solvent was removed in vacuo and the residue was purified by flash chromatography on silica gel to afford 3,3-dideuterio-5-chloro-2,2-dimethyl-2,3-dihydrobenzofuran (727).

Step C: Compound (728) was prepared in a similar manner as that described for the synthesis of (545).

Step D: Compound (729) was prepared in a similar manner as that described for the synthesis of (546).

Step E: Compound (730) was prepared in a similar manner as that described for the synthesis of (511).

114

Intermediate 64

7-(chloromethyl)-5,6-difluoro-2,2-dimethyl-2,3-dihydrobenzofuran (737)

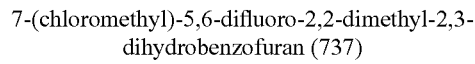

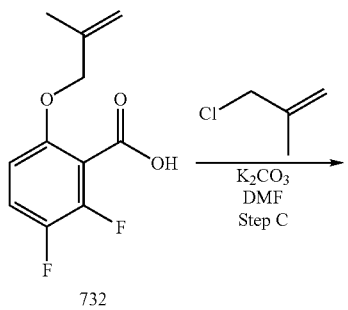
731

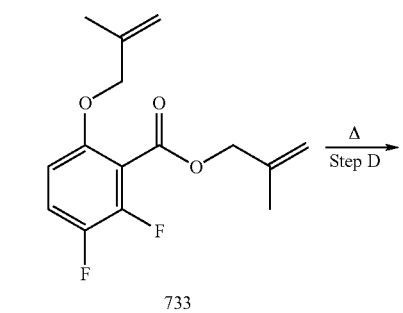
732

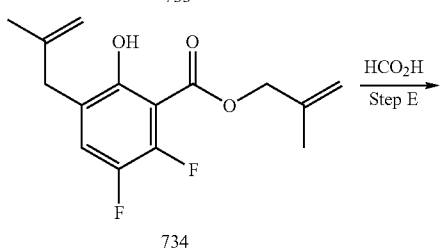
733

734

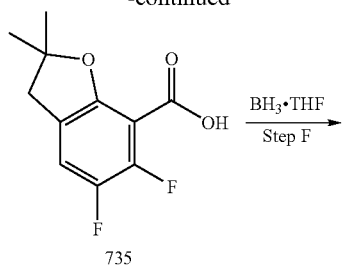

735

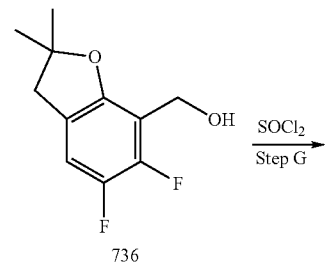

736

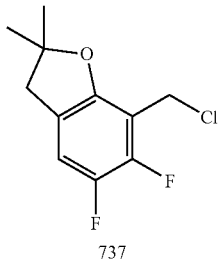

737

Step A: A mixture of 3,4-difluorophenol (2 g, 15.37 mmol), 3-chloro-2-methylpropene (1.66 mL, 16.91 mmol), and potassium carbonate (3.2 g, 23.06 mmol) in DMF (10 mL) was stirred at 85° C. for 6 h. The mixture was filtered and the filtrate was evaporated to dryness. The residue was purified by flash column chromatography eluting with hexanes-EtOAc (2:1) to provide 1,2-difluoro-4-(2-methylallyloxy)benzene (731) (1.78 g, 63%). $^1$H NMR (400 MHz, CDCl$_3$) δ 7.05 (q, J=9.5 Hz, 1H), 6.76-6.71 (m, 1H), 6.63-6.60 (m, 1H), 5.07 (s, 1H), 5.00 (s, 1H), 4.38 (s, 2H), 1.82 (s, 3H).

Step B: To a 1.4 M solution of sec-butyllithium in cyclohexane (6.7 mL) and anhydrous tetrahydrofuran (15 mL) at −75° C. was added 1,2-difluoro-4-(2-methylallyloxy)benzene (731) (1.6 g, 8.68 mmol). The resulting mixture was stirred at −75° C. for 2.5 hours and was then transferred to a round bottom flask containing dry ice. The resulting mixture was shaken for 5 min, and water (10 mL) was added dropwise. The mixture was acidified to pH 1 with concentrated hydrochloric acid and extracted with EtOAc (80 mL×3). The organic phase was washed with brine (60 mL×2), water (60 mL), and dried over anhydrous sodium sulfate, and the solvent removed in vacuo to give an oil 2,3-difluoro-6-(2-methylallyloxy)benzoic acid (732) (1.9 g), The product was used directly in the next step without further purification.

Step C: A mixture of 2,3-difluoro-6-(2-methylallyloxy) benzoic acid (732) (1.45 g, 6.35 mmol), 3-chloro-2-methylpropene (0.77 mL, 7.62 mmol), and potassium carbonate (1.76 g, 12.7 mmol) in anhydrous DMF was stirred at 65° C. under N$_2$ overnight. The mixture was filtered and the filtrate was evaporated to dryness. The residue was purified by flash column chromatography eluting with hexanes-EtOAc (4:1) to provide 2-methylallyl 2,3-difluoro-6-(2-methylallyloxy) benzoate (733) (1.55 g, 87%). $^1$H NMR (400 MHz, CDCl$_3$) δ 7.14 (q, J=9.5 Hz, 1H), 6.63-6.60 (m, 1H), 5.09 (s, 1H), 5.06 (s, 1H), 4.98 (s, 2H), 4.78 (s, 2H), 4.45 (s, 2H), 1.81 (s, 3H), 1.79 (s, 3H).

Step D: A solution of 2-methylallyl 2,3-difluoro-6-(2-methylallyloxy)benzoate (733) (1.53 g, 5.42 mmol) in NMP (3.5 mL) was heated in the microwave at 200° C. for 6 h. The solvent was removed in vacuo to provide 2-methylallyl 2,3-difluoro-6-hydroxy-5-(2-methylallyl)benzoate (734) (1.53 g) which was directly used in the next step reaction without further purification.

Step E: A solution of 2-methylallyl 2,3-difluoro-6-hydroxy-5-(2-methylallyl)benzoate (734) in 96% formic acid (15 mL) was refluxed for 22 hours. The solvent was removed in vacuo, and the residue was purified by flash column chromatography eluting with hexanes-EtOAc (3:1) to afford 5,6-difluoro-2,2-dimethyl-3H-benzofuran-7-carboxylic acid (735) (0.76 g, 61%). $^1$H NMR (400 MHz, DMSO-d$_6$) δ 7.43 (t, J=9.2 Hz, 1H), 2.98 (s, 2H), 1.41 (s, 6H).

Step F: To 5,6-difluoro-2,2-dimethyl-3H-benzofuran-7-carboxylic acid (735) (0.75 g, 3.29 mmol) was added 1.0 M of borane tetrahydrofuran complex solution (12 mL), and the mixture was stirred at room temperature overnight. The reaction was cooled to 0° C., acidified with 5 N HCl to pH 1, and then neutralized to pH 8 with 5 N NaOH. The mixture was extracted with EtOAc (80 mL×3) and the combined organic phase was washed with water (50 mL), dried over anhydrous sodium sulfate, and the solvent removed in vacuo. The product was purified by prep HPLC to yield (5,6-difluoro-2,2-dimethyl-3H-benzofuran-7-yl)methanol (736) (0.4 g, 57%). $^1$H NMR (400 MHz, DMSO-d$_6$) δ 7.18 (t, J=9.0 Hz, 1H), 4.38 (s, 2H), 2.97 (s, 2H), 1.40 (s, 6H).

Step G: To a solution of (5,6-difluoro-2,2-dimethyl-3H-benzofuran-7-yl)methanol (736) (0.18 g, 0.84 mmol) in anhydrous dichloromethane (5 mL) was added SOCl$_2$ dropwise at 0° C. The mixture was stirred at room temperature for 2 h. The solvent was removed in vacuo, and the residue was dissolved in EtOAc (100 mL). The solution was washed with water (30 mL), dried over anhydrous sodium sulfate, and evaporated in vacuo to give a solid 7-(chloromethyl)-5,6-difluoro-2,2-dimethyl-2,3-dihydrobenzofuran (737) (0.194 g, 99%).

Intermediate 65 ethyl 3-(7-hydroxy-2,3-dihydro-1H-inden-4-yl)propanoate (740)

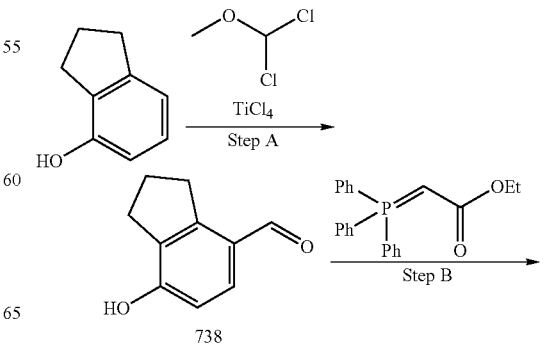

738

-continued

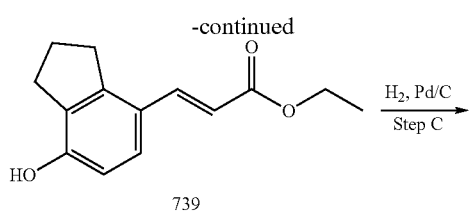

739

Step A: Compound (738) was prepared in a similar manner as that described for the synthesis of (545).
Step B: Compound (739) was prepared in a similar manner as that described for the synthesis of (537).
Step C: Compound (740) was prepared in a similar manner as that described for the synthesis of (513).

Intermediate 66 ethyl 3-(2-bromo-4-hydroxy-5-methoxyphenyl)propanoate (742)

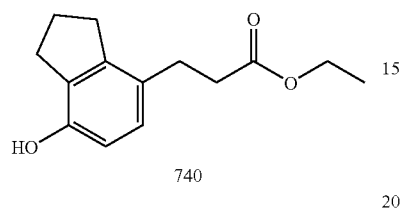

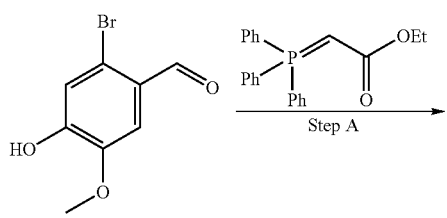

741

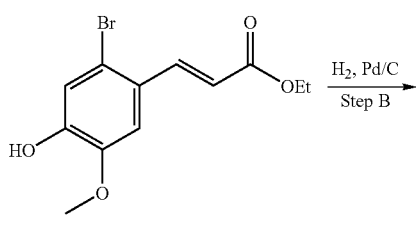

742

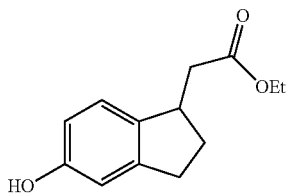

740

Step A: Compound (741) was prepared in a similar manner as that described for the synthesis of (537).
Step B: Compound (742) was prepared in a similar manner as that described for the synthesis of (513).

Intermediate 67

2-(5-hydroxy-2,3-dihydro-1H-inden-1-yl)acetic acid (23)

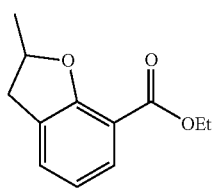

23

The above intermediate was synthesized by a method as disclosed in WO 2004/011445.

Intermediate 68

2-(5-hydroxy-2,3-dihydro-1H-inden-1-yl)acetic acid (24)

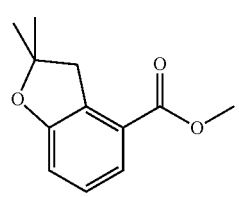

24

The above intermediate was synthesized by a method as disclosed in EP 234872.

Intermediate 69 methyl 2,2-dimethyl-2,3-dihydrobenzofuran-4-carboxylate (25)

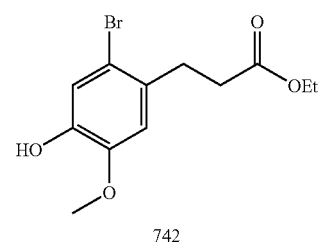

25

The above intermediate was synthesized by a method as disclosed in WO 2007/030061.

Intermediates 70 & 71

The following intermediates were purchased from commercial sources and used to synthesize one or more of the representative compounds of the invention.

Intermediate 72

(2-methylbenzo[d]oxazol-7-yl)methanol (744)

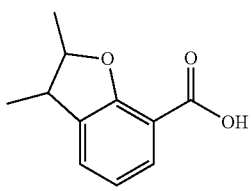
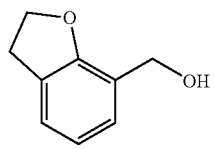
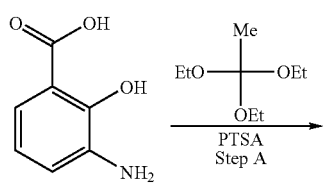
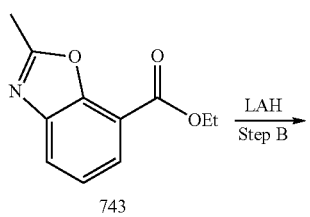
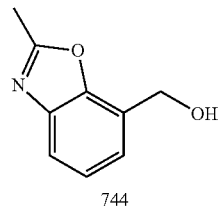

Step A: A solution of 3-amino-2-hydroxybenzoic acid (1 g, 6.53 mmol), triethylorthoacetate (4 mL), and P-toluenesulfonic acid (40 mg) was heated at 100° C. for 18 hours. The reaction was concentrated in vacuo and the crude product was purified by flash column chromatography on silica gel with hexanes and EtOAc (30%) to afford ethyl 2-methylbenzo[d]oxazole-7-carboxylate (743) (1.27 g, 95%).

Step B: To a solution of ethyl 2-methylbenzo[d]oxazole-7-carboxylate (743) (1.27 g, 6.19 mmol) in tetrahydrofuran (61 mL) at 0° C. was added lithium aluminum hydride (7.43 mL, 7.43 mmol, 1M in tetrahydrofuran). The reaction was stirred at 0° C. for 1 hour and quenched with 0.6 mL of water, 0.6 mL of 15% NaOH and 1.8 mL of water. The reaction was warmed to room temperature and diluted with diethyl ether. Magnesium sulfate was added and the solution was filtered, washed with diethyl ether, and the solvent was removed in vacuo to provide (2-methylbenzo[d]oxazol-7-yl)methanol (744) (0.687 g, 68%).

Intermediate 73 methyl 2-(6-methoxybenzofuran-3-yl)acetate (745)

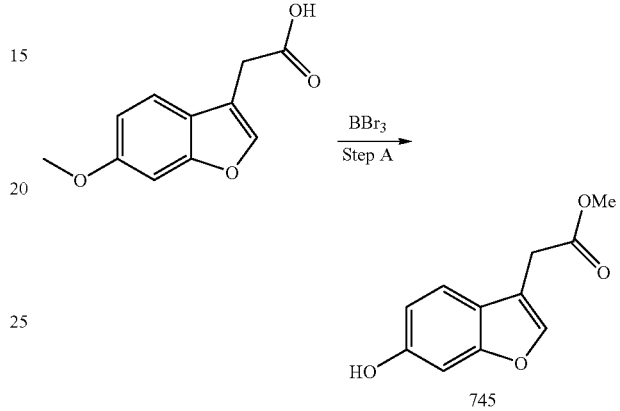

Step A: To a solution of 2-(6-methoxybenzofuran-3-yl) acetic acid (0.6 g, 2.9 mmol) in anhydrous dichloromethane (20 mL) at −78° C. was added boron tribromide (1.5 eq.) The reaction was stirred at −78° C. for 30 minutes, 0° C. for 2 hours, and at room temperature overnight. The reaction mixture was cooled to 0° C. and quenched slowly with methanol. After stirring for 15 minutes a saturated sodium bicarbonate solution was added slowly to the mixture and allowed to stir at 0° C. for 30 minutes. Ethyl acetate was added and the layers were separated. The aqueous layer was extracted with ethyl acetate and the combined organic layers were dried over sodium sulfate, filtered and concentrated in vacuo to give methyl 2-(6-methoxybenzofuran-3-yl)acetate (745) (67%).

Intermediate 74

(R)-4-benzyl-3-((R)-3-(4-hydroxyphenyl)-2-methylpropanoyl)oxazolidin-2-one (748)

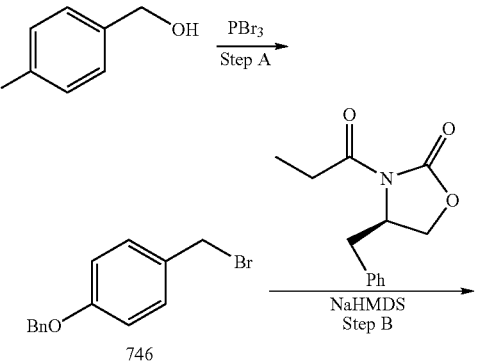

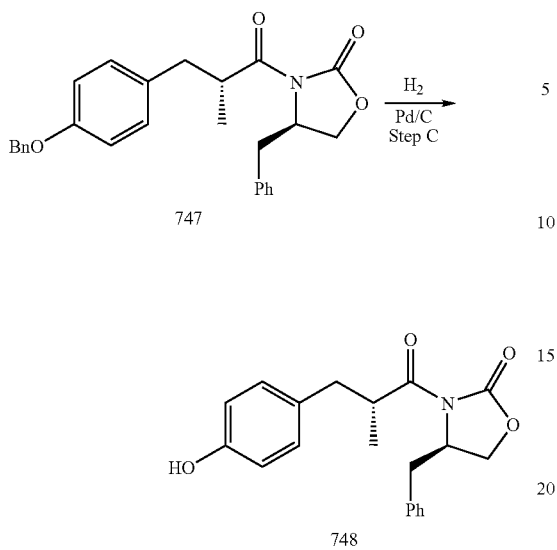

Step A: To a solution of (4-(benzyloxy)phenyl)methanol (21.4 g, 100 mmol) in diethyl ether (250 mL) at 0° C. was added phosphorous tribromide (10.8 g, 40 mmol) and stirred at 0° C. for 30 minutes and at room temperature for 3 hours. The reaction was quenched with water and the layers were separated. The organic layer was washed with water (2×400 mL), saturated sodium bicarbonate (2×400 mL), and brine. The ether layer was dried over sodium sulfate, filtered and concentrated in vacuo to afford 1-(benzyloxy)-4-(bromomethyl)benzene (746).

Step B: To a solution of (R)-4-benzyl-3-propionyloxazolidin-2-one (17.0 g, 72.8 mmol) in tetrahydrofuran (200 mL) at −78° C. was added sodium bis(trimethylsilyl)amide (80 mL, 79.4 mmol) and stirred for 1 hour. A solution of 1-(benzyloxy)-4-(bromomethyl)benzene (746) (20.0 g, 72.2 mmol) in tetrahydrofuran (50 mL) was added slowly to the oxazolidinone solution at −78° C. and allowed to warm to room temperature overnight. The solvent was removed in vacuo and the residue was dissolved with ethyl acetate. The organic layer was washed with water, brine, dried over sodium sulfate, filtered, and concentrated in vacuo. The crude compound was purified by flash column chromatography on silica gel with hexanes and EtOAc (20%) to afford (R)-4-benzyl-3-((R)-3-(4-(benzyloxy)phenyl)-2-methylpropanoyl)oxazolidin-2-one (747).

Step C: Compound (748) was prepared in a similar manner as that described for the synthesis of (513).

Intermediate 75

(S)-4-benzyl-3-((S)-3-(4-hydroxyphenyl)-2-methylpropanoyl)oxazolidin-2-one (751)

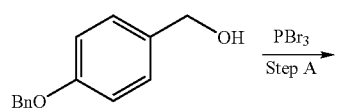

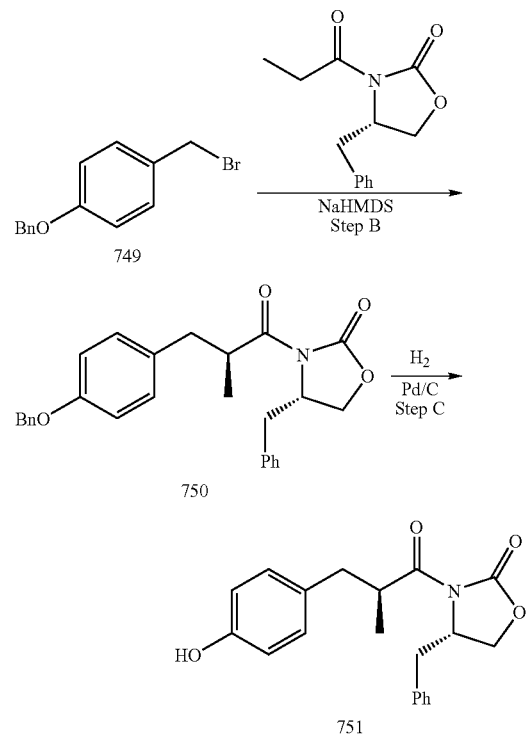

Step A: The synthesis of intermediate (749) was previously described in intermediate 75.

Step B: Compound (750) was prepared in a similar manner as that described for the synthesis of (747).

Step C: Compound (751) was prepared in a similar manner as that described for the synthesis of (513).

Intermediate 76 & Intermediate 77

(R)-4-benzyl-3-((S)-3-(3,5-difluoro-4-hydroxyphenyl)-2-methylpropanoyl)oxazolidin-2-one (754) and
(R)-4-benzyl-3-((R)-3-(3,5-difluoro-4-hydroxyphenyl)-2-methylpropanoyl)oxazolidin-2-one (755)

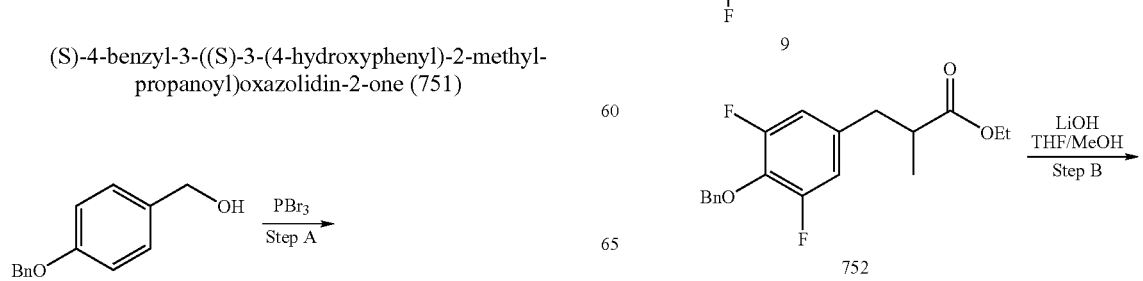

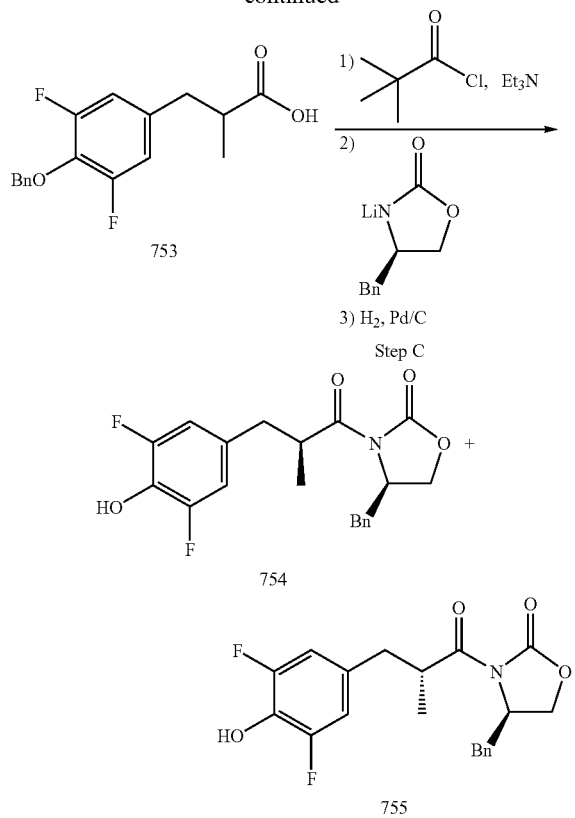

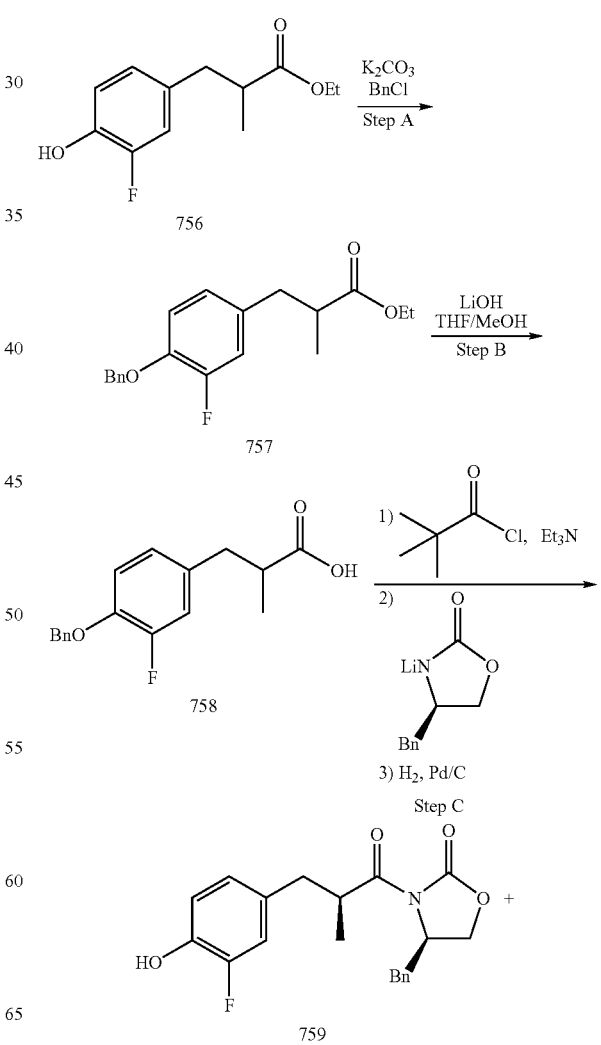

with saturated ammonium chloride and extracted with ethyl acetate. The organic layer was dried over sodium sulfate, filtered, and concentrated in vacuo. The residue was purified by flash column chromatography on silica gel with hexanes and EtOAc to afford the two diastereomers (R)-4-benzyl-3-((S)-3-(4-(benzyloxy)-3,5-difluorophenyl)-2-methylpropanoyl)oxazolidin-2-one and (R)-4-benzyl-3-((R)-3-(4-(benzyloxy)-3,5-difluorophenyl)-2-methylpropanoyl) oxazolidin-2-one. The benzyl group was removed with Pd/C under a hydrogen atmosphere as previously described for the synthesis of compound (9) to provide (R)-4-benzyl-3-((S)-3-(3,5-difluoro-4-hydroxyphenyl)-2-methylpropanoyl)oxazolidin-2-one (754) and (R)-4-benzyl-3-((R)-3-(3,5-difluoro-4-hydroxyphenyl)-2-methylpropanoyl)oxazolidin-2-one (755).

Intermediate 78 & Intermediate 79

(R)-4-benzyl-3-((S)-3-(3-fluoro-4-hydroxyphenyl)-2-methylpropanoyl)oxazolidin-2-one (759) and (R)-4-benzyl-3-((R)-3-(3-fluoro-4-hydroxyphenyl)-2-methylpropanoyl)oxazolidin-2-one (760)

Step A: To a mixture of ethyl 3-(3,5-difluoro-4-hydroxyphenyl)-2-methylpropanoate (9) (930 mg, 3.81 mmol) and potassium carbonate (1.05 g, 7.62 mmol) in DMF (8 mL) was added benzyl chloride (0.53 mL, 4.57 mmol) and stirred overnight at 50° C. The reaction was diluted with water and extracted with ethyl acetate (3×25 mL). The organic layer was dried over sodium sulfate, filtered, and concentrated in vacuo. The residue was purified by flash column chromatography on silica gel with hexanes and EtOAc to afford ethyl 3-(4-(benzyloxy)-3,5-difluorophenyl)-2-methylpropanoate (752).

Step B: To a mixture of 3-(4-(benzyloxy)-3,5-difluorophenyl)-2-methylpropanoate (752) (1.09 g, 3.26 mmol) in tetrahydrofuran (10 mL), water (10 mL), and methanol (20 mL) was added lithium hydroxide (547 mg, 13.04 mmol) and the solution was stirred overnight at 80° C. The reaction was concentrated, acidified with 1N hydrochloric acid, and extracted with ethyl acetate. The organic layer was dried over sodium sulfate, filtered, and concentrated in vacuo to yield 3-(4-(benzyloxy)-3,5-difluorophenyl)-2-methylpropanoic acid (753).

Step C: To a solution of 3-(4-(benzyloxy)-3,5-difluorophenyl)-2-methylpropanoic acid (753) (0.99 g, 3.23 mmol) in tetrahydrofuran (2.5 mL) at 0° C. was added triethylamine (0.50 mL, 3.57 mmol) and pivaloyl chloride (0.44 mL, 3.57 mmol) and the reaction was stirred for 30 minutes. In a separate flask (R)-4-benzyloxazolidin-2-one (0.48 g, 2.69 mmol) was dissolved in tetrahydrofuran (4 mL) and cooled to −78° C. n-butyllithium (1.77 mL, 2.69 mmol, 1.52 M in hexanes) was added and the reaction was stirred for 30 minutes. The solution of 3-(4-(benzyloxy)-3,5-difluorophenyl)-2-methylpropanoic acid was added to the (R)-4-benzyloxazolidin-2-one solution and stirred at −78° C. for 3 hours and at room temperature for 30 minutes. The reaction was quenched -continued

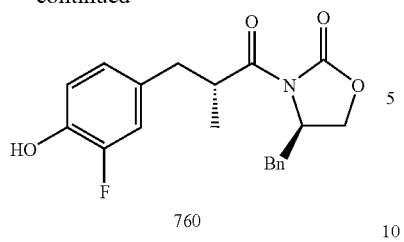
760

Step A: Compound (757) was prepared in a similar manner as that described for the synthesis of (752).

Step B: Compound (758) was prepared in a similar manner as that described for the synthesis of (753).

Step C: Compounds (759) and (760) were prepared in a similar manner as that described for the synthesis of (754) and (755).

Intermediate 80 & Intermediate 81

(R)-4-benzyl-3-((S)-3-(4-hydroxy-3-(trifluoromethyl)phenyl)-2-methylpropanoyl)oxazolidin-2-one (764) and (R)-4-benzyl-3-((R)-3-(4-hydroxy-3-(trifluoromethyl)phenyl)-2-methylpropanoyl)oxazolidin-2-one (765)

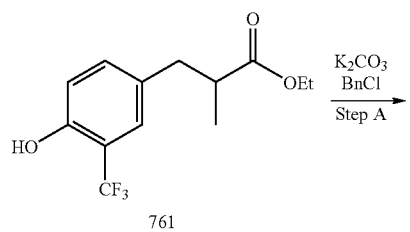
761

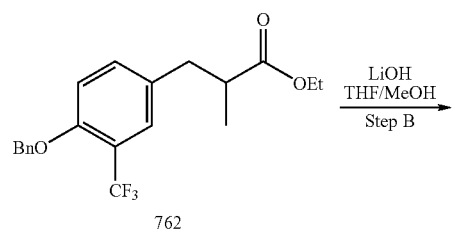
762

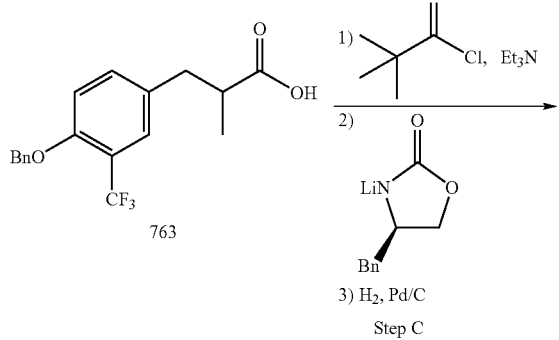
763

-continued

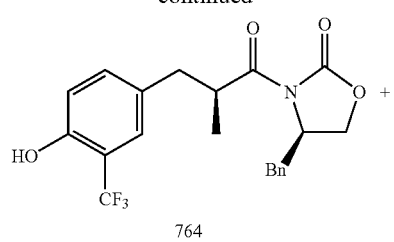
764

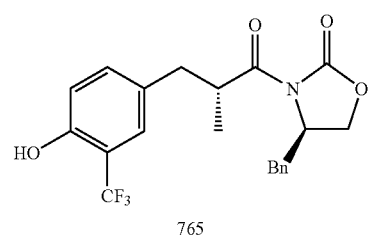
765

Step A: Compound (762) was prepared in a similar manner as that described for the synthesis of (752)

Step B: Compound (763) was prepared in a similar manner as that described for the synthesis of (753)

Step C: Compounds (764) and (765) were prepared in a similar manner as that described for the synthesis of (754) and (755).

Intermediate 82

(7-fluoro-2,2-dimethyl-2,3-dihydrobenzofuran-4-yl)methanol (779)

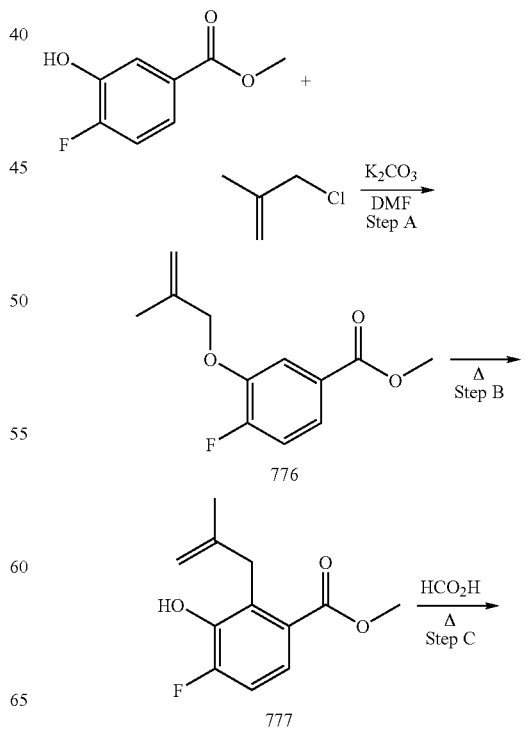
776

777

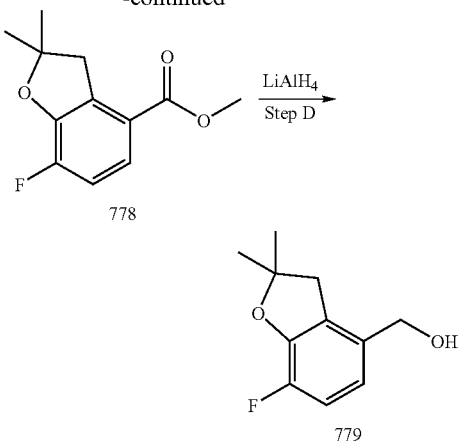

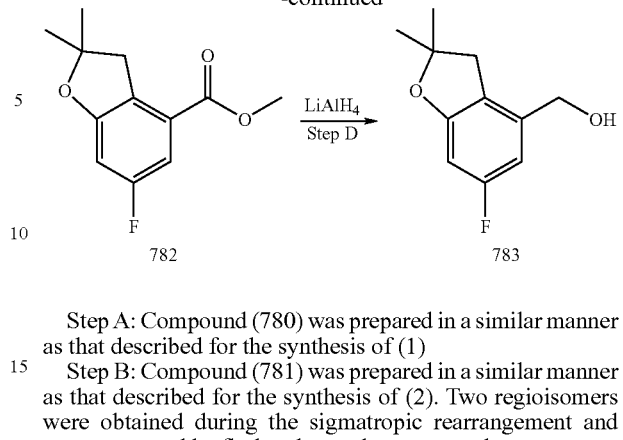

Step A: Compound (780) was prepared in a similar manner as that described for the synthesis of (1)

Step B: Compound (781) was prepared in a similar manner as that described for the synthesis of (2). Two regioisomers were obtained during the sigmatropic rearrangement and were separated by flash column chromatography Step C: Compounds (782) were prepared in a similar manner as that described for the synthesis of (3). The acid obtained after the cyclization was esterified by adding 20 equivalents of thionyl chloride to a solution of the acid in methanol.

Step D: Compound (783) was prepared in a similar manner as that described for the synthesis of (4).

Step A: Compound (776) was prepared in a similar manner as that described for the synthesis of (1)

Step B: Compound (777) was prepared in a similar manner as that described for the synthesis of (2)

Step C: Compounds (778) were prepared in a similar manner as that described for the synthesis of (3).

Step D: Compound (779) was prepared in a similar manner as that described for the synthesis of (4).

Intermediate 83

(6-fluoro-2,2-dimethyl-2,3-dihydrobenzofuran-4-yl)methanol (783)

Intermediate 84

(5-fluoro-2,2-dimethyl-2,3-dihydrobenzofuran-4-yl)methanol (787)

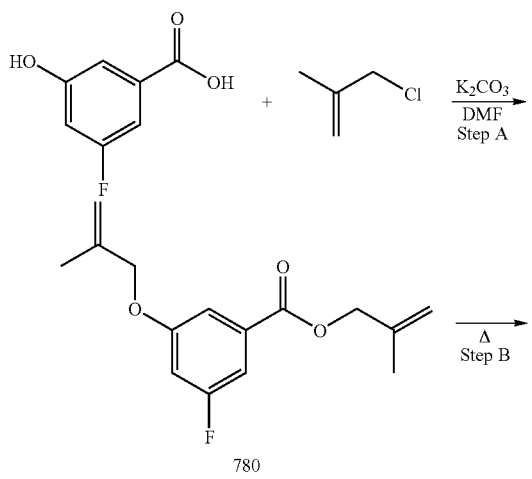

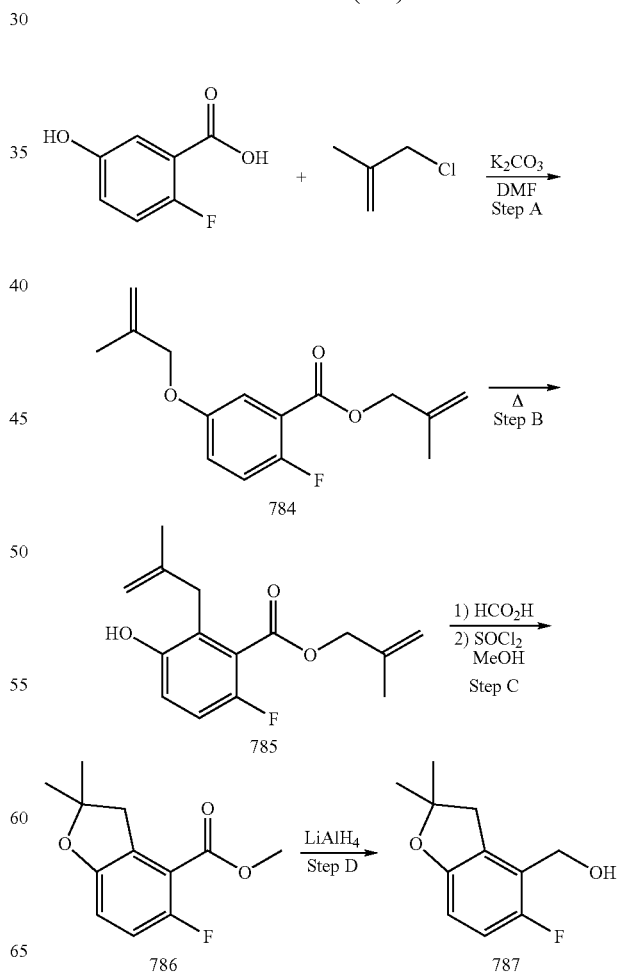

Step A: Compound (784) was prepared in a similar manner as that described for the synthesis of (1).

Step B: Compound (785) was prepared in a similar manner as that described for the synthesis of (2). Two regioisomers were obtained during the sigmatropic rearrangement and were separated by flash column chromatography Step C: Compounds (786) were prepared in a similar manner as that described for the synthesis of (3). The acid obtained after the cyclization was esterified by adding 20 equivalents of thionyl chloride to a solution of the acid in methanol.

Step D: Compound (787) was prepared in a similar manner as that described for the synthesis of (4).

Intermediate 85

(5-chloro-2,2-dimethyl-2,3-dihydrobenzofuran-4-yl)methanol (791)

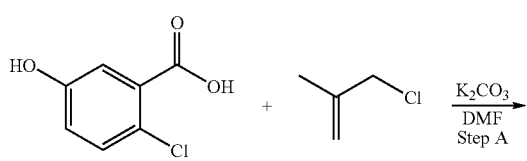

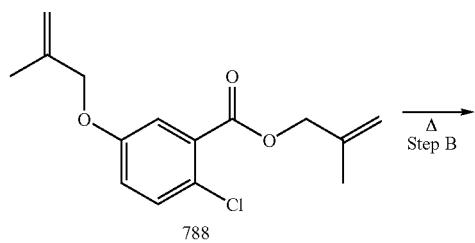
788

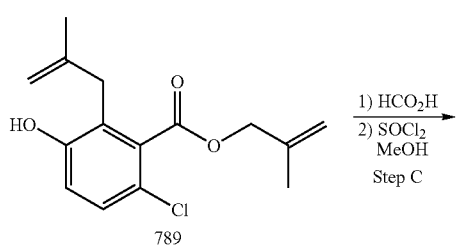
789

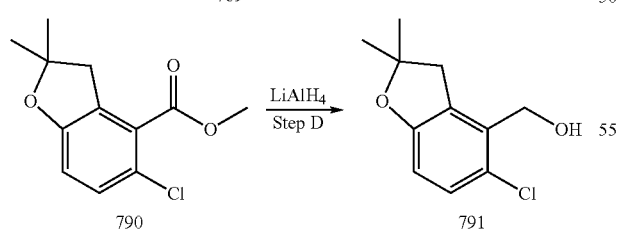
790          791

Step A: Compound (788) was prepared in a similar manner as that described for the synthesis of (1).

Step B: Compound (789) was prepared in a similar manner as that described for the synthesis of (2). Two regioisomers were obtained during the sigmatropic rearrangement and were separated by flash column chromatography Step C: Compounds (790) were prepared in a similar manner as that described for the synthesis of (3). The acid obtained after the cyclization was esterified by adding 20 equivalents of thionyl chloride to a solution of the acid in methanol.

Step D: Compound (791) was prepared in a similar manner as that described for the synthesis of (4).

Intermediate 86 dideuterio(5-chloro-2,2-dimethyl-2,3-dihydrobenzofuran-7-yl)methanol (792)

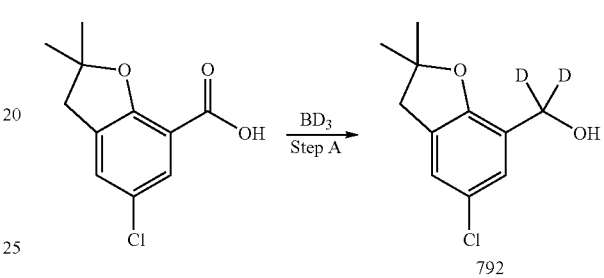
792

Step A: Compound (792) was prepared in a similar manner as that described for the synthesis of (510).

Intermediate 87 ethyl 2,3-dideuterio-3-(4-hydroxyphenyl)propanoate (794)

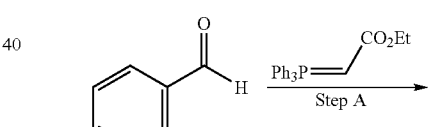

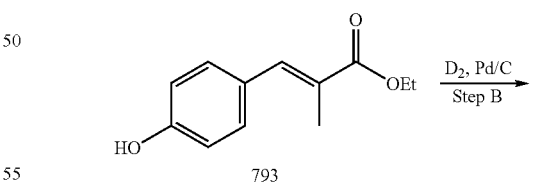
793

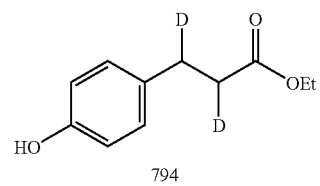
794

Step A: Compound (793) is prepared in a similar manner as that described for the synthesis of (537).

Step B: Compound (794) is prepared in a similar manner as that described for the synthesis of (513) (except D$_2$ balloon is used).

Intermediate 88 deuterio(5-chloro-2,2-dimethyl-2,3-dihydrobenzofuran-7-yl)methanol (796)

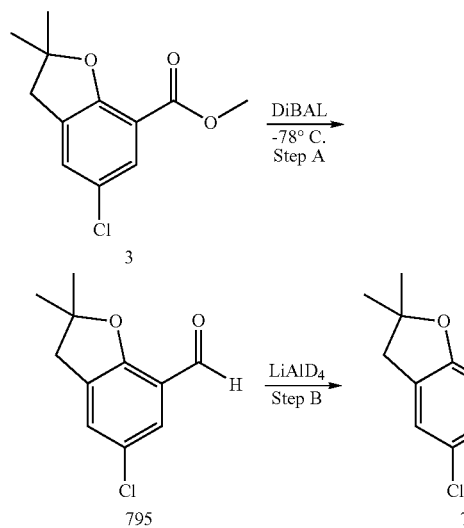

Step A: A solution of (3) in toluene is cooled to −78° C. and diisobutylaluminum hydride is added under dry nitrogen. The solution is kept at −78° C. before saturated sodium bisulfite is added. The solution is allowed to warm to room temperature and the layers are separated. The toluene layer is extracted with portions of bisulfite which is combined with the aqueous layer, basified with 2 M sodium hydroxide to pH 8-9 (with cooling) and extracted with ether. The ether is washed with water, dried, and evaporated to give (795).

Step B: Compound (796) is prepared in a similar manner as that described for the synthesis of (4).

Intermediate 89

(3-deuterio-5-chloro-2,2-dimethyl-2,3-dihydrobenzofuran-7-yl)methanol (800)

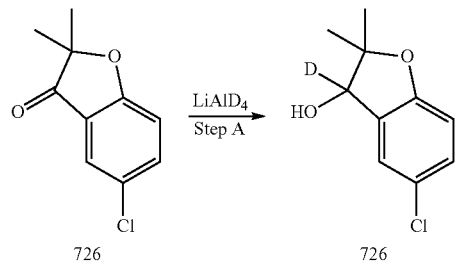

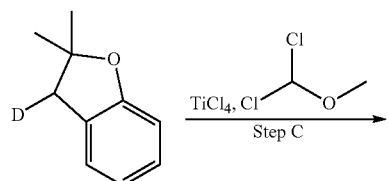

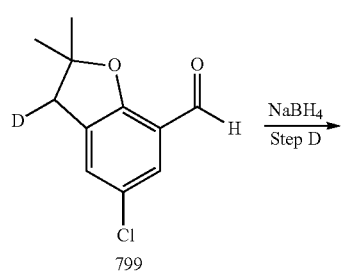

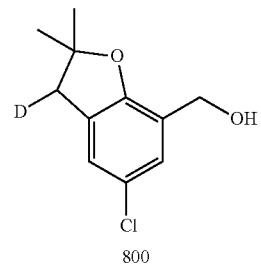

Step A: Compound (797) is prepared in a similar manner as that described for the synthesis of (4).

Step B: To a solution of 3-deuterio-5-chloro-2,2-dimethyl-2,3-dihydrobenzofuran-3-ol (797), triethylsilane and dichloromethane at 0° C. is added boron trifluoride diethyl etherate and stirred at room temperature. The reaction is quenched with saturated sodium bicarbonate and extracted with ethyl. The organic layer is dried over sodium sulfate, filtered, and concentrated in vacuo to give 3-deuterio-5-chloro-2,2-dimethyl-2,3-dihydrobenzofuran (798).

Step C: Compound (799) is prepared in a similar manner as that described for the synthesis of (545).

Step D: Compound (800) is prepared in a similar manner as that described for the synthesis of (546).

Intermediate 90

7-(chloromethyl)-5-fluoro-2,2-dimethyl-2,3-dihydrobenzofuran

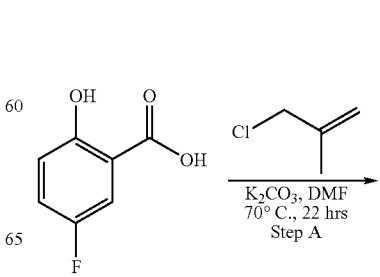

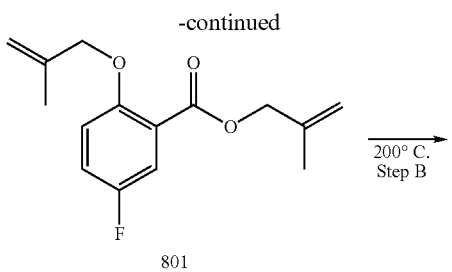
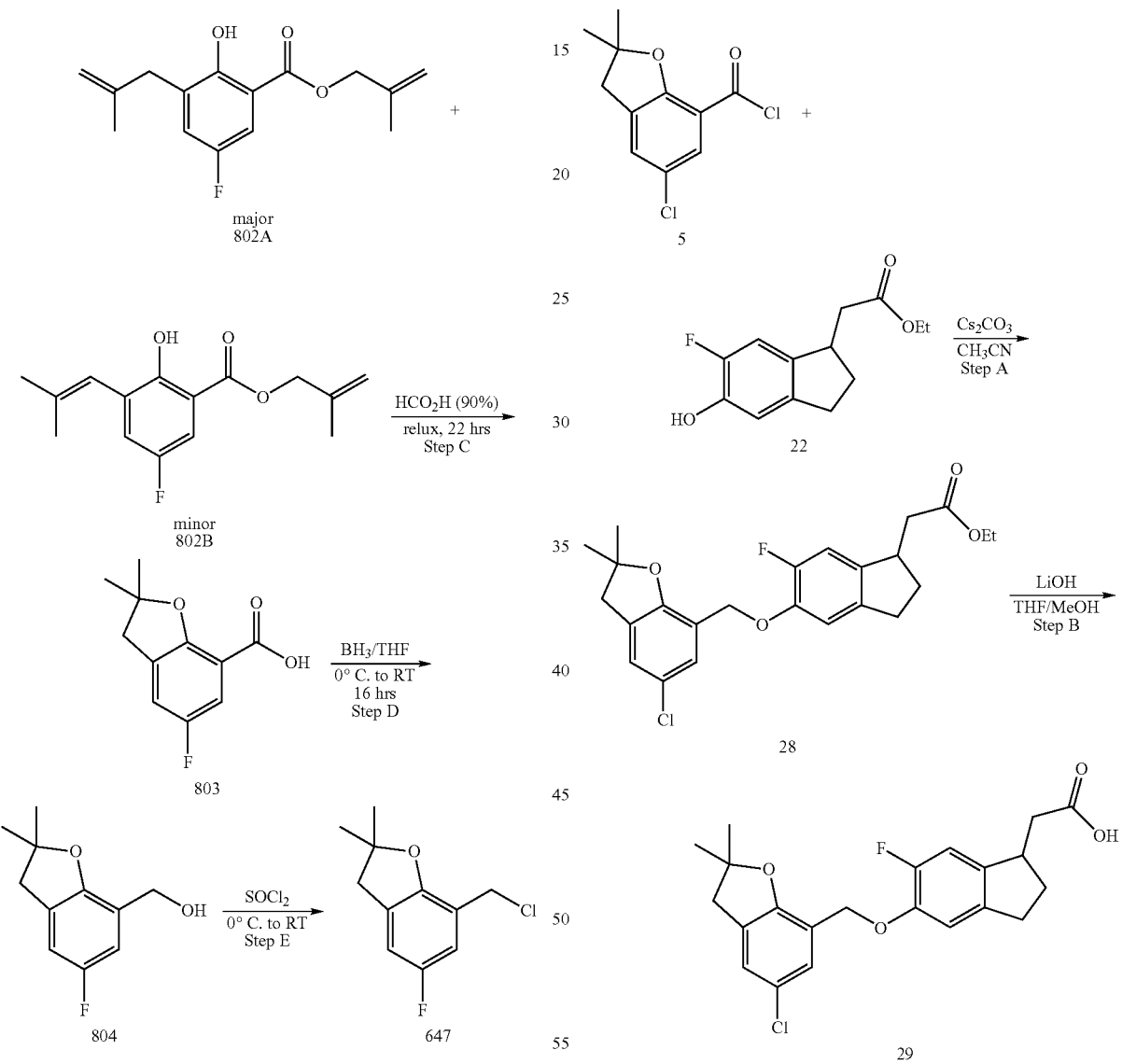

Step E: Compound (647) was prepared in a similar manner as that described for the synthesis of (5)

Preparation of GPR120 Agonists

Example 1

2-(5-(((5-chloro-2,2-dimethyl-2,3-dihydrobenzofuran-7-yl)methoxy)-6-fluoro-2,3-dihydro-1H-inden-1-yl)acetic acid (29)

Step A: Compound (801) was prepared in a similar manner as that described for the synthesis of (1)

Step B: Compound (802A) and (802B) were prepared in a similar manner as that described for the synthesis of (2). The two compounds were carried on to the next step as a mixture.

Step C: Compounds (803) were prepared in a similar manner as that described for the synthesis of (3).

Step D: Compound (804) was prepared in a similar manner as that described for the synthesis of (510)

Step A: To a solution of intermediate (5) (0.100 g, 0.43 mmol) in acetonitrile (3 mL) was added intermediate 22 (0.103 g, 0.43 mmol) and cesium carbonate (0.169 g, 0.52 mmol). The resulting suspension was stirred at 75° C. for 5 h. The reaction was cooled to room temperature and filtered through a pad of celite. The filtrate was concentrated in vacuo and the residue was purified by silica gel chromatography (0-20% EtOAc in hexanes) to yield intermediate (28).

Step B: To a solution of intermediate (28) (0.100 g, 0.231 mmol) in tetrahydrofuran (1 mL) and methanol (1 mL) was added a solution of lithium hydroxide (1.0 M, 1.0 mL). The reaction was stirred at room temperature for 4 h. The mixture was acidified with 1M HCl and diluted with ethyl acetate (5 mL). The organic layer was washed with brine (5 mL), dried over sodium sulfate and filtered. The filtrate was concentrated in vacuo and the residue was purified by silica gel chromatography (0-100% EtOAc in hexanes) to isolate the title compound (29). $^1$H NMR (400 MHz, CDCl$_3$) δ: 7.05 (s, 1H), 6.94-6.90 (m, 3H), 5.03 (s, 2H), 3.54-3.51 (m, 1H), 3.00 (s, 2H), 2.86-2.72 (m, 3H), 2.50-2.40 (m, 2H), 1.80-1.75 (m, 1H), 1.48 (s, 6H).

Example 2

3-(4-((2,2-dimethylchroman-8-yl)methoxy)-3,5-difluorophenyl)-2-methylpropanoic acid (31)

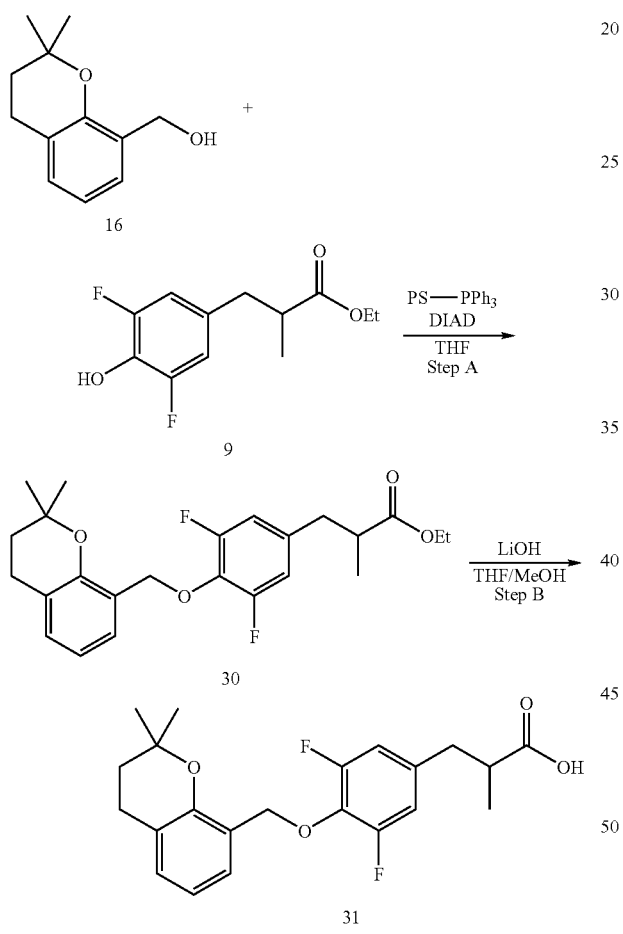

Step A: To a solution of intermediate (16) (0.140 g, 0.73 mmol) in tetrahydrofuran (3 mL) was added intermediate 9 (0.178 g, 0.73 mmol), polymer supported triphenylphosphine (3 mmol/g, 0.36 g, 1.1 mmol) and diisopropylazodicarboxylate (0.214 mL, 1.1 mmol). The resulting suspension was stirred for 18 h. The reaction was diluted with ethyl acetate and filtered through a pad of celite. The filtrate was concentrated in vacuo and the residual was purified by silica gel chromatography (0-20% EtOAc in hexanes) to yield the intermediate (30).

Step B: To a solution of intermediate (30) (0.100 g, 0.256 mmol) in tetrahydrofuran (1 mL) and methanol (1 mL) was added a solution of lithium hydroxide (1.0 M, 1.0 mL). The reaction was stirred at room temperature for 4 h. The mixture was acidified with 1M HCl and diluted with ethyl acetate (5 mL). The organic layer was washed with brine (5 mL), dried over sodium sulfate and filtered. The filtrate was concentrated in vacuo and the residue was purified by silica gel chromatography (0-100% EtOAc in hexanes) to isolate the title compound (31). $^1$H NMR (400 MHz, CDCl$_3$) δ: 7.28 (d, 1H), 7.03 (d, 1H), 6.82 (t, 1H), 6.71 (d, 2H), 5.15 (s, 2H), 3.00-2.95 (m, 1H), 2.77 (t, 2H), 2.73-2.70 (m, 1H), 2.62-2.57 (m, 1H), 1.77 (t, 2H), 1.19 (d, 3H), 0.89 (s, 6H).

Representative compounds of the invention, prepared by following procedures described in the above examples using appropriate starting materials that will be apparent to those skilled in the art, are shown below.

Example 3

3-(4-((2,3-dihydrobenzofuran-7-yl)methoxy)-3,5-difluorophenyl)-2-methylpropanoic acid (32)

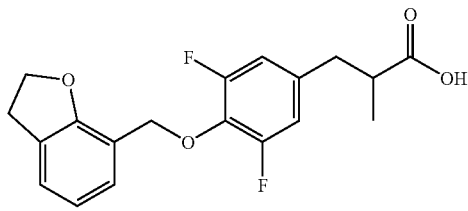

$^1$H NMR (400 MHz, CDCl$_3$) δ: 7.21-7.16 (m, 2H), 6.83 (t, 1H), 6.70 (d, 2H), 5.13 (s, 2H), 4.57 (t, 2H), 3.21 (t, 2H), 2.99-2.94 (m, 1H), 2.74-2.69 (m, 1H), 2.62-2.56 (m, 1H), 1.19 (d, 3H).

Example 4

2-methyl-3-(4-((2,2,5-trimethyl-2,3-dihydrobenzofuran-7-yl)methoxy)phenyl)propanoic acid (33)

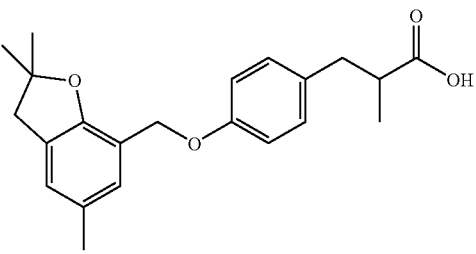

$^1$H NMR (400 MHz, CDCl$_3$) δ: 7.09-7.05 (m, 3H), 6.95-6.90 (m, 3H), 4.98 (s, 2H), 3.03-2.99 (m, 1H), 2.98 (2H, s), 2.78-2.51 (m, 1H), 2.63-2.58 (m, 1H), 2.27 (s, 3H), 1.47 (s, 6H), 1.16 (d, 3H).

Example 5

3-(3,5-difluoro-4-((2,2,5-trimethyl-2,3-dihydrobenzofuran-7-yl)methoxy)phenyl)-2-methylpropanoic acid (34)

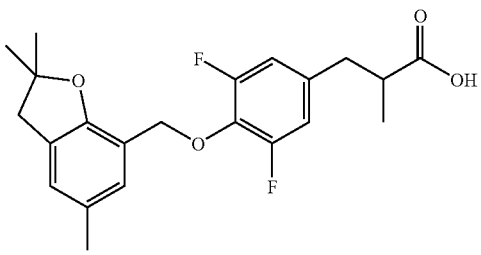

$^1$H NMR (400 MHz, CDCl$_3$) δ: 7.03 (s, 1H), 6.90 (s, 1H), 6.69 (d, 2H), 5.10 (s, 2H), 2.99-2.96 (m, 1H), 2.94 (s, 2H), 2.74-2.69 (m, 1H), 2.61-2.56 (m, 1H), 2.26 (s, 3H), 1.40 (s, 6H), 1.18 (d, 3H).

Example 6

3-(4-((5-fluoro-2,2-dimethyl-2,3-dihydrobenzofuran-7-yl)methoxy)-3-methylphenyl)-2-methylpropanoic acid (35)

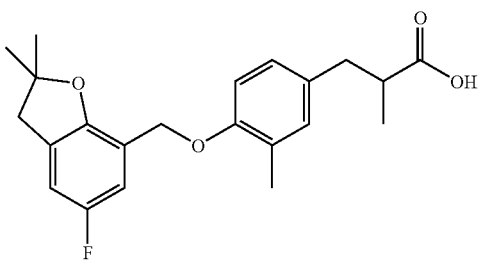

$^1$H NMR (400 MHz, CDCl$_3$) δ: 7.00-6.78 (m, 5H), 4.98 (s, 2H), 3.00 (s, 2H), 2.96-3.00 (m, 1H), 2.76-2.70 (m, 1H), 2.61-2.55 (m, 1H), 2.26 (s, 3H), 1.48 (s, 6H), 1.18 (d, J=7.2 Hz, 3H). LC-MS ESI m/z: found 371.2 [M−H]$^-$

Example 7

3-(4-((5-fluoro-2,2-dimethyl-2,3-dihydrobenzofuran-7-yl)methoxy)-3-methoxyphenyl)-2-methylpropanoic acid (36)

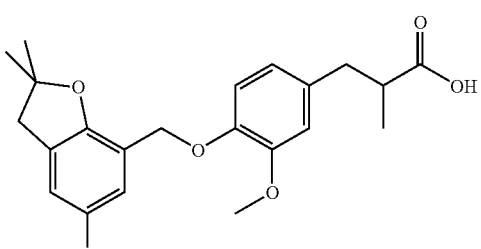

$^1$H NMR (400 MHz, CDCl$_3$) δ: 7.02-6.99 (dd, J=10.0 Hz, 2.4 Hz, 1H), 6.84 (d, J=8.4 Hz, 1H), 6.78-6.75 (dd, J=5.2 Hz, 2.4 Hz, 1H), 6.71 (s, 1H), 6.66-6.64 (m, 1H), 5.06 (s, 2H), 3.87 (s, 3H), 3.02-2.97 (m, 3H), 2.76-2.70 (m, 1H), 2.62-2.57 (m, 1H), 1.48 (s, 6H), 1.16 (d, J=7.2 Hz, 3H).

Example 8

3-(3-fluoro-4-((5-fluoro-2,2-dimethyl-2,3-dihydrobenzofuran-7-yl)methoxy)phenyl)-2-methylpropanoic acid (37)

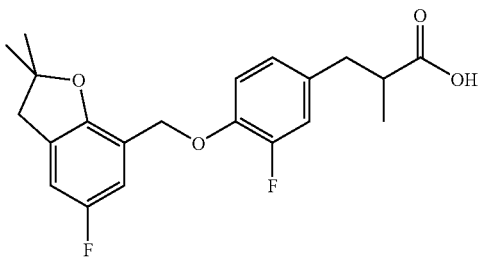

$^1$H NMR (400 MHz, CDCl$_3$) δ: 6.90-6.70 (m, 3H), 6.79-6.83 (m, 2H), 5.04 (s, 2H), 2.99 (s, 2H), 2.95-2.99 (m, 1H), 2.68-2.74 (m, 1H), 2.57-2.62 (m, 1H), 1.47 (s, 6H), 1.17 (d, J=7.2 Hz, 3H). LC-MS ESI m/z: found 375.1 [M−H]$^-$

Example 9

3-(4-((5-chloro-2,2-dimethyl-2,3-dihydrobenzofuran-7-yl)methoxy)-3-(trifluoromethyl)phenyl)-2-methylpropanoic acid (38)

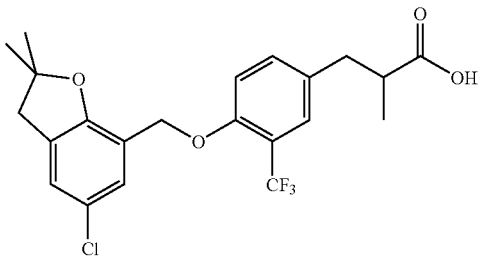

$^1$H NMR (400 MHz, CDCl$_3$) δ: 7.39 (s, 1H), 7.26 (m, 2H), 7.05 (s, 1H), 7.01 (d, J=9.2 Hz, 1H), 5.06 (s, 2H), 3.00 (s, 2H), 3.04-2.99 (m, 1H), 2.77-2.72 (m, 1H), 2.69-2.64 (m, 1H), 1.48 (s, 6H), 1.19 (d, J=6.8 Hz, 3H). LC-MS ESI m/z: found 441.1 [M−H]$^-$

Example 10

3-(4-((5-chloro-2,2-dimethyl-2,3-dihydrobenzofuran-7-yl)methoxy)-3-fluorophenyl)-2-methylpropanoic acid (39)

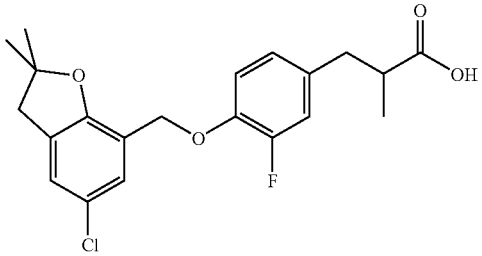

¹H NMR (400 MHz, CDCl₃) δ: 7.25 (s, 1H), 7.04 (s, 1H), 6.97-6.91 (m, 2H), 6.84-6.82 (m, 1H), 5.03 (s, 2H), 3.00 (s, 2H), 2.99-2.95 (m, 1H), 2.75-2.70 (m, 1H), 2.63-2.58 (m, 1H), 1.48 (s, 6H), 1.18 (d, J=6.4 Hz, 3H). LC-MS ESI m/z: found 390.1 [M−H]⁻

Example 11

3-(4-((5-chloro-2,2-dimethyl-2,3-dihydrobenzofuran-7-yl)methoxy)-3-methylphenyl)-2-methylpropanoic acid (40)

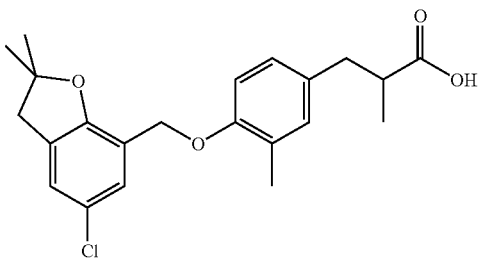

¹H NMR (400 MHz, CDCl₃) δ: 7.25 (s, 1H), 7.04 (s, 1H), 6.97-6.93 (m, 2H), 6.82 (d, J=8.0 Hz, 1H), 4.96 (s, 2H), 3.00 (s, 2H), 2.99-2.96 (m, 1H), 2.76-2.70 (m, 1H), 2.63-2.58 (m, 1H), 2.26 (s, 3H), 1.48 (s, 6H), 1.18 (d, J=7.2 Hz, 3H).

Example 12

3-(3-chloro-4-((5-chloro-2,2-dimethyl-2,3-dihydrobenzofuran-7-yl)methoxy)phenyl)-2-methylpropanoic acid (41)

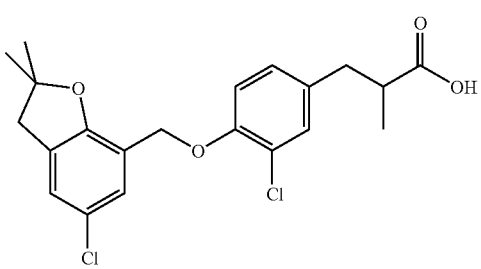

¹H NMR (400 MHz, CDCl₃) δ: 7.30 (s, 1H), 7.21 (d, J=2.0 Hz, 1H), 7.05 (s, 1H), 6.98 (dd, J=8.4, 2.0 Hz, 1H), 6.92 (d, J=8.4 Hz, 1H), 5.04 (s, 2H), 3.00 (s, 2H), 2.98-2.94 (m, 1H), 2.74-2.70 (m, 1H), 2.63-2.58 (m, 1H), 1.48 (s, 6H), 1.18 (d, J=6.4 Hz, 3H). LC-MS ESI m/z: found 407.0 [M−H]⁻

Example 13

3-(3,5-dichloro-4-((5-chloro-2,2-dimethyl-2,3-dihydrobenzofuran-7-yl)methoxy)phenyl)-2-methylpropanoic acid (42)

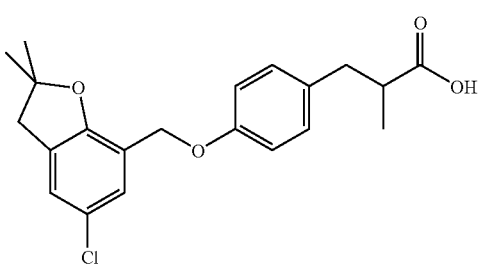

¹H NMR (400 MHz, CDCl₃) δ: 7.24 (s, 1H), 7.09 (d, J=8.8 Hz, 2H), 7.04 (s, 1H), 6.91 (d, J=8.8 Hz, 2H), 4.96 (s, 2H), 3.00 (s, 2H), 3.03-2.98 (m, 1H), 2.76-2.73 (m, 1H), 2.65-2.60 (m, 1H), 1.48 (s, 6H), 1.18 (d, J=6.8 Hz, 3H). LC-MS ESI m/z: found 373.2 [M−H]⁻

Example 14

3-(3,5-dichloro-4-((5-chloro-2,2-dimethyl-2,3-dihydrobenzofuran-7-yl)methoxy)phenyl)-2-methylpropanoic acid (43)

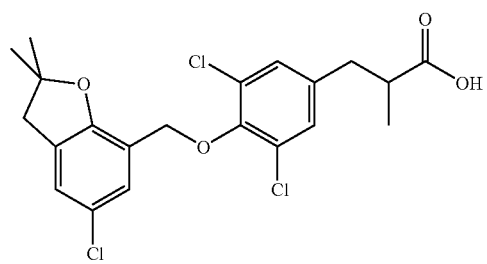

¹H NMR (400 MHz, CDCl₃) δ: 7.38 (s, 1H), 7.13 (s, 2H), 7.07 (s, 1H), 4.98 (s, 2H), 2.99 (s, 2H), 3.02-2.96 (m, 1H), 2.77-2.73 (m, 1H), 2.63-2.60 (m, 1H), 1.44 (s, 6H), 1.21 (d, J=6.8 Hz, 3H). LC-MS ESI m/z: found 441.0, 443.3, 445.3 [M−H]⁻

Example 15

3-(4-((5-chloro-2,2-dimethyl-2,3-dihydrobenzofuran-7-yl)methoxy)-3-methoxyphenyl)-2-methylpropanoic acid (44)

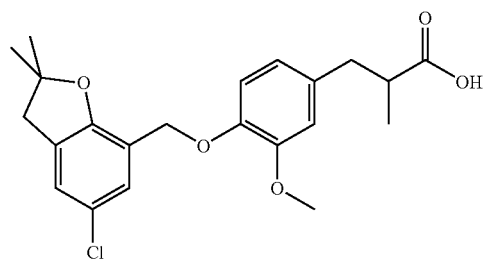

¹H NMR (400 MHz, CDCl₃) δ: 7.27 (s, 1H), 7.02 (s, 1H), 6.84 (d, J=8.4 Hz, 1H), 6.72 (d, J=1.6 Hz, 1H), 6.64 (dd, J=8.4, 1.6 Hz, 1H), 5.04 (s, 2H), 3.87 (s, 3H), 2.99 (s, 2H), 3.01-2.97 (m, 1H), 2.76-2.71 (m, 1H), 2.63-2.58 (m, 1H), 1.48 (s, 6H), 1.18 (d, J=6.8 Hz, 3H). LC-MS ESI m/z: found 403.0 [M−H]⁻

Example 16

3-(4-((5-fluoro-2,2-dimethyl-2,3-dihydrobenzofuran-7-yl)methoxy)phenyl)-2-methylpropanoic acid (45)

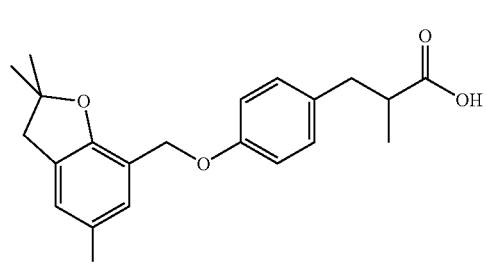

¹H NMR (400 MHz, CDCl₃) δ: 7.09 (d, J=8.6 Hz, 2H), 6.97 (d, J=10.0 Hz, 1H), 6.91 (d, J=8.6 Hz, 2H), 6.79 (d, J=7.6 Hz, 1H), 4.98 (s, 2H), 3.00 (s, 2H), 3.03-2.98 (m, 1H), 2.76-2.71 (m, 1H), 2.65-2.59 (m, 1H), 1.48 (s, 6H), 1.17 (d, J=7.2 Hz, 3H). LC-MS ESI m/z: found 357.1 [M−H]⁻

Example 17

3-(4-((2,2-dimethyl-2,3-dihydrobenzofuran-4-yl)methoxy)phenyl)-2-methylpropanoic acid (46)

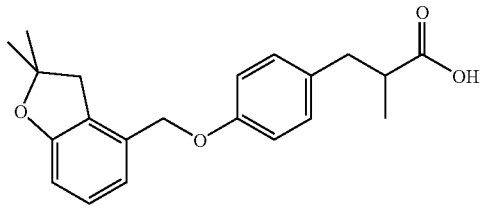

¹H NMR (400 MHz, CDCl₃) δ: 7.15-7.10 (m, 3H), 6.90-6.88 (m, 3H), 6.72 (d, J=8.4 Hz, 1H), 4.95 (s, 2H), 3.04 (s, 2H), 3.03-2.98 (m, 1H), 2.75-2.72 (m, 1H), 2.67-2.62 (m, 1H), 1.48 (s, 6H), 1.18 (d, J=6.8 Hz, 3H).

Example 18

3-(3,5-difluoro-4-((5-fluoro-2,2-dimethyl-2,3-dihydrobenzofuran-7-yl)methoxy)phenyl)-2-methylpropanoic acid (47)

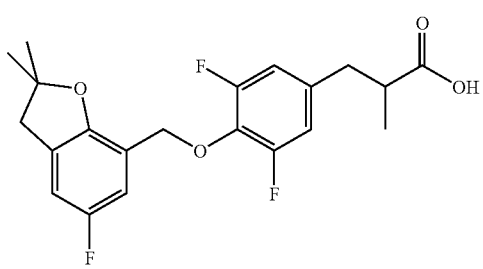

¹H NMR (400 MHz, CDCl₃) δ: 6.97 (dd, J=9.2, 2.4 Hz, 1H), 6.8 (dd, J=9.2, 2.4 Hz, 1H), 6.71 (d, J=8.8 Hz, 2H), 5.08 (s, 2H), 2.96 (s, 2H), 2.99-2.94 (m, 1H), 2.74-2.66 (m, 1H), 2.59 (dd, J=13.6, 6.8 Hz, 1H), 1.41 (s, 6H), 1.18 (d, J=6.8 Hz, 3H).

Example 19

2-(3,5-difluoro-4-((5-fluoro-2,2-dimethyl-2,3-dihydrobenzofuran-7-yl)methoxy)phenyl)cyclopropanecarboxylic acid (48)

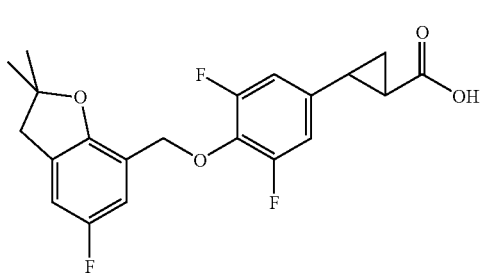

¹H NMR (400 MHz, CDCl₃) δ: 6.96 (dd, J=9.6, 2.4 Hz, 1H), 6.8 (dd, J=9.6, 2.4 Hz, 1H), 6.62 (d, J=8.4 Hz, 2H), 5.08 (s, 2H), 2.96 (s, 2H), 2.54-2.46 (m, 1H), 1.84-1.8 (m, 1H), 1.68-1.62 (m, 1H), 1.41 (s, 6H), 1.38-1.30 (m, 1H).

Example 20

3-(3,5-difluoro-4-((2-methyl-2,3-dihydrobenzofuran-7-yl)methoxy)phenyl)-2-methylpropanoic acid (49)

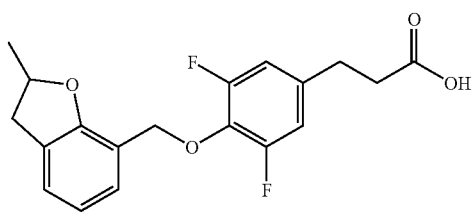

¹H NMR (400 MHz, CDCl₃) δ: 7.21 (d, J=7.6 Hz, 1H), 7.11 (d, J=7.2 Hz, 1H), 6.81 (t, J=7.6 Hz, 1H), 6.72 (d, J=8.8 Hz, 2H), 5.15 (d, J=11.4 Hz, 1H), 5.12 (d, J=11.4 Hz, 1H), 4.95-4.88 (m, 1H), 3.30 (dd, J=15.2, 7.6 Hz, 1H), 2.86 (t, J=7.6 Hz, 2H), 2.79 (dd, J=15.2, 7.6 Hz, 1H), 2.64 (t, J=7.6 Hz, 2H), 1.41 (d, J=6.4 Hz, 3H).

Example 21

3-(4-((2,2-dimethyl-2,3-dihydrobenzofuran-4-yl)methoxy)-3,5-difluorophenyl)-2-methylpropanoic acid (50)

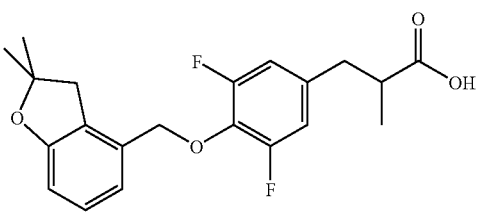

¹H NMR (400 MHz, CDCl₃) δ: 7.08 (t, J=8.0 Hz, 1H), 6.84 (d, J=8.0 Hz, 1H), 6.76-6.68 (m, 3H), 5.04 (s, 2H), 3.11 (s, 2H), 2.96 (dd, J=13.6, 7.4 Hz, 1H), 2.74-2.66 (m, 1H), 2.59 (dd, J=13.6, 7.4 Hz, 1H), 1.48 (s, 6H), 1.18 (d, J=6.8 Hz, 3H).

Example 22

2-(4-((2,2-dimethyl-2,3-dihydrobenzofuran-4-yl)methoxy)-3,5-difluorophenyl)cyclopropanecarboxylic acid (51)

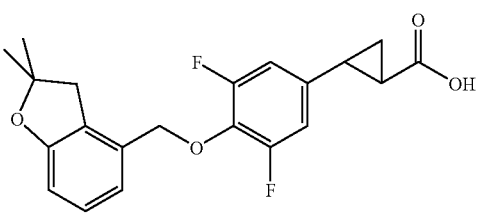

¹H NMR (400 MHz, CDCl₃) δ: 7.08 (t, J=7.8 Hz, 1H), 6.83 (d, J=7.2 Hz, 1H), 6.71 (d, J=8 Hz, 1H), 6.63 (d, J=8.8 Hz, 2H), 5.04 (s, 2H), 3.11 (s, 2H), 2.52-2.46 (m, 1H), 1.88-1.8 (m, 1H), 1.68-1.62 (m, 1H), 1.48 (s, 6H), 1.34-1.3 (m, 1H).

Example 23

3-(4-((2,2-dimethyl-2,3-dihydrobenzofuran-7-yl)methoxy)-3,5-difluorophenyl)-2-methylpropanoic acid (52)

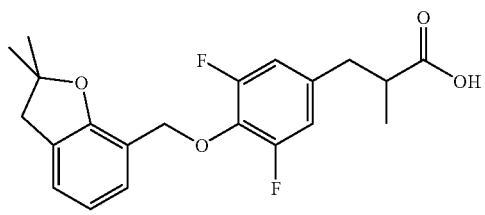

¹H NMR (400 MHz, CDCl₃) δ 7.21 (d, J=7.6 HZ, 1H), 7.06 (dd, J=7.2, 1.2 HZ, 1H), 6.79 (t, J=7.4 Hz, 1H), 6.70 (m, 2H), 5.14 (s, 2H), 2.98 (s, 2H,). 2.97-2.93 (m, 1H), 2.72-2.68 (m, 1H), 2.60-2.55 (m, 1H), 1.42 (s, 6H), 1.19 (d, J=6.8 Hz, 3H).

Example 24

2-(4-((2,2-dimethyl-2,3-dihydrobenzofuran-7-yl)methoxy)-3,5-difluorophenyl)cyclopropanecarboxylic acid (53)

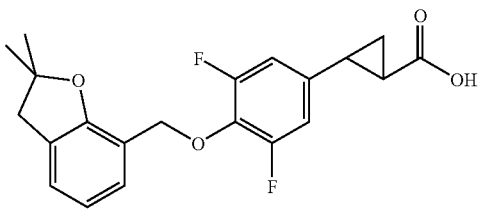

¹H NMR (400 MHz, CDCl₃) δ 7.21 (d, J=7.6 HZ, 1H), 7.08 (dd, J=7.2, 1.2 HZ, 1H), 6.79 (t, J=7.4 Hz, 1H), 6.61 (m, 2H), 5.13 (s, 2H), 2.98 (s, 2H), 2.49-2.45 (m, 1H), 1.84-1.80 (m, 1H), 1.66-1.61 (m, 1H), 1.41 (s, 6H), 1.33-1.28 (m, 1H).

Example 25

3-(4-((2,2-dimethyl-2,3-dihydrobenzofuran-7-yl)methoxy)-3,5-difluorophenyl)propanoic acid (54)

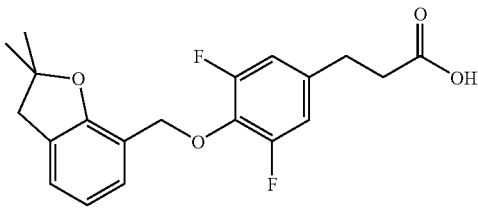

¹H NMR (400 MHz, DMSO-d₆) δ 12.14 (s, 1H), 7.14-7.09 (m, 2H), 6.96 (s, 1H), 6.93 (br s, 1H), 6.76 (t, J=7.5 Hz, 1H), 5.00 (s, 2H), 2.95 (s, 2H), 2.73 (t, J=7.6 Hz, 2H), 2.49 (m, 2H), 1.31 (s, 6H).

Example 26

3-(2-chloro-4-((5-chloro-2,2-dimethyl-2,3-dihydrobenzofuran-7-yl)methoxy)phenyl)-2-methylpropanoic acid (55)

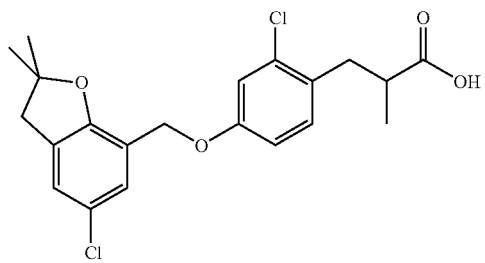

¹H NMR (400 MHz, DMSO-d₆) δ 12.18 (s, 1H), 7.22-7.17 (m, 3H), 7.07 (d, J=2.5 Hz, 1H), 6.90 (dd, J=8.5, 2.5 Hz, 1H), 4.93 (s, 2H), 3.03 (s, 2H), 2.96-2.89 (m, 1H), 2.66-2.60 (m, 2H), 1.43 (s, 6H), 1.03 (d, J=6.3 Hz, 3H). LC-MS ESI m/z: found 407.1 [M−H]⁻

Example 27

2-(3,5-difluoro-4-((4-fluoro-2,2-dimethyl-2,3-dihydrobenzofuran-7-yl)methoxy)phenyl)cyclopropanecarboxylic acid (56)

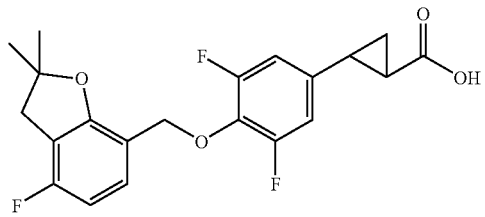

¹H NMR (400 MHz, DMSO-d₆) δ 12.34 (s, 1H), 7.16-7.12 (m, 1H), 6.95-6.91 (m, 2H), 6.63-6.59 (m, 1H), 4.96 (s, 2H), 2.99 (s, 2H), 2.37-2.32 (m, 1H), 1.81-1.77 (m, 1H), 1.41-1.28 (m, 8H). LC-MS ESI m/z: found 390.9 [M−H]⁻

Example 28

3-(3,5-difluoro-4-((4-fluoro-2,2-dimethyl-2,3-dihydrobenzofuran-7-yl)methoxy)phenyl)-2-methylpropanoic acid (57)

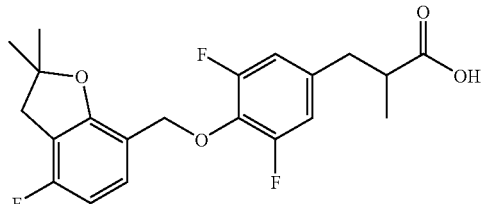

¹H NMR (400 MHz, DMSO-d₆) δ 12.18 (s, 1H), δ 7.16-7.12 (m, 1H), 6.93-6.90 (m, 2H), 6.63-6.58 (m, 1H), 4.98 (s, 2H), 3.00 (s, 2H), 2.80 (dd, J=12.9, 6.6, 1H), 2.63-2.51 (m, 2H), 1.34 (s, 6H), 1.00 (d, J=6.7 Hz, 3H). LC-MS ESI m/z: found 392.8 [M−H]⁻

Example 29

3-(3-fluoro-4-((4-fluoro-2,2-dimethyl-2,3-dihydrobenzofuran-7-yl)methoxy)phenyl)-2-methylpropanoic acid (58)

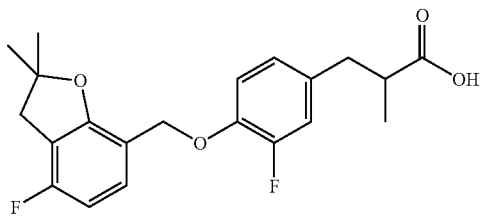

¹H NMR (400 MHz, DMSO-d₆) δ 12.12 (s, 1H), 7.24-7.21 (m, 1H), 7.14-7.10 (m, 1H), 7.03-7.01 (m, 1H), 6.91-6.89 (m, 1H), 6.66 (t, J=8.6 Hz, 1H), 4.95 (s, 2H), 3.06 (s, 2H), 2.80 (m, 1H), 2.59-2.53 (m, 2H), 1.42 (s, 6H), 1.00 (d, J=6.5 Hz, 3H). LC-MS ESI m/z: found 375.0 [M−H]⁻

Example 30

3-(4-((4-fluoro-2,2-dimethyl-2,3-dihydrobenzofuran-7-yl)methoxy)phenyl)-2-methylpropanoic acid (59)

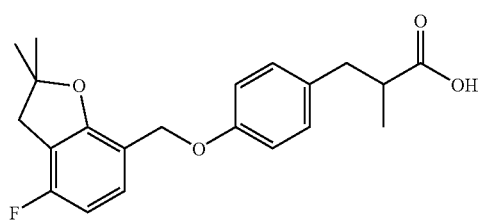

¹H NMR (400 MHz, DMSO-d₆) δ 12.07 (s, 1H), 7.23-7.20 (m, 1H), 7.07 (d, J=8.4 Hz, 2H), 6.87 (d, J=8.5 Hz, 2H), 6.65 (t, J=8.6 Hz, 1H), 4.87 (s, 2H), 3.06 (s, 2H), 2.81-2.78 (m, 1H), 2.56-2.51 (m, 2H), 1.45 (s, 6H), 1.00 (d, J=6.5 Hz, 3H). LC-MS ESI m/z: found 357.2 [M−H]⁻

Example 31

2-(4-((2,2-dimethyl-4-(trifluoromethyl)-2,3-dihydrobenzofuran-7-yl)methoxy)-3,5-difluorophenyl)cyclopropanecarboxylic acid (60)

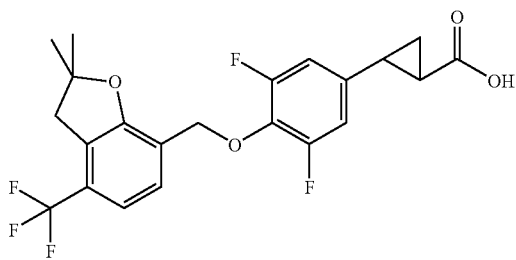

¹H NMR (400 MHz, DMSO-d₆) δ 12.27 (s, 1H), 7.36 (d, J=7.9 Hz, 1H), 7.12 (d, J=7.9 Hz, 1H), 6.97-6.95 (m, 2H), 5.06 (s, 2H), 3.12 (s, 2H), 2.38-2.32 (m, 1H), 1.81-1.79 (m, 1H), 1.42-1.30 (m, 8H). LC-MS ESI m/z: found 441.3 [M−H]⁻

Example 32

3-(4-((2,2-dimethyl-4-(trifluoromethyl)-2,3-dihydrobenzofuran-7-yl)methoxy)-3,5-difluorophenyl)-2-methylpropanoic acid (61)

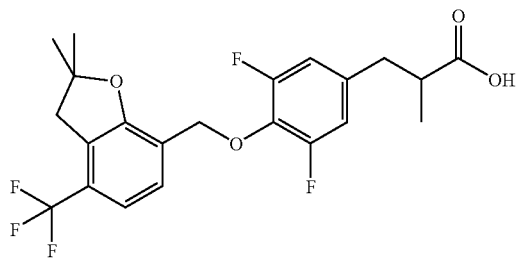

¹H NMR (400 MHz, DMSO-d₆) δ 12.19 (s, 1H), 7.36 (d, J=8.1 Hz, 1H), 7.12 (d, J=7.9 Hz, 1H), 6.96-6.94 (m, 2H), 5.07 (s, 2H), 3.13 (s, 2H), 2.81 (dd, J=12.8, 6.6 Hz, 1H), 2.68-2.48 (m, 2H), 1.37 (s, 6H), 1.00 (d, J=6.7 Hz, 3H). LC-MS ESI m/z: found 443.2 [M−H]⁻

Example 33

3-(4-((2,2-dimethyl-4-(trifluoromethyl)-2,3-dihydrobenzofuran-7-yl)methoxy)-3-fluorophenyl)-2-methylpropanoic acid (62)

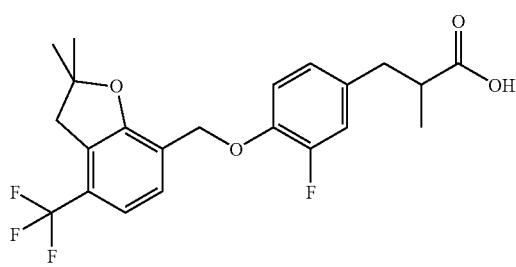

¹H NMR (400 MHz, DMSO-d₆) δ 12.13 (s, 1H), 7.40 (d, J=7.9 Hz, 1H), 7.16-7.03 (m, 3H), 6.91 (d, J=8.3 Hz, 1H), 5.06 (s, 2H), 3.18 (s, 2H), 2.81-2.79 (m, 1H), 2.62-2.51 (m, 2H), 1.46 (s, 6H), 1.00 (d, J=6.6 Hz, 3H). LC-MS ESI m/z: found 425.0 [M−H]⁻

Example 34

3-(4-((2,2-dimethyl-4-(trifluoromethyl)-2,3-dihydrobenzofuran-7-yl)methoxy)phenyl)-2-methylpropanoic acid (63)

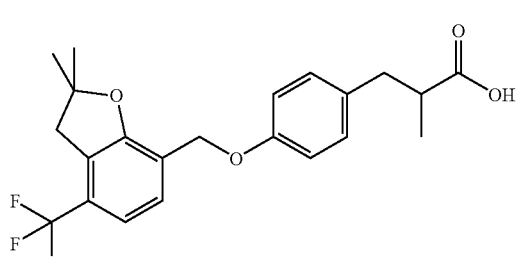

¹H NMR (400 MHz, DMSO-d₆) δ 12.07 (s, 1H), 7.39 (d, J=8.2 Hz, 1H), 7.12-7.07 (m, 3H), 6.89 (d, J=8.5 Hz, 2H), 4.99 (s, 2H), 3.18 (s, 2H), 2.81-2.78 (m, 1H), 2.58-2.51 (m, 2H), 1.46 (s, 6H), 1.00 (d, J=6.5 Hz, 3H). LC-MS ESI m/z: found 407.1 [M−H]⁻

Example 35A and 35B 2-(4-((5-chloro-2,2-dimethyl-2,3-dihydrobenzofuran-7-yl)methoxy)-3,5-difluoro phenyl)cyclopropanecarboxylic acid (64)

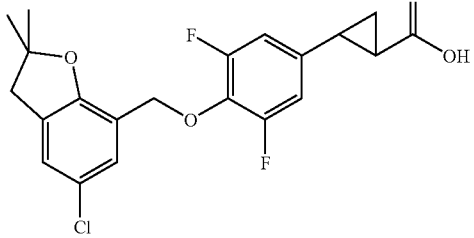

¹H NMR (400 MHz, CDCl₃) δ 7.21 (s, 1H), 7.05 (s, 1H), 6.65-6.60 (m, 2H), 5.03 (s, 2H), 2.51-2.47 (m, 1H), 1.84-1.81 (m, 1H), 1.67-1.62 (m, 1H), 1.38 (s, 6H), 1.33-1.30 (m, 1H). Chiral separation of (64), using preparative Regis Pack, 5/100, 250×21.1 mm, flow rate 30 mL/min, solvent system 2.5:97.5:0.1 of iso-Propanol:Hexanes:Acetic acid, provided (64A) (RT=15-25 minutes) and (64B) (RT=26-35 minutes). (64A): ¹H NMR (400 MHz, CDCl₃) δ 7.21 (s, 1H), 7.04 (s, 1H), 6.62 (d, J=7.2 Hz, 2H), 5.05 (s, 2H), 2.96 (s, 2H), 2.48 (s, 1H), 1.83 (s, 1H), 1.64 (s, 1H), 1.40 (s, 6H), 1.31 (s, 1H). LC-MS ESI m/z: found 407.0 (M−H)⁻.
Chiral separation of (64), using preparative Regis Pack, 5/100, 250×21.1 mm, flow rate 30 mL/min, solvent system 2.5:97.5:0.1 of iso-Propanol:Hexanes:Acetic acid, provided (64A) (RT=15-25 minutes) and (64B) (RT=26-35 minutes). (64B): ¹H NMR (400 MHz, CDCl₃) δ 7.21 (s, 1H), 7.05 (s, 1H), 6.62 (d, J=7.8 Hz, 2H), 5.05 (s, 2H), 2.95 (s, 2H), 2.54-2.40 (m, 1H), 1.86-1.80 (m, 1H), 1.66-1.60 (m, 1H), 1.40 (s, 6H), 1.35-1.27 (m, 1H). LC-MS ESI m/z: found 407.0 (M−H)⁻.

Example 36

2-(5-((5-chloro-2,2-dimethyl-2,3-dihydrobenzofuran-7-yl)methoxy)-2,3-dihydro-1H-inden-1-yl)acetic acid (65)

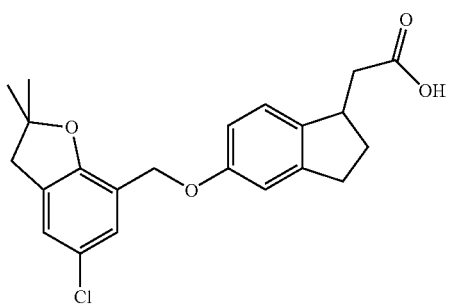

¹H NMR (400 MHz, CDCl₃) δ 7.24 (s, 1H), 7.09 (d, J=8.3 Hz, 1H), 7.04 (s, 1H), 6.87 (s, 1H), 6.81 (d, J=8.3 Hz, 1H), 4.96 (s, 2H), 3.61-3.45 (m, 1H), 3.00 (s, 2H), 2.95-2.77 (m, 3H), 2.50-2.38 (m, 2H), 1.82-1.75 (m, 1H), 1.48 (s, 6H).

Example 37

2-(5-((5-fluoro-2,2-dimethyl-2,3-dihydrobenzofuran-7-yl)methoxy)-2,3-dihydro-1H-inden-1-yl)acetic acid (66)

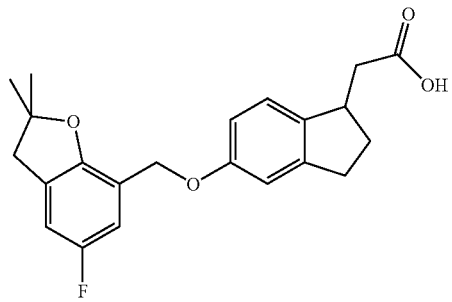

¹H NMR (400 MHz, CDCl₃) δ 7.08 (m, 1H), 7.02-6.93 (m, 1H), 6.87 (s, 1H), 6.80 (m, 2H), 4.97 (s, 2H), 3.61-3.45 (m, 1H), 2.99 (s, 2H), 2.92-2.74 (m, 3H), 2.50-2.35 (m, 2H), 1.77 (m, 1H), 1.48 (s, 6H).

Example 38

3-(4-((5-chloro-2,2-dimethyl-2,3-dihydrobenzofuran-7-yl)methoxy)-3,5-difluorophenyl)-2-methylpropanoic acid (67)

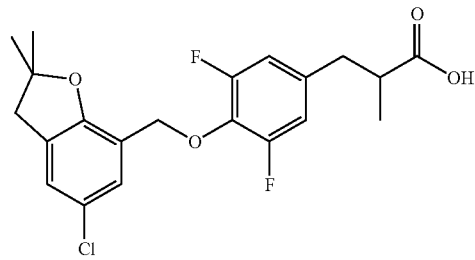

¹H NMR (400 MHz, CDCl₃) δ 7.22 (s, 1H), 7.04 (s, 1H), 6.72 (s, 1H), 6.70 (s, 1H), 5.07 (s, 2H), 3.03-2.91 (m, 3H), 2.72 (m, 1H), 2.59 (m, 1H), 1.42 (s, 6H), 1.19 (d, J=7.0 Hz, 3H).

Example 39

3-(4-((5-chloro-2,2-dimethyl-2,3-dihydrobenzofuran-7-yl)methoxy)-2-methoxyphenyl)-2-methylpropanoic acid (68)

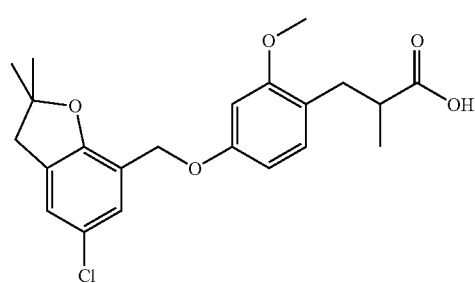

¹H NMR (400 MHz, CDCl₃) δ 7.05-6.99 (m, 3H), 6.52-6.48 (m, 2H), 4.96 (s, 2H), 3.79 (s, 3H), 3.00 (s, 2H), 2.98-2.94 (m, 1H), 2.84-2.80 (m, 1H), 2.66-2.61 (m, 1H), 1.48 (s, 6H), 1.15 (d, J=7.0 Hz, 3H).

Example 40

3-(4-((2,3-dimethyl-2,3-dihydrobenzofuran-7-yl)methoxy)-3,5-difluorophenyl)-2-methylpropanoic acid (69)

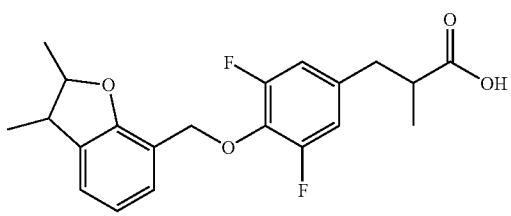

LC-MS ESI m/z: found 375.1 [M–H]⁻

Example 41

2-(2-(4-((5-chloro-2,2-dimethyl-2,3-dihydrobenzofuran-7-yl)methoxy)-3,5-difluorophenyl)cyclopropyl)acetic acid (70)

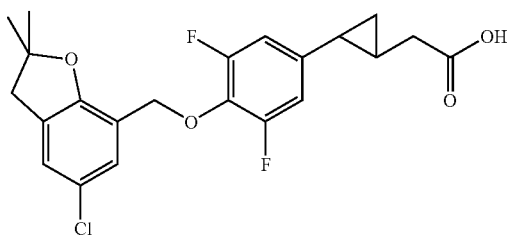

¹H NMR (400 MHz, CDCl₃) δ 7.23 (s, 1H), 7.04 (s, 1H), 6.61 (d, J=8.9 Hz, 2H), 5.04 (s, 2H), 2.95 (s, 2H), 2.50-2.38 (m, 2H), 1.74-1.65 (m, 1H), 1.40 (s, 6H), 1.30-1.25 (m, 1H), 0.98-0.88 (m, 2H).

Example 42

3-(4-((5,6-difluoro-2,2-dimethyl-2,3-dihydrobenzofuran-7-yl)methoxy)-3,5-difluorophenyl)-2-methylpropanoic acid (71)

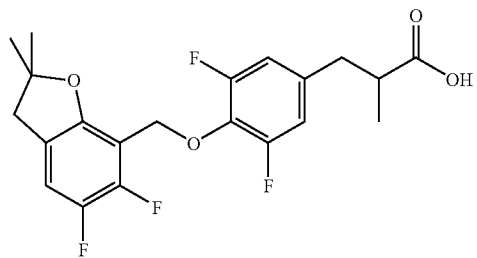

¹H NMR (400 MHz, DMSO-d₆) δ 7.27 (t, J=9.2 Hz, 1H), 6.91 (d, J=9.2 Hz, 2H), 5.04 (s, 2H), 2.91 (s, 2H), 2.82-2.77 (m, 1H), 2.61-2.51 (m, 2H), 1.25 (s, 6H), 0.98 (d, J=6.4 Hz, 3H). LC-MS ESI m/z: found 411.1 [M–H]⁻.

Example 43

3-(4-((5,6-difluoro-2,2-dimethyl-2,3-dihydrobenzofuran-7-yl)methoxy)phenyl)-2-methylpropanoic acid (72)

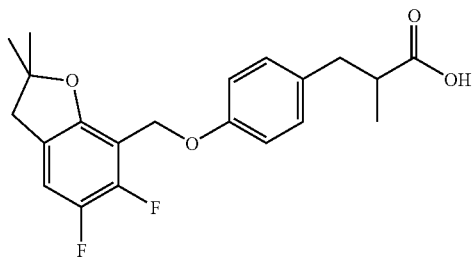

¹H NMR (400 MHz, DMSO-d₆) δ 7.31 (t, J=9.0 Hz, 1H), 7.07 (d, J=8.8 Hz, 2H), 6.90 (d, J=8.8 Hz, 2H), 4.93 (s, 2H), 3.00 (s, 2H), 2.79 (m, 1H), 2.54 (m, 2H), 1.31 (s, 6H), 0.99 (d, J=6.4 Hz, 3H). LC-MS ESI m/z: found 375.1 [M–H]⁻.

Example 44

3-(4-(((2,2-dimethyl-2,3-dihydrobenzofuran-7-yl)oxy)methyl)-3-fluorophenyl)-2-methylpropanoic acid (73)

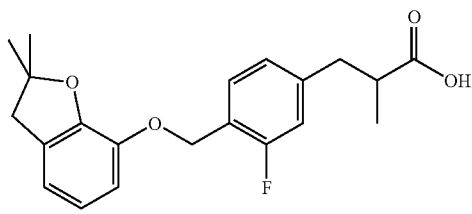

¹H NMR (400 MHz, DMSO-d₆) δ 12.20 (s, 1H), 7.41-7.37 (m, 1H), 7.08-7.02 (m, 2H), 6.84 (d, J=8.0 Hz, 1H), 6.77 (d, J=7.2 Hz, 1H), 6.71-6.67 (m, 1H), 5.03 (s, 2H), 2.96 (s, 2H), 2.89-2.85 (m, 1H), 2.64-2.60 (m, 2H), 1.37 (s, 6H), 1.02 (d, J=6.0 Hz, 3H). LC-MS ESI m/z: found 357.1 [M–H]⁻.

Example 45

3-(4-((6-fluoro-4H-benzo[d][1,3]dioxin-8-yl)methoxy)phenyl)-2-methylpropanoic acid (74)

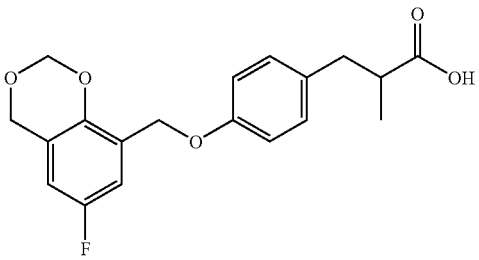

¹H NMR (400 MHz, DMSO-d₆) δ 12.08 (s, 1H), 7.12-7.07 (m, 3H), 6.94 (d, J=8.4 Hz, 1H), 6.89 (d, J=7.6 Hz, 2H), 5.28 (s, 2H), 4.96 (s, 2H), 4.88 (s, 2H), 2.80-2.79 (m, 1H), 2.57-2.54 (m, 2H), 0.99 (d, J=6.0 Hz, 3H). LC-MS ESI m/z: found 345.1 [M−H]⁻.

Example 46

3-(4-((5-fluoro-2,2-dimethyl-2,3-dihydrobenzofuran-7-yl)methoxy)-2-methylphenyl)propanoic acid (75)

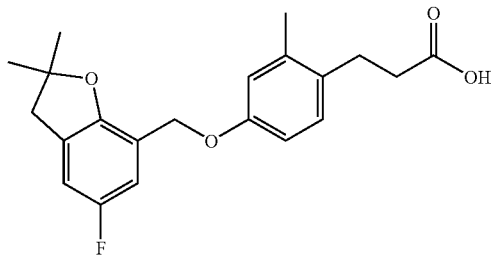

¹H NMR (400 MHz, DMSO-d₆) δ 12.09 (s, 1H), 7.01-6.99 (m, 2H), 6.95-6.92 (m, 1H), 6.76 (s, 1H), 6.71-6.69 (m, 1H), 4.86 (s, 2H), 3.01 (s, 2H), 2.70 (t, J=7.6 Hz, 2H), 2.40 (t, J=7.6 Hz, 2H), 2.20 (s, 3H), 1.41 (s, 6H). LC-MS ESI m/z: found 357.5 [M−H]⁻.

Example 47

3-(2-chloro-4-((5-fluoro-2,2-dimethyl-2,3-dihydrobenzofuran-7-yl)methoxy)phenyl)propanoic acid (76)

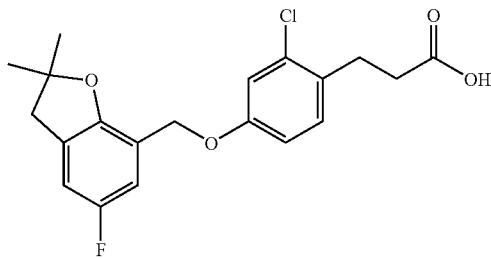

¹H NMR (400 MHz, DMSO-d₆) δ 12.20 (s, 1H), 7.23-7.20 (m, 1H), 7.05-7.01 (m, 2H), 6.97-6.95 (m, 1H), 6.90-6.88 (m, 1H), 4.92 (s, 2H), 3.01 (s, 2H), 2.84-2.79 (m, 2H), 2.48-2.43 (m, 2H), 1.41 (s, 6H). LC-MS ESI m/z: found 377.1 [M−H]⁻.

Example 48

3-(2-fluoro-4-((5-fluoro-2,2-dimethyl-2,3-dihydrobenzofuran-7-yl)methoxy)phenyl)propanoic acid (77)

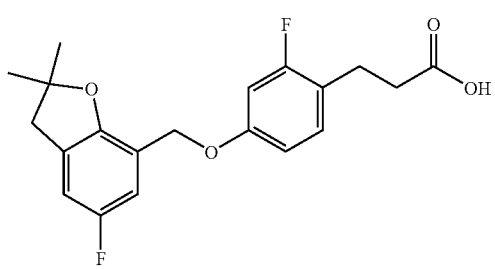

¹H NMR (400 MHz, DMSO-d₆) δ 12.15 (s, 1H), 7.16 (t, J=8.6 Hz, 1H), 7.02 (d, J=7.6 Hz, 1H), 6.96 (d, J=10.0 Hz, 1H), 6.81 (d, J=12.0 Hz, 1H), 6.73 (d, J=8.4 Hz, 1H), 4.90 (s, 2H), 3.01 (s, 2H), 2.72 (t, J=7.6 Hz, 2H), 2.44 (t, J=7.6 Hz, 2H), 1.40 (s, 6H). LC-MS ESI m/z: found 361.4 [M−H]⁻.

Example 49

3-(2,6-difluoro-4-((5-fluoro-2,2-dimethyl-2,3-dihydrobenzofuran-7-yl)methoxy)phenyl)propanoic acid (78)

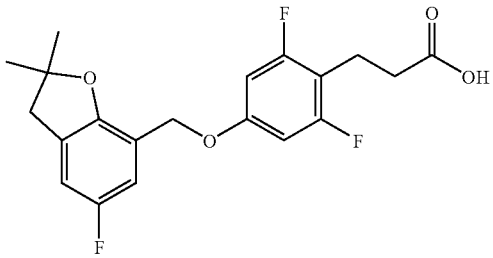

¹H NMR (400 MHz, DMSO-d₆) δ 12.20 (s, 1H), 7.04 (d, J=8.4 Hz, 1H), 6.98 (d, J=9.6 Hz, 1H), 6.75 (d, J=9.2 Hz, 1H), 4.91 (s, 2H), 3.01 (s, 2H), 2.73 (t, J=7.6 Hz, 2H), 2.39 (t, J=7.4 Hz, 2H), 1.40 (s, 6H). LC-MS ESI m/z: found 379.1 [M−H]⁻.

Example 50

3-(4-((5-fluoro-2,2-dimethyl-2,3-dihydrobenzofuran-7-yl)methoxy)-2-methoxyphenyl)propanoic acid (79)

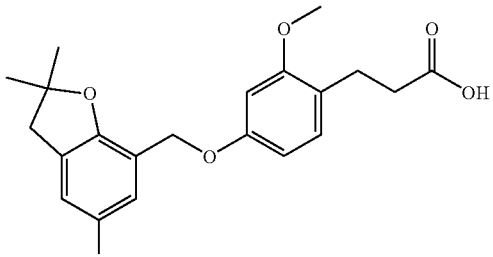

¹H NMR (400 MHz, DMSO-d₆) δ 12.02 (s, 1H), 7.02-6.95 (m, 3H), 6.56 (s, 1H), 6.47 (d, J=8.0 Hz, 1H), 4.89 (s, 2H), 3.73 (s, 3H), 3.01 (s, 2H), 2.66 (t, J=7.6 Hz, 2H), 2.37 (t, J=7.4 Hz, 2H), 1.40 (s, 6H). LC-MS ESI m/z: found 373.4 [M−H]⁻.

Example 51

3-(4-((5-chloro-2,2-dimethyl-2,3-dihydrobenzofuran-7-yl)methoxy)-2-methylphenyl)propanoic acid (80)

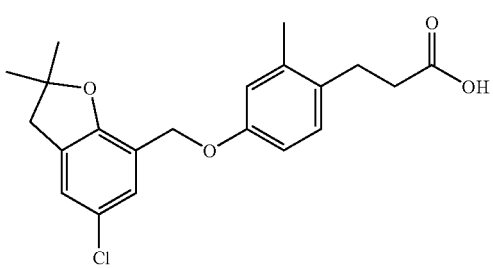

¹H NMR (400 MHz, DMSO-d₆) δ 12.10 (s, 1H), 7.17 (d, J=10.4 Hz, 2H), 7.00 (d, J=8.4 Hz, 1H), 6.77 (d, J=8.4 Hz, 1H), 6.71 (d, J=8.4 Hz, 1H), 4.86 (s, 2H), 3.01 (s, 2H), 2.70 (t, J=7.6 Hz, 2H), 2.40 (t, J=7.8 Hz, 2H), 2.20 (s, 3H), 1.41 (s, 6H). LC-MS ESI m/z: found 373.2 [M–H]⁻.

Example 52

3-(2-chloro-4-((5-chloro-2,2-dimethyl-2,3-dihydrobenzofuran-7-yl)methoxy)phenyl)-propanoic acid (81)

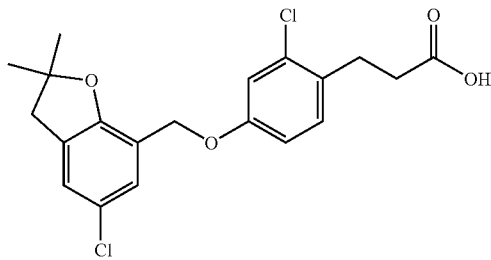

¹H NMR (400 MHz, DMSO-d₆) δ 12.18 (s, 1H), 7.23-7.18 (m, 3H), 7.05 (s, 1H), 6.89 (d, J=8.4 Hz, 1H), 4.92 (s, 2H), 3.01 (s, 2H), 2.81 (t, J=7.6 Hz, 2H), 2.45 (t, J=8.0 Hz, 2H), 1.41 (s, 6H). LC-MS ESI m/z: found 393.3 [M–H]⁻.

Example 53

3-(4-((5-chloro-2,2-dimethyl-2,3-dihydrobenzofuran-7-yl)methoxy)-2-fluorophenyl)-propanoic acid (82)

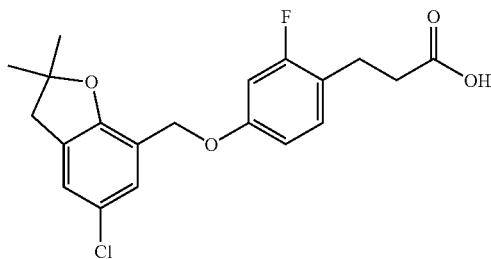

¹H NMR (400 MHz, DMSO-d₆) δ 12.14 (s, 1H), 7.20-7.14 (m, 3H), 6.82 (d, J=11.6 Hz, 1H), 6.74 (d, J=8.4 Hz, 1H), 4.90 (s, 2H), 3.02 (s, 2H), 2.73 (t, J=7.6 Hz, 2H), 2.44 (t, J=7.6 Hz, 2H), 1.41 (s, 6H). LC-MS ESI m/z: found 377.2 [M–H]⁻.

Example 54

3-(4-((5-chloro-2,2-dimethyl-2,3-dihydrobenzofuran-7-yl)methoxy)-2,6-difluorophenyl)propanoic acid (83)

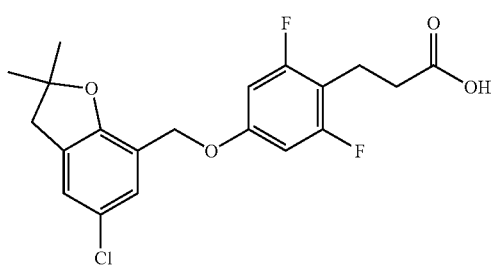

¹H NMR (400 MHz, DMSO-d₆) δ 12.19 (br, 1H), 7.27-7.20 (m, 2H), 6.75 (d, J=9.2 Hz, 2H), 4.92 (s, 2H), 3.02 (s, 2H), 2.74 (t, J=7.6 Hz, 2H), 2.40 (t, J=7.6 Hz, 2H), 1.41 (s, 6H). LC-MS ESI m/z: found 395.1 [M–H]⁻.

Example 55

3-(4-((5-chloro-2,2-dimethyl-2,3-dihydrobenzofuran-7-yl)methoxy)-2-methoxyphenyl)propanoic acid (84)

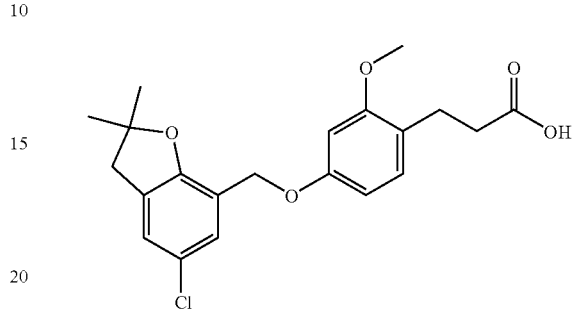

¹H NMR (400 MHz, DMSO-d₆) δ 12.03 (br, 1H), 7.21-7.17 (m, 2H), 6.98 (d, J=8.0 Hz, 1H), 6.56 (s, 1H), 6.47 (d, J=8.0 Hz, 1H), 4.89 (s, 2H), 3.74 (s, 3H), 3.02 (s, 2H), 2.66 (t, J=7.6 Hz, 2H), 2.38 (t, J=7.8 Hz, 2H), 1.41 (s, 6H). LC-MS ESI m/z: found 389.4 [M–H]⁻.

Example 56

3-(2-bromo-4-((5-fluoro-2,2-dimethyl-2,3-dihydrobenzofuran-7-yl)methoxy)-5-methoxyphenyl) propanoic acid (85)

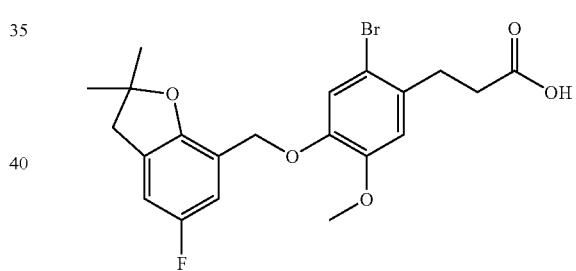

¹H NMR (400 MHz, DMSO-d₆) δ 12.20 (br, 1H), 7.14 (s, 1H), 7.03-6.92 (m, 3H), 4.90 (s, 2H), 3.72 (s, 3H), 3.01 (s, 2H), 2.80 (m, 2H), 2.47 (m, 2H), 1.40 (s, 6H). LC-MS ESI m/z: found 452.1 [M–H]⁻.

Example 57

3-(2-bromo-4-((5-chloro-2,2-dimethyl-2,3-dihydrobenzofuran-7-yl)methoxy)-5-methoxyphenyl) propanoic acid (86)

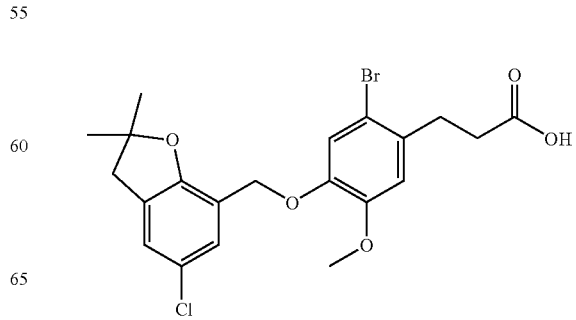

¹H NMR (400 MHz, DMSO-d₆) δ 12.21 (br, 1H), 7.20-7.14 (m, 3H), 6.96 (s, 1H), 4.90 (s, 2H), 3.71 (s, 3H), 3.01 (s, 2H), 2.80 (m, 2H), 2.47 (m, 2H), 1.41 (s, 6H). LC-MS ESI m/z: found 467.0 [M−H]⁻.

Example 58

2-((4-((5-fluoro-2,2-dimethyl-2,3-dihydrobenzofuran-7-yl)methoxy)phenyl)thio)-acetic acid (87)

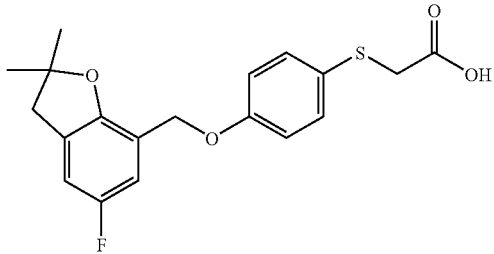

¹H NMR (400 MHz, DMSO-d₆) δ 12.58 (br, 1H), 7.30 (d, J=7.2 Hz, 2H), 7.02-6.94 (m, 4H), 4.90 (s, 2H), 3.61 (s, 2H), 3.00 (s, 2H), 1.40 (s, 6H). LC-MS ESI m/z: found 361.2 [M−H]⁻.

Example 59

2-((4-((5-chloro-2,2-dimethyl-2,3-dihydrobenzofuran-7-yl)methoxy)phenyl)thio)-acetic acid (88)

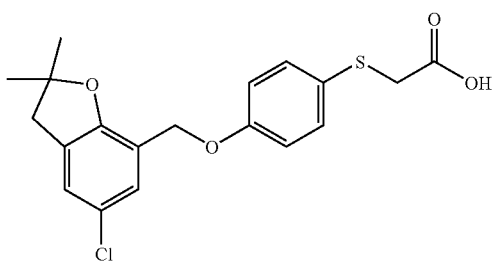

¹H NMR (400 MHz, DMSO-d₆) δ 12.60 (br, 1H), 7.30 (d, J=7.2 Hz, 2H), 7.23-7.18 (m, 2H), 6.95 (d, J=8.0 Hz, 2H), 4.90 (s, 2H), 3.61 (s, 2H), 3.01 (s, 2H), 1.41 (s, 6H). LC-MS ESI m/z: found 377.0 [M−H]⁻.

Example 60

(E)-3-(2-ethyl-4-((5-fluoro-2,2-dimethyl-2,3-dihydrobenzofuran-7-yl)methoxy)phenyl)acrylic acid (89)

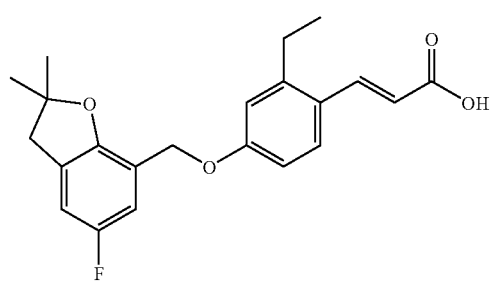

¹H NMR (400 MHz, DMSO-d₆) δ 12.27 (br, 1H), 7.77-7.73 (m, 1H), 7.68-7.62 (m, 1H), 7.04-7.00 (m, 1H), 6.99-6.96 (m, 1H), 6.87-6.84 (m, 2H), 6.29 (d, J=15.6 Hz, 1H), 4.95 (s, 2H), 3.01 (s, 2H), 2.69-2.67 (m, 2H), 1.41 (s, 6H), 1.10-1.08 (m, 3H). LC-MS ESI m/z: found 369.2 [M−H]⁻.

Example 61

3-(4-((5-fluoro-2,2-dimethyl-2,3-dihydrobenzofuran-7-yl)methoxy)-2-(trifluoromethyl)phenyl)propanoic acid (90)

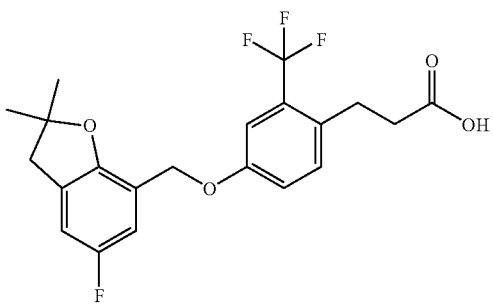

¹H NMR (400 MHz, DMSO-d₆) δ 12.22 (br, 1H), 7.39-7.37 (m, 1H), 7.23-7.20 (m, 2H), 7.03-6.97 (m, 2H), 4.98 (s, 2H), 3.00 (s, 2H), 2.89-2.86 (m, 2H), 2.49-2.44 (m, 2H), 1.40 (s, 6H). LC-MS ESI m/z: found 411.5 [M−H]⁻.

Example 62

3-(4-((5-chloro-2,2-dimethyl-2,3-dihydrobenzofuran-7-yl)methoxy)-2-(trifluoromethyl)phenyl)propanoic acid (91)

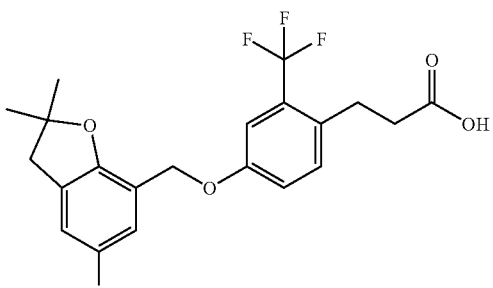

¹H NMR (400 MHz, DMSO-d₆) δ 12.22 (br, 1H), 7.40-7.38 (m, 1H), 7.23-7.19 (m, 4H), 4.98 (s, 2H), 3.01 (s, 2H), 2.89-2.86 (m, 2H), 2.49-2.45 (m, 2H), 1.40 (s, 6H). LC-MS ESI m/z: found 427.4 [M−H]⁻.

Example 63

3-(7-((5-fluoro-2,2-dimethyl-2,3-dihydrobenzofuran-7-yl)methoxy)-2,3-dihydro-1H-inden-4-yl)propanoic acid (92)

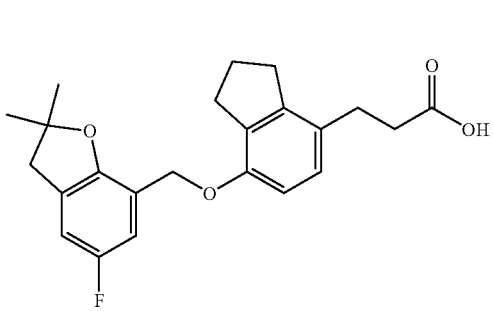

¹H NMR (400 MHz, CDCl₃) δ 6.99-6.96 (m, 1H), 6.94-6.90 (m, 1H), 6.79-6.77 (m, 1H), 6.72-6.68 (m, 1H), 5.00 (s, 2H), 3.00 (s, 2H), 2.98-2.85 (m, 6H), 2.62 (t, J=8.0 Hz, 2H), 2.12-2.06 (m, 2H), 1.48 (s, 6H). LC-MS ESI m/z: found 383.1 [M–H]⁻.

Example 64

3-(7-((5-chloro-2,2-dimethyl-2,3-dihydrobenzofuran-7-yl)methoxy)-2,3-dihydro-1H-inden-4-yl)propanoic acid (93)

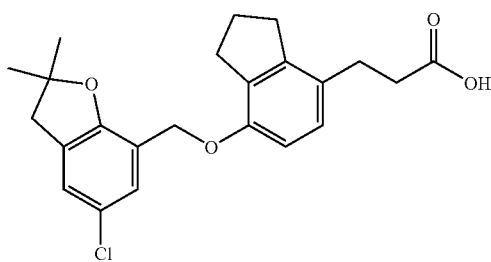

¹H NMR (400 MHz, CDCl₃) δ 7.26-7.24 (m, 1H), 7.05-7.02 (m, 1H), 6.92 (d, J=8.2 Hz, 1H), 6.71 (d, J=8.2 Hz, 1H), 4.98 (s, 2H), 3.00 (s, 2H), 2.97-2.83 (m, 6H), 2.62 (t, J=7.8 Hz, 2H), 2.10 (t, J=7.8 Hz, 2H), 1.48 (s, 6H). LC-MS ESI m/z: found 399.3 [M–H]⁻.

Example 65

(R)-3-(4-((5-fluoro-2,2-dimethyl-2,3-dihydrobenzofuran-7-yl)methoxy)phenyl)-2-methylpropanoic acid (94)

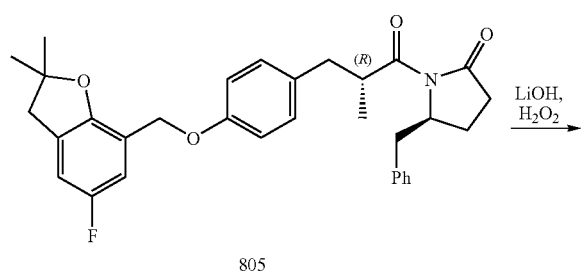

To a solution of lithium hydroxide (65 mg, 1.55 mmol) in water (2 mL) was added 30% hydrogen peroxide (0.4 mL, 3.88 mmol) and stirred for 30 minutes. The solution was cooled to 0° C. and was added to a solution of (S)-5-benzyl-1-((R)-3-(4-((5-fluoro-2,2-dimethyl-2,3-dihydrobenzofuran-7-yl)methoxy)phenyl)-2-methylpropanoyl)pyrrolidin-2-one (805) (500 mg, 0.97 mmol) in 4:1 tetrahydrofuran/water (5 mL) at 0° C. The reaction was stirred for 1 hour at 0° C. and was quenched with sodium sulfite (489 mg, 3.88 mmol) in water (3 mL). The solvent was removed in vacuo at room temperature. The solution was cooled to 0° C. and was acidified with 6N HCl. The aqueous layer was extracted with ethyl acetate, dried over sodium sulfate, filtered, and concentrated in vacuo. The crude compound was purified by flash column chromatography on silica gel with hexanes and EtOAc (20%) to afford (R)-3-(4-((5-fluoro-2,2-dimethyl-2,3-dihydrobenzofuran-7-yl)methoxy)phenyl)-2-methylpropanoic acid (94). ¹H NMR (400 MHz, CDCl₃) δ: 7.09 (d, J=8.5 Hz, 2H), 6.97 (d, J=9.7 Hz, 1H), 6.91 (d, J=8.5 Hz, 2H), 6.79 (d, J=7.6 Hz, 1H), 4.97 (s, 2H), 3.05-2.95 (m, 3H), 2.75-2.58 (m, 2H), 1.48 (s, 6H), 1.16 (d, J=4.0 Hz, 3H). LC-MS ESI m/z: found 357.0 [M–H]⁻.

Example 66

(S)-3-(4-((5-fluoro-2,2-dimethyl-2,3-dihydrobenzofuran-7-yl)methoxy)phenyl)-2-methylpropanoic acid (95)

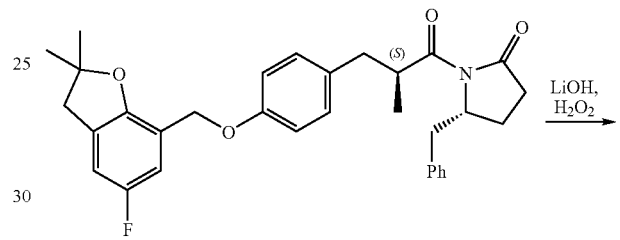

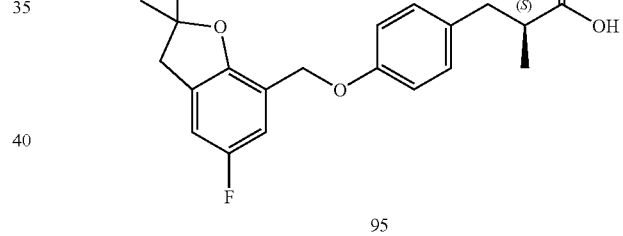

Compound (95) was prepared in a similar manner as that described for the synthesis of (94). ¹H NMR (400 MHz, CDCl₃) δ: 7.09 (d, J=8.5 Hz, 2H), 6.94 (d, J=9.7 Hz, 1H), 6.91 (d, J=8.5 Hz, 2H), 6.79 (d, J=7.6 Hz, 1H), 4.97 (s, 2H), 3.05-2.95 (m, 3H), 2.75-2.58 (m, 2H), 1.48 (s, 6H), 1.16 (d, J=4.0 Hz, 3H). LC-MS ESI m/z: found 357.0 [M–H]⁻.

Example 67

3-(4-(((5-fluoro-2,2-dimethyl-2,3-dihydrobenzofuran-7-yl)methyl)amino)phenyl)-2-methylpropanoic acid (96)

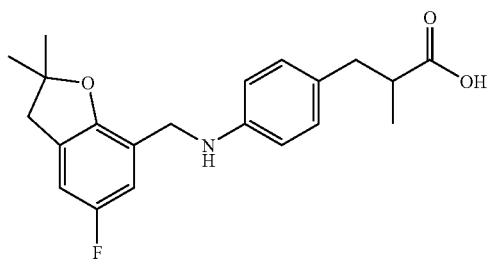

$^1$H NMR (400 MHz, DMSO-$d_6$) δ 6.93-6.77 (m, 4H), 6.49 (d, J=7.8 Hz, 2H), 4.05 (s, 2H), 2.98 (s, 2H), 2.70-2.66 (m, 1H), 2.47-2.39 (m, 2H), 1.40 (s, 6H), 0.95 (d, J=8.0 Hz, 3H). LC-MS ESI m/z: found 356.3 [M−H]$^−$.

Example 68

3-(4-(5-fluoro-2,2-dimethyl-2,3-dihydrobenzofuran-7-carboxamido)phenyl)-2-methylpropanoic acid (97)

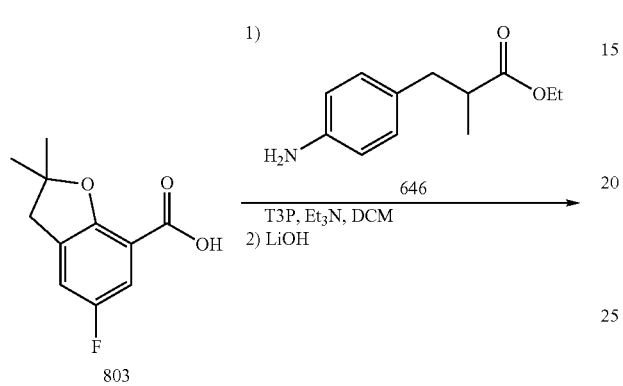

5-fluoro-2,2-dimethyl-2,3-dihydrobenzofuran-7-carboxylic acid (803) (Compound was prepared in a similar manner as that described for the synthesis of (735) (101.3 mg, 0.482 mmol) was dissolved in dichloromethane (4 mL) and ethyl 3-(4-aminophenyl)-2-methylpropanoate (646) (100 mg, 0.482 mmol), triethyl amine (0.4 mL, 2.89 mmol), and 1-propanephosphonic acid cyclic anhydride (0.34 mL, 0.58 mmol, 50% in ethyl acetate) were added and stirred overnight at room temperature. The reaction was purified in vacuo and purified by flash column chromatography on silica gel with hexanes and EtOAc to give ethyl 3-(4-(5-fluoro-2,2-dimethyl-2,3-dihydrobenzofuran-7-carboxamido)phenyl)-2-methylpropanoate. The ester was dissolved in tetrahydrofuran (1.0 mL), methanol (1.0 mL) and water (3 mL). Lithium hydroxide was added and the reaction was stirred at room temperature for 4 h. The mixture was acidified with 1M HCl and diluted with EtOAc (3 mL). The organic layer was washed with brine (3 mL), dried over sodium sulfate and filtered. The filtrate was concentrated in vacuo to yield 3-(4-(5-fluoro-2,2-dimethyl-2,3-dihydrobenzofuran-7-carboxamido)phenyl)-2-methylpropanoic acid (97). $^1$H NMR (400 MHz, CDCl$_3$) δ 9.53 (br, 1H), 7.66 (dd, J=9.9, 2.6 Hz, 1H), 7.57 (d, J=8.4 Hz, 2H), 7.19 (d, J=8.4 Hz, 2H), 7.02 (dd, J=9.9, 2.6 Hz, 1H), 3.13-3.00 (m, 3H), 2.72 (m, 2H), 1.60 (s, 6H), 1.19 (d, J=8.0 Hz, 3H).

Example 69

3-(3,5-difluoro-4-((5-fluoro-2,2-dimethyl-2,3-dihydrobenzofuran-7-yl)methoxy)phenyl)-2-ethoxypropanoic acid (98)

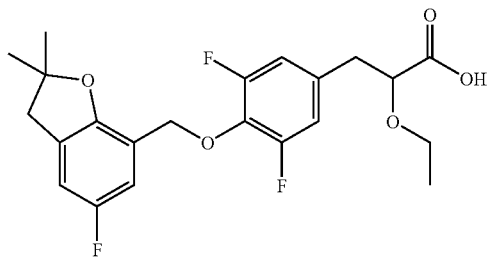

$^1$H NMR (400 MHz, CDCl$_3$) δ 6.94 (d, J=9.4 Hz, 1H), 6.77 (m, 3H), 5.09 (s, 2H), 4.03 (m, 1H), 3.62 (m, 1H), 3.44 (m, 1H), 3.09-2.82 (m, 4H), 1.42 (s, 6H), 1.19 (t, J=7.0 Hz, 3H). LC-MS ESI m/z: found 423.4 [M−H]$^−$.

Example 70

2-(4-(2-(5-fluoro-2,2-dimethyl-2,3-dihydrobenzofuran-7-yl)ethyl)phenoxy)acetic acid (99)

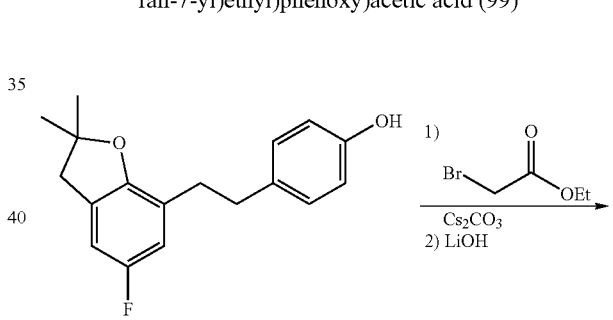

A solution of 4-(2-(5-fluoro-2,2-dimethyl-2,3-dihydrobenzofuran-7-yl)ethyl)phenol (650) (164.1 mg, 0.573 mmol), ethyl bromoacetate (95.7 mg, 0.573 mmol), cesium carbonate (265 mg, 0.688 mmol) and acetonitrile (5 mL) was heated at 50° C. for 18 hours. The reaction was concentrated in vacuo and then purified by flash column chromatography with hexanes and EtOAc (30%). The ester was dissolved in tetrahydrofuran (1.0 mL), methanol (1.0 mL) and water (3 mL). Lithium hydroxide was added and the reaction was stirred at room temperature for 24 hours. The mixture was acidified with 1M HCl and diluted with EtOAc (3 mL). The organic layer was washed with brine (3 mL), dried over sodium sulfate and filtered. The filtrate was concentrated in vacuo to yield 2-(4-(2-(5-fluoro-2,2-dimethyl-2,3-dihydrobenzofuran-7-yl)ethyl)phenoxy)acetic acid (99). $^1$H NMR (400 MHz, CDCl$_3$) δ 7.11 (d, J=7.8 Hz, 2H), 6.83 (d, J=8.4 Hz, 2H), 6.69 (d, J=8.4 Hz, 1H), 6.56 (d, J=8.4 Hz, 1H), 4.65 (s, 2H), 2.96 (s, 2H), 2.88-2.73 (m, 4H), 1.43 (s, 6H). LC-MS ESI m/z: found 343.4 [M−H]$^-$.

Example 71

3-(5-((5-chloro-2,2-dimethyl-2,3-dihydrobenzofuran-7-yl)methoxy)-[1,1'-biphenyl]-2-yl)propanoic acid (100)

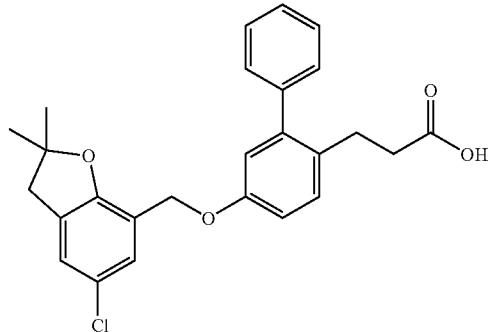

$^1$H NMR (400 MHz, DMSO-d$_6$) δ 7.48-7.12 (m, 8H), 6.92 (s, 1H), 6.73 (s, 1H), 4.92 (s, 2H), 2.99 (s, 2H), 2.66 (m, 2H), 2.26 (m, 2H), 1.33 (s, 6H). LC-MS ESI m/z: found 435.4 [M−H]$^-$.

Example 72

3-(5-((5-fluoro-2,2-dimethyl-2,3-dihydrobenzofuran-7-yl)methoxy)-[1,1'-biphenyl]-2-yl)propanoic acid (101)

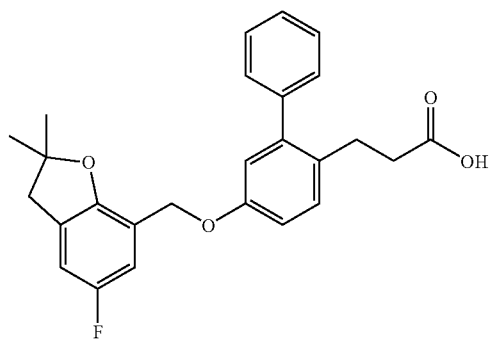

$^1$H NMR (400 MHz, DMSO-d$_6$) δ 12.00 (br, 1H), 7.48-7.13 (m, 6H), 6.95-6.90 (m, 3H), 6.73 (s, 1H), 4.91 (s, 2H), 2.98 (s, 2H), 2.66 (m, 2H), 2.26 (m, 2H), 1.33 (s, 6H). LC-MS ESI m/z: found 419.3 [M−H]$^-$.

Example 73

3-(4-((5-chloro-2,2-dimethyl-2,3-dihydrobenzofuran-7-yl)methoxy)-5-fluoro-2-propylphenyl)propanoic acid (102)

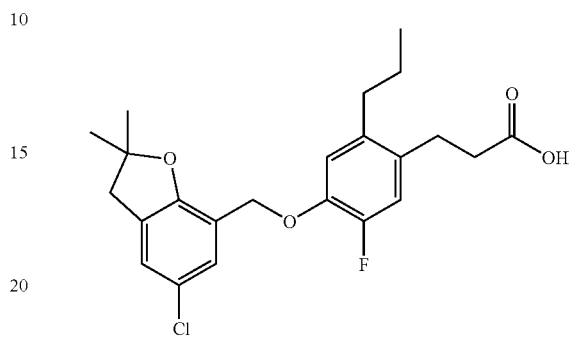

$^1$H NMR (400 MHz, DMSO-d$_6$) δ 12.15 (br, 1H), 7.18 (m, 2H), 6.96 (m, 2H), 4.96 (s, 2H), 3.01 (s, 2H), 2.70 (m, 2H), 2.42 (m, 4H), 1.47 (m, 2H), 1.40 (s, 6H), 0.87 (t, J=8.0 Hz, 3H). LC-MS ESI m/z: found 419.4 [M−H]$^-$.

Example 74

3-(5-fluoro-4-((5-fluoro-2,2-dimethyl-2,3-dihydrobenzofuran-7-yl)methoxy)-2-propylphenyl)propanoic acid (103)

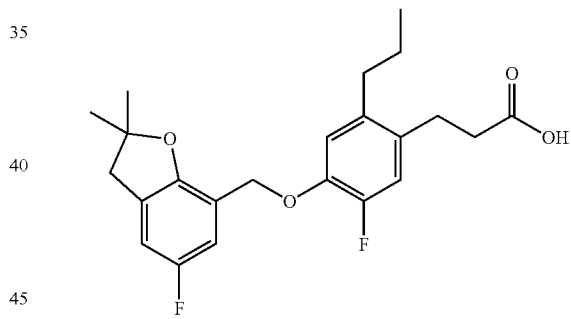

$^1$H NMR (400 MHz, DMSO-d$_6$) δ 12.14 (br, 1H), 6.99 (m, 2H), 6.96 (m, 2H), 4.95 (s, 2H), 3.00 (s, 2H), 2.70 (m, 2H), 2.45 (m, 4H), 1.46 (m, 2H), 1.39 (s, 6H), 0.87 (d, J=7.2 Hz, 3H). LC-MS ESI m/z: found 403.4 [M−H]$^-$.

Example 75

3-(4-((5-chloro-2,2-dimethyl-3-oxo-2,3-dihydrobenzofuran-7-yl)methoxy)-2-ethyl-3-fluorophenyl)propanoic acid (104)

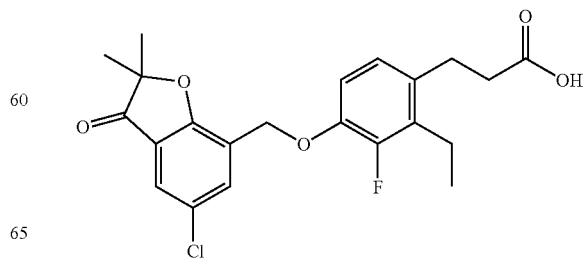

¹H NMR (400 MHz, DMSO-d₆) δ 12.16 (br, 1H), 7.85 (s, 1H), 7.70 (s, 1H), 7.03 (m, 1H), 6.92 (m, 1H), 5.14 (s, 2H), 2.76 (m, 2H), 2.58 (m, 2H), 1.38 (s, 6H), 1.06 (m, 3H). LC-MS ESI m/z: found 419.3 [M−H]⁻.

Example 76

3-(4-((5-chloro-2,2-dimethyl-3-oxo-2,3-dihydrobenzofuran-7-yl)methoxy)-2-propylphenyl)propanoic acid (105)

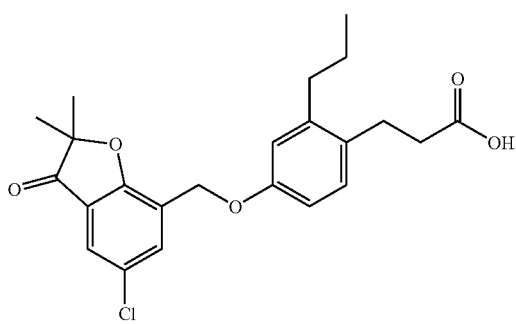

¹H NMR (400 MHz, DMSO-d₆) δ 12.11 (br, 1H), 7.85 (s, 1H), 7.67 (s, 1H), 7.05 (m, 1H), 6.80 (m, 2H), 5.07 (s, 2H), 2.73 (m, 2H), 2.41 (m, 4H), 1.50 (m, 2H), 1.40 (s, 6H), 0.89 (t, J=8.0 Hz, 3H). LC-MS ESI m/z: found 415.1 [M−H]⁻.

Example 77

3-(4-((5-chloro-2,2-dimethyl-3-oxo-2,3-dihydrobenzofuran-7-yl)methoxy)-3-fluorophenyl)-2-methylpropanoic acid (106)

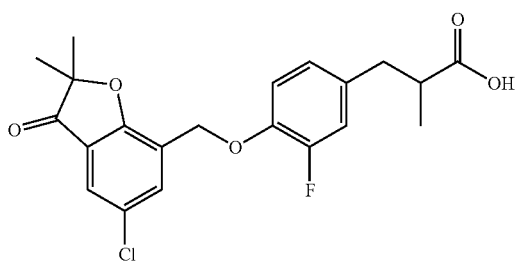

¹H NMR (400 MHz, DMSO-d₆) δ 12.12 (br, 1H), 7.86 (s, 1H), 7.70 (s, 1H), 7.20-7.16 (m, 1H), 7.04 (d, J=12.0 Hz, 1H), 6.93 (d, J=8.0 Hz, 1H), 5.16 (s, 2H), 2.78 (m, 1H), 2.56 (m, 2H), 1.39 (s, 6H), 1.00 (d, J=4.0 Hz, 3H). LC-MS ESI m/z: found 405.3 [M−H]⁻.

Example 78

3-(3-fluoro-4-((5-fluoro-2,2-dimethyl-3-oxo-2,3-dihydrobenzofuran-7-yl)methoxy)phenyl)-2-methylpropanoic acid (107)

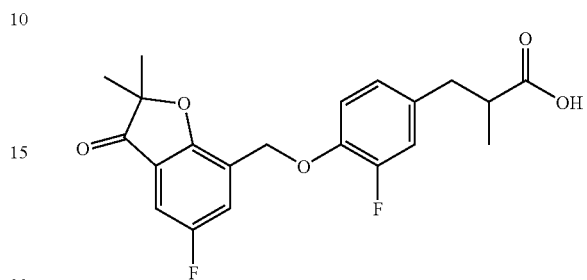

¹H NMR (400 MHz, DMSO-d₆) δ 12.14 (br, 1H), 7.73 (dd, J=8.0, 4.0 Hz, 1H), 7.48 (dd, J=8.0, 4.0 Hz, 1H), 7.19 (t, J=8.0 Hz, 1H), 7.02 (d, J=12.0 Hz, 1H), 6.93 (d, J=8.0 Hz, 1H), 5.16 (s, 2H), 2.79-2.75 (m, 1H), 2.56-2.51 (m, 2H), 1.39 (s, 6H), 1.00 (d, J=6.3 Hz, 3H). LC-MS ESI m/z: found 389.1 [M−H]⁻.

Example 79

3-(4-((5-chloro-2,2-dimethyl-3-oxo-2,3-dihydrobenzofuran-7-yl)methoxy)-3-(trifluoromethyl)phenyl)-2-methylpropanoic acid (108)

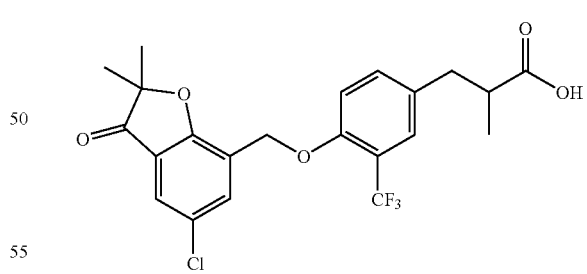

¹H NMR (400 MHz, CDCl₃) δ 7.77 (s, 1H), 7.58 (s, 1H), 7.43 (s, 1H), 7.32 (d, J=8.4 Hz, 1H), 7.04 (d, J=8.4 Hz, 1H), 5.19 (s, 2H), 3.09-2.97 (m, 1H), 2.76-2.68 (m, 2H), 1.48 (s, 6H), 1.20 (d, J=6.7 Hz, 3H). LC-MS ESI m/z: found 455.0 [M−H]⁻.

Example 80

3-(4-((5-chloro-3-hydroxy-2,2-dimethyl-2,3-dihydrobenzofuran-7-yl)methoxy)-3-fluorophenyl)-2-methylpropanoic acid (109)

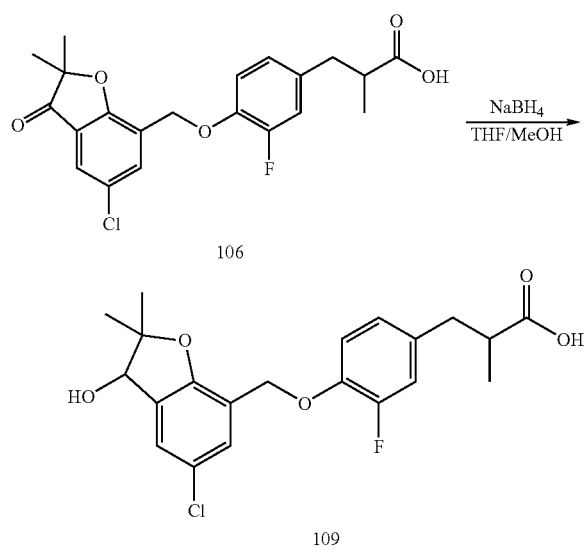

To a solution of 3-(4-((5-chloro-2,2-dimethyl-3-oxo-2,3-dihydrobenzofuran-7-yl)methoxy)-3-fluorophenyl)-2-methylpropanoic acid (106) (80 mg, 0.197 mmol) in tetrahydrofuran/methanol (2:1, 2 mL) was added sodium borohydride (15 mg, 0.393 mmol). After the reaction was stirred at room temperature for 1.5 hours water was added and the solution was extracted with ethyl acetate, dried over sodium sulfate and filtered. The filtrate was concentrated in vacuo to yield 3-(4-((5-chloro-3-hydroxy-2,2-dimethyl-2,3-dihydrobenzofuran-7-yl)methoxy)-3-fluorophenyl)-2-methylpropanoic acid (109). $^{1}$H NMR (400 MHz, CDCl$_3$) δ 7.40 (s, 1H), 7.31 (s, 1H), 6.92 (m, 2H), 6.82 (d, J=12.0 Hz, 1H), 5.04 (s, 2H), 4.75 (s, 1H), 2.93 (m, 1H), 2.71 (m, 1H), 2.64 (m, 1H), 1.49 (s, 3H), 1.34 (s, 3H), 1.18 (d, J=6.9 Hz, 3H). LC-MS ESI m/z: found 407.3 [M−H]$^{-}$.

Example 81

3-(4-((5-bromo-2,2-dimethyl-2,3-dihydrobenzofuran-7-yl)methoxy)phenyl)-2-methylpropanoic acid (110)

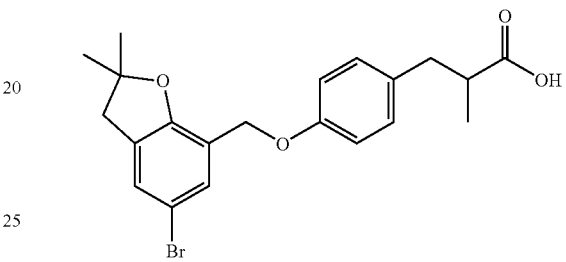

$^{1}$H NMR (400 MHz, CDCl$_3$) δ 7.31 (s, 1H), 7.11 (s, 1H), 7.02 (d, J=8.2 Hz, 2H), 6.84 (d, J=8.2 Hz, 2H), 4.89 (s, 2H), 2.95-2.91 (m, 3H), 2.73-2.47 (m, 2H), 1.41 (s, 6H), 1.10 (d, J=6.8 Hz, 3H). LC-MS ESI m/z: found 418.0 [M−H]$^{-}$.

Example 82

3-(4-((5-(4-chlorophenyl)-2,2-dimethyl-2,3-dihydrobenzofuran-7-yl)methoxy)phenyl)-2-methylpropanoic acid (111)

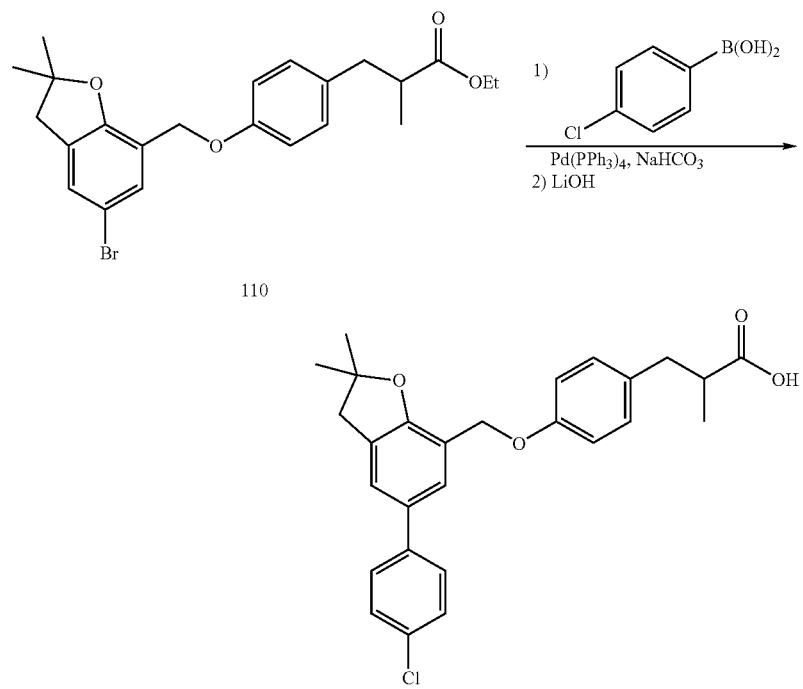

A solution of ethyl 3-(4-((5-bromo-2,2-dimethyl-2,3-dihydrobenzofuran-7-yl)methoxy)phenyl)-2-methylpropanoate (110) (80 mg, 0.179 mmol), 4-chlorophenyl boronic acid (30.8 mg, 0.197 mmol), Pd(PPh$_3$)$_4$ (7 mg, 00.006 mmol), saturated sodium bicarbonate (0.64 mL), methanol (1.5 mL), and toluene (0.64 mL) was heated in a microwave reactor for 40 minutes at 110° C. To the solution was added water and ethyl acetate and the two layers were separated. The crude compound was purified by flash column chromatography on silica gel with hexanes and EtOAc (30%) to afford ethyl 3-(4-((5-(4-chlorophenyl)-2,2-dimethyl-2,3-dihydrobenzofuran-7-yl)methoxy)phenyl)-2-methylpropanoate. The ester was dissolved in tetrahydrofuran (1.0 mL), methanol (1.0 mL) and water (3 mL). Lithium hydroxide was added and the reaction was stirred at room temperature for 24 hours. The mixture was acidified with 1M HCl and diluted with EtOAc (3 mL). The organic layer was washed with brine (3 mL), dried over sodium sulfate and filtered. The filtrate was concentrated in vacuo to yield 3-(4-((5-(4-chlorophenyl)-2,2-dimethyl-2,3-dihydrobenzofuran-7-yl)methoxy)phenyl)-2-methylpropanoic acid (111). $^1$H NMR (400 MHz, CDCl$_3$) δ 7.43-7.39 (m, 3H), 7.34 (d, J=8.3 Hz, 2H), 7.28 (d, J=8.3 Hz, 1H), 7.09 (d, J=8.2 Hz, 2H), 6.94 (d, J=8.3 Hz, 2H), 5.05 (s, 2H), 3.07 (s, 2H), 3.00 (dd, J=13.4, 6.4 Hz, 1H), 2.73-2.67 (m, 1H), 2.62-2.58 (m, 1H), 1.51 (s, 6H), 1.17 (d, J=6.8 Hz, 3H). LC-MS ESI m/z: found 449.1 [M−H]$^−$.

Example 83

3-(4-((5-(4-fluorophenyl)-2,2-dimethyl-2,3-dihydrobenzofuran-7-yl)methoxy)phenyl)-2-methylpropanoic acid (112)

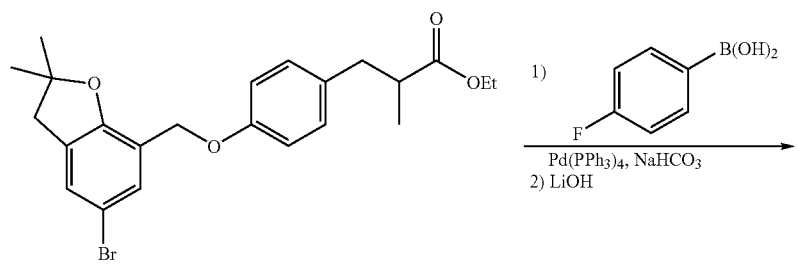

110

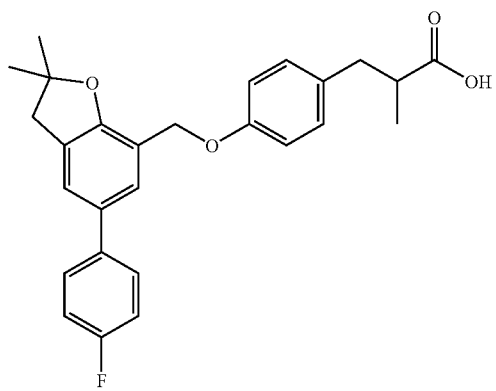

112

Compound (112) was prepared in a similar manner as that described for the synthesis of (111). $^1$H NMR (400 MHz, CDCl$_3$) δ 7.44-7.38 (m, 4H), 7.16-7.02 (m, 4H), 6.95 (d, J=8.3 Hz, 2H), 5.05 (s, 2H), 3.07 (s, 2H), 3.03 (dd, J=13.4, 6.4 Hz, 1H), 2.80-2.68 (m, 1H), 2.67-2.56 (m, 1H), 1.51 (s, 6H), 1.17 (d, J=6.8 Hz, 3H). LC-MS ESI m/z: found 433.2 [M−H]$^−$.

Example 84

3-(4-((5-(3-chlorophenyl)-2,2-dimethyl-2,3-dihydrobenzofuran-7-yl)methoxy)phenyl)-2-methylpropanoic acid (113)

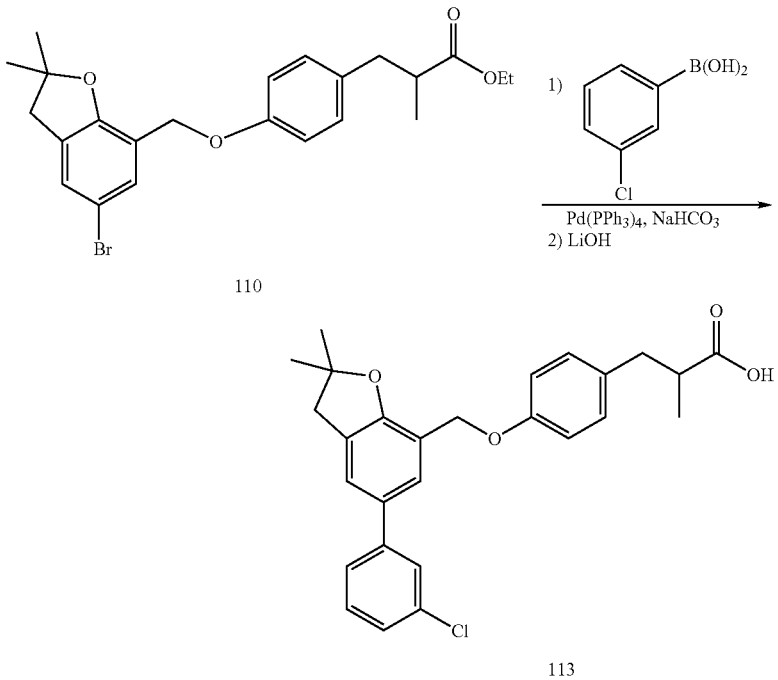

Compound (113) was prepared in a similar manner as that described for the synthesis of (111). $^1$H NMR (400 MHz, CDCl$_3$) δ 7.49-7.46 (m, 2H), 7.38 (d, J=7.8 Hz, 1H), 7.34-7.17 (m, 3H), 7.09 (d, J=8.4 Hz, 2H), 6.95 (d, J=8.4 Hz, 2H), 5.05 (s, 2H), 3.07 (s, 2H), 3.02-2.97 (m, 1H), 2.75-2.71 (m, 1H), 2.64-2.59 (m, 1H), 1.52 (s, 6H), 1.17 (d, J=6.9 Hz, 3H). LC-MS ESI m/z: found 449.0 [M−H]$^−$.

Example 85

3-(4-((5-(2-chlorophenyl)-2,2-dimethyl-2,3-dihydrobenzofuran-7-yl)methoxy)phenyl)-2-methylpropanoic acid (114)

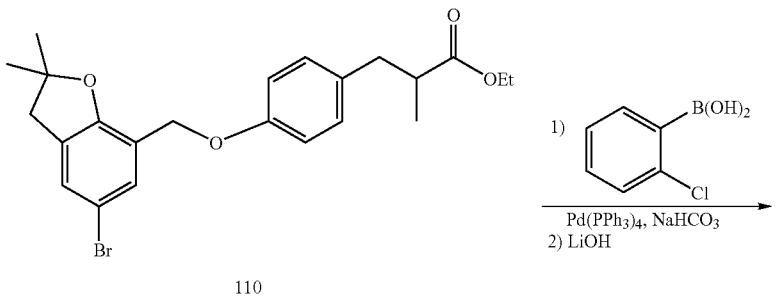

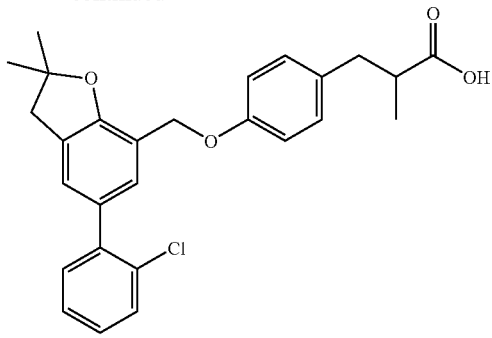
114
Compound (114) was prepared in a similar manner as that described for the synthesis of (111). ¹H NMR (400 MHz, CDCl₃) δ 7.47-7.38 (m, 1H), 7.35-7.27 (m, 3H), 7.24-7.19 (m, 2H), 7.08 (d, J=6.9 Hz, 2H), 6.93 (d, J=6.6 Hz, 2H), 5.05 (s, 2H), 3.08 (s, 2H), 3.04-2.93 (m, 1H), 2.74-2.71 (m, 1H), 2.65-2.60 (m, 1H), 1.52 (s, 6H), 1.15 (d, J=8.0 Hz, 3H). LC-MS ESI m/z: found 449.2 [M−H]⁻.
Example 86
3-(4-((5-(3-methoxyphenyl)-2,2-dimethyl-2,3-dihydrobenzofuran-7-yl)methoxy)phenyl)-2-methylpropanoic acid (115)
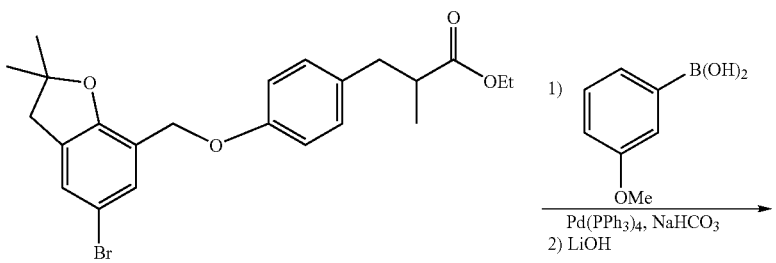
110
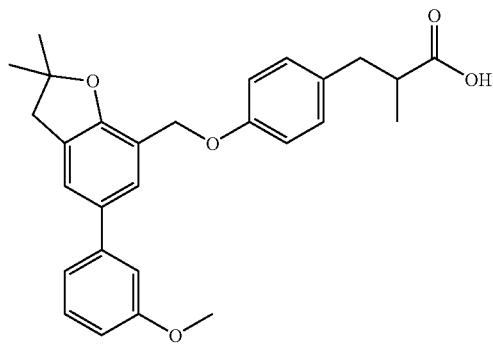
115

Compound (115) was prepared in a similar manner as that described for the synthesis of (111). ¹H NMR (400 MHz, CDCl₃) δ 7.46 (s, 1H), 7.30-7.28 (m, 2H), 7.15-7.08 (m, 3H), 7.02 (s, 1H), 6.94 (d, J=7.7 Hz, 2H), 6.82 (d, J=8.0 Hz, 1H), 5.06 (s, 2H), 3.84 (s, 3H), 3.07 (s, 2H), 3.01-2.96 (m, 1H), 2.79-2.53 (m, 2H), 1.51 (s, 6H), 1.17 (d, J=6.7 Hz, 3H). LC-MS ESI m/z: found 445.2 [M−H]⁻.

Example 87

3-(4-((2,2-dimethyl-5-(3-(trifluoromethyl)phenyl)-2,3-dihydrobenzofuran-7-yl)methoxy)phenyl)-2-methylpropanoic acid (116)

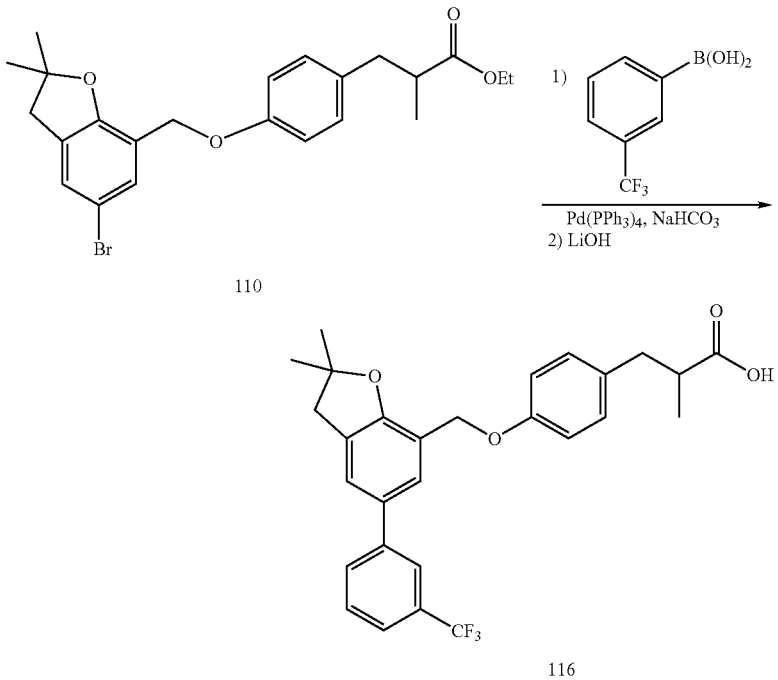

Compound (116) was prepared in a similar manner as that described for the synthesis of (111). ¹H NMR (400 MHz, CDCl₃) δ 7.74 (s, 1H), 7.68 (d, J=8.0 Hz, 1H), 7.51-7.49 (m, 3H), 7.32 (s, 1H), 7.10 (d, J=8.6 Hz, 2H), 6.95 (d, J=8.4 Hz, 2H), 5.06 (s, 2H), 3.09 (s, 2H), 3.03-2.98 (m, 1H), 2.76-2.59 (m, 2H), 1.52 (s, 6H), 1.17 (d, J=6.9 Hz, 3H). LC-MS ESI m/z: found 483.1 [M−H]⁻.

Example 88

3-(4-((5-chloro-2,2-dimethyl-2,3-dihydrobenzofuran-7-yl)methoxy)-3-((dimethylamino)methyl)phenyl)-2-methylpropanoic acid (117)

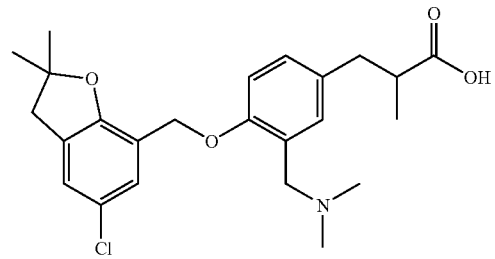

$^1$H NMR (400 MHz, DMSO-d$_6$) δ 9.24 (s, 1H), 7.30 (s, 1H), 7.24-7.23 (m, 3H), 7.11 (d, J=8.8 Hz, 1H), 5.00 (s, 2H), 4.20 (d, J=4.7 Hz, 2H), 3.03 (s, 2H), 2.89-2.76 (m, 1H), 2.70 (s, 6H), 2.57-2.48 (m, 2H), 1.42 (s, 6H), 1.02 (d, J=6.4 Hz, 3H). LC-MS ESI m/z: found 431.7 [M−H]$^−$.

Example 89

3-(4-((5-(diethylamino)-2,2-dimethyl-2,3-dihydrobenzofuran-7-yl)methoxy)phenyl)-2-methylpropanoic acid (118)

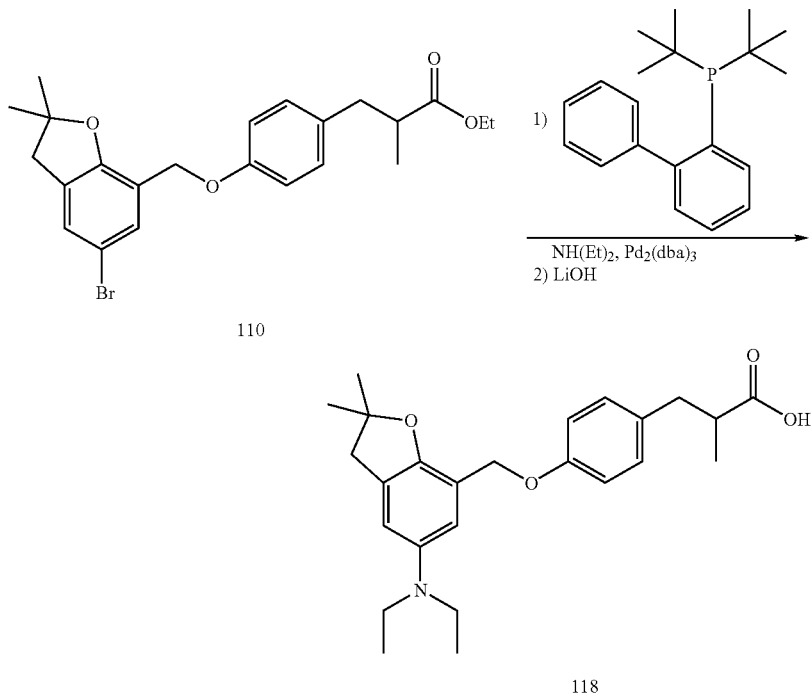

A mixture of ethyl 3-(4-((5-bromo-2,2-dimethyl-2,3-dihydrobenzofuran-7-yl)methoxy)phenyl)-2-methylpropanoate (110) (78 mg, 0.17 mmol), diethylamine (0.08 mL, 0.78 mmol), [1,1'-biphenyl]-2-yldi-tert-butylphosphine (16 mg, 0.052 mmol), tris(dibenzylideneacetone) dipalladium (47.6 mg, 0.052 mmol), and sodium t-butoxide (25 mg, 0.26 mmol) in toluene (2 mL) was heated in a pressure tube at 80° C. overnight. Water was added and the reaction was extracted with ethyl acetate and the combined organic layers dried over sodium sulfate, filtered and concentrated in vacuo. The crude compound was purified by flash column chromatography on silica gel with hexanes and EtOAc (50%) to give ethyl 3-(4-((5-(diethylamino)-2,2-dimethyl-2,3-dihydrobenzofuran-7-yl)methoxy)phenyl)-2-methylpropanoate. The ester was dissolved in tetrahydrofuran (1.0 mL), methanol (1.0 mL) and water (3 mL). Lithium hydroxide was added and the reaction was stirred at room temperature for 24 hours. The mixture was acidified with 1M HCl and diluted with EtOAc (3 mL). The organic layer was washed with brine (3 mL), dried over sodium sulfate and filtered. The filtrate was concentrated in vacuo to yield 3-(4-((5-(diethylamino)-2,2-dimethyl-2,3-dihydrobenzofuran-7-yl)methoxy)phenyl)-2-methylpropanoic acid (118). $^1$H NMR (400 MHz, CDCl$_3$) δ 7.38 (s, 1H), 7.18 (s, 1H), 7.09 (d, J=8.1 Hz, 2H), 6.87 (d, J=8.3 Hz, 2H), 5.04 (s, 2H), 3.84-3.47 (m, 2H), 3.34-3.09 (m, 2H), 3.06 (s, 2H), 3.01-2.89 (m, 1H), 2.78-2.57 (m, 2H), 1.51 (s, 6H), 1.18 (d, J=6.7 Hz, 3H), 1.07 (t, J=6.9 Hz, 6H). LC-MS ESI m/z: found 410.4 [M−H]$^−$.

Example 90

3-(4-((2,2-dimethyl-5-(1H-tetrazol-1-yl)-2,3-dihydrobenzofuran-7-yl)methoxy)phenyl)-2-methylpropanoic acid (119)

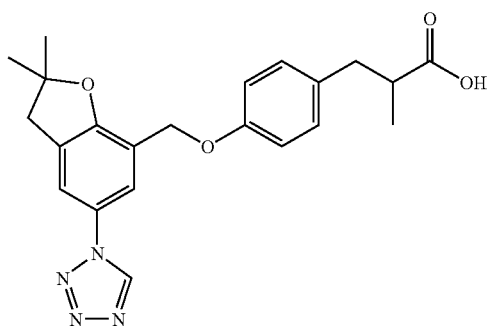

¹H NMR (400 MHz, CDCl₃) δ 8.86 (s, 1H), 7.52 (s, 1H), 7.41 (s, 1H), 7.11 (d, J=7.8 Hz, 2H), 6.92 (d, J=8.5 Hz, 2H), 5.06 (s, 2H), 3.12 (s, 2H), 3.02-2.98 (m, 1H), 2.77-2.62 (m, 2H), 1.55 (s, 6H), 1.18 (d, J=6.9 Hz, 3H). LC-MS ESI m/z: found 408.9 [M+H]⁺.

Example 91

3-(4-((7-fluoro-2,2-dimethyl-2,3-dihydrobenzofuran-4-yl)methoxy)phenyl)-2-methylpropanoic acid (120)

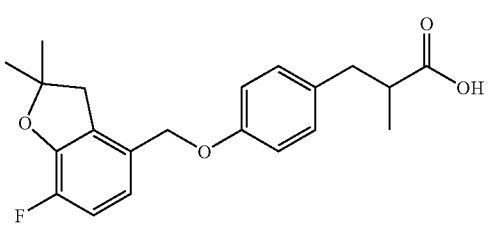

¹H NMR (400 MHz, CDCl₃) δ 7.10 (d, 2H), 6.92 (m, 1H), 6.87 (d, 2H), 6.79 (m, 1H), 4.89 (s, 2H), 3.07 (s, 2H), 3.00 (m, 1H), 2.76-2.61 (m, 3H), 1.51 (s, 6H), 1.17 (d, 3H).

Example 92

3-(3,5-difluoro-4-((7-fluoro-2,2-dimethyl-2,3-dihydrobenzofuran-4-yl)methoxy)phenyl)-2-methylpropanoic acid (121)

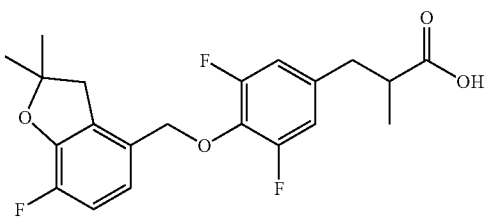

¹H NMR (400 MHz, CDCl₃) δ 6.86 (t, 1H), 6.76-6.70 (m, 3H), 4.99 (s, 2H), 3.16 (s, 2H), 2.95 (m, 1H), 2.71 (m, 1H), 2.59 (m, 1H), 1.52 (s, 6H), 1.18 (d, 3H).

Example 93

2-(3,5-difluoro-4-((7-fluoro-2,2-dimethyl-2,3-dihydrobenzofuran-4-yl)methoxy)phenyl)cyclopropanecarboxylic acid (122)

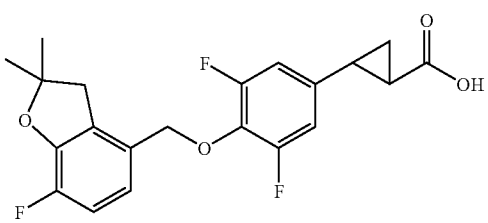

¹H NMR (400 MHz, CDCl₃) δ 6.86 (t, 1H), 6.75-6.72 (m, 1H), 6.62 (d, 2H), 4.99 (s, 2H), 3.15 (s, 2H), 2.49 (m, 1H), 1.83 (m, 1H), 1.64 (m, 1H), 1.52 (s, 6H), 1.31 (m, 1H).

Example 94

2-(5-((7-fluoro-2,2-dimethyl-2,3-dihydrobenzofuran-4-yl)methoxy)-2,3-dihydro-1H-inden-1-yl)acetic acid (123)

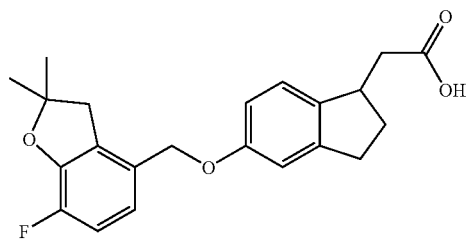

¹H NMR (400 MHz, CDCl₃) δ 7.11 (d, 1H), 6.92 (t, 1H), 6.83-6.76 (m, 3H), 4.89 (s, 2H), 3.54 (m, 1H), 3.08 (s, 2H), 2.92-2.77 (m, 3H), 2.51-2.41 (m, 2H), 1.83-1.74 (m, 1H), 1.52 (s, 6H).

Example 95

3-(3,5-difluoro-4-((5-fluoro-2,2-dimethyl-2,3-dihydrobenzofuran-4-yl)methoxy)phenyl)-2-methylpropanoic acid (124)

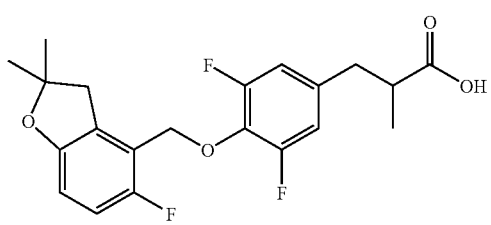

¹H NMR (400 MHz, CDCl₃) δ 6.80-6.70 (m, 3H), 6.63-6.60 (m, 1H), 5.10 (s, 2H), 3.12 (s, 2H), 2.96 (m, 1H), 2.72 (m, 1H), 2.60 (m, 1H), 1.46 (s, 6H), 1.19 (d, 3H).

Example 96

3-(4-((5-fluoro-2,2-dimethyl-2,3-dihydrobenzofuran-4-yl)methoxy)phenyl)-2-methylpropanoic acid (125)

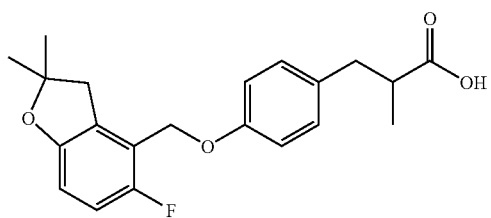

¹H NMR (400 MHz, CDCl₃) δ 7.10 (d, 2H), 6.89 (d, 2H), 6.82 (t, 1H), 6.62 (dd, 1H), 5.03 (s, 2H), 3.07 (s, 2H), 3.04-2.98 (m, 1H), 2.76-2.71 (m, 1H), 2.66-2.60 (m, 1H), 1.45 (s, 6H), 1.18 (d, 3H).

Example 97

(R)-3-(3,5-difluoro-4-((5-fluoro-2,2-dimethyl-2,3-dihydrobenzofuran-4-yl)methoxy)phenyl)-2-methylpropanoic acid (126)

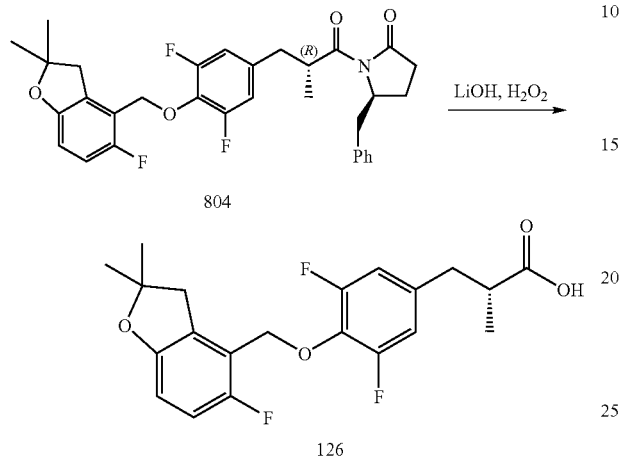

Compound (126) was prepared in a similar manner as that described for the synthesis of (94). ¹H NMR (400 MHz, CDCl₃) δ 6.80-6.70 (m, 3H), 6.63-6.60 (m, 1H), 5.10 (s, 2H), 3.12 (s, 2H), 2.99-2.94 (m, 1H), 2.75-2.70 (m, 1H), 2.63-2.57 (m, 1H), 1.46 (s, 6H), 1.18 (d, 3H).

Example 98

3-(4-((5-chloro-2,2-dimethyl-2,3-dihydrobenzofuran-7-yl)methoxy)-2-methoxyphenyl)-2-methylpropanoic acid (127)

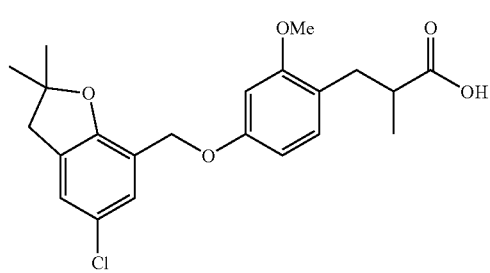

¹H NMR (400 MHz, CDCl₃) δ 7.05-6.99 (m, 3H), 6.52-6.48 (m, 2H), 4.96 (s, 2H), 3.79 (s, 3H), 3.00 (s, 2H), 2.98-2.94 (m, 1H), 2.84-2.80 (m, 1H), 2.66-2.61 (m, 1H), 1.46 (s, 6H), 1.15 (d, 3H).

Example 99

2-(3,5-difluoro-4-((5-fluoro-2,2-dimethyl-2,3-dihydrobenzofuran-4-yl)methoxy)phenyl)cyclopropanecarboxylic acid (128)

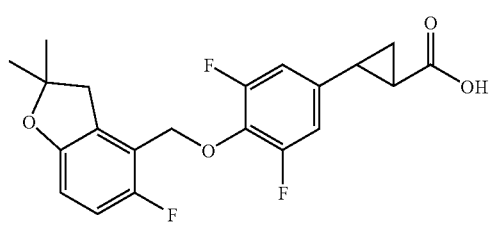

¹H NMR (400 MHz, CDCl₃) δ 6.81-6.76 (m, 1H), 6.66-6.61 (m, 3H), 5.10 (s, 2H), 3.11 (s, 2H), 2.52-2.47 (m, 1H), 1.87-1.82 (m, 1H), 1.68-1.63 (m, 1H), 1.46 (s, 6H), 1.35-1.30 (m, 1H).

Example 100

3-(4-((5-chloro-2,2-dimethyl-2,3-dihydrobenzofuran-4-yl)methoxy)-3,5-difluorophenyl)-2-methylpropanoic acid (129)

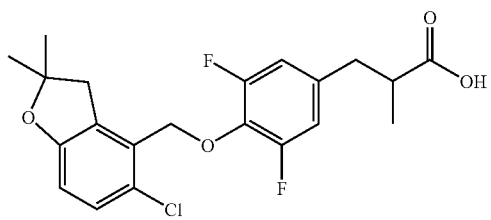

¹H NMR (400 MHz, CDCl₃) δ 7.11 (d, 1H), 6.74 (d, 2H), 6.64 (d, 1H), 5.17 (s, 2H), 3.14 (s, 2H), 3.00-2.95 (m, 1H), 2.75-2.70 (m, 1H), 2.63-2.58 (m, 1H), 1.46 (s, 6H), 1.19 (d, 3H).

Example 101

3-(3,5-difluoro-4-((6-fluoro-2,2-dimethyl-2,3-dihydrobenzofuran-4-yl)methoxy)phenyl)-2-methylpropanoic acid (130)

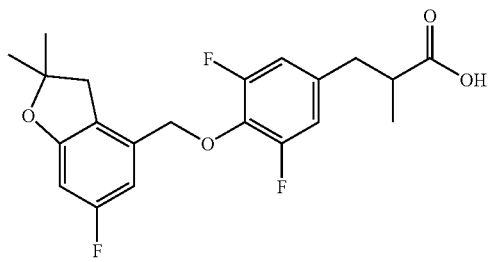

¹H NMR (400 MHz, CDCl₃) δ 6.73 (d, 2H), 6.59 (d, 1H), 6.42 (d, 1H), 4.98 (s, 2H), 3.03 (s, 2H), 2.98-2.93 (m, 1H), 2.73-2.70 (m, 1H), 2.63-2.58 (m, 1H), 1.47 (s, 6H), 1.19 (d, 3H).

Example 102

3-(4-((5-chloro-2,2-dimethyl-2,3-dihydrobenzofuran-4-yl)methoxy)phenyl)-2-methylpropanoic acid (131)

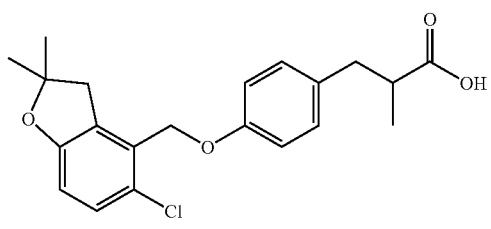

¹H NMR (400 MHz, CDCl₃) δ 7.15-7.10 (m, 3H), 6.89 (d, 2H), 6.64 (d, 1H), 5.10 (s, 2H), 3.09 (s, 2H), 3.03-2.98 (m, 1H), 2.74-2.71 (m, 1H), 2.66-2.61 (m, 1H), 1.44 (s, 6H), 1.17 (d, 3H).

Example 103

2-(4-((5-chloro-2,2-dimethyl-2,3-dihydrobenzofuran-7-yl)methoxy)-3-methylphenoxy)acetic acid (132)

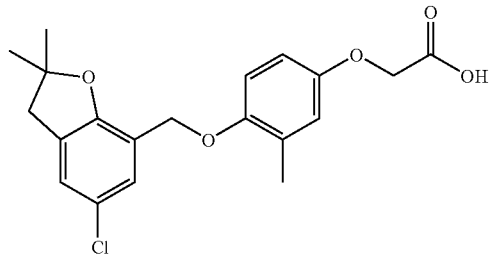

¹H NMR (400 MHz, CDCl₃) δ: 10.07 (br, 1H), 7.25 (d, 1H), 7.04 (s, 1H), 6.76-6.66 (m, 3H), 4.94 (s, 2H), 4.63 (s, 2H), 3.00 (s, 2H), 2.12 (s, 3H), 1.49 (s, 6H). LC-MS ESI m/z: found 375.0 [M−H]⁻.

Example 104

2-(4-((4-chloro-2,2-dimethyl-2,3-dihydrobenzofuran-7-yl)methoxy)-2-methylphenoxy)acetic acid (133)

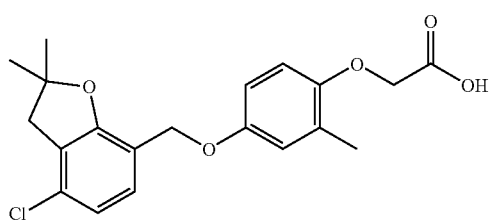

¹H NMR (400 MHz, CDCl₃) δ: 7.24 (s, 1H), 7.04 (s, 1H), 6.85 (d, 1H), 6.76-6.73 (m, 1H), 6.67 (s, 1H), 4.93 (s, 2H), 4.64 (s, 2H), 3.00 (s, 2H), 2.27 (s, 3H), 1.49 (s, 6H). LC-MS ESI m/z: found 375.0 [M−H]⁻.

Example 105

2-(4-((5-chloro-2,2-dimethyl-2,3-dihydrobenzofuran-7-yl)methoxy)phenoxy)acetic acid (134)

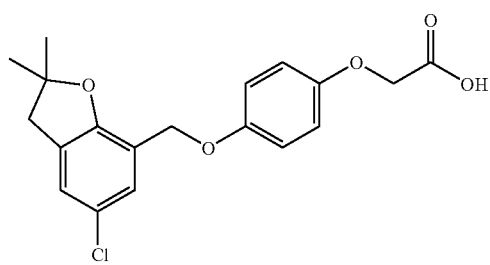

¹H NMR (400 MHz, CDCl₃) δ: 7.20 (s, 1H), 7.01 (s, 1H), 6.90 (d, 2H), 6.84 (d, 2H), 4.91 (s, 2H), 4.54 (s, 2H), 2.97 (s, 2H), 1.45 (s, 6H). LC-MS ESI m/z: found 363.1 [M−H]⁻.

Example 106

3-(4-((5-chloro-2,2-dimethyl-2,3-dihydrobenzofuran-7-yl)methoxy)-3,5-difluorophenyl)butanoic acid (135)

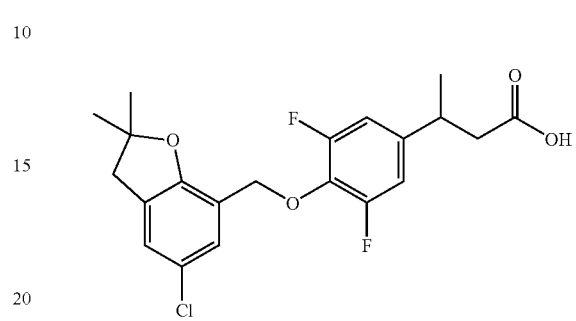

¹H NMR (400 MHz, CDCl₃) δ: 7.20 (s, 1H), 7.01 (s, 1H), 6.75-6.69 (m, 2H), 5.03 (s, 2H), 2.93 (s, 2H), 2.56-2.44 (m, 3H), 1.37 (s, 6H), 1.23 (d, 3H). LC-MS ESI m/z: found 409.2 [M−H]⁻.

Example 107

3-(3,5-difluoro-4-((5-methoxy-2,2-dimethyl-2,3-dihydrobenzofuran-7-yl)methoxy)phenyl)-2-methylpropanoic acid (136)

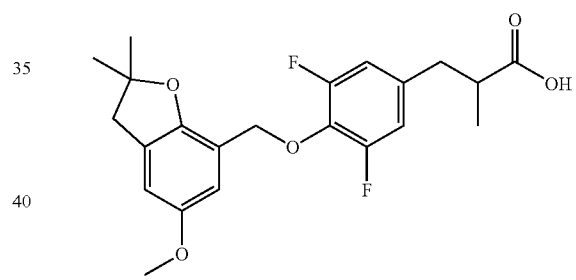

¹H NMR (400 MHz, CDCl₃) δ: 6.81 (s, 1H), 6.71-6.69 (m, 3H), 5.11 (s, 2H), 3.74 (s, 3H), 2.98-2.94 (m, 3H), 2.70 (m, 1H), 2.60-2.55 (m, 1H), 1.40 (s, 6H), 1.17 (d, 3H). LC-MS ESI m/z: found 405.1 [M−H]⁻.

Example 108

3-(4-((5-methoxy-2,2-dimethyl-2,3-dihydrobenzofuran-7-yl)methoxy)phenyl)-2-methylpropanoic acid (137)

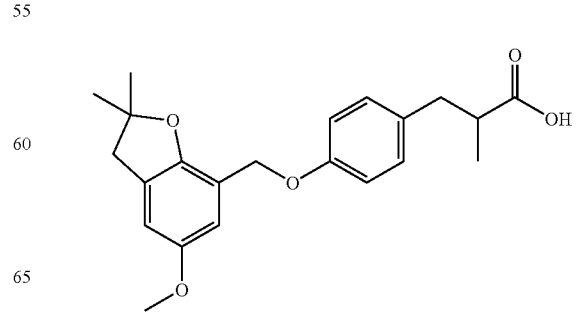

¹H NMR (400 MHz, CDCl₃) δ: 7.08 (d, 2H), 6.93 (d, 2H), 6.81 (s, 1H), 6.69 (s, 1H), 4.99 (s, 2H), 3.74 (s, 3H), 3.02-2.99 (m, 3H), 2.71 (m, 1H), 2.63-2.59 (m, 1H), 1.47 (s, 6H), 1.16 (d, 3H). LC-MS ESI m/z: found 369.3 [M−H]⁻.

Example 109

3-(4-((5-chloro-2,3,3-trimethyl-2,3-dihydrobenzofuran-7-yl)methoxy)-3,5-difluorophenyl)-2-methylpropanoic acid (138)

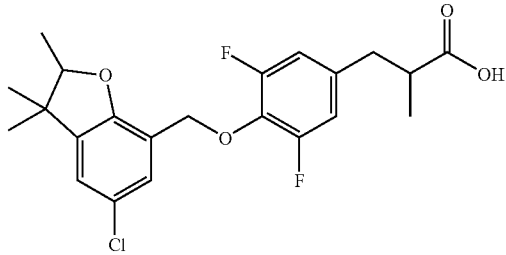

¹H NMR (400 MHz, CDCl₃) δ: 7.23 (s, 1H), 6.97 (s, 1H), 6.70 (d, 2H), 5.08-5.04 (m, 2H), 4.35 (m, 1H), 2.99-2.94 (m, 1H), 2.71-2.56 (m, 2H), 1.30 (d, 3H), 1.27 (s, 3H), 1.19 (d, 3H), 1.05 (s, 3H). LC-MS ESI m/z: found 423.4 [M−H]⁻.

Example 110

3-(4-((5-ethoxy-2,2-dimethyl-2,3-dihydrobenzofuran-7-yl)methoxy)-3,5-difluorophenyl)-2-methylpropanoic acid (139)

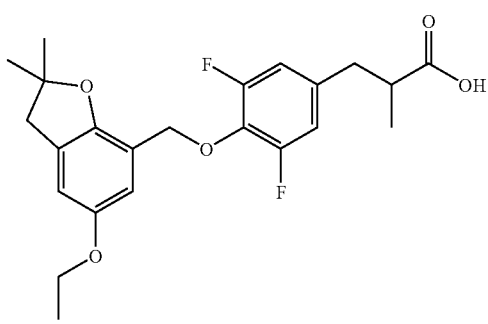

¹H NMR (400 MHz, CDCl₃) δ: 6.78 (s, 1H), 6.68 (m, 3H), 5.09 (s, 2H), 3.97-3.92 (m, 2H), 2.96-2.91 (m, 3H), 2.70 (m, 1H), 2.60-2.57 (m, 1H), 1.39-1.34 (m, 9H), 1.17 (d, 3H). LC-MS ESI m/z: found 419.3 [M−H]⁻.

Example 111

3-(4-((5-(benzyloxy)-2,2-dimethyl-2,3-dihydrobenzofuran-7-yl)methoxy)-3,5-difluorophenyl)-2-methylpropanoic acid (140)

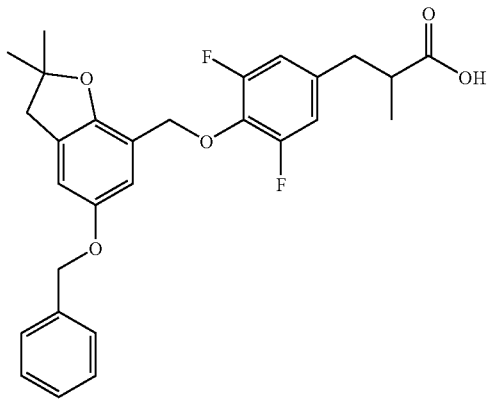

¹H NMR (400 MHz, CDCl₃) δ: 7.43-7.31 (m, 5H), 6.92 (s, 1H), 6.76 (s, 1H), 6.69 (d, 2H), 5.11 (s, 2H), 4.98 (s, 2H), 2.97-2.93 (m, 3H), 2.76-2.66 (m, 2H), 2.60-2.56 (m, 1H), 1.39 (s, 6H), 1.17 (d, 3H). LC-MS ESI m/z: found 481.2 [M−H]⁻.

Example 112

5-((5-chloro-2,2-dimethyl-2,3-dihydrobenzofuran-7-yl)methoxy)-2,3-dihydro-1H-indene-2-carboxylic acid (141)

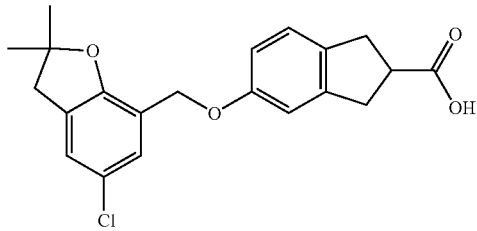

¹H NMR (400 MHz, CDCl₃) δ: 7.25 (s, 1H), 7.09 (d, 1H), 7.03 (s, 1H), 6.86 (s, 1H), 6.80 (d, 1H), 4.95 (s, 2H), 3.40-3.36 (m, 1H), 3.28-3.15 (m, 4H), 2.99 (s, 2H), 1.47 (s, 6H). LC-MS ESI m/z: found 371.0 [M−H]⁻.

Example 113

5-((5-fluoro-2,2-dimethyl-2,3-dihydrobenzofuran-7-yl)methoxy)-2,3-dihydro-1H-indene-2-carboxylic acid (142)

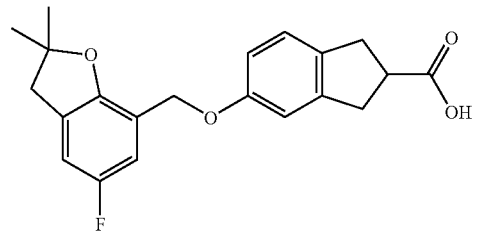

¹H NMR (400 MHz, CDCl₃) δ: 7.08 (d, 1H), 6.97 (d, 1H), 6.85 (s, 1H), 6.81-6.77 (m, 2H), 4.97 (s, 2H), 3.98-3.34 (m, 1H), 3.28-3.14 (m, 4H), 2.99 (s, 2H), 1.48 (s, 6H). LC-MS ESI m/z: found 355.2 [M−H]⁻.

Example 114

6-((5-fluoro-2,2-dimethyl-2,3-dihydrobenzofuran-7-yl)methoxy)-2-naphthoic acid (143)

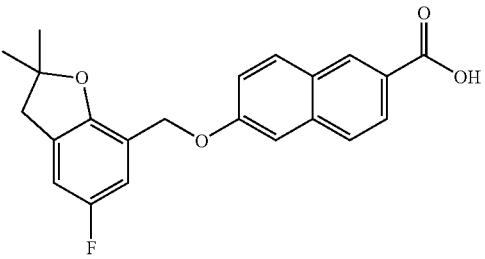

¹H NMR (400 MHz, DMSO-d₆) δ: 12.88 (br, 1H), 8.50 (s, 1H), 8.00 (d, 1H), 7.91-7.83 (m, 2H), 7.49 (s, 1H), 7.27 (d, 1H), 7.04 (m, 2H), 5.07 (s, 2H), 3.03 (s, 2H), 1.43 (s, 6H). LC-MS ESI m/z: found 365.0 [M−H]⁻.

Example 115

3-(4-((5-fluoro-2,2-dimethyl-2,3-dihydrobenzofuran-7-yl)methoxy)-2-isopropoxyphenyl)propanoic acid (144)

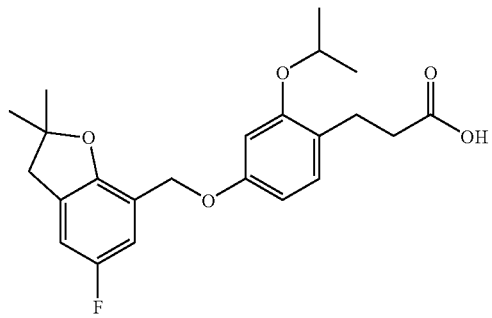

¹H NMR (400 MHz, CDCl₃) δ: 7.02 (d, 1H), 6.96 (d, 1H), 6.78 (d, 1H), 6.50-6.46 (m, 2H), 4.95 (s, 2H), 4.51 (m, 1H), 2.99 (s, 2H), 2.83 (m, 2H), 2.62 (m, 2H), 1.47 (s, 6H), 1.32 (d, 6H). LC-MS ESI m/z: found 401.8 [M−H]⁻.

Example 116

3-(4-((5-chloro-2,2-dimethyl-2,3-dihydrobenzofuran-7-yl)methoxy)-2-isopropoxyphenyl)propanoic acid (145)

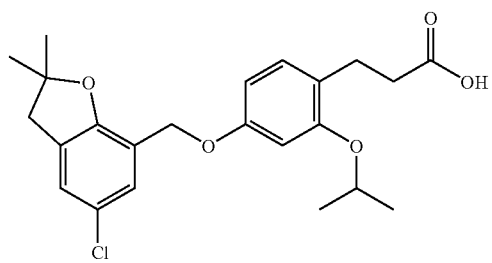

¹H NMR (400 MHz, CDCl₃) δ: 7.24 (d, 1H), 7.02 (s, 2H), 6.48 (m, 2H), 4.94 (s, 2H), 4.51 (m, 1H), 2.99 (s, 2H), 2.83 (m, 2H), 2.62 (m, 2H), 1.47 (s, 6H), 1.32 (d, 6H). LC-MS ESI m/z: found 417.0 [M−H]⁻.

Example 117

3-(4-((5-chloro-2,2-dimethyl-2,3-dihydrobenzofuran-7-yl)methoxy)-2-ethoxyphenyl)propanoic acid (146)

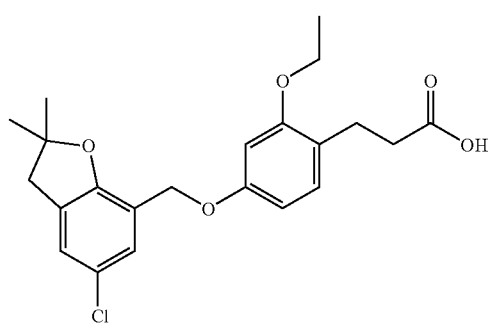

¹H NMR (400 MHz, CDCl₃) δ: 7.24 (s, 1H), 7.02 (s, 2H), 6.48 (s, 2H), 4.94 (s, 2H), 3.99 (m, 2H), 2.99 (s, 2H), 2.87 (m, 2H), 2.63 (m, 2H), 1.47 (s, 6H), 1.40 (t, 3H). LC-MS ESI m/z: found 403.3 [M−H]⁻.

Example 118

3-(2-ethoxy-4-((5-methoxy-2,2-dimethyl-2,3-dihydrobenzofuran-7-yl)methoxy)phenyl)propanoic acid (147)

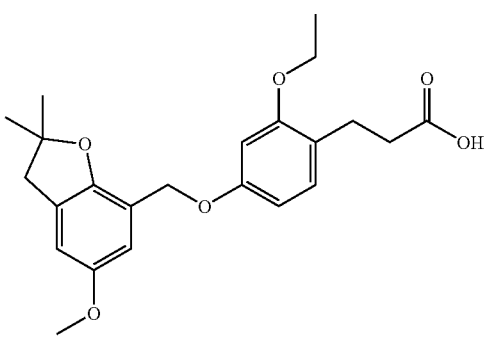

¹H NMR (400 MHz, CDCl₃) δ: 7.01 (m, 1H), 6.80 (s, 1H), 6.68 (s, 1H), 6.50 (s, 2H), 4.97 (s, 2H), 4.00 (m, 2H), 3.73 (s, 3H), 2.98 (s, 2H), 2.85 (m, 2H), 2.63 (m, 2H), 1.45 (s, 6H), 1.38 (m, 3H). LC-MS ESI m/z: found 399.2 [M−H]⁻.

Example 119

3-(4-((5-chloro-2-methylbenzofuran-7-yl)methoxy)-2-ethylphenyl)propanoic acid (148)

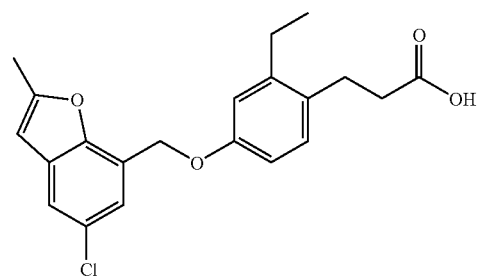

¹H NMR (400 MHz, CDCl₃) δ: 7.38 (s, 1H), 7.32 (s, 1H), 7.09 (d, 1H), 6.88 (s, 1H), 6.80 (d, 1H), 6.35 (s, 1H), 5.28 (s, 2H), 2.93 (m, 2H), 2.67-2.60 (m, 4H), 2.46 (s, 3H), 1.23 (m, 3H). LC-MS ESI m/z: found 370.9 [M−H]⁻.

Example 120

3-(4-((5-chloro-2-methylbenzofuran-7-yl)methoxy)-3-fluorophenyl)-2-methylpropanoic acid (149)

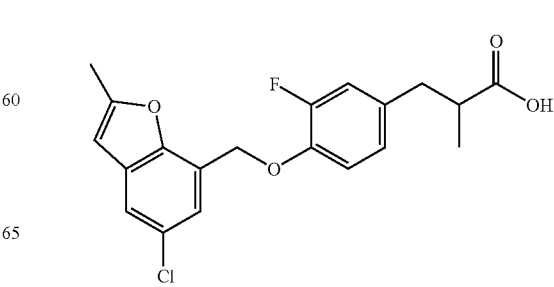

¹H NMR (400 MHz, CDCl₃) δ: 7.38 (s, 1H), 7.31 (s, 1H), 6.99-6.93 (m, 2H), 6.85 (d, 1H), 6.34 (s, 1H), 5.34 (s, 2H), 3.02-2.96 (m, 1H), 2.73-2.71 (m, 1H), 2.65-2.59 (m, 1H), 2.45 (s, 3H), 1.18 (m, 3H). LC-MS ESI m/z: found 375.2 [M–H]⁻.

Example 121

3-(4-((5-fluoro-2,2-dimethyl-2,3-dihydrobenzofuran-7-yl)methoxy)naphthalen-1-yl)propanoic acid (150)

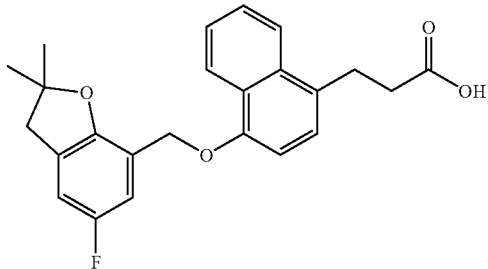

¹H NMR (400 MHz, DMSO-d₆) δ: 8.41 (d, 1H), 7.95 (d, 1H), 7.58-7.49 (m, 2H), 7.25 (m, 1H), 7.09 (d, 1H), 6.86-6.81 (m, 2H), 5.17 (s, 2H), 3.36 (m, 2H), 3.02 (s, 2H), 2.79 (m, 2H), 1.48 (s, 6H). LC-MS ESI m/z: found 393.4 [M–H]⁻.

Example 122

3-(2-((dimethylamino)methyl)-4-((5-fluoro-2,2-dimethyl-2,3-dihydrobenzofuran-7-yl)methoxy)phenyl)propanoic acid (151)

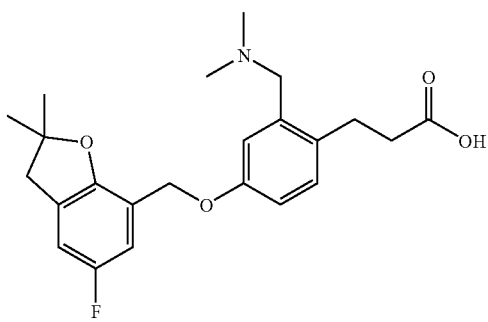

¹H NMR (400 MHz, DMSO-d₆) δ: 7.21 (d, 1H), 7.03 (d, 1H), 6.93 (s, 2H), 6.80 (d, 1H), 4.92 (s, 2H), 4.26 (s, 2H), 3.00 (s, 2H), 2.89 (m, 2H), 2.83 (s, 6H), 2.78 (m, 2H), 1.47 (s, 6H). LC-MS ESI m/z: found 400.4 [M–H]⁻.

Example 123

3-(4-((5-acetamido-2,2-dimethyl-2,3-dihydrobenzofuran-7-yl)methoxy)phenyl)-2-methylpropanoic acid (152)

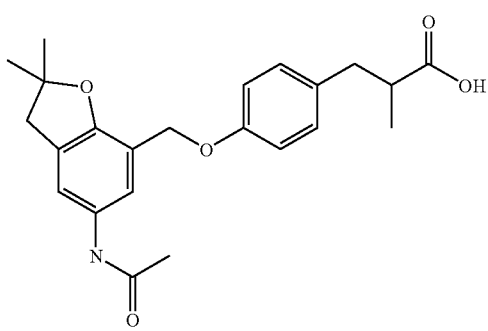

¹H NMR (400 MHz, DMSO-d₆) δ: 7.44 (s, 1H), 7.31 (br, 1H), 7.06 (d, 2H), 6.99 (s, 1H), 6.87 (d, dH), 4.97 (s, 2H), 3.02-2.92 (m, 3H), 2.74-2.61 (m, 2H), 2.11 (s, 3H), 1.47 (s, 6H), 1.17 (d, 3H). LC-MS ESI m/z: found 396.5 [M–H]⁻.

Example 124

3-(4-((2,2-dimethyl-5-(trifluoromethoxy)-2,3-dihydrobenzofuran-7-yl)methoxy)phenyl)-2-methylpropanoic acid (153)

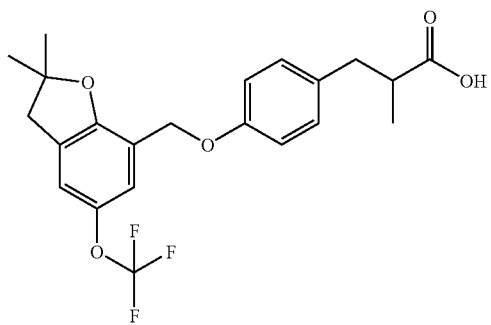

¹H NMR (400 MHz, DMSO-d₆) δ: 7.14-7.08 (m, 3H), 6.95-6.91 (m, 3H), 4.98 (s, 2H), 3.05-2.95 (m, 3H), 2.74-2.69 (m, 1H), 2.64-2.59 (m, 1H), 1.49 (s, 6H), 1.16 (d, 3H). LC-MS ESI m/z: found 423.4 [M–H]⁻.

Example 125

3-(4-((5-fluoro-2,2-dimethyl-2,3-dihydrobenzofuran-7-yl)methoxy)-2-methylbenzofuran-7-yl)propanoic acid (154)

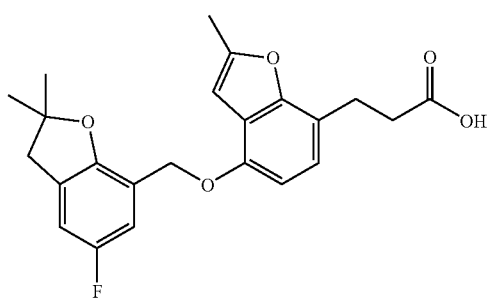

¹H NMR (400 MHz, DMSO-d₆) δ: 7.07-6.99 (m, 3H), 6.82 (d, 1H), 6.51 (s, 1H), 5.13 (s, 2H), 3.03-3.00 (m, 4H), 2.66-2.63 (m, 2H), 2.42 (s, 3H), 1.45 (s, 6H). LC-MS ESI m/z: found 397.3 [M–H]⁻.

Example 126

2-acetamidoethyl 3-(4-((5-chloro-2,2-dimethyl-2,3-dihydrobenzofuran-7-yl)methoxy)-3-(trifluoromethyl)phenyl)-2-methylpropanoate (155)

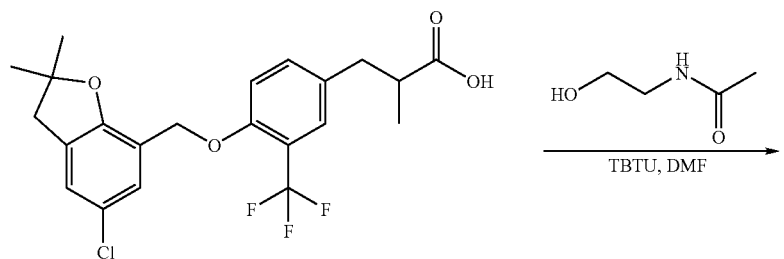

38

HPLC to afford 2-acetamidoethyl 3-(4-((5-chloro-2,2-dimethyl-2,3-dihydrobenzofuran-7-yl)methoxy)-3-(trifluoromethyl)phenyl)-2-methylpropanoate (155) (45 mg, 70%). $^1$H NMR (400 MHz, CDCl$_3$) δ: 7.39 (s, 1H), 7.04 (m, 2H), 7.05-7.00 (m, 2H), 5.47 (br, 1H), 5.06 (s, 2H), 4.10 (m, 2H), 3.44-3.37 (m, 2H), 3.05 (s, 2H), 2.96-2.91 (m, 1H), 2.76-2.66

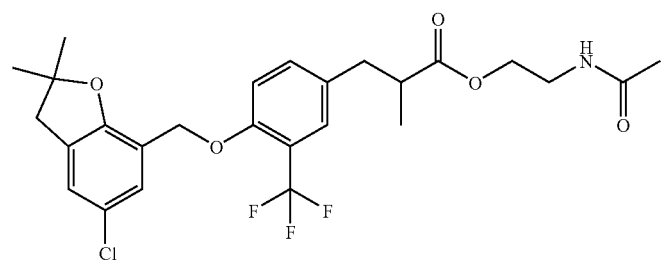

155

A solution of 3-(4-((5-chloro-2,2-dimethyl-2,3-dihydrobenzofuran-7-yl)methoxy)-3-(trifluoromethyl)phenyl)-2-methylpropanoic acid (38) (50 mg, 0.113 mmol), O-(benzotriazol-1-yl)-N,N,N',N'-tetramethyluronium tetrafluoroborate (54.3 mg, 0.169 mmol), and diisopropylethylamine (39.3 μL, 0.225 mmol) in DMF (1.5 mL) was stirred at room temperature for 30 min, then N-acetylethanolamine (23 mg, 0.226 mmol) was added. The reaction mixture was stirred at room temperature overnight. After evaporation of solvent in vacuo, the residue was purified by preparative (m, 2H), 1.93 (s, 3H), 1.49 (s, 6H), 1.19 (d, J=6.8 Hz, 3H). LC-MS ESI m/z: found 528.0 [M−H]$^-$.

Example 127

3-(4-(((5-chloro-2,2-dimethyl-2,3-dihydrobenzofuran-7-yl)methyl)amino)phenyl)propanoic acid (156)

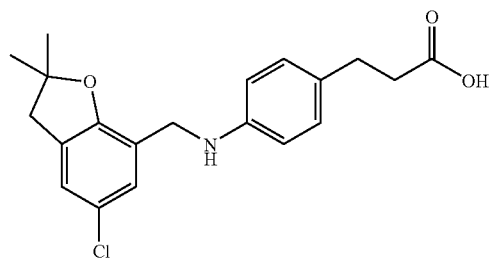

$^1$H NMR (400 MHz, CDCl$_3$) δ 7.27 (bs, 1H), 7.08 (s, 1H), 7.01 (d, J=8.2 Hz, 2H), 7.00 (s, 1H), 6.60 (d, J=8.2 Hz, 2H), 4.21 (s, 2H), 2.98 (s, 2H), 2.84 (t, J=7.8 Hz, 2H), 2.62 (t, J=7.8 Hz, 2H), 1.48 (s, 6H).

Example 128

3-(4-(((5-fluoro-2,2-dimethyl-2,3-dihydrobenzofuran-7-yl)methyl)amino)phenyl)propanoic acid (157)

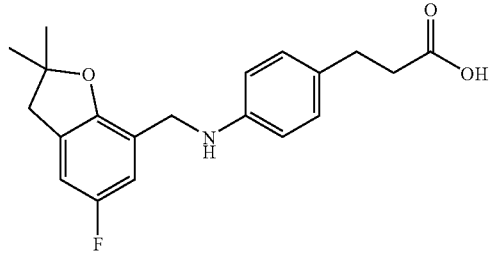

$^1$H NMR (400 MHz, CDCl$_3$) δ 7.00 (d, J=7.8 Hz, 2H), 6.81 (d, J=8.5 Hz, 1H), 6.73 (d, J=8.5 Hz, 1H), 6.59 (d, J=7.8 Hz, 2H), 4.22 (s, 2H), 2.98 (s, 2H), 2.83 (t, J=7.7 Hz, 2H), 2.61 (t, J=7.7 Hz, 2H), 1.47 (s, 6H).

Example 129

3-(4-((5-chloro-2,2-dimethyl-3-oxo-2,3-dihydrobenzofuran-7-yl)methoxy)phenyl)-2-methylpropanoic acid (158)

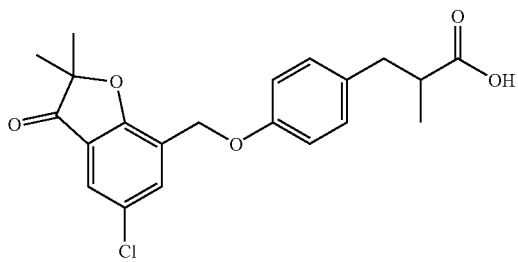

$^1$H NMR (400 MHz, CDCl$_3$) δ 7.76 (d, J=2.1 Hz, 1H), 7.58 (d, J=2.2 Hz, 1H), 7.13 (d, J=8.6 Hz, 2H), 6.94 (d, J=8.6 Hz, 2H), 5.10 (s, 2H), 3.01 (dd, J=13.4, 6.5 Hz, 1H), 2.76-2.60 (m, 2H), 1.48 (s, 6H), 1.18 (d, J=6.9 Hz, 3H).

Example 130

3-(4-((5-chloro-3-hydroxy-2,2-dimethyl-2,3-dihydrobenzofuran-7-yl)methoxy)phenyl)-2-methylpropanoic acid (159)

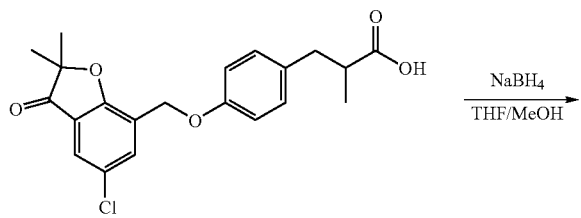

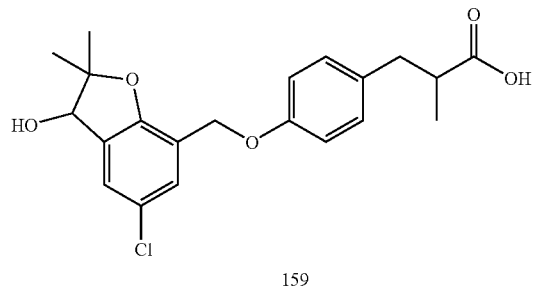

Compound (159) was prepared in a similar manner as that described for the synthesis of 109. $^1$H NMR (400 MHz, CDCl$_3$) δ 7.38 (d, J=1.8 Hz, 1H), 7.29 (d, J=1.8 Hz, 1H), 7.08 (d, J=8.4 Hz, 2H), 6.89 (d, J=8.5 Hz, 2H), 4.96 (s, 2H), 4.74 (s, 1H), 2.97 (dd, J=13.4, 6.6 Hz, 1H), 2.75-2.58 (m, 2H), 1.48 (s, 3H), 1.34 (s, 3H), 1.16 (d, J=6.8 Hz, 3H).

Examples 131A and 131B 2-(4-((5-fluoro-2,2-dimethyl-2,3-dihydrobenzofuran-7-yl)methoxy)phenyl)cyclopropanecarboxylic acid (160)

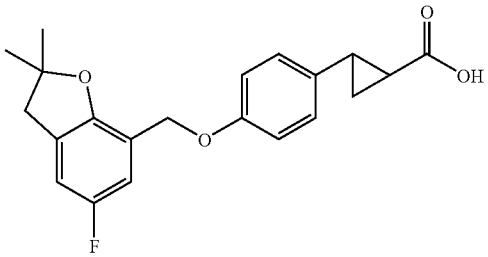

$^1$H NMR (400 MHz, CDCl$_3$) δ 7.02 (d, J=8.6 Hz, 2H), 6.93 (m, 3H), 6.79 (d, J=7.9 Hz, 1H), 4.98 (s, 2H), 3.00 (s, 2H), 2.61-2.45 (m, 1H), 1.88-1.76 (m, 1H), 1.64-1.56 (m, 1H), 1.48 (s, 6H), 1.38-1.30 (m, 1H).

Chiral separation of (160), using preparative Regis Pack, 5/100, 250×21.1 mm, flow rate 30 mL/min, solvent system 2.5:97.5:0.1 of iso-Propanol:Hexanes:Acetic acid provided (160A) (RT=12-15 minutes) and (160B) (RT=20-23 minutes). (160A): $^1$H NMR (400 MHz, CDCl$_3$) δ 7.02 (d, J=7.9 Hz, 2H), 6.92 (dd, J=18.5, 9.6 Hz, 3H), 6.78 (d, J=6.9 Hz, 1H), 4.97 (s, 2H), 2.99 (s, 2H), 2.62-2.44 (m, 1H), 1.86-1.77 (m, 1H), 1.65-1.56 (m, 1H), 1.47 (s, 6H), 1.39-1.29 (m, 1H). LC-MS ESI m/z: found 355.2 (M–H)$^-$.

Chiral separation of (160), using preparative Regis Pack, 5/100, 250×21.1 mm, flow rate 30 mL/min, solvent system 2.5:97.5:0.1 of iso-Propanol:Hexanes:Acetic acid provided (160A) (RT=12-15 minutes) and (160B) (RT=20-23 minutes). (160B): $^1$H NMR (400 MHz, CDCl$_3$) δ 7.02 (d, J=8.5 Hz, 2H), 6.98-6.85 (m, 3H), 6.78 (d, J=7.5 Hz, 1H), 4.97 (s, 2H), 2.99 (s, 2H), 2.61-2.49 (m, 1H), 1.85-1.76 (m, 1H), 1.64-1.58 (m, 1H), 1.47 (s, 6H), 1.38-1.30 (s, 1H). LC-MS ESI m/z: found 355.3 (M–H)⁻.

Example 132

3-(4-((5-fluoro-2,2-dimethyl-2,3-dihydrobenzofuran-7-yl)methoxy)phenyl)propanoic acid (161)

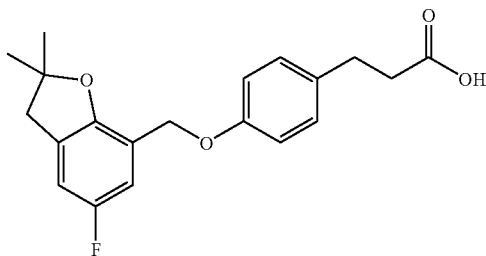

$^1$H NMR (400 MHz, CDCl$_3$) δ 7.11 (d, J=8.4 Hz, 2H), 6.96 (d, J=9.4 Hz, 1H), 6.91 (d, J=8.4 Hz, 2H), 6.79 (d, J=7.8 Hz, 1H), 4.97 (s, 2H), 2.99 (s, 2H), 2.89 (t, J=7.7 Hz, 2H), 2.64 (t, J=7.7 Hz, 2H), 1.48 (s, 6H).

Example 133

2-(4-((5-fluoro-2,2-dimethyl-2,3-dihydrobenzofuran-7-yl)methoxy)phenyl)acetic acid (162)

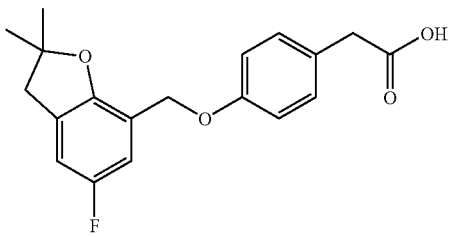

$^1$H NMR (400 MHz, CDCl$_3$) δ 7.17 (d, J=7.7 Hz, 2H), 6.94 (m, 3H), 6.79 (d, J=7.8 Hz, 1H), 4.98 (s, 2H), 3.57 (s, 2H), 2.99 (s, 2H), 1.47 (s, 6H).

Example 134

3-(2-ethyl-4-((5-fluoro-2,2-dimethyl-2,3-dihydrobenzofuran-7-yl)methoxy)phenyl)propanoic acid (163)

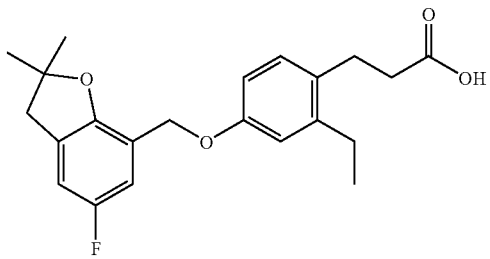

$^1$H NMR (400 MHz, CDCl$_3$) δ 7.05 (d, J=8.3 Hz, 1H), 6.98 (d, J=9.9 Hz, 1H), 6.80 (m, 3H), 4.97 (s, 2H), 2.99 (s, 2H), 2.90 (t, J=7.7 Hz, 2H), 2.67-2.59 (m, 4H), 1.47 (s, 6H), 1.21 (t, J=7.4 Hz, 3H).

Example 135

3-(4-((5-fluoro-2,2-dimethyl-2,3-dihydrobenzofuran-7-yl)methoxy)-2-isopropylphenyl)propanoic acid (164)

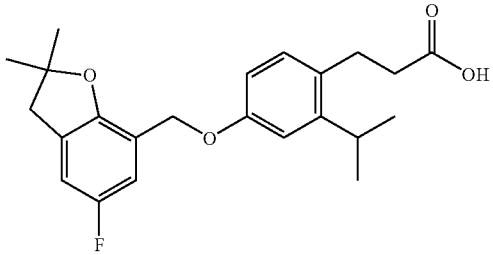

$^1$H NMR (400 MHz, CDCl$_3$) δ 7.05 (d, J=8.0 Hz, 1H), 6.98 (d, J=9.3 Hz, 1H), 6.89 (s, 1H), 6.83-6.70 (m, 2H), 4.97 (s, 2H), 3.14-3.04 (m, 1H), 2.99 (s, 2H), 2.93 (t, J=7.8 Hz, 2H), 2.59 (t, J=7.8 Hz, 2H), 1.47 (s, 6H), 1.22 (d, J=6.6 Hz, 6H).

Example 136

3-(4-((5-fluoro-2,2-dimethyl-2,3-dihydrobenzofuran-7-yl)methoxy)-2-(trifluoromethoxy)phenyl)propanoic acid (165)

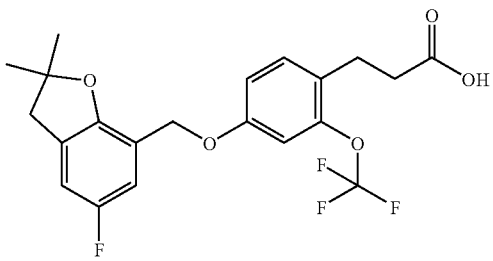

$^1$H NMR (400 MHz, CDCl$_3$) δ 7.16 (d, J=7.6 Hz, 1H), 6.93 (d, J=9.9 Hz, 1H), 6.87-6.77 (m, 3H), 4.97 (s, 2H), 3.00 (s, 2H), 2.91 (d, J=7.4 Hz, 2H), 2.62 (t, J=7.3 Hz, 2H), 1.47 (s, 6H).

Example 137

3-(4-((5-chloro-2,2-dimethyl-2,3-dihydrobenzofuran-7-yl)methoxy)-2-isopropylphenyl)propanoic acid (166)

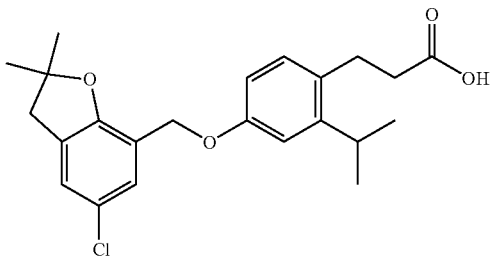

¹H NMR (400 MHz, CDCl₃) δ 7.25 (s, 1H), 7.1-7.0 (m, 2H), 6.89 (s, 1H), 6.76 (d, J=8.0 Hz, 1H), 4.95 (s, 2H), 3.15-3.05 (m, 1H), 2.99 (s, 2H), 2.94 (t, J=7.4 Hz, 2H), 2.60 (t, J=7.5 Hz, 2H), 1.47 (s, 6H), 1.22 (d, J=6.5 Hz, 6H).

Example 138

3-(4-((5-chloro-2,2-dimethyl-2,3-dihydrobenzofuran-7-yl)methoxy)-2-ethylphenyl)propanoic acid (167)

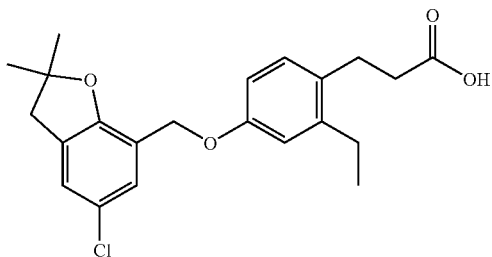

¹H NMR (400 MHz, CDCl₃) δ 7.25 (s, 1H), 7.08-7.02 (m, 2H), 6.83 (s, 1H), 6.77 (d, J=8.4 Hz, 1H), 4.95 (s, 2H), 2.99 (s, 2H), 2.91 (t, J=7.9 Hz, 2H), 2.66-2.56 (m, 4H), 1.47 (s, 6H), 1.22 (t, J=7.5 Hz, 3H).

Example 139

3-(4-((5-chloro-2,2-dimethyl-2,3-dihydrobenzofuran-7-yl)methoxy)-2-(trifluoromethoxy)phenyl)propanoic acid (168)

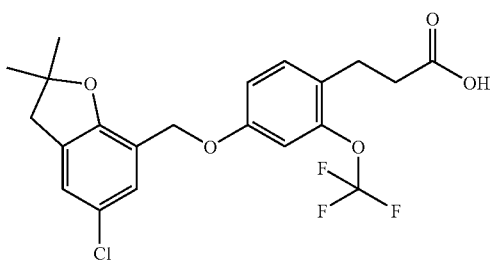

¹H NMR (400 MHz, CDCl₃) δ 7.20 (s, 1H), 7.16 (d, J=8.1 Hz, 1H), 7.05 (s, 1H), 6.90-6.82 (m, 2H), 4.95 (s, 2H), 3.00 (s, 2H), 2.92 (d, J=7.9 Hz, 2H), 2.63 (d, J=7.6 Hz, 2H), 1.47 (s, 6H).

Example 140

3-(4-((2,2-dimethyl-2,3-dihydrobenzofuran-4-yl)methoxy)-2-ethylphenyl)propanoic acid (169)

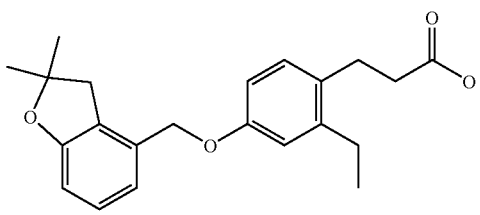

¹H NMR (400 MHz, CDCl₃) δ 7.17-7.16 (m, 2H), 6.90 (d, J=7.1 Hz, 1H), 6.83 (s, 1H), 6.79-6.70 (m, 2H), 4.95 (s, 2H), 3.06 (s, 2H), 2.93 (t, J=6.1 Hz, 2H), 2.7-2.58 (m, 4H), 1.49 (s, 6H), 1.23 (t, J=6.1 Hz, 3H).

Example 141

(R)-3-(4-((5-chloro-2,2-dimethyl-2,3-dihydrobenzofuran-7-yl)methoxy)-3-fluorophenyl)-2-methylpropanoic acid (170)

Compound (170) was prepared in a similar manner as that described for the synthesis of (94). ¹H NMR (400 MHz, CDCl₃) δ 7.24 (s, 1H), 7.03 (s, 1H), 6.98-6.87 (m, 2H), 6.82 (d, J=7.8 Hz, 1H), 5.02 (s, 2H), 3.02-2.92 (m, 3H), 2.75-2.65 (m, 1H), 2.58 (dd, J=12.8, 8.0 Hz, 1H), 1.46 (s, 6H), 1.16 (d, J=6.2 Hz, 3H).

Example 142

(S)-3-(4-((5-chloro-2,2-dimethyl-2,3-dihydrobenzofuran-7-yl)methoxy)-3-fluorophenyl)-2-methylpropanoic acid (171)

197

-continued

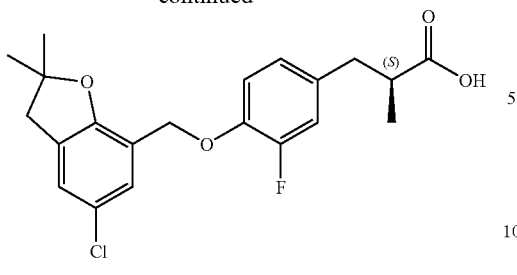

171

Compound (171) was prepared in a similar manner as that described for the synthesis of (94). $^1$H NMR (400 MHz, CDCl$_3$) δ 7.24 (s, 1H), 7.03 (s, 1H), 6.98-6.88 (m, 2H), 6.83 (s, 1H), 5.02 (s, 2H), 3.02-2.92 (m, 3H), 2.75-2.65 (m, 1H), 2.64-2.54 (m, 1H), 1.46 (s, 6H), 1.16 (d, J=6.0 Hz, 3H).

Example 143

(R)-3-(4-((5-chloro-2,2-dimethyl-2,3-dihydrobenzofuran-7-yl)methoxy)-3-(trifluoromethyl)phenyl)-2-methylpropanoic acid (172)

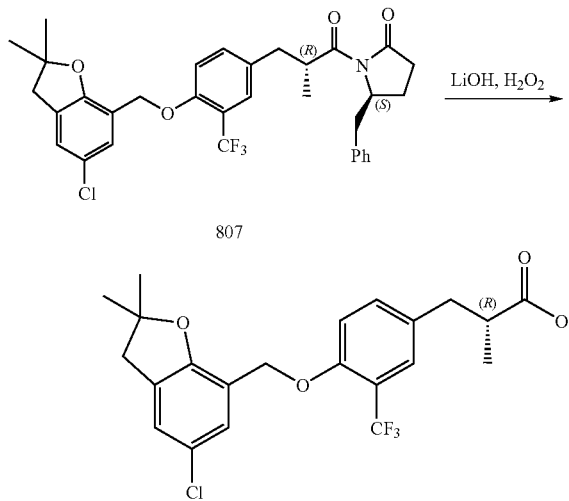

Compound (172) was prepared in a similar manner as that described for the synthesis of (94). $^1$H NMR (400 MHz, CDCl$_3$) δ 7.38 (s, 1H), 7.27-7.23 (m, 2H), 7.11-6.89 (m, 2H), 5.06 (s, 2H), 3.11-2.90 (m, 3H), 2.76-2.60 (m, 2H), 1.48 (s, 6H), 1.18 (d, J=6.7 Hz, 3H).

Example 144

(S)-3-(4-((5-chloro-2,2-dimethyl-2,3-dihydrobenzofuran-7-yl)methoxy)-3-(trifluoromethyl)phenyl)-2-methylpropanoic acid (173)

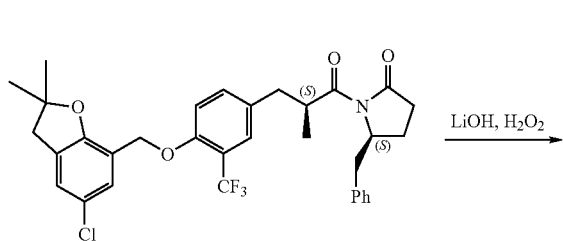

198

-continued

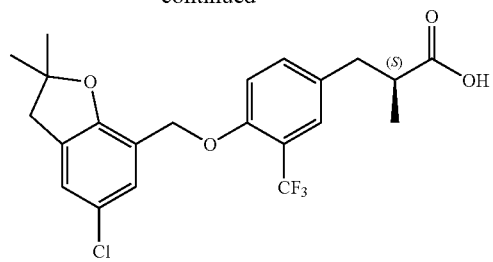

173

Compound (173) was prepared in a similar manner as that described for the synthesis of (94). $^1$H NMR (400 MHz, CDCl$_3$) δ 7.38 (s, 1H), 7.27-7.23 (m, 2H), 7.10-6.93 (m, 2H), 5.06 (s, 2H), 3.08-2.90 (m, 3H), 2.75-2.60 (m, 2H), 1.48 (s, 6H), 1.17 (d, J=6.7 Hz, 3H).

Example 145

3-(4-((3,3-dideuterio-5-fluoro-2,2-dimethyl-2,3-dihydrobenzofuran-7-yl)methoxy)phenyl)-2-methylpropanoic acid (174)

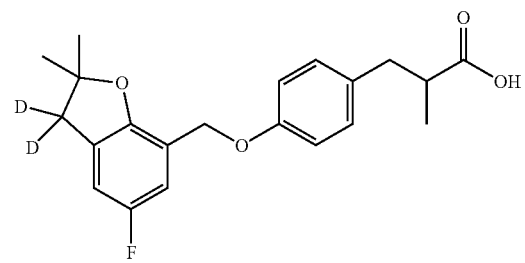

$^1$H NMR (400 MHz, CDCl$_3$) δ 7.09 (d, J=8.4 Hz, 2H), 6.97 (d, J=9 Hz, 1H), 6.91 (d, J=8.6 Hz, 2H), 6.78 (d, J=9 Hz, 1H), 4.97 (s, 2H), 3.13-2.93 (m, 1H), 2.81-2.55 (m, 2H), 1.47 (s, 6H), 1.17 (d, J=6.9 Hz, 3H).

Example 146

3-(4-((3,3-dideuterio-5-chloro-2,2-dimethyl-2,3-dihydrobenzofuran-7-yl)methoxy)-3-fluorophenyl)-2-methylpropanoic acid (175)

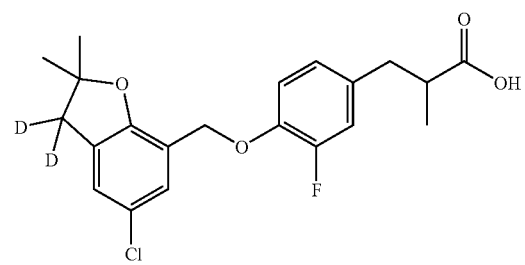

$^1$H NMR (400 MHz, CDCl$_3$) δ 7.26 (s, 1H), 7.04 (s, 1H), 6.98-6.88 (m, 2H), 6.82 (d, J=8.4 Hz, 1H), 5.03 (s, 2H), 2.98

(dd, J=13.6, 6.6 Hz, 1H), 2.76-2.65 (m, 1H), 2.60 (dd, J=13.5, 7.7 Hz, 1H), 1.47 (s, 6H), 1.17 (d, J=6.9 Hz, 3H).

Example 147

3-(4-((3,3-dideuterio-5-chloro-2,2-dimethyl-2,3-dihydrobenzofuran-7-yl)methoxy)-3-(trifluoromethyl)phenyl)-2-methylpropanoic acid (176)

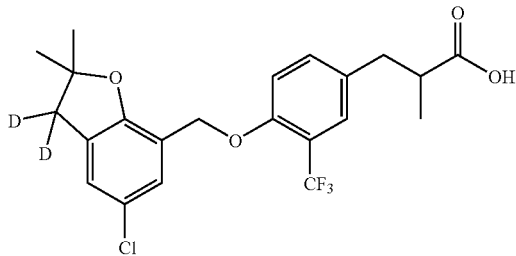

$^1$H NMR (400 MHz, CDCl$_3$) δ 7.40 (s, 1H), 7.3-7.24 (m, 2H), 7.10-6.97 (m, 2H), 5.08 (s, 2H), 3.03 (dd, J=13.4, 6.3 Hz, 1H), 2.8-2.62 (m, 2H), 1.49 (s, 6H), 1.20 (d, J=6.7 Hz, 3H).

Example 148

3-(4-((5-chloro-3,3-dimethyl-2,3-dihydrobenzofuran-7-yl)methoxy)phenyl)-2-methylpropanoic acid (177)

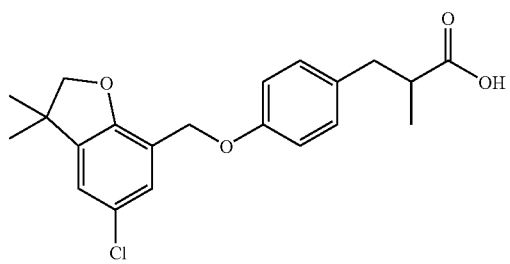

$^1$H NMR (400 MHz, CDCl$_3$) δ 7.26 (s, 1H), 7.10 (d, J=7.3 Hz, 2H), 7.00 (s, 1H), 6.91 (d, J=8.2 Hz, 2H), 4.97 (s, 2H), 4.28 (s, 2H), 3.01 (dd, J=13.4, 6.3 Hz, 1H), 2.76-2.57 (m, 2H), 1.34 (s, 6H), 1.17 (d, J=6.8 Hz, 3H).

Example 149

3-(4-((5-chloro-3,3-dimethyl-2,3-dihydrobenzofuran-7-yl)methoxy)-3-fluorophenyl)-2-methylpropanoic acid (178)

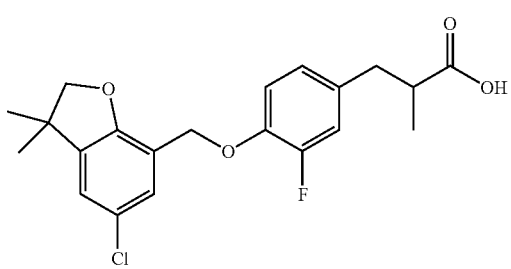

$^1$H NMR (400 MHz, CDCl$_3$) δ 7.26 (s, 1H), 7.00 (s, 1H), 6.97-6.90 (m, 2H), 6.84 (d, J=7.7 Hz, 1H), 5.04 (s, 2H), 4.28 (s, 2H), 2.98 (dd, J=13.4, 6.6 Hz, 1H), 2.76-2.65 (m, 1H), 2.61 (dd, J=13.5, 7.8 Hz, 1H), 1.33 (s, 6H), 1.18 (d, J=6.8 Hz, 3H).

Example 150

3-(4-((2,2-dimethyl-2,3-dihydrobenzofuran-4-yl)methoxy)-2,3-dimethylphenyl)propanoic acid (179)

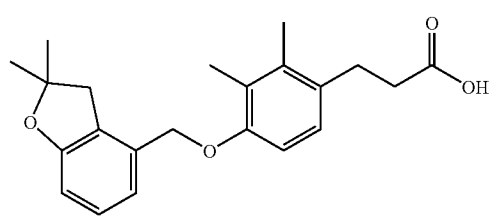

$^1$H NMR (400 MHz, CDCl$_3$) δ 7.13 (t, J=7.8 Hz, 1H), 6.98 (d, J=8.4 Hz, 1H), 6.92 (d, J=7.5 Hz, 1H), 6.75-6.70 (m, 2H), 4.93 (s, 2H), 3.03 (s, 2H), 2.94 (t, J=8.0 Hz, 2H), 2.60 (t, J=8.0 Hz, 2H), 2.24 (s, 3H), 2.20 (s, 3H), 1.48 (s, 6H).

Example 151

3-(3,5-difluoro-4-((2-methylbenzo[b]thiophen-7-yl)methoxy)phenyl)-2-methylpropanoic acid (180)

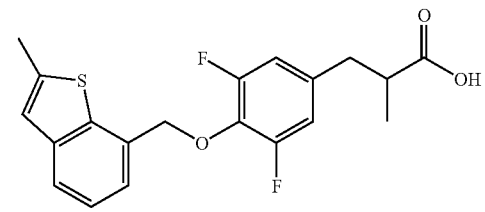

$^1$H NMR (400 MHz, CDCl$_3$) δ 7.63 (d, J=7.6 Hz, 1H), 7.37-7.28 (m, 2H), 7.01 (s, 1H), 6.74 (d, J=8.7 Hz, 2H), 5.33 (s, 2H), 3.01-2.93 (m, 1H), 2.75-2.69 (m, 1H), 2.64-2.56 (m, 4H), 1.19 (d, J=6.9 Hz, 3H). LC-MS ESI m/z: found 375.0 [M−H]$^-$.

Example 152

2-(5-((2-methylbenzo[b]thiophen-7-yl)methoxy)-2,3-dihydro-1H-inden-1-yl)acetic acid (181)

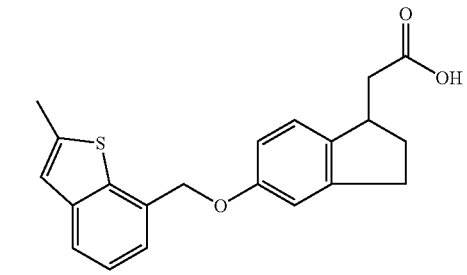

$^1$H NMR (400 MHz, CDCl$_3$) δ 7.67-7.58 (m, 1H), 7.32 (d, J=4.8 Hz, 2H), 7.11 (d, J=8.3 Hz, 1H), 7.02 (s, 1H), 6.92 (s,

1H), 6.86 (d, J=8.2 Hz, 1H), 5.25 (s, 2H), 3.62-3.47 (m, 1H), 2.96-2.77 (m, 3H), 2.60 (s, 3H), 2.51-2.38 (m, 2H), 1.84-1.72 (m, 1H).

Example 153

2-(6-((5-fluoro-2,2-dimethyl-2,3-dihydrobenzofuran-7-yl)methoxy)-1,2,3,4-tetrahydronaphthalen-1-yl)acetic acid (182)

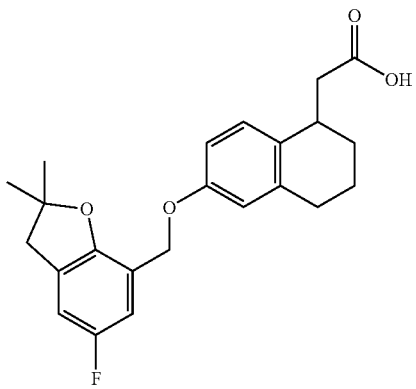

$^1$H NMR (400 MHz, CDCl$_3$) δ 7.08 (d, J=8.5 Hz, 1H), 6.97 (d, J=9.9 Hz, 1H), 6.79 (d, J=8.3 Hz, 2H), 6.70 (s, 1H), 4.96 (s, 2H), 3.37-3.23 (m, 1H), 3.00 (s, 2H), 2.79-2.67 (m, 3H), 2.59-2.50 (m, 1H), 1.98-1.64 (m, 4H), 1.48 (s, 6H). LC-MS ESI m/z: found 385.1 (M+H)$^+$.

Example 154

2-(6-((5-chloro-2,2-dimethyl-2,3-dihydrobenzofuran-7-yl)methoxy)-1,2,3,4-tetrahydronaphthalen-1-yl)acetic acid (183)

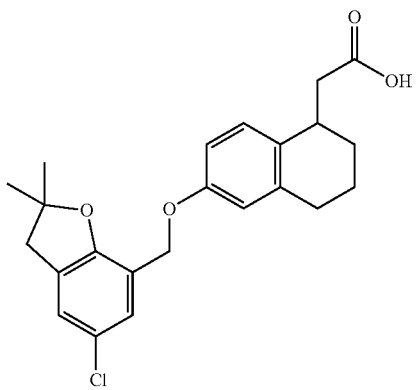

$^1$H NMR (400 MHz, CDCl$_3$) δ 7.24 (s, 1H), 7.09 (d, J=8.5 Hz, 1H), 7.04 (s, 1H), 6.79 (dd, J=8.6, 2.6 Hz, 1H), 6.70 (d, J=2.5 Hz, 1H), 4.95 (s, 2H), 3.40-3.23 (m, 1H), 3.00 (s, 2H), 2.81-2.69 (m, 3H), 2.61-2.50 (m, 1H), 2.01-1.64 (m, 4H), 1.48 (s, 6H). LC-MS ESI m/z: found 401.0 (M+H)$^+$.

Example 155

3-(3-chloro-4-((5-fluoro-2,2-dimethyl-2,3-dihydrobenzofuran-7-yl)methoxy)phenyl)-2-methylpropanoic acid (184)

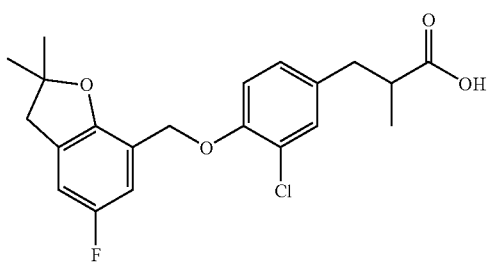

$^1$H NMR (400 MHz, CDCl$_3$) δ 7.21 (s, 1H), 7.08-6.90 (m, 3H), 6.80 (d, J=7.2 Hz, 1H), 5.06 (s, 2H), 3.04-2.91 (m, 3H), 2.76-2.66 (m, 1H), 2.63-2.54 (m, 1H), 1.48 (s, 6H), 1.17 (d, J=6.9 Hz, 3H). LC-MS: 393.0 (M+H$^+$). LC-MS ESI m/z: found 393.0 (M+H)$^+$.

Example 156

3-(4-((5-chloro-2,2-dimethyl-2,3-dihydrobenzofuran-7-yl)methoxy)phenyl)-3-methylbutanoic acid (185)

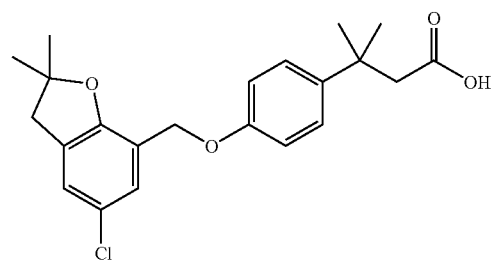

$^1$H NMR (400 MHz, CDCl$_3$) δ 7.32-7.20 (m, 3H), 7.04 (s, 1H), 6.93 (d, J=8.8 Hz, 2H), 4.96 (s, 2H), 3.00 (s, 2H), 2.63 (s, 2H), 1.47 (s, 6H), 1.44 (s, 6H).

Example 157

3-(4-((5-fluoro-2,2-dimethyl-2,3-dihydrobenzofuran-7-yl)methoxy)phenyl)-3-methylbutanoic acid (186)

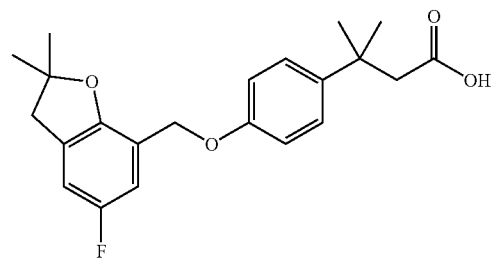

$^1$H NMR (400 MHz, CDCl$_3$) δ 7.27 (d, J=9.6 Hz, 2H), 6.97 (d, J=7.1 Hz, 1H), 6.93 (d, J=9.6 Hz, 2H), 6.79 (d, J=7.1 Hz, 1H), 4.97 (s, 2H), 3.00 (s, 2H), 2.62 (s, 2H), 1.48 (s, 6H), 1.44 (s, 6H).

Example 158

3-methyl-3-(4-((2,2,5-trimethyl-2,3-dihydrobenzofuran-7-yl)methoxy)phenyl)butanoic acid (187)

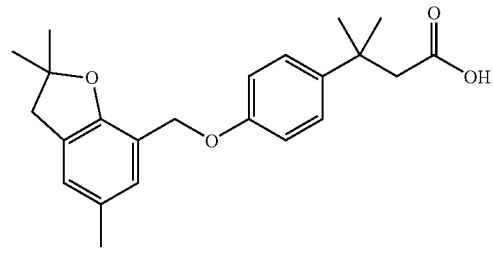

¹H NMR (400 MHz, CDCl₃)) δ 7.27 (d, J=8.8 Hz, 2H), 7.05 (s, 1H), 6.95 (d, J=8.8 Hz, 2H), 6.90 (s, 1H), 4.98 (s, 2H), 2.98 (s, 2H), 2.63 (s, 2H), 2.26 (s, 3H), 1.46 (s, 6H), 1.44 (s, 6H). LC-MS ESI m/z: found 369.0 (M+H)⁺.

Example 159

3-(4-((5-chloro-3H-spiro[benzofuran-2,1'-cyclopentane]-7-yl)methoxy)phenyl)-2-methylpropanoic acid (188)

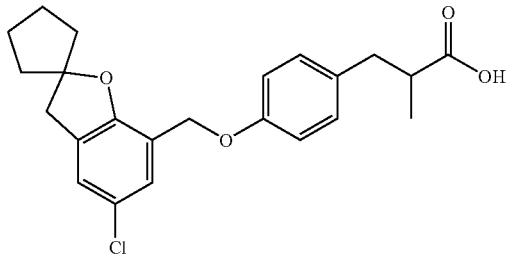

¹H NMR (400 MHz, CDCl₃) δ 7.22 (s, 1H), 7.09 (d, J=8.3 Hz, 2H), 7.04 (s, 1H), 6.91 (d, J=8.3 Hz, 2H), 4.94 (s, 2H), 3.15 (s, 2H), 3.10-2.90 (m, 1H), 2.77-2.66 (m, 1H), 2.65-2.53 (m, 1H), 2.11-2.04 (m, 2H), 1.94-1.82 (m, 2H), 1.80-1.62 (m, 4H), 1.16 (d, J=6.9 Hz, 3H). LC-MS ESI m/z: found 399.3 (M–H)⁻.

Example 160

4-(4-((5-fluoro-2,2-dimethyl-2,3-dihydrobenzofuran-7-yl)methoxy)phenyl)butanoic acid (189)

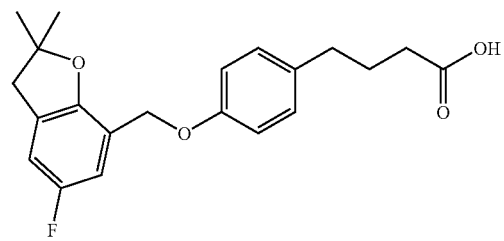

¹H NMR (400 MHz, CDCl₃) δ 7.08 (d, J=8.1 Hz, 2H), 6.97 (d, 1H), 6.90 (d, J=8.1 Hz, 2H), 6.79 (d, 1H), 4.97 (s, 2H), 2.99 (s, 2H), 2.60 (t, J=7.5 Hz, 2H), 2.36 (t, J=7.4 Hz, 2H), 1.98-1.83 (m, 2H), 1.48 (s, 6H). LC-MS ESI m/z: found 357.3 (M–H)⁻.

Example 161

4-(3,5-difluoro-4-((5-fluoro-2,2-dimethyl-2,3-dihydrobenzofuran-7-yl)methoxy)phenyl)butanoic acid (190)

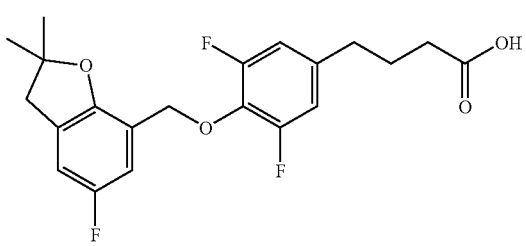

¹H NMR (400 MHz, CDCl₃) δ 6.98 (d, 1H), 6.80 (d, 1H), 6.69 (d, 2H), 5.07 (s, 2H), 2.96 (s, 2H), 2.58 (t, J=7.6 Hz, 2H), 2.36 (t, J=7.3 Hz, 2H), 1.98-1.82 (m, 2H), 1.41 (s, 6H). LC-MS ESI m/z: found 393.1 (M–H)⁻.

Example 162

3-(4-((5-fluoro-3H-spiro[benzofuran-2,1'-cyclopentane]-7-yl)methoxy)phenyl)-2-methylpropanoic acid (191)

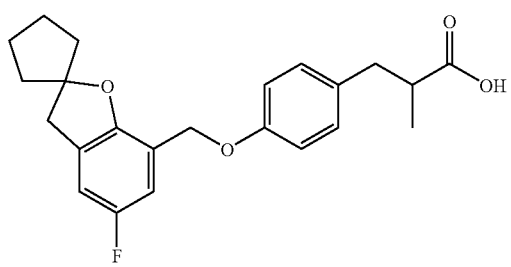

¹H NMR (400 MHz, CDCl₃) δ 7.08 (d, J=8.3, 2H), 6.98-6.87 (m, 3H), 6.79 (d, J=7.7 Hz, 1H), 4.96 (s, 2H), 3.15 (s, 2H), 3.10-2.90 (m, 1H), 2.78-2.66 (m, 1H), 2.66-2.53 (m, 1H), 2.13-2.01 (m, 2H), 1.95-1.84 (m, 2H), 1.80-1.65 (m, 4H), 1.16 (d, J=6.8 Hz, 3H). LC-MS ESI m/z: found 383.2 (M–H)⁻.

Example 163

2-(5-((5-fluoro-3H-spiro[benzofuran-2,1'-cyclopentane]-7-yl)methoxy)-2,3-dihydro-1H-inden-1-yl)acetic acid (192)

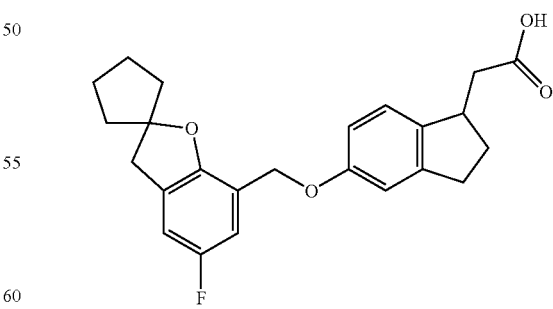

¹H NMR (400 MHz, DMSO) δ 12.16 (s, 1H), 7.06 (d, J=8.3 Hz, 1H), 7.00 (d, 1H), 6.92 (d, 1H), 6.82 (s, 1H), 6.72 (d, J=8.2 Hz, 1H), 4.88 (s, 2H), 3.31-3.23 (m, 1H), 3.17 (s, 2H), 2.84-2.57 (m, 3H), 2.30-2.15 (m, 2H), 1.94 (s, 2H), 1.83-1.51 (m, 7H). LC-MS ESI m/z: found 395.3 (M−H)⁻.

Example 164

3-(4-((5-fluoro-3H-spiro[benzofuran-2,1'-cyclopentane]-7-yl)methoxy)phenyl)propanoic acid (193)

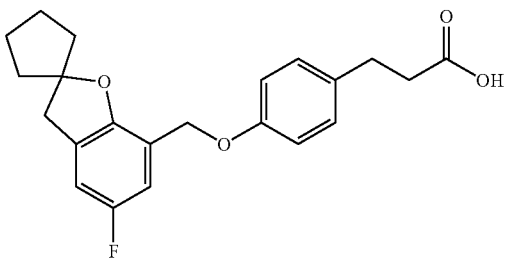

¹H NMR (400 MHz, CDCl₃) δ 7.11 (d, J=8.1 Hz, 2H), 6.98-6.86 (m, 3H), 6.79 (d, J=7.5 Hz, 1H), 4.96 (s, 2H), 3.15 (s, 2H), 2.89 (t, J=7.7 Hz, 2H), 2.64 (t, J=7.8 Hz, 2H), 2.14-2.01 (m, 2H), 1.96-1.80 (m, 2H), 1.81-1.63 (m, 4H). LC-MS ESI m/z: found 369.1 (M−H)⁻.

Example 165

2-(4-((5-fluoro-3H-spiro[benzofuran-2,1'-cyclopentane]-7-yl)methoxy)phenyl)cyclopropanecarboxylic acid (194)

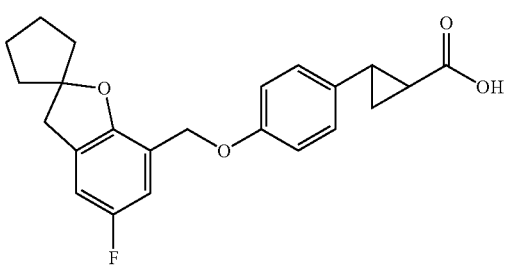

¹H NMR (400 MHz, CDCl₃) δ 7.02 (d, J=8.3 Hz, 2H), 6.96-6.87 (m, 3H), 6.79 (d, J=8.5 Hz, 1H), 4.96 (s, 2H), 3.15 (s, 2H), 2.62-2.48 (m, 1H), 2.12-2.02 (m, 2H), 1.93-1.56 (m, 8H), 1.39-1.29 (m, 1H). LC-MS ESI m/z: found 318.0 (M−H)⁻.

Example 166

3-(4-((5-chloro-3H-spiro[benzofuran-2,1'-cyclopentane]-7-yl)methoxy)phenyl)propanoic acid (195)

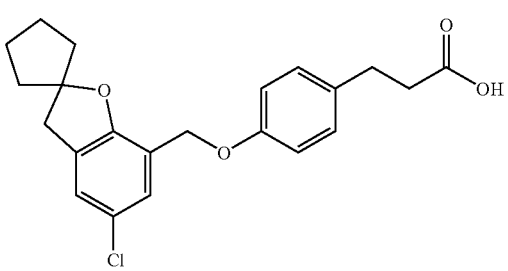

¹H NMR (400 MHz, CDCl₃) δ 7.22 (s, 1H), 7.11 (d, J=8.2 Hz, 2H), 7.04 (s, 1H), 6.91 (d, J=8.2 Hz, 2H), 4.94 (s, 2H), 3.15 (s, 2H), 2.89 (t, J=7.3 Hz, 2H), 2.64 (t, J=7.9 Hz, 2H), 2.15-2.00 (m, 2H), 1.96-1.84 (m, 2H), 1.81-1.65 (m, 4H). LC-MS ESI m/z: found 385.1 (M−H)⁻.

Example 167

4-(4-((2,2,5-trimethyl-2,3-dihydrobenzofuran-7-yl)methoxy)phenyl)butanoic acid (196)

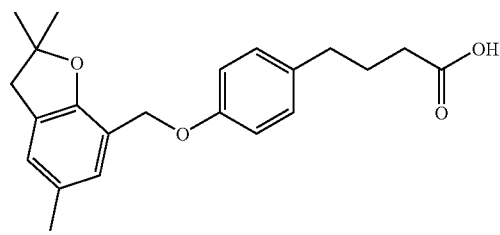

¹H NMR (400 MHz, CDCl₃) δ 7.10-7.00 (m, 3H), 6.96-6.87 (m, 3H), 4.97 (s, 2H), 2.97 (s, 2H), 2.60 (t, J=7.3 Hz, 2H), 2.35 (t, J=7.3 Hz, 2H), 2.26 (s, 3H), 1.98-1.85 (m, 2H), 1.46 (s, 6H). LC-MS ESI m/z: found 353.1 (M−H)⁻.

Example 168

4-(4-((5-chloro-2,2-dimethyl-2,3-dihydrobenzofuran-7-yl)methoxy)phenyl)butanoic acid (197)

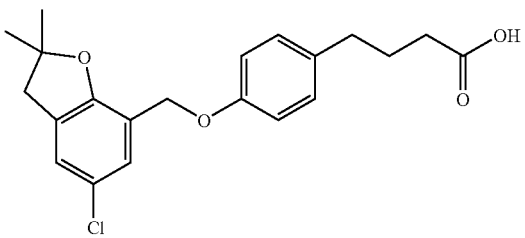

¹H NMR (400 MHz, CDCl₃) δ 7.24 (s, 1H), 7.10-7.01 (m, 3H), 6.91 (d, J=7.9 Hz, 2H), 4.95 (s, 2H), 2.99 (s, 2H), 2.60 (t, J=7.6 Hz, 2H), 2.36 (t, J=7.4 Hz, 2H), 1.95-1.85 (m, 2H), 1.47 (s, 6H). LC-MS ESI m/z: found 373.4 (M−H)⁻.

Example 169

4-(3,5-difluoro-4-((2,2,5-trimethyl-2,3-dihydrobenzofuran-7-yl)methoxy)phenyl)butanoic acid (198)

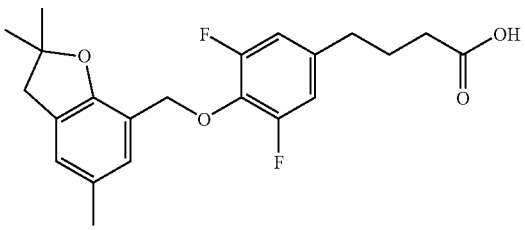

¹H NMR (400 MHz, CDCl₃) δ 7.03 (s, 1H), 6.90 (s, 1H), 6.67 (d, J=8.6 Hz, 2H), 5.08 (s, 2H), 2.93 (s, 2H), 2.57 (t, J=7.6 Hz, 2H), 2.36 (t, J=7.3 Hz, 2H), 2.25 (s, 3H), 1.98-1.81 (m, 2H), 1.39 (s, 6H). LC-MS ESI m/z: found 389.2 (M−H)⁻.

Example 170

4-(4-((5-chloro-2,2-dimethyl-2,3-dihydrobenzofuran-7-yl)methoxy)-3,5-difluorophenyl)butanoic acid (199)

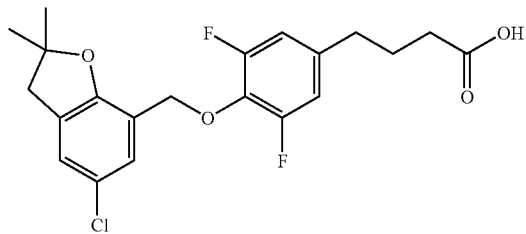

¹H NMR (400 MHz, CDCl₃) δ 7.22 (s, 1H), 7.04 (s, 1H), 6.69 (d, J=8.5 Hz, 2H), 5.05 (s, 2H), 2.96 (s, 2H), 2.58 (t, J=7.6 Hz, 2H), 2.36 (t, J=7.3 Hz, 2H), 1.95-1.83 (m, 2H), 1.41 (s, 6H). LC-MS ESI m/z: found 409.1 (M−H)⁻.

Example 171

4-(4-((5-fluoro-2,2-dimethyl-2,3-dihydrobenzofuran-7-yl)methoxy)phenyl)-2-methylbutanoic acid (200)

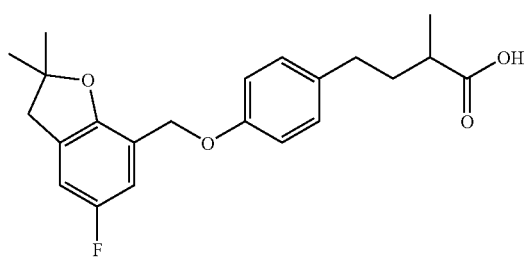

¹H NMR (400 MHz, CDCl₃) δ 7.08 (d, J=8.5 Hz, 2H), 6.97 (d, 1H), 6.90 (d, J=8.5 Hz, 2H), 6.78 (d, 1H), 4.97 (s, 2H), 2.99 (s, 2H), 2.59 (t, J=7.9 Hz, 2H), 2.55-2.44 (m, 1H), 2.08-1.94 (m, 1H), 1.76-1.61 (m, 1H), 1.47 (s, 6H), 1.22 (d, J=7.0 Hz, 3H). LC-MS ESI m/z: found 371.1 (M−H)⁻.

Example 172

4-(4-((5-chloro-2,2-dimethyl-2,3-dihydrobenzofuran-7-yl)methoxy)phenyl)-2-methylbutanoic acid (201)

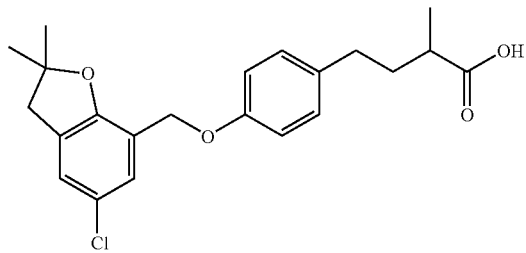

¹H NMR (400 MHz, CDCl₃) δ 7.24 (s, 1H), 7.09 (d, J=7.7 Hz, 2H), 7.03 (s, 1H), 6.90 (d, J=7.7, Hz 2H), 4.95 (s, 2H), 2.99 (s, 2H), 2.60 (t, J=7.9 Hz, 2H), 2.55-2.43 (m, 1H), 2.08-1.93 (m, 1H), 1.79-1.63 (m, 1H), 1.47 (s, 6H), 1.22 (d, J=6.9 Hz, 3H). LC-MS ESI m/z: found 387.5 (M−H)⁻.

Example 173

3-(4-((5-fluoro-2,2-dimethyl-2,3-dihydrobenzofuran-7-yl)methoxy)-3-methoxyphenyl)propanoic acid (202)

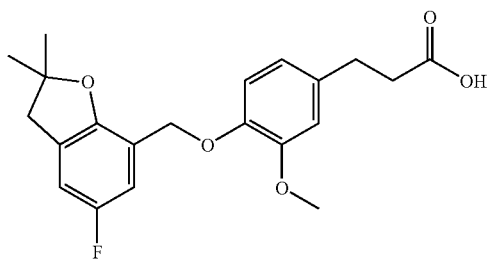

¹H NMR (400 MHz, CDCl₃) δ 6.99 (d, 1H), 6.83 (d, J=8.3 Hz, 1H), 6.80-6.75 (m, 2H), 6.66 (d, J=8.3 Hz, 1H), 5.06 (s, 2H), 3.87 (s, 3H), 2.98 (s, 2H), 2.88 (t, J=7.8 Hz, 2H), 2.65 (t, J=7.7 Hz, 2H), 1.47 (s, 6H). LC-MS ESI m/z: found 373.0 (M−H)⁻.

Example 174

3-(4-((5-chloro-2,2-dimethyl-2,3-dihydrobenzofuran-7-yl)methoxy)-3-methoxyphenyl)propanoic acid (203)

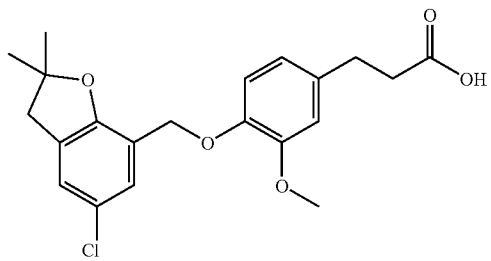

¹H NMR (400 MHz, CDCl₃) δ 7.26 (s, 1H), 7.01 (s, 1H), 6.84 (d, J=8.1 Hz, 1H), 6.73 (s, 1H), 6.66 (d, J=8.1 Hz, 1H), 5.04 (s, 2H), 3.87 (s, 3H), 2.98 (s, 2H), 2.88 (t, J=7.6, Hz 2H), 2.65 (t, J=7.6 Hz, 2H), 1.47 (s, 6H). LC-MS ESI m/z: found 389.2 (M−H)⁻.

Example 175

(S)-2-(5-((5-fluoro-2,2-dimethyl-2,3-dihydrobenzofuran-7-yl)methoxy)-2,3-dihydro-1H-inden-1-yl)acetic acid (204)

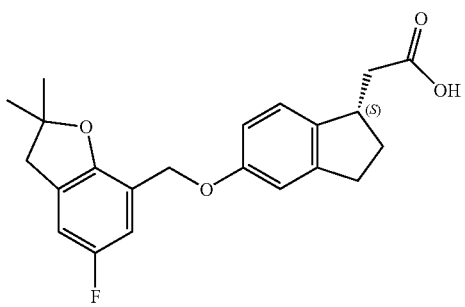

¹H NMR (400 MHz, CDCl₃) δ 7.08 (d, J=8.0 Hz, 1H), 6.97 (d, J=9.6 Hz, 1H), 6.87 (s, 1H), 6.83-6.77 (m, 2H), 4.97 (s, 2H), 3.63-3.41 (m, 1H), 2.99 (s, 2H), 2.97-2.72 (m, 3H), 2.51-2.34 (m, 2H), 1.83-1.71 (m, 1H), 1.48 (s, 6H). LC-MS ESI m/z: found 369.2 (M−H)⁻.

Example 176

(S)-2-(5-((5-chloro-2,2-dimethyl-2,3-dihydrobenzofuran-7-yl)methoxy)-2,3-dihydro-1H-inden-1-yl)acetic acid (205)

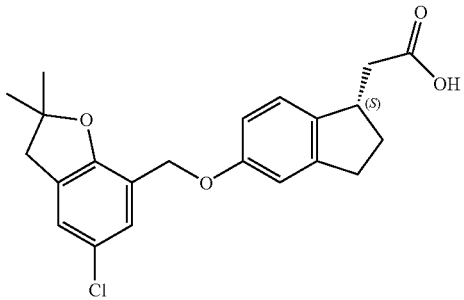

¹H NMR (400 MHz, CDCl₃) δ 7.24 (s, 1H), 7.09 (d, J=8.4 Hz, 1H), 7.03 (s, 1H), 6.87 (s, 1H), 6.80 (d, J=8.4 Hz, 1H), 4.95 (s, 2H), 3.63-3.41 (m, 1H), 3.00 (s, 2H), 2.95-2.73 (m, 3H), 2.54-2.33 (m, 2H), 1.85-1.68 (m, 1H), 1.48 (s, 6H). LC-MS ESI m/z: found 385.1 (M−H)⁻.

Example 177

3-(4-((5-chloro-2,2-dimethyl-2,3-dihydrobenzofuran-7-yl)methoxy)phenyl)propanoic acid (206)

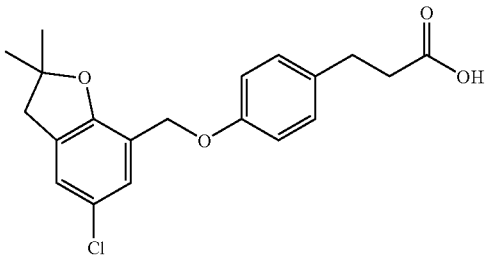

¹H NMR (400 MHz, CDCl₃) δ 7.24 (s, 1H), 7.11 (d, J=7.7 Hz, 2H), 7.04 (s, 1H), 6.91 (d, J=7.7 Hz, 2H), 4.96 (s, 2H), 2.99 (s, 2H), 2.89 (t, J=7.7 Hz, 2H), 2.64 (t, J=7.8 Hz, 2H), 1.47 (s, 6H). LC-MS ESI m/z: found 359.1 (M−H)⁻.

Example 178

(R)-2-(5-((5-fluoro-2,2-dimethyl-2,3-dihydrobenzofuran-7-yl)methoxy)-2,3-dihydro-1H-inden-1-yl)acetic acid (207)

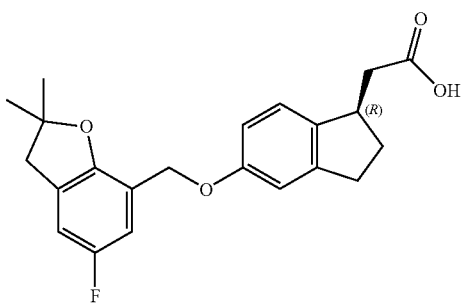

¹H NMR (400 MHz, CDCl₃) δ 7.08 (d, J=8.2 Hz, 1H), 6.97 (d, J=9.9 Hz, 1H), 6.87 (s, 1H), 7.80-7.75 (m, 2H), 4.97 (s, 2H), 3.63-3.41 (m, 1H), 3.00 (s, 2H), 2.95-2.73 (m, 3H), 2.53-2.34 (m, 2H), 1.85-1.70 (m, 1H), 1.48 (s, 6H). LC-MS ESI m/z: found 369.1 (M−H)⁻.

Example 179

(R)-2-(5-((5-chloro-2,2-dimethyl-2,3-dihydrobenzofuran-7-yl)methoxy)-2,3-dihydro-1H-inden-1-yl)acetic acid (208)

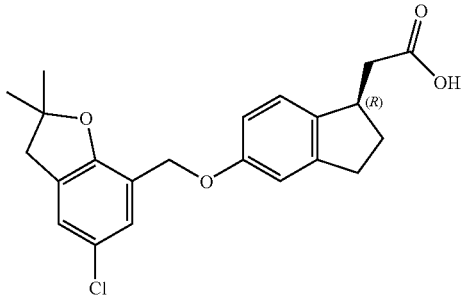

¹H NMR (400 MHz, CDCl₃) δ 7.25 (s, 1H), 7.09 (d, J=8.2 Hz, 1H), 7.04 (s, 1H), 6.87 (s, 1H), 6.81 (d, J=8.2 Hz, 1H), 4.96 (s, 2H), 3.60-3.42 (m, 1H), 3.00 (s, 2H), 2.95-2.74 (m, 3H), 2.54-2.32 (m, 2H), 1.86-1.71 (m, 1H), 1.48 (s, 6H). LC-MS ESI m/z: found 384.9 (M−H)⁻.

Example 180

2-(3-fluoro-4-((5-fluoro-2,2-dimethyl-2,3-dihydrobenzofuran-7-yl)methoxy)phenyl)cyclopropanecarboxylic acid (209)

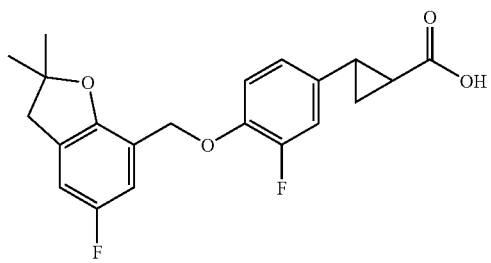

¹H NMR (400 MHz, CDCl₃) δ 7.00-6.88 (m, 2H), 6.85-6.71 (m, 3H), 5.04 (s, 2H), 2.99 (s, 2H), 2.59-2.43 (m, 1H), 1.86-1.74 (m, 1H), 1.69-1.54 (m, 1H), 1.47 (s, 6H), 1.38-1.27 (s, 1H). LC-MS ESI m/z: found 373.1 (M−H)⁻.

Example 181

2-(4-((5-chloro-2,2-dimethyl-2,3-dihydrobenzofuran-7-yl)methoxy)-3-fluorophenyl)cyclopropanecarboxylic acid (210)

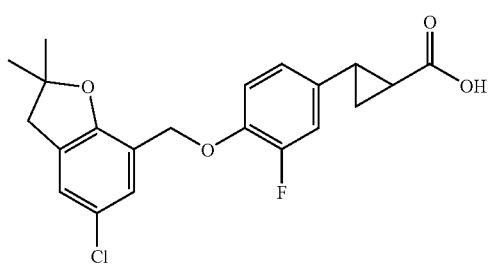

¹H NMR (400 MHz, CDCl₃) δ 7.23 (s, 1H), 7.04 (s, 1H), 6.94 (t, J=8.6 Hz, 1H), 6.80 (t, J=11.7 Hz, 2H), 5.03 (s, 2H), 2.99 (s, 2H), 2.57-2.42 (m, 1H), 1.86-1.72 (m, 1H), 1.68-1.54 (m, 1H), 1.47 (s, 6H), 1.36-1.27 (m, 1H). LC-MS ESI m/z: found 389.2 (M–H)⁻.

Example 182

4-(4-((5-fluoro-2,2-dimethyl-2,3-dihydrobenzofuran-7-yl)methoxy)phenyl)-3-methylbutanoic acid (211)

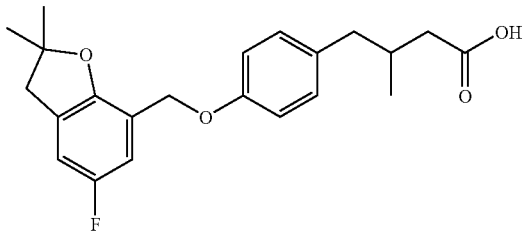

¹H NMR (400 MHz, CDCl₃) δ 7.05 (d, J=7.7 Hz, 2H), 6.97 (d, J=9.5 Hz, 1H), 6.90 (d, J=7.4 Hz, 2H), 6.79 (d, J=7.9 Hz, 1H), 4.97 (s, 2H), 2.99 (s, 2H), 2.61-2.51 (m, 1H), 2.50-2.30 (m, 2H), 2.27-2.09 (m, 2H), 1.47 (s, 6H), 0.96 (d, J=6.2 Hz, 3H). LC-MS ESI m/z: found 371.2 (M–H)⁻.

Example 183

4-(4-((5-chloro-2,2-dimethyl-2,3-dihydrobenzofuran-7-yl)methoxy)phenyl)-3-methylbutanoic acid (212)

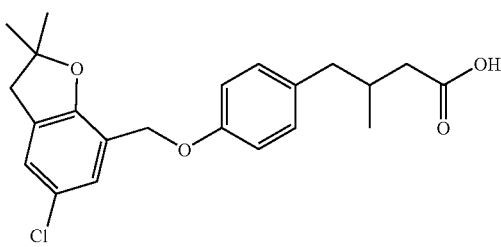

¹H NMR (400 MHz, CDCl₃) δ 7.25 (s, 1H), 7.06 (d, J=8.6 Hz, 3H), 6.90 (d, J=7.9 Hz, 2H), 4.96 (s, 2H), 2.99 (s, 2H), 2.63-2.30 (m, 3H), 2.29-2.08 (m, 2H), 1.48 (s, 6H), 0.96 (d, J=6.2 Hz, 3H). LC-MS ESI m/z: found 387.3 (M–H)⁻.

Examples 184A and 184B 2-(3,5-difluoro-4-((5-fluoro-2,2-dimethyl-2,3-dihydrobenzofuran-7-yl)methoxy)benzyl)cyclopropanecarboxylic acid (213)

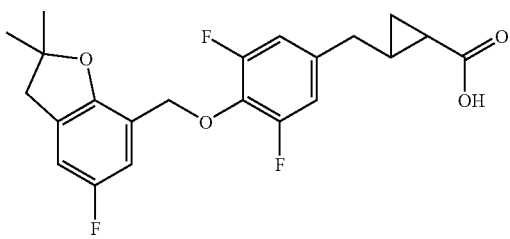

¹H NMR (400 MHz, CDCl₃) δ 6.97 (d, J=9.5 Hz, 1H), 6.79 (d, J=7.5 Hz, 1H), 6.60 (d, J=8.9 Hz, 2H), 5.05 (s, 2H), 2.95 (s, 2H), 2.43 (t, J=6.9 Hz, 2H), 1.75-1.63 (m, 1H), 1.39 (s, 6H), 1.35-1.25 (m, 1H), 1.01-0.82 (m, 2H). LC-MS ESI m/z: found 405.5 (M–H)⁻.

Chiral separation of (213), using preparative Pirkle Covalent (R,R) Whelk-O® 2, 10/100, 250×21.1 mm, flow rate 30 mL/min, solvent system 2:98:0.1 of iso-Propanol:Hexanes:Acetic acid, provided (213A) (RT=12.0 minutes) and (213B) (RT=14.0 minutes). (213A): ¹H NMR (400 MHz, CDCl₃) δ 6.97 (d, J=9.6 Hz, 1H), 6.79 (d, J=8.1 Hz, 1H), 6.60 (d, J=9.0 Hz, 2H), 5.05 (s, 2H), 2.95 (s, 2H), 2.43 (t, J=7.7 Hz, 2H), 1.75-1.63 (m, 1H), 1.39 (s, 6H), 1.35-1.25 (m, 1H), 0.98-0.83 (m, 2H).

Chiral separation of (213), using preparative Pirkle Covalent (R,R) Whelk-O® 2, 10/100, 250×21.1 mm, flow rate 30 mL/min, solvent system 2:98:0.1 of iso-Propanol:Hexanes:Acetic acid, provided (213A) (RT=12.0 minutes) and (213B) (RT=14.0 minutes). (213B): ¹H NMR (400 MHz, CDCl₃) δ 6.97 (d, J=9.9 Hz, 1H), 6.79 (d, J=7.1 Hz, 1H), 6.60 (d, J=8.5 Hz, 2H), 5.05 (s, 2H), 2.95 (s, 2H), 2.51-2.30 (m, 2H), 1.75-1.64 (m, 1H), 1.39 (s, 6H), 1.35-1.26 (m, 1H), 0.91 (ddd, J=11.9, 6.7, 2.0 Hz, 2H).

Example 185

2-(4-((5-chloro-2,2-dimethyl-2,3-dihydrobenzofuran-7-yl)methoxy)-3,5-difluorobenzyl)cyclopropanecarboxylic acid (214)

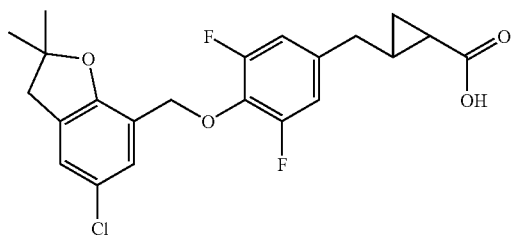

¹H NMR (400 MHz, CDCl₃) δ 7.23 (s, 1H), 7.04 (s, 1H), 6.60 (d, J=9.0 Hz, 2H), 5.03 (s, 2H), 2.95 (s, 2H), 2.43 (t, J=7.5 Hz, 2H), 1.74-1.66 (m, 1H), 1.40 (s, 6H), 1.36-1.26 (s, 1H), 1.00-0.84 (m, 2H). LC-MS ESI m/z: found 421.3 (M–H)⁻.

Example 186

3-(4-((2,2-dimethyl-5-phenyl-2,3-dihydrobenzofuran-7-yl)methoxy)phenyl)propanoic acid (215)

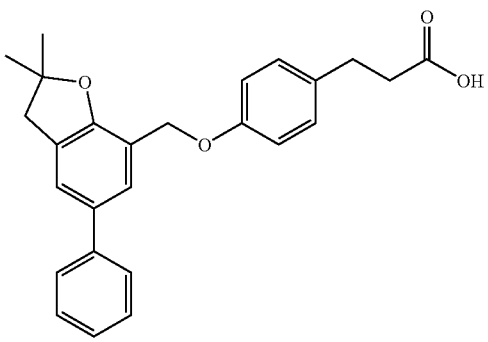

¹H NMR (400 MHz, CDCl₃) δ 7.55-7.46 (m, 3H), 7.38 (t, J=7.5 Hz, 2H), 7.33-7.26 (m, 2H), 7.11 (d, J=8.2 Hz, 2H), 6.95 (d, J=8.4 Hz, 2H), 5.06 (s, 2H), 3.08 (s, 2H), 2.89 (t, J=7.6 Hz, 2H), 2.64 (t, J=7.7 Hz, 2H), 1.51 (s, 6H). LC-MS ESI m/z: found 401.2 (M−H)⁻.

Example 187

2-(5-((2,2-dimethyl-5-phenyl-2,3-dihydrobenzofuran-7-yl)methoxy)-2,3-dihydro-1H-inden-1-yl)acetic acid (216)

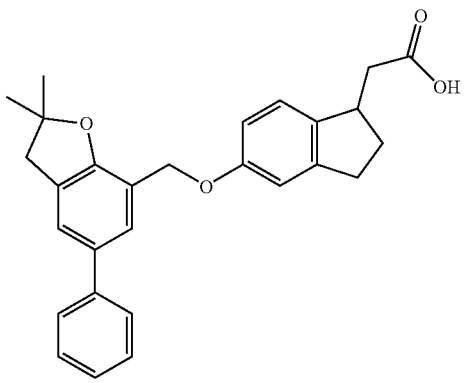

¹H NMR (400 MHz, CDCl₃) δ 7.54-7.47 (m, 3H), 7.39 (t, J=7.3 Hz, 2H), 7.33-7.26 (m, 2H), 7.08 (d, J=8.2 Hz, 1H), 6.92 (s, 1H), 6.84 (d, J=8.6 Hz, 1H), 5.06 (s, 2H), 3.62-3.44 (m, 1H), 3.08 (s, 2H), 2.96-2.76 (m, 3H), 2.51-2.35 (m, 2H), 1.85-1.70 (m, 1H), 1.52 (s, 6H). LC-MS ESI m/z: found 427.2 (M−H)⁻.

Example 188

(R)-2-(5-((6-fluoro-2,2-dimethyl-2,3-dihydrobenzofuran-4-yl)methoxy)-2,3-dihydro-1H-inden-1-yl)acetic acid (217)

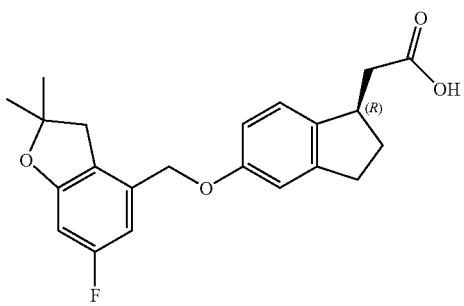

¹H NMR (400 MHz, CDCl₃) δ 7.11 (d, J=7.7 Hz, 1H), 6.83 (s, 1H), 6.76 (d, J=8.3 Hz, 1H), 6.62 (d, J=9.7 Hz, 1H), 6.42 (d, J=9.0 Hz, 1H), 4.92 (s, 2H), 3.65-3.44 (m, 1H), 2.97 (s, 2H), 2.93-2.74 (m, 3H), 2.54-2.36 (m, 2H), 1.87-1.71 (m, 1H), 1.48 (d, J=5.9 Hz, 6H). LC-MS ESI m/z: found 369.0 (M−H)⁻.

Example 189

3-(2-fluoro-4-((5-fluoro-3H-spiro[benzofuran-2,1'-cyclopentane]-7-yl)methoxy)phenyl)propanoic acid (218)

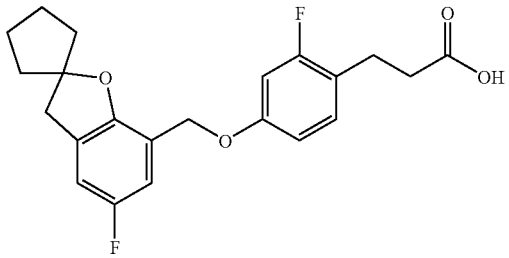

¹H NMR (400 MHz, CDCl₃) δ 7.08 (t, J=8.4 Hz, 1H), 6.92 (d, J=9.3 Hz, 1H), 6.80 (d, J=7.3 Hz, 1H), 6.69 (d, J=9.7 Hz, 2H), 4.95 (s, 2H), 3.15 (s, 2H), 2.89 (t, J=7.4 Hz, 2H), 2.64 (t, J=7.6 Hz, 2H), 2.16-2.01 (m, 2H), 1.95-1.85 (m, 2H), 1.78-1.65 (m, 4H). (M−H⁺). LC-MS ESI m/z: found 387.2 (M−H)⁻.

Example 190

3-(4-((5-fluoro-3H-spiro[benzofuran-2,1'-cyclopentane]-7-yl)methoxy)-2-methoxyphenyl)propanoic acid (219)

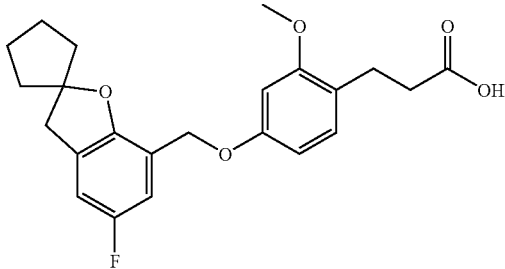

¹H NMR (400 MHz, CDCl₃) δ 7.02 (d, J=8.3 Hz, 1H), 6.95 (d, J=9.4 Hz, 1H), 6.80 (d, J=7.9 Hz, 1H), 6.49 (d, J=9.2 Hz, 2H), 4.96 (s, 2H), 3.78 (s, 3H), 3.15 (s, 2H), 2.86 (t, J=7.7 Hz, 2H), 2.62 (t, J=7.7 Hz, 2H), 2.17-2.00 (m, 2H), 1.97-1.84 (m, 2H), 1.80-1.62 (m, 4H). LC-MS ESI m/z: found 399.3 (M−H)⁻.

Example 191

2-(4-((5-fluoro-2,2-dimethyl-2,3-dihydrobenzofuran-7-yl)methoxy)benzyl)cyclopropanecarboxylic acid (220)

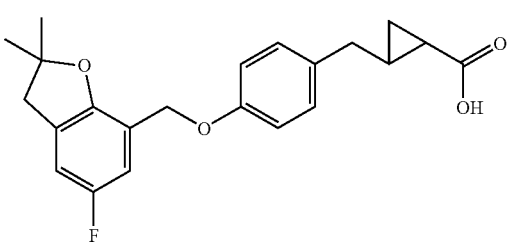

¹H NMR (400 MHz, CDCl₃) δ 7.10 (d, J=7.7 Hz, 2H), 6.97 (d, J=9.9 Hz, 1H), 6.91 (d, J=7.3 Hz, 2H), 6.78 (d, J=7.7 Hz, 1H), 4.97 (s, 2H), 2.99 (s, 2H), 2.75-2.46 (m, 2H), 1.80-1.61 (m, 1H), 1.47 (s, 6H), 1.34-1.18 (m, 2H), 0.98-0.80 (m, 1H). LC-MS ESI m/z: found 369.1 (M−H)⁻.

Example 192

2-(4-((5-chloro-2,2-dimethyl-2,3-dihydrobenzofuran-7-yl)methoxy)benzyl)cyclopropanecarboxylic acid (221)

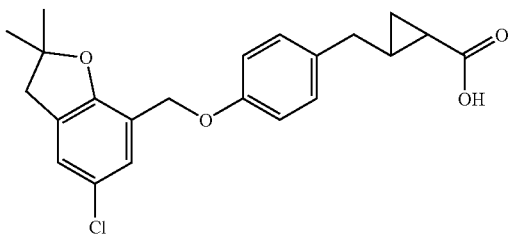

¹H NMR (400 MHz, CDCl₃) δ 7.25 (s, 1H), 7.10 (d, J=7.4 Hz, 2H), 7.03 (s, 1H), 6.92 (d, J=7.1 Hz, 2H), 4.96 (s, 2H), 2.99 (s, 2H), 2.75-2.46 (m, 2H), 1.78-1.65 (m, 1H), 1.47 (s, 6H), 1.34-1.20 (m, 2H), 0.94-0.82 (m, 1H). LC-MS ESI m/z: found 385.0 (M−H)⁻.

Example 193

3-(4-((5-chloro-3H-spiro[benzofuran-2,1'-cyclopentane]-7-yl)methoxy)-2-fluorophenyl)propanoic acid (222)

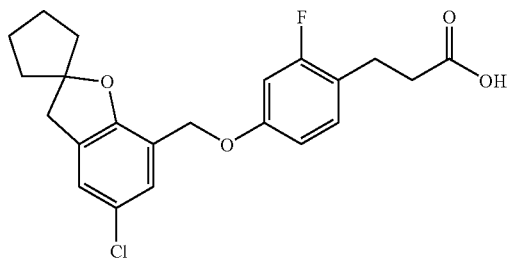

¹H NMR (400 MHz, CDCl₃) δ 7.19 (s, 1H), 7.13-7.02 (m, 2H), 6.69 (d, J=10.0 Hz, 2H), 4.93 (s, 2H), 3.15 (s, 2H), 2.90 (t, J=7.5 Hz, 2H), 2.64 (t, J=7.4 Hz, 2H), 2.14-2.02 (m, 2H), 1.98-1.64 (m, 6H). LC-MS ESI m/z: found 403.4 (M−H)⁻.

Example 194

3-(4-((5-chloro-3H-spiro[benzofuran-2,1'-cyclopentane]-7-yl)methoxy)-2-methoxyphenyl)propanoic acid (223)

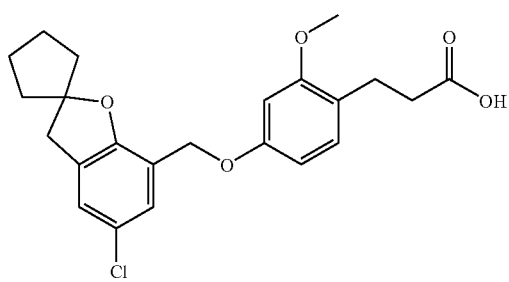

¹H NMR (400 MHz, CDCl₃) δ 7.23 (s, 1H), 7.03 (d, J=9.4 Hz, 2H), 6.50 (d, J=10.3 Hz, 2H), 4.94 (s, 2H), 3.79 (s, 3H), 3.15 (s, 2H), 2.87 (t, J=7.5 Hz, 2H), 2.62 (t, J=7.6 Hz, 2H), 2.13-2.00 (m, 2H), 1.98-1.60 (m, 6H). LC-MS ESI m/z: found 415.0 (M−H)⁻.

Example 195

3-(2-chloro-4-((5-fluoro-3H-spiro[benzofuran-2,1'-cyclopentane]-7-yl)methoxy)phenyl)propanoic acid (224)

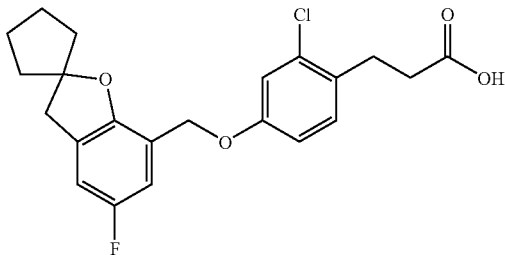

¹H NMR (400 MHz, CDCl₃) δ 7.13 (d, J=8.4 Hz, 1H), 7.00 (s, 1H), 6.92 (d, J=9.6 Hz, 1H), 6.81 (t, J=7.4 Hz, 2H), 4.95 (s, 2H), 3.15 (s, 2H), 2.98 (t, J=7.7 Hz, 2H), 2.66 (t, J=7.5 Hz, 2H), 2.19-2.04 (m, 2H), 1.99-1.85 (m, 2H), 1.80-1.66 (m, 4H). LC-MS ESI m/z: found 402.9 (M−H)⁻.

Example 196

3-(2-chloro-4-((5-chloro-3H-spiro[benzofuran-2,1'-cyclopentane]-7-yl)methoxy)phenyl)propanoic acid (225)

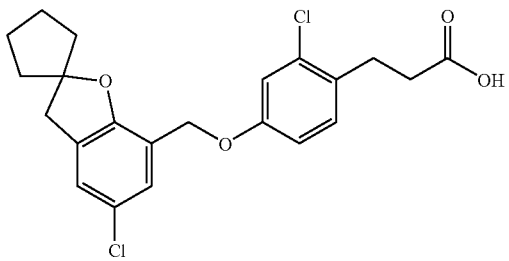

¹H NMR (400 MHz, CDCl₃) δ 7.19 (s, 1H), 7.13 (d, J=8.2 Hz, 1H), 7.05 (s, 1H), 7.00 (s, 1H), 6.82 (d, J=8.1 Hz, 1H), 4.93 (s, 2H), 3.15 (s, 2H), 2.98 (t, J=7.1 Hz, 2H), 2.66 (t, J=7.3 Hz, 2H), 2.21-1.95 (m, 2H), 1.95-1.82 (m, 2H), 1.82-1.62 (m, 4H). LC-MS ESI m/z: found 419.2 (M−H)⁻.

Example 197

3-(2,6-dichloro-4-((5-fluoro-2,2-dimethyl-2,3-dihydrobenzofuran-7-yl)methoxy)phenyl)propanoic acid (226)

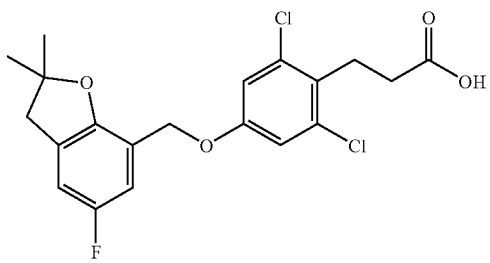

¹H NMR (400 MHz, CDCl₃) δ 6.95 (s, 2H), 6.90 (d, J=9.1 Hz, 1H), 6.81 (d, J=7.6 Hz, 1H), 4.95 (s, 2H), 3.26-3.12 (m, 2H), 3.01 (s, 2H), 2.65-2.51 (m, 2H), 1.50 (s, 6H). LC-MS ESI m/z: found 411.2 (M−H)⁻.

Example 198

3-(2,6-dichloro-4-((5-chloro-2,2-dimethyl-2,3-dihydrobenzofuran-7-yl)methoxy)phenyl)propanoic acid (227)

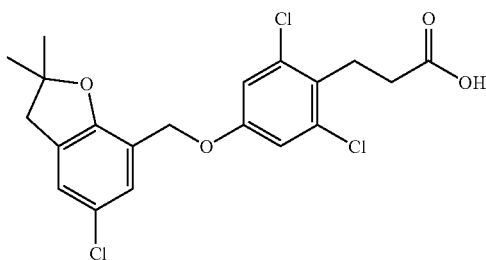

¹H NMR (400 MHz, CDCl₃) δ 7.18 (s, 1H), 7.06 (s, 1H), 6.95 (s, 2H), 4.94 (s, 2H), 3.26-3.09 (m, 2H), 3.01 (s, 2H), 2.66-2.50 (m, 2H), 1.50 (s, 6H). LC-MS ESI m/z: found 430.8 (M−H)⁻.

Example 199

2-(2-(4-((5-fluoro-2,2-dimethyl-2,3-dihydrobenzofuran-7-yl)methoxy)phenyl)cyclopropyl)acetic acid (228)

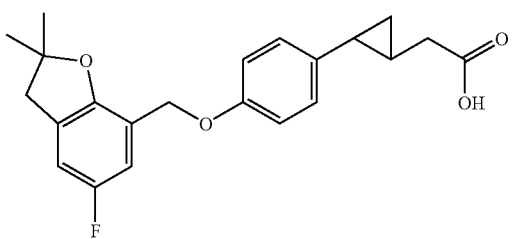

¹H NMR (400 MHz, CDCl₃) δ 6.98 (dd, J=21.4, 8.8 Hz, 3H), 6.88 (d, J=7.1 Hz, 2H), 6.78 (d, J=7.1 Hz, 1H), 4.96 (s, 2H), 2.99 (s, 2H), 2.43 (d, J=6.9 Hz, 2H), 1.77-1.69 (m, 1H), 1.47 (s, 6H), 1.36-1.22 (m, 1H), 0.99-0.90 (m, 1H), 0.85-0.77 (m, 1H). LC-MS ESI m/z: found 368.9 (M−H)⁻.

Example 200

2-(2-(4-((5-chloro-2,2-dimethyl-2,3-dihydrobenzofuran-7-yl)methoxy)phenyl)cyclopropyl)acetic acid (229)

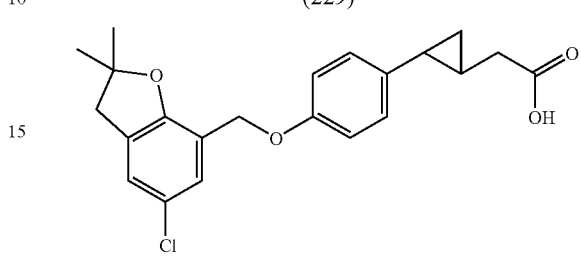

¹H NMR (400 MHz, CDCl₃) δ 7.23 (s, 1H), 7.01 (d, J=8.6 Hz, 3H), 6.88 (d, J=6.9 Hz, 2H), 4.94 (s, 2H), 2.99 (s, 2H), 2.43 (d, J=6.2 Hz, 2H), 1.81-1.68 (m, 1H), 1.47 (s, 6H), 1.38-1.26 (m, 1H), 1.01-0.89 (m, 1H), 0.87-0.76 (m, 1H). LC-MS ESI m/z: found 384.8 (M−H)⁻.

Example 201

2-(2-(4-((5-fluoro-3H-spiro[benzofuran-2,1'-cyclopentane]-7-yl)methoxy)phenyl)cyclopropyl)acetic acid (230)

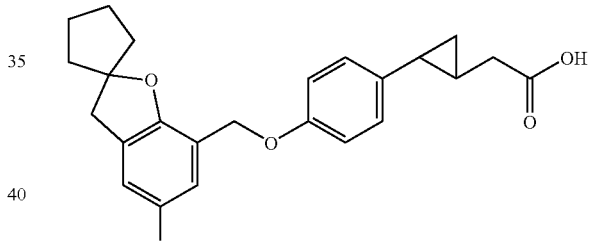

¹H NMR (400 MHz, CDCl₃) δ 7.01 (d, J=6.8 Hz, 2H), 6.94 (d, J=10.3 Hz, 1H), 6.88 (d, J=7.0 Hz, 2H), 6.78 (d, J=7.6 Hz, 1H), 4.95 (s, 2H), 3.14 (s, 2H), 2.43 (d, J=5.5 Hz, 2H), 2.16-2.02 (m, 2H), 1.97-1.83 (m, 2H), 1.80-1.62 (s, 5H), 1.37-1.22 (m, 1H), 0.99-0.89 (m, 1H), 0.86-0.75 (m, 1H). LC-MS ESI m/z: found 395.2 (M−H)⁻.

Example 202

2-(2-(4-((5-chloro-3H-spiro[benzofuran-2,1'-cyclopentane]-7-yl)methoxy)phenyl)cyclopropyl)acetic acid (231)

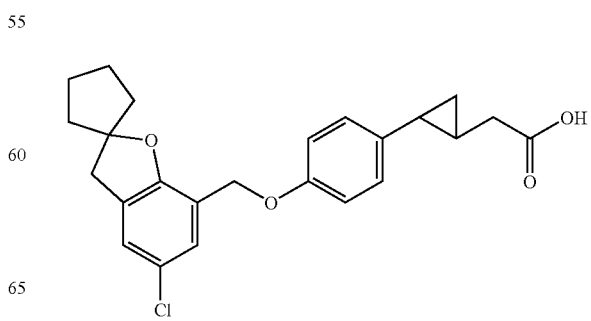

¹H NMR (400 MHz, CDCl₃) δ 6.82 (s, 1H), 6.62 (d, J=9.4 Hz, 3H), 6.49 (d, J=7.3 Hz, 2H), 4.54 (s, 2H), 2.75 (s, 2H), 2.17-1.95 (m, 2H), 1.79-1.62 (m, 2H), 1.57-1.42 (m, 2H), 1.40-1.24 (m, 5H), 0.99-0.87 (m, 1H), 0.61-0.50 (m, 1H), 0.49-0.36 (m, 1H). LC-MS ESI m/z: found 411.1 (M−H)⁻.

Example 203

3-(2-ethyl-4-((5-fluoro-3H-spiro[benzofuran-2,1'-cyclopentane]-7-yl)methoxy)phenyl)propanoic acid (232)

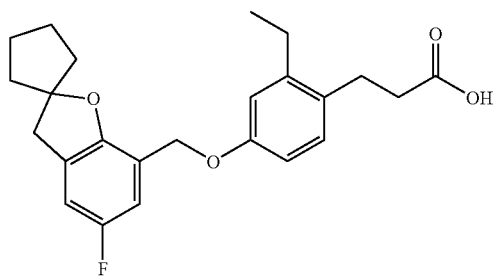

¹H NMR (400 MHz, CDCl₃) δ 7.05 (d, J=8.3 Hz, 1H), 6.96 (d, J=9.7 Hz, 1H), 6.84-6.73 (m, 3H), 4.96 (s, 2H), 3.15 (s, 2H), 2.91 (t, J=7.8 Hz, 2H), 2.71-2.50 (m, 4H), 2.15-2.00 (m, 2H), 1.98-1.82 (m, 2H), 1.81-1.61 (m, 4H), 1.21 (t, J=7.3 Hz, 3H). LC-MS ESI m/z: found 397.0 (M−H)⁻.

Example 204

3-(4-((5-fluoro-2,2-dimethyl-2,3-dihydrobenzofuran-7-yl)methoxy)-2,6-dimethylphenyl)propanoic acid (233)

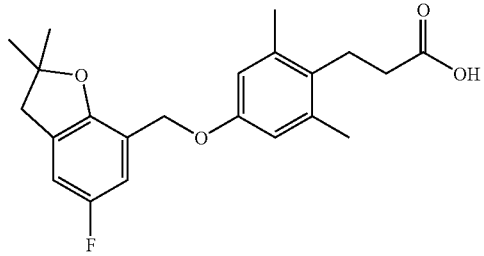

¹H NMR (400 MHz, CDCl₃) δ 6.97 (d, J=9.7 Hz, 1H), 6.79 (s, 1H), 6.67 (s, 2H), 4.95 (s, 2H), 3.00 (s, 2H), 2.92 (s, 2H), 2.47 (d, J=8.4 Hz, 2H), 2.30 (s, 6H), 1.48 (s, 6H). LC-MS ESI m/z: found 371.3 (M−H)⁻.

Example 205

3-(4-((5-chloro-2,2-dimethyl-2,3-dihydrobenzofuran-7-yl)methoxy)-2,6-dimethylphenyl)propanoic acid (234)

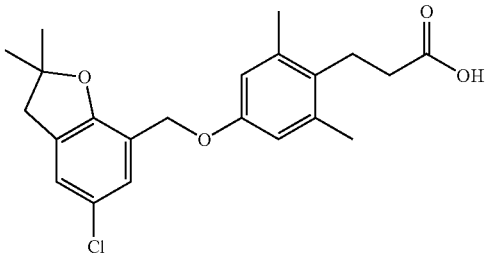

¹H NMR (400 MHz, CDCl₃) δ 7.03 (s, 1H), 6.67 (s, 2H), 4.93 (s, 2H), 3.00 (s, 2H), 2.92 (s, 2H), 2.47 (s, 2H), 2.30 (s, 6H), 1.48 (s, 6H). LC-MS ESI m/z: found 387.3 (M−H)⁻.

Example 206

3-(4-((5-fluoro-2,2-dimethyl-2,3-dihydrobenzofuran-7-yl)methoxy)-2,5-dimethylphenyl)propanoic acid (235)

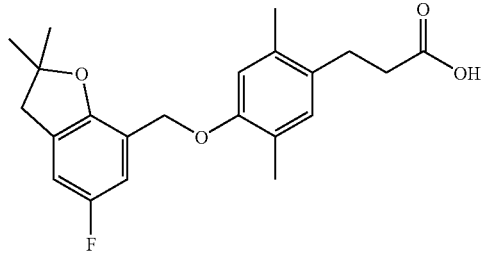

¹H NMR (400 MHz, CDCl₃) δ 7.00 (d, J=8.5 Hz, 1H), 6.92 (s, 1H), 6.79 (s, 1H), 6.72 (s, 1H), 4.97 (s, 2H), 3.00 (s, 2H), 2.90-2.81 (m, 2H), 2.63-2.53 (m, 2H), 2.27 (s, 3H), 2.23 (s, 3H), 1.48 (s, 6H). LC-MS ESI m/z: found 371.0 (M−H)⁻.

Example 207

3-(4-((5-chloro-2,2-dimethyl-2,3-dihydrobenzofuran-7-yl)methoxy)-2,5-dimethylphenyl)propanoic acid (236)

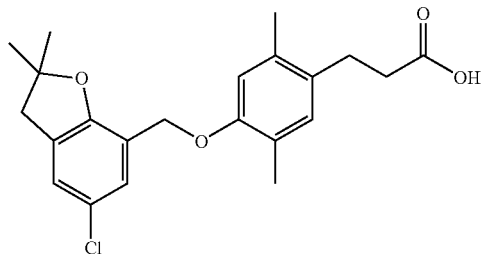

¹H NMR (400 MHz, CDCl₃) δ 7.26 (s, 1H), 7.04 (s, 1H), 6.92 (s, 1H), 6.71 (s, 1H), 4.95 (s, 2H), 3.00 (s, 2H), 2.86 (s, 2H), 2.60 (d, J=6.6 Hz, 2H), 2.27 (s, 3H), 2.22 (s, 3H), 1.48 (s, 6H). LC-MS ESI m/z: found 387.3 (M−H)⁻.

Example 208

3-(4-((5-fluoro-2,2-dimethyl-2,3-dihydrobenzofuran-7-yl)methoxy)-2,3-dimethylphenyl)propanoic acid (237)

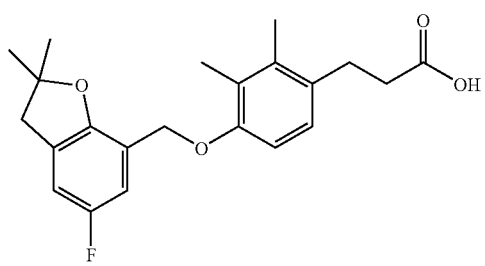

¹H NMR (400 MHz, CDCl₃) δ 6.99-6.95 (m, 2H), 6.75 (d, J=9.8 Hz, 2H), 4.97 (s, 2H), 2.99 (s, 2H), 2.93 (s, 2H), 2.59 (d, J=7.5 Hz, 2H), 2.23 (s, 6H), 1.47 (s, 6H). LC-MS ESI m/z: found 371.3 (M−H)⁻.

Example 209

3-(4-((5-chloro-2,2-dimethyl-2,3-dihydrobenzofuran-7-yl)methoxy)-2,3-dimethylphenyl)propanoic acid (238)

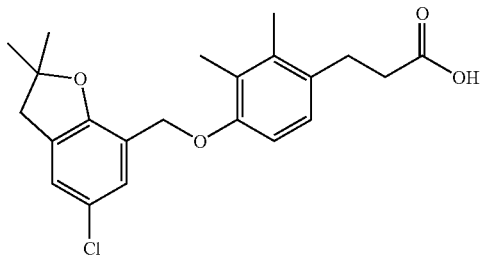

$^1$H NMR (400 MHz, CDCl$_3$) δ 7.25 (s, 1H), 7.04 (s, 1H), 6.94 (d, J=8.3 Hz, 1H), 6.75 (d, J=8.1 Hz, 1H), 4.95 (s, 2H), 2.99 (s, 2H), 2.94 (d, J=4.5 Hz, 2H), 2.59 (s, 2H), 2.23 (s, 6H), 1.47 (s, 6H). LC-MS ESI m/z: found 387.3 (M−H)$^-$.

Example 210

2-(2-(2-fluoro-4-((5-fluoro-2,2-dimethyl-2,3-dihydrobenzofuran-7-yl)methoxy)phenyl)cyclopropyl)acetic acid (239)

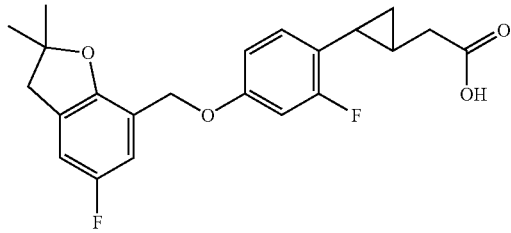

$^1$H NMR (400 MHz, CDCl$_3$) δ 6.97-6.74 (m, 3H), 6.66 (s, 2H), 4.94 (s, 2H), 2.99 (s, 2H), 2.61-2.32 (m, 2H), 1.90-1.76 (m, 1H), 1.48 (s, 6H), 1.40-1.28 (m, 1H), 1.01-0.90 (m, 1H), 0.90-0.79 (m, 1H). LC-MS ESI m/z: found 387.0 (M−H)$^-$.

Example 211

2-(2-(4-((5-chloro-2,2-dimethyl-2,3-dihydrobenzofuran-7-yl)methoxy)-2-fluorophenyl)cyclopropyl)acetic acid (240)

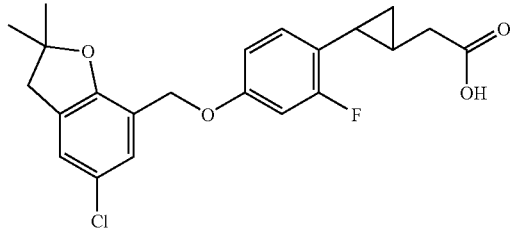

$^1$H NMR (400 MHz, CDCl$_3$) δ 7.20 (s, 1H), 7.04 (s, 1H), 6.91-6.79 (m, 1H), 6.67 (s, 2H), 4.93 (s, 2H), 2.99 (s, 2H), 2.61-2.30 (m, 2H), 1.90-1.73 (m, 1H), 1.48 (s, 6H), 1.41-1.28 (m, 1H), 1.01-0.90 (m, 1H), 0.90-0.77 (m, 1H). LC-MS ESI m/z: found 403.1 (M−H)$^-$.

Example 212

3-(4-((5-fluoro-2,2-dimethyl-2,3-dihydrobenzofuran-7-yl)methoxy)-2-propylphenyl)propanoic acid (241)

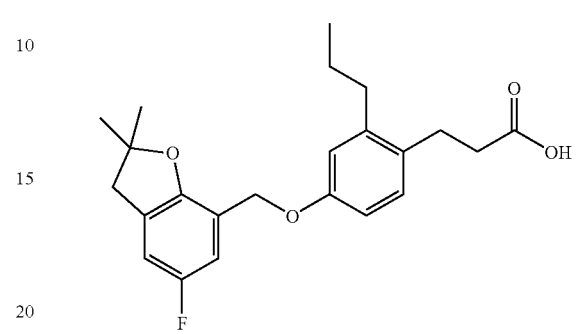

$^1$H NMR (400 MHz, CDCl$_3$) δ 7.05 (d, J=8.3 Hz, 1H), 6.97 (d, J=9.5 Hz, 1H), 6.79 (s, 3H), 4.96 (s, 2H), 2.99 (s, 2H), 2.95-2.83 (m, 2H), 2.66-2.50 (m, 4H), 1.67-1.53 (m, 2H), 1.47 (s, 6H), 1.02-0.89 (m, 3H). LC-MS ESI m/z: found 385.0 (M−H)$^-$.

Example 213

3-(4-((5-chloro-2,2-dimethyl-2,3-dihydrobenzofuran-7-yl)methoxy)-2-propylphenyl)propanoic acid (242)

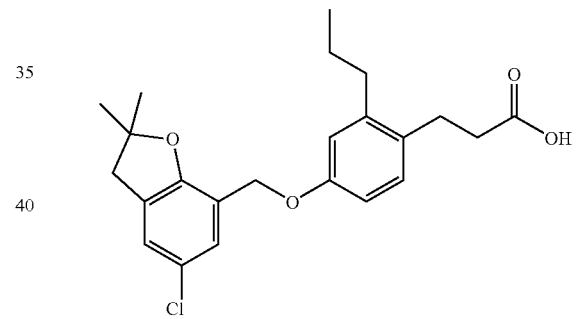

$^1$H NMR (400 MHz, CDCl$_3$) δ 7.25 (s, 1H), 7.16-6.96 (m, 2H), 6.90-6.68 (m, 2H), 4.94 (s, 2H), 2.99 (s, 2H), 2.94-2.84 (m, 2H), 2.68-2.43 (m, 4H), 1.75-1.55 (m, 2H), 1.47 (s, 6H), 1.04-0.91 (m, 3H). LC-MS ESI m/z: found 401.2 (M−H)$^-$.

Example 214

3-(5-fluoro-4-((5-fluoro-2,2-dimethyl-2,3-dihydrobenzofuran-7-yl)methoxy)-2-methylphenyl)propanoic acid (243)

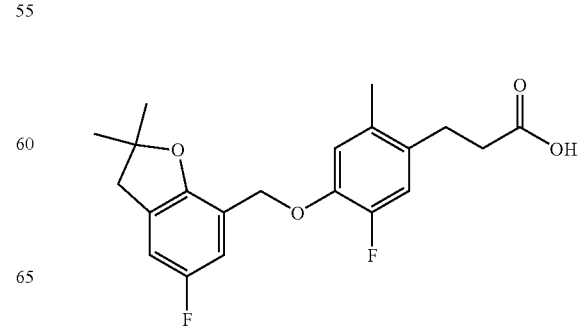

¹H NMR (400 MHz, CDCl₃) δ 6.99 (d, J=9.3 Hz, 1H), 6.90-6.73 (m, 3H), 5.03 (s, 2H), 2.99 (s, 2H), 2.84 (t, J=7.5 Hz, 2H), 2.59 (t, J=7.5 Hz, 2H), 2.23 (s, 3H), 1.48 (s, 6H). LC-MS ESI m/z: found 375.0 (M−H)⁻.

Example 215

3-(4-((5-chloro-2,2-dimethyl-2,3-dihydrobenzofuran-7-yl)methoxy)-5-fluoro-2-methylphenyl)propanoic acid (244)

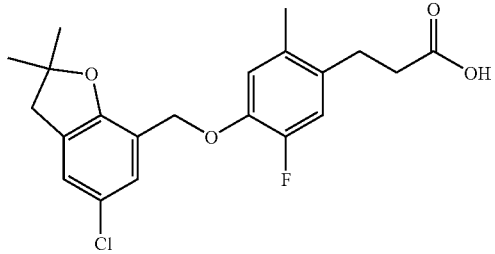

¹H NMR (400 MHz, CDCl₃) δ 7.26 (s, 1H), 7.04 (s, 1H), 6.87-6.84 (m, 2H), 5.01 (s, 2H), 2.99 (s, 2H), 2.84 (t, J=7.8 Hz, 2H), 2.59 (t, J=7.7 Hz, 2H), 2.23 (s, 3H), 1.48 (s, 6H). LC-MS ESI m/z: found 391.3 (M−H)⁻.

Example 216

3-(2-ethyl-3-fluoro-4-((5-fluoro-2,2-dimethyl-2,3-dihydrobenzofuran-7-yl)methoxy)phenyl)propanoic acid (245)

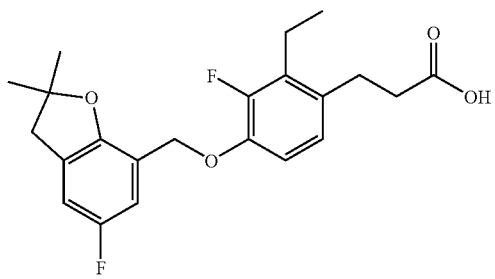

¹H NMR (400 MHz, CDCl₃) δ 7.00 (d, J=9.5 Hz, 1H), 6.86-6.71 (m, 3H), 5.03 (s, 2H), 2.99 (s, 2H), 2.90 (t, J=6.7 Hz, 2H), 2.73-2.56 (m, 4H), 1.47 (s, 6H), 1.18 (t, J=6.6 Hz, 3H). LC-MS ESI m/z: found 389.4 (M−H)⁻.

Example 217

3-(4-((5-chloro-2,2-dimethyl-2,3-dihydrobenzofuran-7-yl)methoxy)-2-ethyl-3-fluorophenyl)propanoic acid (246)

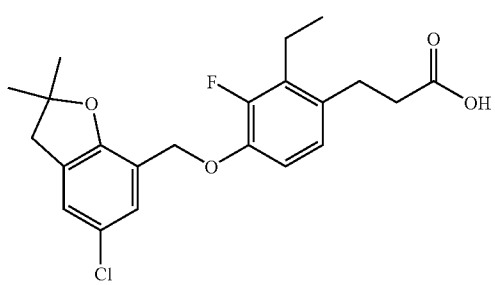

¹H NMR (400 MHz, CDCl₃) δ 7.26 (s, 1H), 7.03 (s, 1H), 6.81 (s, 2H), 5.01 (s, 2H), 2.99 (s, 2H), 2.90 (t, J=7.6 Hz, 2H), 2.76-2.53 (m, 4H), 1.47 (d, J=1.3 Hz, 6H), 1.18 (t, J=6.9 Hz, 3H). LC-MS ESI m/z: found 405.3 (M−H)⁻.

Example 218

3-(4-((5-fluoro-2,2-dimethyl-2,3-dihydrobenzofuran-7-yl)methoxy)-5,6,7,8-tetrahydronaphthalen-1-yl)propanoic acid (247)

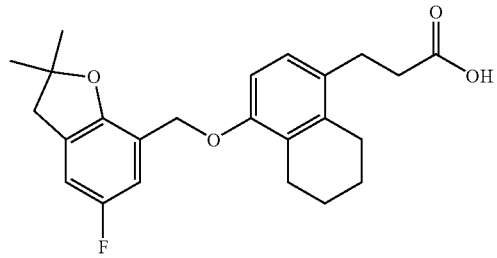

¹H NMR (400 MHz, DMSO) δ 12.11 (s, 1H), 7.09-6.65 (m, 4H), 4.87 (s, 2H), 3.00 (s, 2H), 2.81-2.26 (m, 9H), 2.17 (s, 1H), 1.66 (s, 2H), 1.39 (s, 6H). LC-MS ESI m/z: found 397.3 (M−H)⁻.

Example 219

3-(4-((5-chloro-2,2-dimethyl-2,3-dihydrobenzofuran-7-yl)methoxy)-5,6,7,8-tetrahydronaphthalen-1-yl)propanoic acid (248)

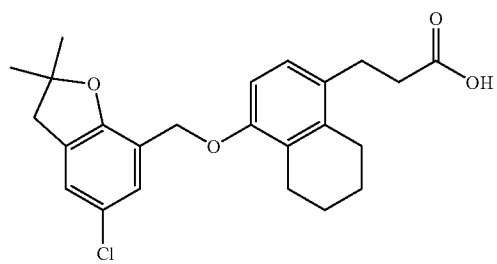

¹H NMR (400 MHz, DMSO) δ 12.08 (s, 1H), 7.17 (s, 2H), 7.05-6.64 (m, 2H), 4.88 (s, 2H), 3.01 (s, 2H), 2.81-2.30 (m, 9H), 2.22-2.08 (m, 1H), 1.65 (s, 2H), 1.40 (s, 6H). LC-MS ESI m/z: found 413.2 (M−H)⁻.

Example 220

3-(2-ethyl-5-fluoro-4-((5-fluoro-2,2-dimethyl-2,3-dihydrobenzofuran-7-yl)methoxy)phenyl)propanoic acid (249)

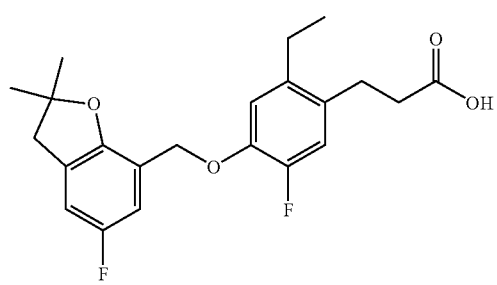

¹H NMR (400 MHz, CDCl₃) δ 7.00 (d, J=9.6 Hz, 1H), 6.93-6.71 (m, 3H), 5.04 (s, 2H), 2.99 (s, 2H), 2.87 (t, J=7.8 Hz, 2H), 2.68-2.45 (m, 4H), 1.47 (s, 6H), 1.16 (dd, J=8.4, 6.6 Hz, 3H). LC-MS ESI m/z: found 389.4 (M−H)⁻.

Example 221

3-(4-((5-chloro-2,2-dimethyl-2,3-dihydrobenzofuran-7-yl)methoxy)-2-ethyl-5-fluorophenyl)propanoic acid (250)

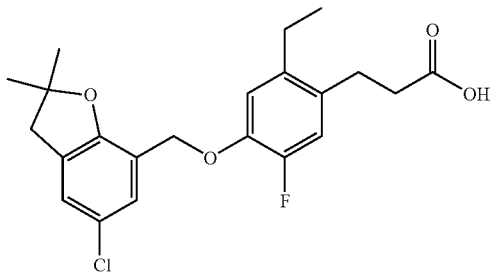

$^1$H NMR (400 MHz, CDCl$_3$) δ 7.25 (s, 1H), 7.04 (s, 1H), 6.85 (dd, J=18.8 Hz, 10.4, 2H), 5.03 (s, 2H), 2.99 (s, 2H), 2.87 (t, J=7.6 Hz, 2H), 2.67-2.45 (m, 4H), 1.47 (s, 6H), 1.17 (t, J=7.5 Hz, 3H). LC-MS ESI m/z: found 405.4 (M−H)$^-$.

Example 222

3-(3-fluoro-4-((5-fluoro-2,2-dimethyl-2,3-dihydrobenzofuran-7-yl)methoxy)-2-propylphenyl)propanoic acid (251)

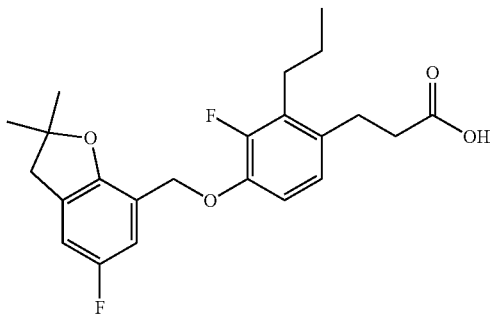

$^1$H NMR (400 MHz, CDCl$_3$) δ 6.99 (d, J=9.7 Hz, 1H), 6.87-6.73 (m, 3H), 5.03 (s, 2H), 2.99 (s, 2H), 2.89 (t, J=7.2 Hz, 2H), 2.67-2.53 (m, 4H), 1.57 (dd, J=15.1, 8.1 Hz, 2H), 1.47 (d, J=1.6 Hz, 6H), 0.98 (t, J=7.0 Hz, 3H). LC-MS ESI m/z: found 403.0 (M−H)$^-$.

Example 223

3-(4-((5-chloro-2,2-dimethyl-2,3-dihydrobenzofuran-7-yl)methoxy)-3-fluoro-2-propylphenyl)propanoic acid (252)

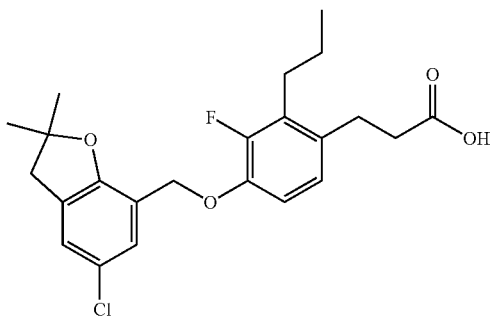

$^1$H NMR (400 MHz, CDCl$_3$) δ 7.25 (d, J=2.2 Hz, 1H), 7.03 (s, 1H), 6.81 (s, 2H), 5.01 (s, 2H), 2.98 (s, 2H), 2.89 (t, J=7.0 Hz, 2H), 2.82-2.36 (m, 4H), 1.57 (d, J=6.7 Hz, 2H), 1.47 (s, 6H), 0.98 (t, J=7.2 Hz, 3H). LC-MS ESI m/z: found 419.4 (M−H)$^-$.

Example 224

3-(3-fluoro-4-((5-fluoro-2,2-dimethyl-2,3-dihydrobenzofuran-7-yl)methoxy)-2-pentylphenyl)propanoic acid (253)

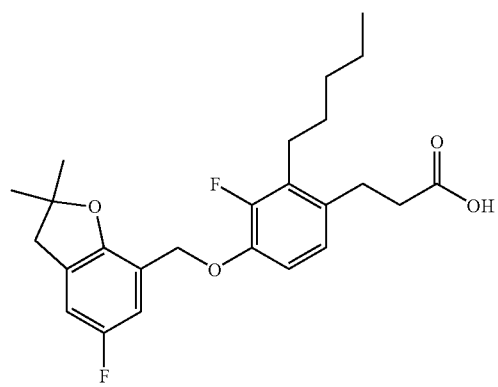

$^1$H NMR (400 MHz, CDCl$_3$) δ 6.99 (d, J=9.7 Hz, 1H), 6.85-6.70 (m, 3H), 5.02 (s, 2H), 2.98 (s, 2H), 2.90-2.85 (m, 2H), 2.68-2.53 (m, 4H), 1.64-1.42 (m, 8H), 1.35 (s, 4H), 0.89 (s, 3H). LC-MS ESI m/z: found 431.1 (M−H)$^-$.

Example 225

3-(4-((5-chloro-2,2-dimethyl-2,3-dihydrobenzofuran-7-yl)methoxy)-3-fluoro-2-pentylphenyl)propanoic acid (254)

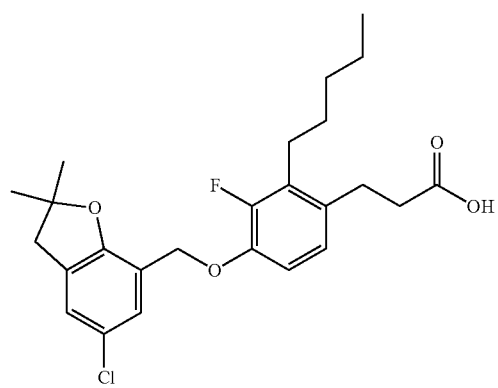

$^1$H NMR (400 MHz, CDCl$_3$) δ 7.26 (s, 1H), 7.03 (s, 1H), 6.83-6.80 (m, 2H), 5.01 (s, 2H), 2.98 (s, 2H), 2.89 (t, J=7.7

Hz, 2H), 2.67-2.51 (m, 4H), 1.65-1.42 (m, 8H), 1.36 (s, 4H), 0.89 (s, 3H). LC-MS ESI m/z: found 447.1 (M–H)⁻.

Example 226

3-(2-ethyl-3-fluoro-4-((5-fluoro-2,2-dimethyl-2,3-dihydrobenzofuran-7-yl)methoxy)phenyl)-2-methyl-propanoic acid (255)

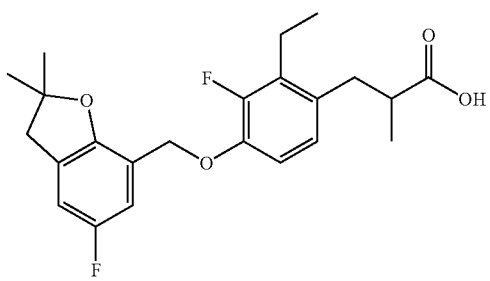

$^1$H NMR (400 MHz, CDCl$_3$) δ 7.00 (d, J=8.2 Hz, 1H), 6.88-6.71 (m, 3H), 5.03 (s, 2H), 3.10-2.95 (m, 3H), 2.78-2.52 (m, 4H), 1.47 (s, 6H), 1.17 (t, J=7.2 Hz, 6H). LC-MS ESI m/z: found 403.4 (M–H)⁻.

Example 227

3-(4-((5-chloro-2,2-dimethyl-2,3-dihydrobenzofuran-7-yl)methoxy)-2-ethyl-3-fluorophenyl)-2-methylpropanoic acid (256)

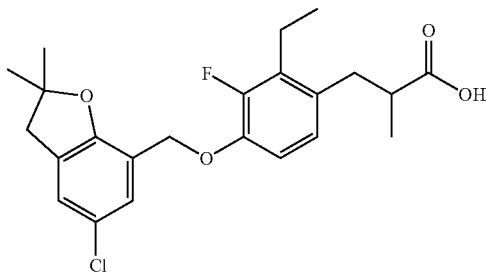

$^1$H NMR (400 MHz, CDCl$_3$) δ 7.26 (s, 1H), 7.04 (s, 1H), 6.83-6.78 (m, 2H), 5.01 (s, 2H), 3.12-2.88 (m, 3H), 2.82-2.48 (m, 4H), 1.47 (s, 6H), 1.17 (t, J=7.3 Hz, 6H). LC-MS ESI m/z: found 419.4 (M–H)⁻.

Example 228

3-(4-(dideuterio(5-fluoro-2,2-dimethyl-2,3-dihydrobenzofuran-7-yl)methoxy)-3-fluoro-2-ethylphenyl)propanoic acid (257)

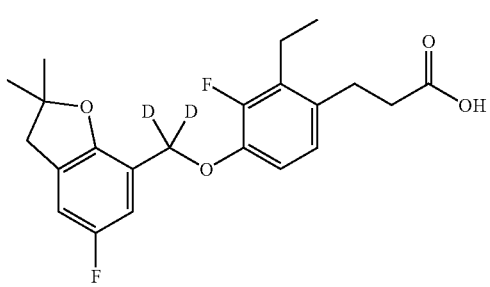

$^1$H NMR (400 MHz, CDCl$_3$) δ 7.00 (d, J=9.6 Hz, 1H), 6.88-6.73 (m, 3H), 2.99 (s, 2H), 2.90 (t, J=7.9 Hz, 2H), 2.75-2.55 (m, 4H), 1.47 (s, 6H), 1.18 (t, J=7.5 Hz, 3H). LC-MS ESI m/z: found 391.3 (M–H)⁻.

Example 229

3-(4-(dideuterio(5-fluoro-2,2-dimethyl-2,3-dihydrobenzofuran-7-yl)methoxy)-3-fluoro-2-propylphenyl)propanoic acid (258)

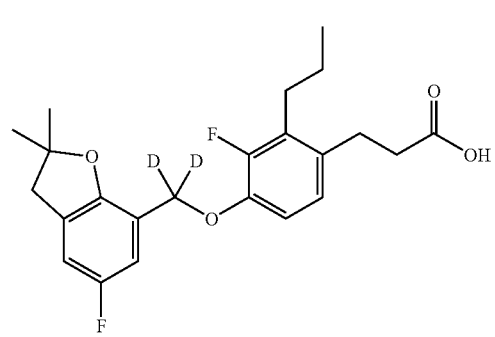

$^1$H NMR (400 MHz, CDCl$_3$) δ 6.99 (d, J=9.5 Hz, 1H), 6.87-6.73 (m, 3H), 2.99 (s, 2H), 2.89 (t, J=8.0 Hz, 2H), 2.70-2.52 (m, 4H), 1.57 (dd, J=15.1, 7.4 Hz, 2H), 1.47 (s, 6H), 0.99 (t, J=7.3 Hz, 3H). LC-MS ESI m/z: found 405.4 (M–H)⁻.

Example 230

3-(4-(dideuterio(5-fluoro-2,2-dimethyl-2,3-dihydrobenzofuran-7-yl)methoxy)-3-fluorophenyl)-2-methylpropanoic acid (259)

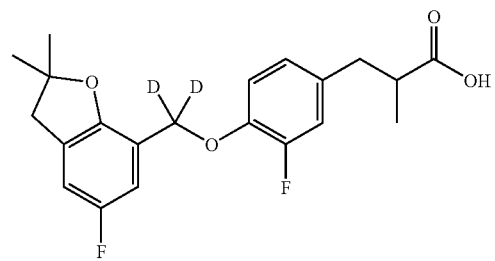

$^1$H NMR (400 MHz, CDCl$_3$) δ 7.04-6.88 (m, 3H), 6.80 (t, J=8.7 Hz, 2H), 3.05-2.91 (m, 3H), 2.70 (dd, J=14.0, 7.0 Hz, 1H), 2.61-2.57 (m, 1H), 1.47 (s, 6H), 1.16 (d, J=6.9 Hz, 3H). LC-MS ESI m/z: found 377.2 (M–H)⁻.

Example 231

3-(4-(dideuterio(5-fluoro-2,2-dimethyl-2,3-dihydrobenzofuran-7-yl)methoxy)-3-(trifluoromethyl)phenyl)-2-methylpropanoic acid (260)

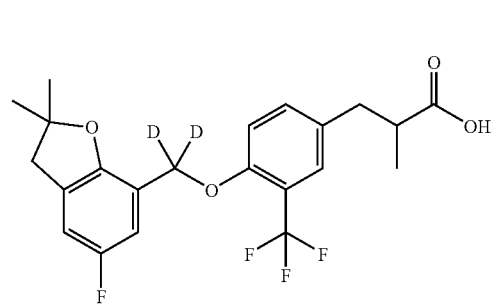

¹H NMR (400 MHz, CDCl₃) δ 7.38 (s, 1H), 7.25 (d, J=6.3 Hz, 1H), 7.06-6.95 (m, 2H), 6.79 (d, J=7.8 Hz, 1H), 3.10-2.93 (m, 3H), 2.68 (d, J=7.3 Hz, 2H), 1.48 (s, 6H), 1.18 (d, J=6.8 Hz, 3H). LC-MS ESI m/z: found 427.1 (M−H)⁻.

Example 232

3-(3-fluoro-4-((5-fluoro-2,2-dimethyl-2,3-dihydrobenzofuran-7-yl)methoxy)-2-isopentylphenyl)propanoic acid (261)

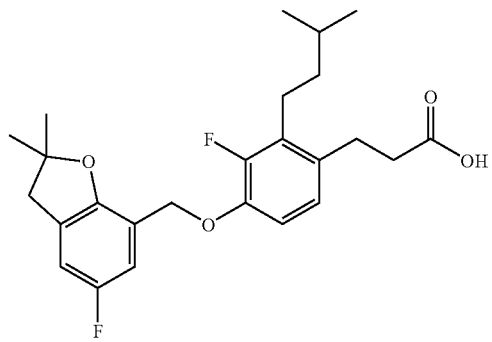

¹H NMR (400 MHz, CDCl₃) δ 7.00 (d, J=9.5 Hz, 1H), 6.87-6.72 (m, 3H), 5.03 (s, 2H), 2.99 (s, 2H), 2.89 (t, J=7.9 Hz, 2H), 2.65-2.58 (m, 4H), 1.74-1.57 (m, 1H), 1.47 (s, 6H), 1.44-1.34 (m, 2H), 0.96 (d, J=6.6 Hz, 6H). LC-MS ESI m/z: found 431.3 (M−H)⁻.

Example 233

3-(4-((5-chloro-2,2-dimethyl-2,3-dihydrobenzofuran-7-yl)methoxy)-3-fluoro-2-isopentylphenyl)propanoic acid (262)

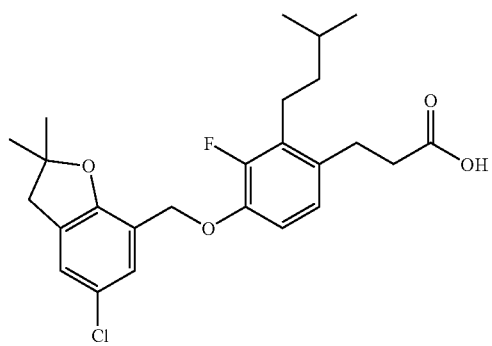

¹H NMR (400 MHz, CDCl₃) δ 7.26 (s, 1H), 7.03 (s, 1H), 6.81 (s, 2H), 5.01 (s, 2H), 2.99 (s, 2H), 2.89 (t, J=7.9 Hz, 2H), 2.64-2.59 (m, 4H), 1.68-1.62 (m, 1H), 1.47 (s, 6H), 1.44-1.33 (m, 2H), 0.96 (d, J=6.6 Hz, 6H). LC-MS ESI m/z: found 447.1 (M−H)⁻.

Example 234

3-(4-(dideuterio(5-chloro-2,2-dimethyl-2,3-dihydrobenzofuran-7-yl)methoxy)-3-fluoro-2-ethylphenyl)propanoic acid (263)

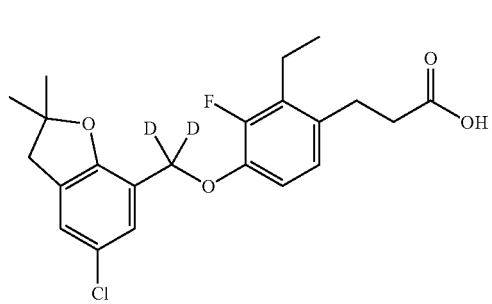

¹H NMR (400 MHz, CDCl₃) δ 7.26 (s, 1H), 7.04 (s, 1H), 6.81 (s, 2H), 2.99 (s, 2H), 2.90 (t, J=7.9 Hz, 2H), 2.75-2.54 (m, 4H), 1.47 (s, 6H), 1.18 (t, J=7.5 Hz, 3H). LC-MS ESI m/z: found 407.2 (M−H)⁻.

Example 235

3-(4-(dideuterio(5-chloro-2,2-dimethyl-2,3-dihydrobenzofuran-7-yl)methoxy)-3-fluoro-2-propylphenyl)propanoic acid (264)

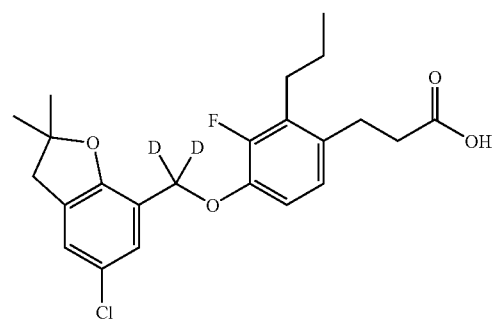

¹H NMR (400 MHz, CDCl₃) δ 7.26 (s, 1H), 7.04 (s, 1H), 6.86-6.77 (m, 2H), 2.99 (s, 2H), 2.90 (t, J=7.9 Hz, 2H), 2.69-2.53 (m, 4H), 1.57 (dd, J=15.4, 7.8 Hz, 2H), 1.47 (s, 6H), 0.99 (t, J=7.3 Hz, 3H). LC-MS ESI m/z: found 421.4 (M−H)⁻.

Example 236

3-(4-(dideuterio(5-chloro-2,2-dimethyl-2,3-dihydrobenzofuran-7-yl)methoxy)-3-fluorophenyl)-2-methylpropanoic acid (265)

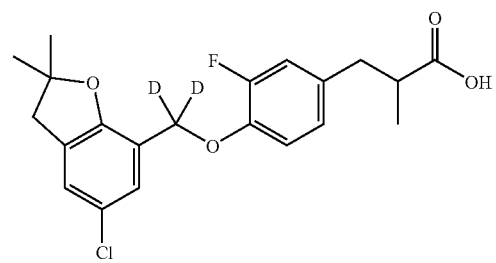

¹H NMR (400 MHz, CDCl₃)) δ 7.24 (s, 1H), 7.04 (s, 1H), 6.97-6.87 (m, 2H), 6.82 (d, J=7.9 Hz, 1H), 3.04-2.92 (m, 3H), 2.79-2.50 (m, 2H), 1.47 (s, 6H), 1.17 (d, J=6.9 Hz, 3H). LC-MS ESI m/z: found 393.2 (M−H)⁻.

Example 237

3-(4-(dideuterio(5-chloro-2,2-dimethyl-2,3-dihydrobenzofuran-7-yl)methoxy)-3-(trifluoromethyl)phenyl)-2-methylpropanoic acid (266)

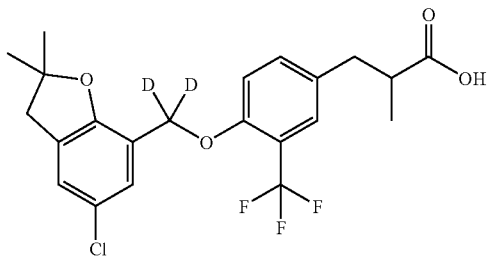

¹H NMR (400 MHz, CDCl₃) δ 7.38 (s, 1H), 7.25-7.21 (m, 2H), 7.07-6.97 (m, 2H), 3.06-2.93 (m, 3H), 2.68 (d, J=7.5 Hz, 2H), 1.48 (s, 6H), 1.18 (d, J=6.6 Hz, 3H). LC-MS ESI m/z: found 443.1 (M–H)⁻.

Example 238

3-(2-butyl-3-fluoro-4-((5-fluoro-2,2-dimethyl-2,3-dihydrobenzofuran-7-yl)methoxy)phenyl)propanoic acid (267)

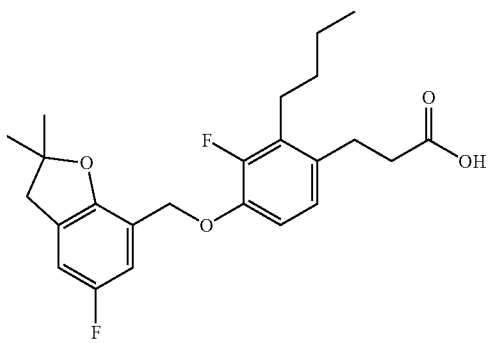

¹H NMR (400 MHz, CDCl₃) δ 7.00 (d, J=9.7 Hz, 1H), 6.89-6.74 (m, 3H), 5.03 (s, 2H), 2.99 (s, 2H), 2.96-2.84 (m, 2H), 2.71-2.54 (m, 4H), 1.61-1.33 (m, 10H), 0.94 (t, J=7.2 Hz, 3H). LC-MS ESI m/z: found 417.3 (M–H)⁻.

Example 239

3-(2-butyl-4-((5-chloro-2,2-dimethyl-2,3-dihydrobenzofuran-7-yl)methoxy)-3-fluorophenyl)propanoic acid (268)

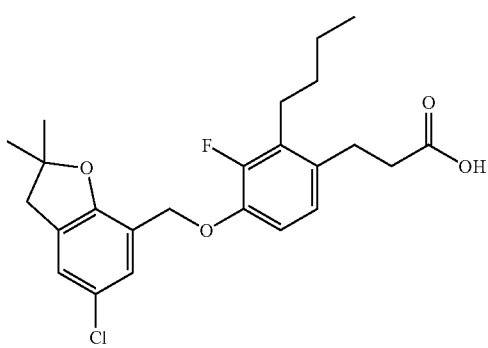

¹H NMR (400 MHz, CDCl₃) δ 7.26 (s, 1H), 7.03 (s, 1H), 6.86-6.77 (m, 2H), 5.01 (s, 2H), 2.99 (s, 2H), 2.90 (t, J=8.0 Hz, 2H), 2.72-2.54 (m, 4H), 1.61-1.31 (m, 10H), 0.94 (t, J=7.2 Hz, 3H). LC-MS ESI m/z: found 433.3 (M–H)⁻.

Example 240

3-(4-((5-fluoro-2,2-dimethyl-2,3-dihydrobenzofuran-7-yl)methoxy)-3-(trifluoromethyl)phenyl)-2-methylpropanoic acid (269)

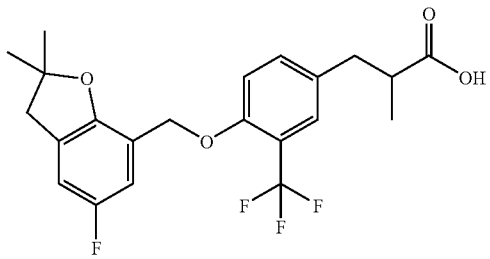

¹H NMR (400 MHz, CDCl₃) δ 7.38 (s, 1H), 7.24 (s, 1H), 7.01 (d, J=7.8 Hz, 2H), 6.79 (d, J=8.1 Hz, 1H), 5.08 (s, 2H), 3.04-2.91 (m, 3H), 2.80-2.55 (m, 2H), 1.48 (s, 6H), 1.18 (d, J=6.8 Hz, 3H). LC-MS ESI m/z: found 425.0 (M–H)⁻.

Example 241

3-(4-((5-chloro-2,2-dimethyl-2,3-dihydrobenzofuran-7-yl)methoxy)-3-fluorophenyl)-2,2,3,3-tetradeuteriopropanoic acid (270)

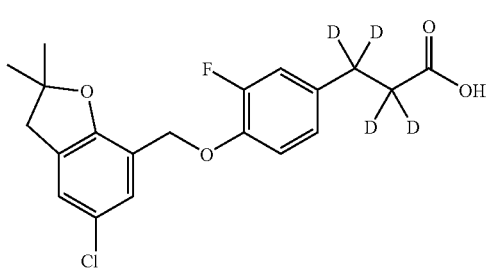

¹H NMR (400 MHz, CDCl₃) δ 7.24 (s, 1H), 7.04 (s, 1H), 6.99-6.78 (m, 3H), 5.03 (s, 2H), 2.99 (s, 2H), 1.47 (s, 6H). LC-MS: 399.3 (M–H⁺). LC-MS ESI m/z: found 381.2 (M–H)⁻.

Example 242

3-(3-fluoro-4-((5-fluoro-2,2-dimethyl-2,3-dihydrobenzofuran-7-yl)methoxy)-2-propylphenyl)-2,2,3,3-tetradeuteriopropanoic acid (271)

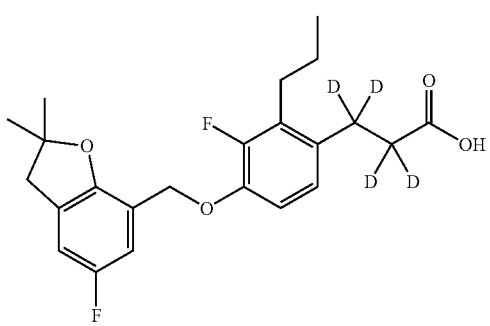

¹H NMR (400 MHz, CDCl₃) δ 6.99 (d, J=10.0 Hz, 1H), 6.87-6.71 (m, 3H), 5.03 (s, 2H), 2.99 (s, 2H), 2.62 (t, J=7.3 Hz, 2H), 1.59-1.53 (m, 2H), 1.47 (s, 6H), 0.99 (t, J=7.3 Hz, 3H). LC-MS ESI m/z: found 407.4 (M–H)⁻.

Example 243

3-(2-ethyl-3-fluoro-4-((5-fluoro-2,2-dimethyl-2,3-dihydrobenzofuran-7-yl)methoxy)phenyl)-2,2,3,3-tetradeuteriopropanoic acid (272)

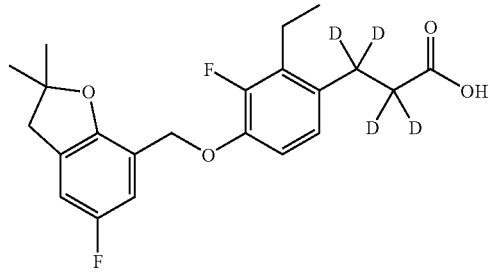

¹H NMR (400 MHz, CDCl₃) δ 7.00 (d, J=10.3 Hz, 1H), 6.87-6.73 (m, 3H), 5.03 (s, 2H), 2.99 (s, 2H), 2.75-2.61 (m, 2H), 1.47 (s, 6H), 1.18 (t, J=7.5 Hz, 3H). LC-MS ESI m/z: found 393.3 (M–H)⁻.

Example 244

3-(3-fluoro-4-((5-fluoro-2,2-dimethyl-2,3-dihydrobenzofuran-7-yl)methoxy)-2-methylphenyl)propanoic acid (273)

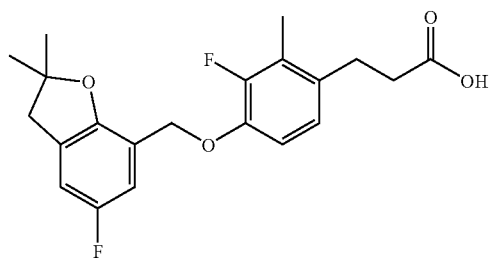

¹H NMR (400 MHz, CDCl₃) δ 6.98 (d, J=9.6 Hz, 1H), 6.85-6.71 (m, 3H), 5.04 (s, 2H), 2.99 (s, 2H), 2.88 (t, J=7.9 Hz, 2H), 2.58 (t, J=7.8 Hz, 2H), 2.23 (s, 3H), 1.47 (s, 6H). LC-MS ESI m/z: found 375.3 (M–H)⁻.

Example 245

3-(4-((5-chloro-2,2-dimethyl-2,3-dihydrobenzofuran-7-yl)methoxy)-3-fluoro-2-methylphenyl)propanoic acid (274)

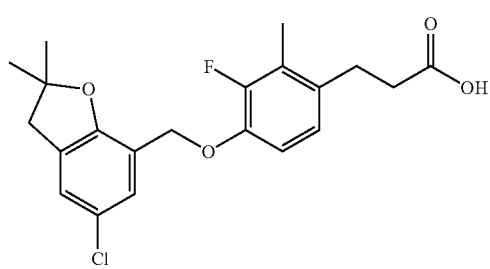

¹H NMR (400 MHz, CDCl₃) δ 7.25 (s, 1H), 7.03 (s, 1H), 6.80 (s, 2H), 5.02 (s, 2H), 2.99 (s, 2H), 2.88 (t, J=7.8 Hz, 2H), 2.59 (t, J=7.8 Hz, 2H), 2.23 (s, 3H), 1.47 (s, 6H). LC-MS ESI m/z: found 391.4 (M–H)⁻.

Example 246

3-(3-ethyl-4-((5-fluoro-2,2-dimethyl-2,3-dihydrobenzofuran-7-yl)methoxy)phenyl)propanoic acid (275)

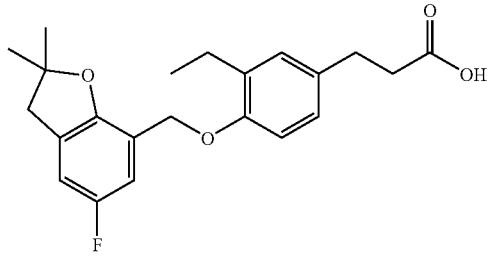

¹H NMR (400 MHz, CDCl₃) δ 7.00-6.90 (m, 3H), 6.83 (d, J=8.4 Hz, 1H), 6.77 (d, J=6.9 Hz, 1H), 4.96 (s, 2H), 2.98 (s, 2H), 2.87 (t, J=7.9 Hz, 2H), 2.72-2.55 (m, 4H), 1.46 (s, 6H), 1.20 (t, J=7.5 Hz, 3H). LC-MS ESI m/z: found 371.2 (M–H)⁻.

Example 247

3-(4-((5-chloro-2,2-dimethyl-2,3-dihydrobenzofuran-7-yl)methoxy)-3-ethylphenyl)propanoic acid (276)

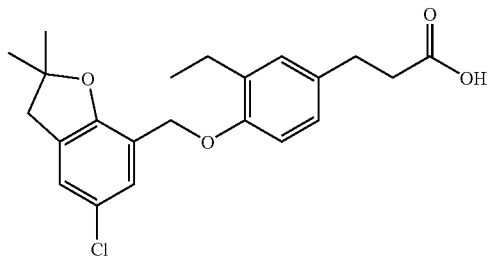

¹H NMR (400 MHz, CDCl₃) δ 7.17 (s, 1H), 6.97-6.89 (m, 3H), 6.78 (d, J=8.2 Hz, 1H), 4.89 (s, 2H), 2.93 (s, 2H), 2.82 (t, J=7.6 Hz, 2H), 2.67-2.51 (m, 4H), 1.41 (s, 6H), 1.14 (t, J=7.5 Hz, 3H). LC-MS ESI m/z: found 387.2 (M–H)⁻.

Example 248

3-(3-ethyl-4-((5-fluoro-2,2-dimethyl-2,3-dihydrobenzofuran-7-yl)methoxy)phenyl)-2-methylpropanoic acid (277)

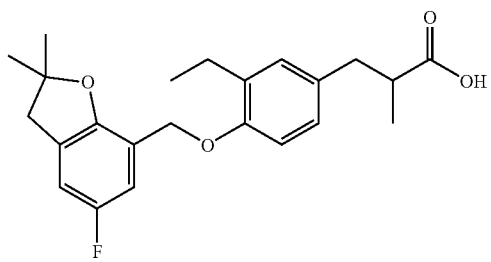

¹H NMR (400 MHz, CDCl₃) δ 6.98-6.93 (m, 3H), 6.82-6.79 (m, 2H), 4.96 (s, 2H), 3.05-2.89 (m, 3H), 2.79-2.49 (m, 4H), 1.46 (s, 6H), 1.25-1.08 (m, 6H). LC-MS ESI m/z: found 385.3 (M–H)⁻.

Example 249

3-(4-((5-chloro-2,2-dimethyl-2,3-dihydrobenzofuran-7-yl)methoxy)-3-ethylphenyl)-2-methylpropanoic acid (278)

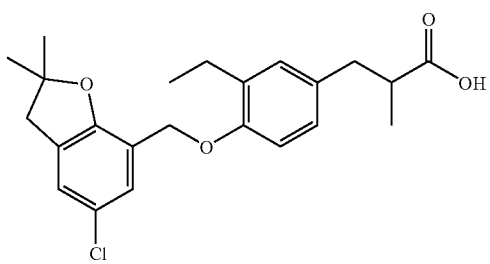

$^1$H NMR (400 MHz, CDCl$_3$) δ 7.17 (s, 1H), 6.97 (s, 1H), 6.92-6.84 (m, 2H), 6.77 (d, J=8.2 Hz, 1H), 4.89 (s, 2H), 3.00-2.84 (m, 3H), 2.74-2.43 (m, 4H), 1.40 (s, 6H), 1.17-0.99 (m, 6H). LC-MS ESI m/z: found 401.2 (M−H)$^-$.

Example 250

3-(2-((5-chloro-2,2-dimethyl-2,3-dihydrobenzofuran-7-yl)methoxy)phenyl)propanoic acid (279)

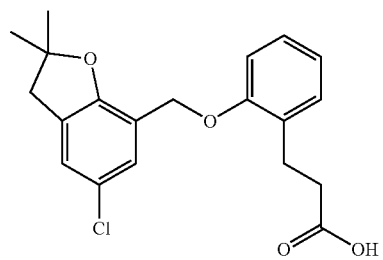

$^1$H NMR (400 MHz, CDCl$_3$) δ 7.22 (s, 1H), 7.18 (t, J=6.6 Hz, 2H), 7.06 (s, 1H), 6.94 (d, J=8.4 Hz, 1H), 6.89 (t, J=7.4 Hz, 1H), 4.99 (s, 2H), 3.05-2.93 (m, 4H), 2.70 (t, J=7.7 Hz, 2H), 1.48 (s, 6H).

Example 251

3-(3-((5-chloro-2,2-dimethyl-2,3-dihydrobenzofuran-7-yl)methoxy)phenyl)-2-methylpropanoic acid (280)

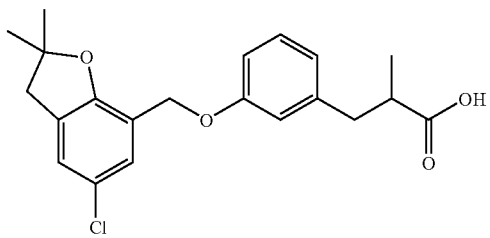

$^1$H NMR (400 MHz, CDCl$_3$) δ 7.25-7.22 (m, 1H), 7.19 (t, J=7.8 Hz, 1H), 7.04 (s, 1H), 6.88-6.75 (m, 3H), 4.97 (s, 2H), 3.05 (dd, J=13.5, 6.1 Hz, 1H), 3.00 (s, 2H), 2.81-2.77 (m, 1H), 2.66-2.63 (m, 1H), 1.48 (s, 6H), 1.18 (d, J=6.9 Hz, 3H).

Example 252

3-(4-((2,2-dimethyl-2,3-dihydrobenzofuran-7-yl)methoxy)phenyl)propanoic acid (281)

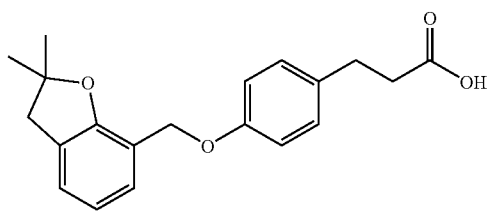

$^1$H NMR (400 MHz, CDCl$_3$) δ 7.28-7.20 (m, 1H), 7.09 (t, J=8.4 Hz, 3H), 6.93 (d, J=8.6 Hz, 2H), 6.82 (t, J=7.5 Hz, 1H), 5.02 (s, 2H), 3.02 (s, 2H), 2.89 (t, J=7.8 Hz, 2H), 2.64 (t, J=7.8 Hz, 2H), 1.48 (s, 6H).

Example 253

3-(4-((2,2-dimethyl-2,3-dihydrobenzofuran-7-yl)methoxy)phenyl)-2-methylpropanoic acid (282)

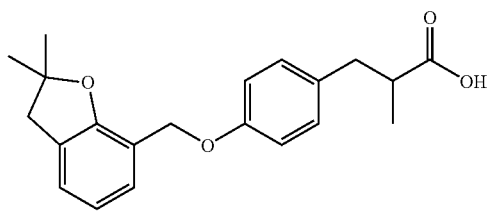

$^1$H NMR (400 MHz, CDCl$_3$) δ 7.25 (d, J=11.0 Hz, 1H), 7.08 (d, J=8.4 Hz, 3H), 6.93 (d, J=8.5 Hz, 2H), 6.83 (t, J=7.5 Hz, 1H), 5.02 (s, 2H), 3.06-2.94 (m, 3H), 2.75-2.69 (m, 1H), 2.63-2.58 (m, 1H), 1.48 (s, 6H), 1.16 (d, J=6.9 Hz, 3H).

Example 254

3-(4-((5-fluoro-2,2-dimethyl-2,3-dihydrobenzofuran-7-yl)methoxy)-2,3,5-trimethylphenyl) propanoic acid (283)

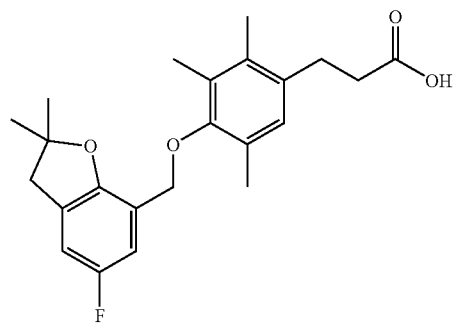

¹H NMR (400 MHz, CDCl₃) δ 7.06 (d, J=9.7 Hz, 1H), 6.89-6.75 (m, 2H), 4.66 (s, 2H), 3.00 (s, 2H), 2.97-2.87 (m, 2H), 2.60 (t, J=8.0 Hz, 2H), 2.27 (s, 3H), 2.24 (s, 3H), 2.19 (s, 3H), 1.45 (s, 6H). LC-MS ESI m/z: found 385.0 (M–H)⁻.

Example 255

3-(4-((5-chloro-2,2-dimethyl-2,3-dihydrobenzofuran-7-yl)methoxy)-2,3,5-trimethylphenyl)propanoic acid (284)

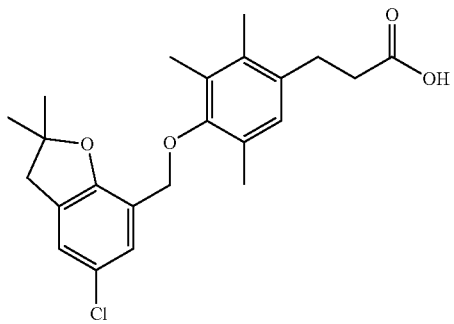

¹H NMR (400 MHz, CDCl₃) δ 7.32 (s, 1H), 7.07 (s, 1H), 6.85 (s, 1H), 4.64 (s, 2H), 3.00 (s, 2H), 2.98-2.84 (m, 2H), 2.66-2.53 (m, 2H), 2.27 (s, 3H), 2.24 (s, 3H), 2.19 (s, 3H), 1.45 (s, 6H). LC-MS ESI m/z: found 401.3 (M–H)⁻.

Example 256

3-(4-((5-fluoro-3H-spiro[benzofuran-2,1'-cyclopentan]-7-yl)methoxy)-2,3-dimethylphenyl)propanoic acid (285)

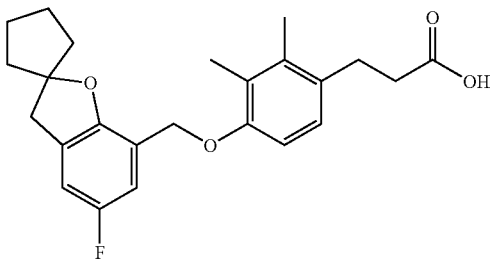

¹H NMR (400 MHz, CDCl₃) δ 7.05-6.90 (m, 2H), 6.79-6.75 (m, 2H), 4.96 (s, 2H), 3.15 (s, 2H), 2.98-2.87 (m, 2H), 2.64-2.53 (m, 2H), 2.23 (s, 6H), 2.12-2.04 (m, 2H), 1.96-1.84 (m, 2H), 1.81-1.63 (m, 4H). LC-MS ESI m/z: found 397.4 (M–H)⁻.

Example 257

2-(5-((5-chloro-2-isopropoxybenzyl)oxy)-6-fluoro-2,3-dihydro-1H-inden-1-yl)acetic acid (286)

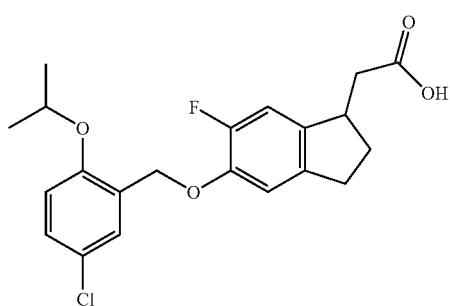

¹H NMR (400 MHz, CDCl₃) δ 7.48 (s, 1H), 7.22-7.19 (m, 1H), 6.97-6.94 (m, 1H), 6.88-6.86 (m, 1H), 6.83-6.81 (m, 1H), 5.08 (s, 2H), 4.59-4.53 (m, 1H), 3.58-3.51 (m, 1H), 2.92-2.74 (m, 3H), 2.52-2.39 (m, 2H), 1.84-1.75 (m, 1H), 1.34 (d, 6H).

Example 258

2-(5-((5-chloro-2-isopropoxybenzyl)oxy)-2,3-dihydro-1H-inden-1-yl)acetic acid (287)

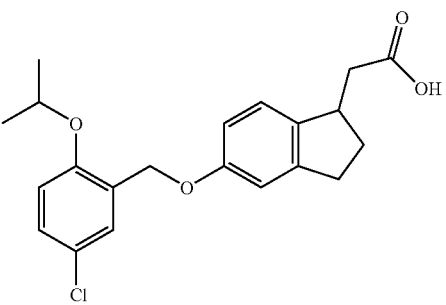

¹H NMR (400 MHz, CDCl₃) δ 7.45 (s, 1H), 7.20-7.18 (m, 1H), 7.11-7.09 (m, 1H), 6.87-6.79 (m, 3H), 5.02 (s, 2H), 4.59-4.53 (m, 1H), 3.56-3.53 (m, 1H), 2.93-2.79 (m, 3H), 2.51-2.41 (m, 2H), 1.81-1.74 (m, 1H), 1.34 (d, 6H).

Example 259

2-(5-((2-isopropoxypyridin-3-yl)methoxy)-2,3-dihydro-1H-inden-1-yl)acetic acid (288)

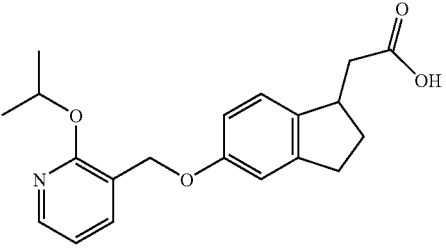

¹H NMR (400 MHz, DMSO-d₆) δ: 12.18 (br, 1H), 8.10 (d, J=4.4 Hz, 1H), 7.73 (d, J=6.4 Hz, 1H), 7.10 (d, J=8.4 Hz, 1H), 6.97-6.94 (m, 1H), 6.85 (s, 1H), 6.75 (d, J=8.4 Hz, 1H), 5.32-5.29 (m, 1H), 4.96 (s, 2H), 2.82-2.79 (m, 1H), 2.76-2.62 (m, 3H), 2.30-2.24 (m, 2H), 1.66-1.61 (m, 1H), 1.28 (d, J=7.1 Hz, 6H). LC-MS ESI m/z: found 340.2 (M–H)⁻.

Example 260

3-(4-((1H-indazol-7-yl)methoxy)-3,5-difluorophenyl)-2-methylpropanoic acid (289)

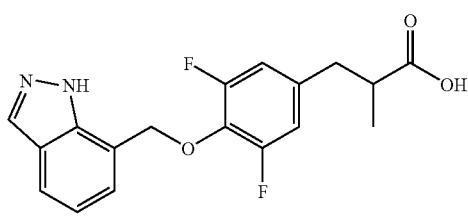

¹H NMR (400 MHz, CDCl₃) δ: 8.14 (s, 1H), 7.76 (d, 1H), 7.31 (d, 1H), 7.26 (s, 1H), 7.15 (m, 1H), 6.82-6.78 (m, 1H), 5.45 (s, 2H), 2.98-2.93 (m, 1H), 2.78-2.73 (m, 1H), 2.67-2.63 (m, 1H), 1.22 (d, 3H). LC-MS ESI m/z: found 347.1 [M+H]⁺.

Example 261

3-(3,5-difluoro-4-((2-methylbenzo[d]oxazol-7-yl)methoxy)phenyl)-2-methylpropanoic acid (290)

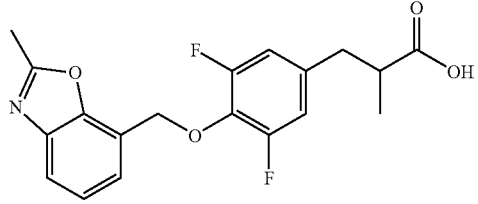

¹H NMR (400 MHz, CDCl₃) δ 7.62 (d, J=7.6 Hz, 1H), 7.38 (d, J=7.2 Hz, 1H), 7.29 (d, J=7.6 Hz, 1H), 6.72 (d, J=9.2 Hz, 2H), 5.41 (s, 2H), 2.99-2.93 (m, 1H), 2.73-2.71 (m, 1H), 2.65 (s, 3H), 2.63-2.58 (m, 1H), 1.18 (d, J=7.2 Hz, 3H). LC-MS ESI m/z: found 361.7 [M+H]⁺.

Example 262

2-(6-((5-fluoro-2,2-dimethyl-2,3-dihydrobenzofuran-7-yl)methoxy)benzofuran-3-yl)acetic acid (291)

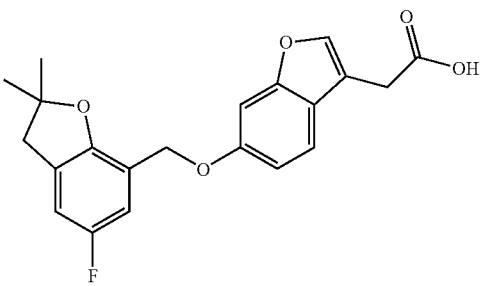

¹H NMR (400 MHz, DMSO-d₆) δ: 12.46 (br, 1H), 7.76 (s, 1H), 7.45 (d, 1H), 7.24 (s, 1H), 7.04-7.00 (m, 2H), 6.93 (d, 1H), 4.99 (s, 2H), 3.63 (s, 2H), 3.04 (s, 2H), 2.50 (s, 3H), 1.45 (s, 6H). LC-MS ESI m/z: found 369.0 [M–H]⁻.

Example 263

2-(7-((5-fluoro-2,2-dimethyl-2,3-dihydrobenzofuran-7-yl)methoxy)-2-oxo-2H-chromen-4-yl)acetic acid (292)

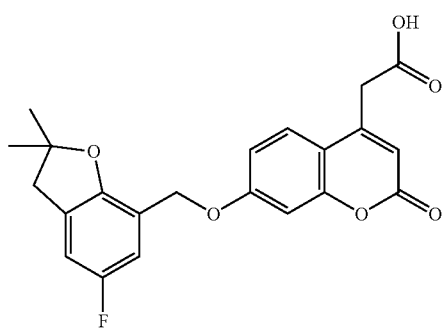

¹H NMR (400 MHz, CDCl₃) δ: 6.93 (d, 3H), 6.82 (m, 1H), 6.64 (m, 1H), 6.34 (s, 1H), 5.06 (d, 2H), 3.15 (m, 1H), 3.08-3.01 (m, 2H), 2.95 (m, 2H), 1.51-1.44 (m, 6H). LC-MS ESI m/z: found 398.8 [M+H]⁺.

Example 264

3-(4-((5-fluoro-2,2-dimethyl-2,3-dihydrobenzofuran-7-yl)methoxy)phenyl)-N-hydroxy-2-methylpropanamide (293)

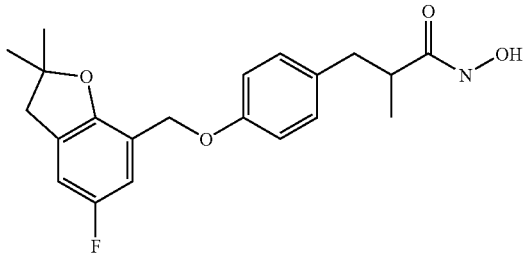

¹H NMR (400 MHz, CDCl₃) δ 7.03 (d, J=8.1 Hz, 2H), 6.95 (d, J=10.4 Hz, 1H), 6.89 (d, J=8.1 Hz, 2H), 6.79 (d, J=7.8 Hz, 1H), 4.96 (s, 2H), 2.99 (s, 2H), 2.91-2.84 (m, 1H), 2.79 (s, 1H), 2.67-2.58 (m, 1H), 2.41-2.29 (m, 1H), 1.47 (s, 6H), 1.19 (d, J=6.7 Hz, 3H). LC-MS ESI m/z: found 372.4 (M–H)⁻.

Example 265

3-(4-((5-fluoro-2,2-dimethyl-2,3-dihydrobenzofuran-7-yl)methoxy)phenyl)-N-hydroxypropanamide (294)

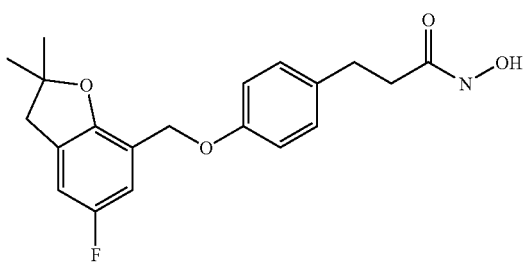

¹H NMR (400 MHz, CDCl₃) δ 7.07 (d, J=7.8 Hz, 2H), 6.98-6.88 (m, 3H), 6.79 (d, J=8.0 Hz, 1H), 4.97 (s, 2H), 2.99 (s, 2H), 2.91 (t, J=7.5 Hz, 2H), 2.80 (s, 1H), 2.41 (t, J=10.4 Hz, 2H), 1.47 (s, 6H). LC-MS ESI m/z: found 358.4 (M–H)⁻.

Example 266

3-(4-((5-chloro-2,2-dimethyl-2,3-dihydrobenzofuran-7-yl)methoxy)phenyl)-4-methylpentanoic acid (295)

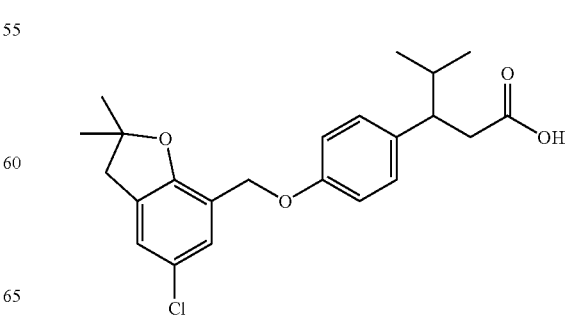

¹H NMR (400 MHz, CDCl₃) δ 7.25 (s, 1H), 7.06-7.03 (m, 3H), 6.90 (d, J=8.0 Hz, 2H), 4.95 (s, 2H), 2.99 (s, 2H), 2.89-2.70 (m, 2H), 2.59-2.54 (m, 1H), 1.88-1.74 (m, 1H), 0.91 (d, J=6.6 Hz, 3H), 0.74 (d, J=6.6 Hz, 3H).

Example 267

3-(4-((6-chloro-2,2-dimethyl-2,3-dihydrobenzofuran-4-yl)methoxy)-2,3-dimethylphenyl)propanoic acid (296)

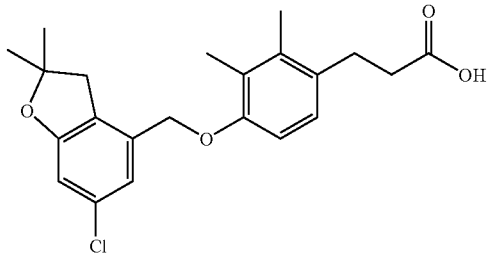

¹H NMR (400 MHz, CDCl₃) δ 6.97 (d, J=8.1 Hz, 1H), 6.92 (s, 1H), 6.70-6.66 (m, 2H), 4.87 (s, 2H), 2.99-2.88 (m, 4H), 2.60 (t, J=8.4 Hz, 2H), 2.23 (s, 3H), 2.20 (s, 3H), 1.47 (s, 6H).

Example 268

3-(2-ethoxy-4-((5-fluoro-2,2-dimethyl-2,3-dihydrobenzofuran-7-yl)methoxy)phenyl)propanoic acid (297)

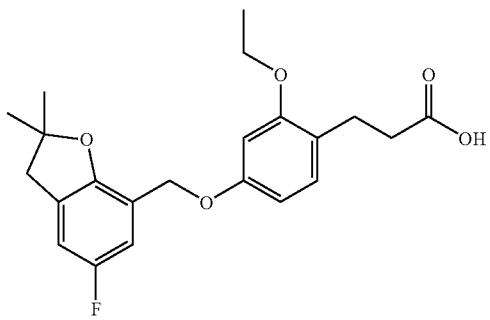

¹H NMR (400 MHz, DMSO-d₆) δ: 12.00 (br, s), 7.01-6.94 (m, 3H), 6.53 (s, 1H), 6.45-6.43 (m, 1H), 4.87 (s, 2H), 3.98-3.96 (m, 2H), 3.00 (s, 2H), 2.68-2.66 (m, 2H), 2.37-2.35 (m, 2H), 1.40 (s, 6H), 1.28-1.26 (m, 3H). LC-MS ESI m/z: found 387.3 [M−H]⁻.

BIOLOGICAL EXAMPLES

Biological Example 1

GPR120 Stable Cell Line

Human GPR120 stable cell line was purchased from Multispan Inc (26219 Eden Landing Road, Hayward, Calif. 94545). This GPR120 cell line was generated in HEK293 cells co-expressing Gqi5. In this cell line, the Flag epitope tag (DYKDDDDK) was fused to the amino terminus of human GPR120 protein.

Assay

The concentration of intracellular $Ca^{2+}$ was measured as described below. Human GPR120 cells were plated in 96 well plates (Poly-D-Lysine coated black/clear Plate, Greiner Bio-One) at 70,000 cells per well and cultured overnight in conditions of 37° C. and 5% $CO_2$. A $Ca^{2+}$ assay dye stock solution was prepared by adding 10 mL of assay buffer (HBSS/20 mM HEPES, pH 7.4) to FLIPR Calcium 4 Assay Bulk Kit (Molecular Devices). The 10 mL of $Ca^{2+}$ assay dye solution was prepared by further diluting 0.5 mL of $Ca^{2+}$ assay dye stock solution with 10 mL of assay buffer. The medium of the cells was removed and immediately 100 μL of the $Ca^{2+}$ assay dye solution was dispensed into each well followed by incubation at 37° C. and 5% $CO_2$ for 50 minutes to incorporate the $Ca^{2+}$ dye into the cells. The cell plate was then placed in the Flexstation (Molecular Devices) for 20 minutes at 37° C. Compounds were dissolved in 100% DMSO and diluted to desired concentrations with assay buffer and placed in the Flexstation simultaneously with the cell plate for 20 minute incubation at 37° C. prior to reading. Fluorescence intensity was measured immediately following compound addition (25 μL/well) on the Flexstation at an excitation wavelength of 485 nm and an emission wavelength of 525 with 515 nm auto cutoff. The resulting increase in fluorescence intensities corresponds to increases in intracellular $Ca^{2+}$ levels.

Determination of Activity of Compounds

Compounds were dissolved in 100% DMSO to a concentration of 20 mM to provide stock solutions. To determine activity against human GPR120, compounds were added with human GPR120 stably expressing cells (described above), at eight desired concentrations ranging from 0.00001 to 20 μM, in 96 well plates and fluorescence intensities were measured for 90 seconds with 2-second intervals. An $EC_{50}$ value (concentration of the GPR120 agonist where 50% of the agonist's maximal activity is observed) was calculated using the changes (Max-Min) of fluorescence intensity.

To determine percent activity for a tested compound, the fluorescence intensity value obtained at a particular concentration were compared to the maximal fluorescence intensity value obtained for reference compound GW9508 (4-[[(3-phenoxyphenyl)methyl]amino]benzene propanoic acid; British Journal of Pharmacology 2006 148, 619-628) or the compound of Example 25. When GW9508 was used as the reference compound, the maximal activity of GW9508 at 6.7 μM was designated as 100% activity. When the compound of Example 25 was used as the reference compound, the maximal activity of the compound of Example 25 at 2.5 μM was designated as 100% activity. Typically, the GW9508 activity reached a maximum at a concentration of approximately 6.7 μM and typically the compound of Example 25 reached a maximum activity at approximately 2.5 μM. Activities of compounds that were tested according to this method are shown in Table 1 below. Table 1 shows the activity expressed as % activity at 5 μM compared to the maximal activity of GW9508 at 6.7 μM or % activity at 2.5 μM compared to the maximal activity of the reference compound of Example 25.

TABLE 1

| Ex. | % Activity (GW9508 Reference Compound) | Ex. | % Activity (Ex. 25 Reference Compound) | Ex. | % Activity (Ex. 25 Reference Compound) | Ex. | % Activity (Example 25 Reference Compound) |
|---|---|---|---|---|---|---|---|
| 2 | 134.6745 | 41 | 116.46 | 115 | 151.78 | 184 | 97.04 |
| 3 | 123.7995 | 42 | 140.94 | 116 | 145.6 | 184A | 95.58 |
| 4 | 110.75072 | 44 | 157.14 | 120 | 104.49 | 184B | 130.66 |
| 5 | 149.18855 | 45 | 79.58 | 122 | 3.58 | 188 | 104.04 |
| 6 | 147.28395 | 46 | 113.55 | 123 | 47.01 | 194 | 148.21 |
| 7 | 168.22715 | 47 | 111.18 | 124 | 131.64 | 197 | 151.44 |
| 8 | 135.3906 | 50 | 129.78 | 125 | 32.57 | 206 | 111.45 |
| 9 | 112.83125 | 53 | 143.19 | 126 | 47.02 | 208 | 147.47 |
| 10 | 106.7955 | 54 | 138.97 | 127 | 152.93 | 209 | 142.22 |
| 11 | 124.2119 | 56 | 108.51 | 130 | 103.85 | 214 | 143.21 |
| 12 | 116.1354 | 59 | 117.58 | 131A | 103.75 | 216 | 144.23 |
| 13 | 119.0442 | 63 | 95.03 | 131B | 105.8 | 218 | 114.48 |
| 14 | 84.491935 | 65 | 141.04 | 133 | 103.4 | 220 | 115.86 |
| 15 | 109.19585 | 67 | 141.82 | 134 | 151.44 | 228 | 119.11 |
| 16 | 110.8294 | 68 | 69.03 | 136 | 140.51 | 230 | 86.25 |
| 17 | 72.210235 | 69 | 78.46 | 140 | 146.18 | 231 | 101.01 |
| 18 | 130.0714 | 70 | 117.72 | 141 | 143.3 | 241 | 159.62 |
| 19 | 125.53955 | 71 | 133.8 | 143 | 90.56 | 243 | 155.23 |
| 20 | 138.03915 | 73 | 114.85 | 143 | 90.56 | 250 | 10.23 |
| 21 | 112.58335 | 77 | 109.62 | 145 | 143.69 | 251 | 61.14 |
| 22 | 126.02425 | 79 | 3.85 | 146 | 140.72 | 254 | 146.14 |
| 23 | 112.7429 | 80 | 86.25 | 147 | 138.65 | 257 | 124.62 |
| 24 | 100.346555 | 82 | 24 | 148 | 113.89 | 258 | 139.95 |
| 25 | 101.766095 | 86 | 5.23 | 151 | 117.38 | 259 | 118.5 |
| 26 | 163.71235 | 88 | 118.92 | 152 | 83.81 | 260 | 16.67 |
| 27 | 143.8489 | 89 | 82.28 | 153 | 106.81 | 261 | 108.78 |
| 28 | 109.58505 | 90 | 75.86 | 156 | 148.87 | 262 | 137.39 |
| 29 | 133.53445 | 91 | 121.29 | 159 | 164.79 | 263 | 5.98 |
| 30 | 176.57625 | 94 | 98.45 | 160 | 172.13 | 264 | 110.24 |
| 31 | 149.52665 | 96 | 124.82 | 162 | 154.48 | 266 | 42.73 |
| 32 | 143.07365 | 99 | 101.53 | 165 | 158.08 | 267 | 140.82 |
| 33 | 142.9517 | 103 | 98.96 | 171 | 98.97 | | |
| 34 | 117.88768 | 106 | 154.51 | 173 | 159.06 | | |
| 35 | 60.108775 | 108 | 143.85 | 175 | 152.44 | | |
| 36 | 122.91405 | 109 | 72.36 | 176 | 138.42 | | |
| 37 | 124.67965 | 111 | 51.55 | 178 | 106 | | |
| 38 | 83.43202 | 112 | 115.42 | 179 | 105.44 | | |
| 40 | 95.33438 | 114 | 123.58 | 182 | 98.43 | | |

Compounds of Examples 1-29, 35-39, 70-79, 81, 84-85, 92-110, 112-116, 118-121, 124, 127-129, 131-132, 134-163, 165-170, 172, 174-182, 184-249 and 252-266 were found to have an $EC_{50}$ of less than or equal to 1 µM. Compounds of Examples 30-33, 42, 44, 46-67, 80, 82, 86-91, 111, 123, 125-126, 130, 133, 171, 173, 183, and 251 were found to have an $EC_{50}$ of greater than 1 µM and less than or equal to 10 µM. Compounds of Examples 34, 40-41, 43, 45, 68-69, and 250 were found to have an $EC_{50}$ of greater than 10 µM.

Biological Example 2

Glucose Uptake in 3T3-L1 Adipocytes

3T3-L1 fibroblasts are plated into growth medium (DMEM supplemented with 10% FBS, 1% Penicillin-Streptomycin) and grown to confluence for 7 days, with media changes every 2 to 3 days. Differentiation into adipocytes is induced by incubating the cells in DMEM supplemented with 10% FBS, 1% Penicillin-Streptomycin, 698 nM Bovine Insulin, 518 µM IBMX and 248 nM Dexamethasone. Glucose uptake activity is determined by measuring the uptake of 2-deoxy-D-[$^3$H]glucose. Briefly, 3T3-L1 adipocytes are washed two times with PBS, once with Fat Cell Buffer (FCB: 125 mM NaCl, 5 mM KCl, 1.8 mM $CaCl_2$, 2.6 mM $MgSO_4$, 25 mM Hepes, 2 mM pyruvate and 2% BSA, 0.2 µm sterile filtered) and are incubated with GPR120 agonists in FCB at 37° C. for 30 minutes. Insulin is prepared at the indicated concentrations in FCB, added to the cells and incubated for 20 minutes at 37° C. Glucose uptake is initiated by the addition of 2-deoxy-D-[$^3$H]glucose (0.083 µCi/mL and 1.1 mM 2-deoxy-D-glucose in FCB) and incubated for 10 minutes at 37° C. Glucose uptake is terminated by removing the contents of the wells and washing the cells three times with cold PBS. The cells are lysed with scintillation solution and 2-deoxy-D-[$^3$H]glucose retained by the cells is counted (MicroBeta TriLux 1450—Perkin Elmer). Cell viability is assessed independently with the CellTitre-Glo Luminescent Cell Viability Assay Kit (Promega) as per manufacturer's instructions. Glucose uptake is quantified by normalizing the glucose uptake measurement for each compound treatment to the corresponding cell viability value. The fold induction of glucose uptake is calculated by normalizing all values against the average value of the basal value (taken as 1-fold).

Biological Example 3

Insulin Secretion (Islet Perifusion)

To determine the effect of GPR120 agonists on insulin secretion from islets, islets from Sprague Dawley rats are isolated and incubated in vitro with GPR120 agonists in the presence of low and high glucose. 200-250 g Sprague Dawley rats are obtained from Charles River laboratories and maintained on regular chow (Purina 5001). Before the procedure, rats are anesthetized with intraperitoneal injection of pentobarbital at 200 mg/kg. The bile duct is clamped where it enters the duodenum, then a catheter is placed in the bile duct between the liver and the pancreas. The pancreas is infused through the catheter with a solution of 0.75 mg/mL collagenase P (Roche) in HBSS buffer (Biowhitaker) supplemented with 0.1% glucose and 0.02% BSA. The pancreas is then excised from the rat and placed in 5 mL of the collagenase P solution in a 37° C. waterbath for 8 minutes. After 8 minutes the digested pancreas is shaken vigorously by hand for 30 seconds. The resulting digest is washed four times in the HBSS buffer, then applied to a discontinuous ficoll gradient. To make the gradient, the digest is re-suspended in 7.5 mL of ficoll DL400 solution (Sigma) density 1.108, in a 15 mL tube. Three 2 mL layers of ficoll solution of decreasing density (1.096, 1.069, 1.037) are then added to the tube to create a density gradient. The gradient is centrifuged at 1500 rpm for 15 minutes after which islets are picked from the top two layers. Islets are washed four times in HBSS buffer, then cultured in RPMI 1640 media (Gibco) supplemented with 1% fetal bovine serum. The following day, 25 size-matched islets are placed in a perifusion chamber and exposed to Krebs Ringer Buffer (KRB; 119 mM NaCl, 4.7 mM KCl, 25 mM $NaHCO_3$, 2.5 mM $CaCl_2$, 1.2 mM $MgSO_4$, 1.2 mM $KH_2PO_4$) at a rate of 1 mL/minute, using a Cellex Acu-Sys S perifusion culture system. The islets are exposed to KRB containing glucose at 2 mM for 30 minutes, followed with buffer containing 16 mM glucose for 30 minutes, then returned to 2 mM glucose for a further 30 minutes, in the presence of 0.1-100 uM of the GPR120 agonist or vehicle (DMSO). Perifusate is collected at 1 minute intervals using a fraction collector, and assayed for insulin using an ELISA kit (Mercodia Ultrasensitive Rat Insulin ELISA Kit, ALPCO). Insulin secretion rate in response to glucose is plotted against time, and the AUC of the curve determined in order to quantify the insulin secretory response to 16 mM glucose during the 30 minute perifusion. Statistical significance of differences in AUC between treated and untreated islets are determined by paired Students t test.

Biological Example 4

Oral Glucose Tolerance 8-10 week old male C57BL/6J mice (Harlan) were maintained on regular chow diet from Harlan (2018 Teklad Global). On the day of the experiment mice were fasted for 6 hours, then randomized into groups (n=10-15) to receive the tested GPR120 agonist at doses ranging from 100 mg/kg or the vehicle (1% CMC, 2% TWEEN 80). Compounds were delivered orally via gavage at 10 mL/kg. Blood glucose levels were measured by glucometer (Ascensia Elite XL, Bayer) at time −30 minutes before administration of compound. Blood glucose was measured again after 30 minutes (at time 0), and then the mice were dosed orally with 3 g/kg glucose at 10 mL/kg. Blood glucose measurements were taken 20, 40, 60, 90 and 120 minutes after glucose administration, by glucometer (Ascensia Elite XL, Bayer).

Glucose levels were plotted against time, and the incremental area under the curve (AUC) of the glucose excursion was determined from time 0 using Graphpad Prism 5.01. Outliers were excluded using Tukey's box plot outlier test, and statistical significance of differences in AUC of compound treatment compared to vehicle was determined by non-parametric Kruskal-Wallis test with Dunn's post test.

Tables 2 and 3 below show the mean percentage inhibition of the glucose excursion for the fifteen animals tested in each group. The compounds were tested at 100 mg/kg and the levels of blood glucose were determined in the presence and absence of the tested compounds. The percentage of glucose reduction is reported. The tested compounds were selected as examples from the exemplified compounds. These results demonstrate that the GPR120 agonists can lower blood glucose in response to an oral glucose challenge.

TABLE 2

| Compound | % reduction AUC glucose excursion at 100 mg/kg |
|---|---|
| Sitagliptin (1 mg/kg) | 58.6 |
| Example 10 | 58.1 |
| Example 13 | 61.9 |

TABLE 3

| Compound | % reduction AUC glucose excursion at 100 mg/kg |
|---|---|
| Sitagliptin (1 mg/kg) | 48.6 |
| Example 35 (racemic) | 27.7 |
| Example 36 | 33.6 |
| Example 16 | 52.4 |

Biological Example 5

Incretin and Enteroendocrine Hormone Measurement

The effect of GPR120 agonists on the secretion of insulin, Glucagon-like peptide-1 (GLP-1), glucose dependent insulinotropic peptide (GIP), Cholecystokinin (CCK) and Peptide YY (PYY) in C57BL/6J mice are determined as follows.

8-10 week old male C57BL/6J mice (Harlan) are maintained on a regular chow diet from Harlan (2018 Teklad Global). On the day of the experiment, mice are fasted for 6 hours then randomized into treatment groups (n=15). All groups are treated with the DPPIV inhibitor sitagliptin at 1 mg/kg to prevent degradation of active GLP-1. GPR120 agonist compounds are dosed at concentrations ranging from 3-100 mg/kg in 1% CMC, 2% TWEEN 80 either by oral gavage or intraperitoneal injection (i.p.) at −30 minutes. Sitagliptin is administered in the same dosing solution. Oral glucose at 3 g/kg is administered at 0 minutes. At 3 minutes after glucose administration, animals are anesthetized with pentobarbital (40 mg/mL in 10% ethanol) and at 4 minutes blood collected by heart puncture in microtainer tubes (BD) with potassium EDTA. For Glucose-independent incretin studies the same procedure is used but in the absence of oral glucose administration. Dosing of GPR120 agonist compounds and blood collection are as described above. For the GLP-1 assay, the collection tubes also contain a DPP-IV inhibitor provided in the GLP-1 assay kit.

Insulin is measured using the Mercodia mouse Insulin ELISA Kit (ALPCO) according to the manufacturer's instructions. Bioactive GLP-1 is measured using Glucagon-like peptide-1 (active) ELISA assay kit (Linco) according to the manufacturer's instructions. Total GIP (bioactive plus inactive) is measured using rat/mouse total GIP ELISA assay kit (Linco), according to the manufacturer's instructions. CCK (Nonsulfated Cholecystokinin Octapeptide, 26-33) is measured using human, rat, mouse CCK ELISA assay kit (Phoenix Pharmaceuticals), according to the manufacturer's instructions. PYY is measured using canine, mouse, porcine, rat PYY ELISA assay kit (Peninsula Laboratories), according to the manufacturer's instructions.

Biological Example 6

Gastric Emptying

To evaluate the effects of GPR120 agonists on gastric emptying, 8-10 week old male C57BL/6J mice (Harlan) are fasted for 16-18 hours, then treated orally or by intraperitoneal injection with either GPR120 agonists (1-100 mg/kg) or vehicle (1% CMC, 2% TWEEN 80) 30 minutes prior to initiation of the gastric emptying study. Phenol red (0.05% PR in deionized water) is administered either in an aqueous or glucose solution (0.05% in 20% glucose). Immediately after phenol red (PR) administration (0 min), control group animals are sacrificed by cervical dislocation and the average amount of phenol red recovered is measured as 100% phenol red retention. The remainder of the animals from each group are sacrificed at various time-points following phenol red administration. The stomachs are isolated after clamping at both the pyloric and the cardiac ends. Clamped stomachs are transferred to a 50 mL conical tube containing 5 mL deionized water. Clamps are removed and each stomach is cut into fine pieces with scissors and stomach content is extracted by centrifugation at 3000 rpm for 10 minutes and supernatant is filtered to remove particulates. 1 mL of 1N NAOH is added to each 2 mL of filtered supernatant for color development. The concentration of phenol read is determined by measuring the absorbance of the extracted material at a wavelength of 558 nm and then converted to concentration by using the extinction coefficient of phenol red in aqueous solution.

The gastric emptying is calculated by the formula:
% Gastric emptying=$((A-B)/A) \times 100$, where A is the average amount (absorbance) of phenol red recovered immediately after ingestion (the 100% retained group) and B is the amount (absorbance) of phenol red remaining in the stomach at a given time after ingestion.

Biological Example 7

Improvement of Diabetes Parameters in Animal Models of Diabetes

Female ZDF rats (Charles River laboratories) are obtained at 6 weeks of age and acclimatized for 1 week before being placed on a high fat diet (RD 13004, Research Diets). GPR120 compounds are administered to the rats by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer) and insulin is measured using rat insulin ELISA kit (ALPCO). Insulin and glucose levels are compared to those of vehicle treated animals to determine efficacy.

Male high-fat diet-fed mice (Jackson), that have been placed on a high fat Diet D12492 (Research diets, 60 kcal % fat) at the age of 4-weeks are obtained at 10 weeks of age and acclimatized for 1 week. GPR120 compounds are administered by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer), insulin is measured using mouse insulin ELISA kit (ALPCO). Insulin and glucose levels are compared to those of vehicle treated animals to determine efficacy.

The ob/ob mice (Jackson) are obtained at 6 weeks of age and acclimatized for 1-2 week. GPR120 compounds are administered by daily gavage at concentrations ranging from 0.3-300 mg/kg in 1% CMC, 2% TWEEN 80. Body weight and food intake is monitored daily. After 14 days of dosing, blood samples are taken from overnight fasted animals to measure glucose and insulin. Glucose is measured using a glucometer (Ascensia Elite XL, Bayer), insulin is measured using mouse insulin ELISA kit (ALPCO). Insulin and glucose levels are compared to those of vehicle treated animals to determine efficacy.

Biological Example 8

Intra Peritoneal Glucose Tolerance Test 8-10 week old male C57BL/6J mice (Harlan) were maintained on regular chow diet from Harlan (2018 Teklad Global). On the day before the experiment mice were fasted overnight, then randomized into groups (n=10-15) to receive the tested GPR120 agonist at doses ranging from 100 mg/kg or the vehicle (1% CMC, 2% TWEEN 80). Compounds were delivered orally via gavage at 10 mL/kg. Blood glucose levels were measured by glucometer (Ascensia Elite XL, Bayer) at time −30 minutes before administration of compound. Blood glucose was measured again after 30 minutes (at time 0), and then the mice were dosed intra peritoneally with 2 g/kg glucose at 10 mL/kg. Blood glucose measurements were taken 20, 40, 60, 90 and 120 minutes after glucose administration, by glucometer (Ascensia Elite XL, Bayer).

Glucose levels were plotted against time, and the incremental area under the curve (AUC) of the glucose excursion was determined from time 0 using Graphpad Prism 5.01. Outliers were excluded using Tukey's box plot outlier test, and statistical significance of differences in AUC of compound treatment compared to vehicle was determined by non-parametric Kruskal-Wallis test with Dunn's post test.

Table 4 below shows the mean percentage inhibition of the glucose excursion for the ten animals tested in each group. The compounds were tested at 30 mg/kg and the levels of blood glucose were determined in the presence and absence of the tested compounds. The percentage of glucose reduction is reported. The tested compounds were selected as Examples from the exemplified compounds. These results demonstrate that the GPR120 agonists can lower blood glucose in response to an IP glucose challenge.

TABLE 4

| Example | % reduction IPGTT at 30 mg/kg |
|---|---|
| Example 10 | 30.7 |
| Example 142 | 36.2 |
| Example 141 | 30.55 |
| Example 65 | 22.2 |
| Example 16 | 19.4 |
| Example 132 | 6.5 |
| Example 134 | 30.2 |
| Example 208 | 41.7 |
| Example 77 | 10.4 |
| Example 13 | 31 |
| Example 209 | 43.6 |
| Example 268 | 23 |
| Example 64 | 24.9 |
| Example 131 (racemic) | 23.1 |

TABLE 4-continued

| Example | % reduction IPGTT at 30 mg/kg |
|---|---|
| Example 178 | 16.3 |
| Example 9 | 19.8 |
| Example 50 | 26.2 |

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound of Formula (B-1) or (B-2):

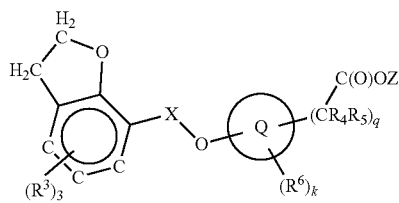

(B-1)

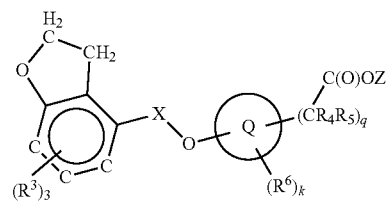

(B-2)

wherein, the ring Q is selected from the group consisting of aryl and

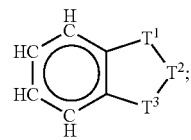

$T^1$, $T^2$, and $T^3$ are independently selected from the group consisting of CH and $CH_2$, with the proviso that if one of $T^1$, $T^2$, and $T^3$ is CH, then $—CR^4R^5-$ is attached to that $T^1$, $T^2$, or $T^3$;

X is $—CH_2—$, $—CHD-$ and $—CD_2-$;

Z is selected from the group consisting of H, alkyl and substituted alkyl;

each $R^3$ is independently selected from the group consisting of H, halo, and aryl;

each $R^4$ and $R^5$ are independently selected from the group consisting of H and deuterium;

each $R^6$ is independently a halo;

the subscript k is 0, 1, 2 or 3; and the subscript q is 0, 1, or 2;

or a pharmaceutically acceptable salt thereof.

2. The compound of claim 1 of Formula (C-1):

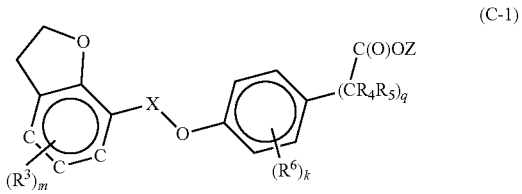

(C-1)

or a pharmaceutically acceptable salt thereof wherein X, $R^3$—$R^6$, k, q, and Z are defined as in claim 1.

3. The compound of claim 2, wherein the subscript q is 2.
4. The compound of claim 3, wherein Z is H.
5. The compound of claim 4, wherein, each $R^3$ is independently selected from the group consisting of F and Cl.
6. The compound of claim 5, wherein the subscript k is 0, 1 or 2.
7. The compound of claim 6, wherein each $R^6$ is independently selected from the group consisting of fluoro and chloro.
8. The compound of claim 1, wherein, the ring Q is

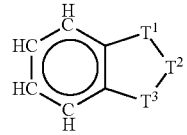

wherein $T^1$-$T^3$ are defined as in claim 1.

9. A compound of or a pharmaceutically acceptable salt thereof, which compound is selected from the group consisting of
2-(5-((5-chloro-2,2-dimethyl-2,3-dihydrobenzofuran-7-yl)methoxy)-6-fluoro-2,3-dihydro-1H-inden-1-yl)acetic acid (29);
2-(5-((5-chloro-2,2-dimethyl-2,3-dihydrobenzofuran-7-yl)methoxy)-2,3-dihydro-1H-inden-1-yl)acetic acid (65);
2-(5-((5-fluoro-2,2-dimethyl-2,3-dihydrobenzofuran-7-yl)methoxy)-2,3-dihydro-1H-inden-1-yl)acetic acid (66);
3-(7-((5-fluoro-2,2-dimethyl-2,3-dihydrobenzofuran-7-yl)methoxy)-2,3-dihydro-1H-inden-4-yl)propanoic acid (92);
3-(7-((5-chloro-2,2-dimethyl-2,3-dihydrobenzofuran-7-yl)methoxy)-2,3-dihydro-1H-inden-4-yl)propanoic acid (93);
2-(5-((7-fluoro-2,2-dimethyl-2,3-dihydrobenzofuran-4-yl)methoxy)-2,3-dihydro-1H-inden-1-yl)acetic acid (123);
5-((5-chloro-2,2-dimethyl-2,3-dihydrobenzofuran-7-yl)methoxy)-2,3-dihydro-1H-indene-2-carboxylic acid (141);
5-((5-fluoro-2,2-dimethyl-2,3-dihydrobenzofuran-7-yl)methoxy)-2,3-dihydro-1H-indene-2-carboxylic acid (142);
(S)-2-(5-((5-fluoro-2,2-dimethyl-2,3-dihydrobenzofuran-7-yl)methoxy)-2,3-dihydro-1H-inden-1-yl)acetic acid (204);
(S)-2-(5-((5-chloro-2,2-dimethyl-2,3-dihydrobenzofuran-7-yl)methoxy)-2,3-dihydro-1H-inden-1-yl)acetic acid (205);
(R)-2-(5-((5-fluoro-2,2-dimethyl-2,3-dihydrobenzofuran-7-yl)methoxy)-2,3-dihydro-1H-inden-1-yl)acetic acid (207);

(R)-2-(5-((5-chloro-2,2-dimethyl-2,3-dihydrobenzofuran-7-yl)methoxy)-2,3-dihydro-1H-inden-1-yl)acetic acid (208);

2-(5-((2,2-dimethyl-5-phenyl-2,3-dihydrobenzofuran-7-yl)methoxy)-2,3-dihydro-1H-inden-1-yl)acetic acid (216);

(R)-2-(5-((6-fluoro-2,2-dimethyl-2,3-dihydrobenzofuran-4-yl)methoxy)-2,3-dihydro-1H-inden-1-yl)acetic acid (217);.

10. A composition comprising a compound of claim 1 and a pharmaceutically acceptable carrier.

11. A method of treating a disease or condition selected from the group consisting of Type I diabetes, Type II diabetes and metabolic syndrome, said method comprising administering to a mammal in need of such treatment a therapeutically effective amount of a compound of claim 1.

12. The method of claim 11, wherein said disease is Type II diabetes.

13. A method of lowering blood glucose in a mammal, said method comprising administering a therapeutically effective amount of a compound claim 1 to a mammal in need of such treatment.

14. The method of claim 13, wherein said mammal is a human.

15. A compound or a pharmaceutically acceptable salt thereof, which compound is selected from the group consisting of 3-(4-((2,2-dimethylchroman-8-yl)methoxy)-3,5-difluorophenyl)-2-methylpropanoic acid (31);

3-(4-((2,3-dihydrobenzofuran-7-yl)methoxy)-3,5-difluorophenyl)-2-methylpropanoic acid (32);

2-methyl-3-(4-((2,2,5-trimethyl-2,3-dihydrobenzofuran-7-yl)methoxy)phenyl)propanoic acid (33);

3-(3,5-difluoro-4-((2,2,5-trimethyl-2,3-dihydrobenzofuran-7-yl)methoxy)phenyl)-2-methylpropanoic acid (34);

3-(4-((5-fluoro-2,2-dimethyl-2,3-dihydrobenzofuran-7-yl)methoxy)-3-methylphenyl)-2-methylpropanoic acid (35);

3-(4-((5-fluoro-2,2-dimethyl-2,3-dihydrobenzofuran-7-yl)methoxy)-3-methoxyphenyl)-2-methylpropanoic acid (36);

3-(3-fluoro-4-((5-fluoro-2,2-dimethyl-2,3-dihydrobenzofuran-7-yl)methoxy)phenyl)-2-methylpropanoic acid (37);

3-(4-((5-chloro-2,2-dimethyl-2,3-dihydrobenzofuran-7-yl)methoxy)-3-(trifluoromethyl)phenyl)-2-methylpropanoic acid (38);

3-(4-((5-chloro-2,2-dimethyl-2,3-dihydrobenzofuran-7-yl)methoxy)-3-fluorophenyl)-2-methylpropanoic acid (39);

3-(4-((5-chloro-2,2-dimethyl-2,3-dihydrobenzofuran-7-yl)methoxy)-3-methylphenyl)-2-methylpropanoic acid (40);

3-(3-chloro-4-((5-chloro-2,2-dimethyl-2,3-dihydrobenzofuran-7-yl)methoxy)phenyl)-2-methylpropanoic acid (41);

3-(3,5-dichloro-4-((5-chloro-2,2-dimethyl-2,3-dihydrobenzofuran-7-yl)methoxy)phenyl)-2-methylpropanoic acid (42);

3-(3,5-dichloro-4-((5-chloro-2,2-dimethyl-2,3-dihydrobenzofuran-7-yl)methoxy)phenyl)-2-methylpropanoic acid (43);

3-(4-((5-chloro-2,2-dimethyl-2,3-dihydrobenzofuran-7-yl)methoxy)-3-methoxyphenyl)-2-methylpropanoic acid (44);

3-(4-((5-fluoro-2,2-dimethyl-2,3-dihydrobenzofuran-7-yl)methoxy)phenyl)-2-methylpropanoic acid (45);

3-(4-((2,2-dimethyl-2,3-dihydrobenzofuran-4-yl)methoxy)phenyl)-2-methylpropanoic acid (46);

3-(3,5-difluoro-4-((5-fluoro-2,2-dimethyl-2,3-dihydrobenzofuran-7-yl)methoxy)phenyl)-2-methylpropanoic acid (47);

2-(3,5-difluoro-4-((5-fluoro-2,2-dimethyl-2,3-dihydrobenzofuran-7-yl)methoxy) phenyl)cyclopropanecarboxylic acid (48);

3-(3,5-difluoro-4-((2-methyl-2,3-dihydrobenzofuran-7-yl)methoxy)phenyl)-2-methylpropanoic acid (49);

3-(4-((2,2-dimethyl-2,3-dihydrobenzofuran-4-yl)methoxy)-3,5-difluorophenyl)-2-methylpropanoic acid (50);

2-(4-((2,2-dimethyl-2,3-dihydrobenzofuran-4-yl)methoxy)-3,5-difluorophenyl) cyclopropanecarboxylic acid (51);

3-(4-((2,2-dimethyl-2,3-dihydrobenzofuran-7-yl)methoxy)-3,5-difluorophenyl)-2-methylpropanoic acid (52);

2-(4-((2,2-dimethyl-2,3-dihydrobenzofuran-7-yl)methoxy)-3,5-difluorophenyl)cyclopropanecarboxylic acid (53);

3-(4-((2,2-dimethyl-2,3-dihydrobenzofuran-7-yl)methoxy)-3,5-difluorophenyl)propanoic acid (54);

3-(2-chloro-4-((5-chloro-2,2-dimethyl-2,3-dihydrobenzofuran-7-yl)methoxy)phenyl)-2-methylpropanoic acid (55);

2-(3,5-difluoro-4-((4-fluoro-2,2-dimethyl-2,3-dihydrobenzofuran-7-yl)methoxy)phenyl)cyclopropanecarboxylic acid (56);

3-(3,5-difluoro-4-((4-fluoro-2,2-dimethyl-2,3-dihydrobenzofuran-7-yl)methoxy)phenyl)-2-methylpropanoic acid (57);

3-(3-fluoro-4-((4-fluoro-2,2-dimethyl-2,3-dihydrobenzofuran-7-yl)methoxy)phenyl)-2-methylpropanoic acid (58);

3-(4-((4-fluoro-2,2-dimethyl-2,3-dihydrobenzofuran-7-yl)methoxy)phenyl)-2-methylpropanoic acid (59);

2-(4-((2,2-dimethyl-4-(trifluoromethyl)-2,3-dihydrobenzofuran-7-yl)methoxy)-3,5-difluorophenyl)cyclopropanecarboxylic acid (60);

3-(4-((2,2-dimethyl-4-(trifluoromethyl)-2,3-dihydrobenzofuran-7-yl)methoxy)-3,5-difluorophenyl)-2-methylpropanoic acid (61);

3-(4-((2,2-dimethyl-4-(trifluoromethyl)-2,3-dihydrobenzofuran-7-yl)methoxy)-3-fluorophenyl)-2-methylpropanoic acid (62);

3-(4-((2,2-dimethyl-4-(trifluoromethyl)-2,3-dihydrobenzofuran-7-yl)methoxy)phenyl)-2-methylpropanoic acid (63);

2-(4-((5-chloro-2,2-dimethyl-2,3-dihydrobenzofuran-7-yl)methoxy)-3,5-difluorophenyl)cyclopropanecarboxylic acid (64);

3-(4-((5-chloro-2,2-dimethyl-2,3-dihydrobenzofuran-7-yl)methoxy)-3,5-difluorophenyl)-2-methylpropanoic acid (67);

3-(4-((5-chloro-2,2-dimethyl-2,3-dihydrobenzofuran-7-yl)methoxy)-2-methoxyphenyl)-2-methylpropanoic acid (68);

3-(4-((2,3-dihydrobenzofuran-7-yl)methoxy)-3,5-difluorophenyl)-2-methylpropanoic acid (69);

2-(2-(4-((5-chloro-2,2-dimethyl-2,3-dihydrobenzofuran-7-yl)methoxy)-3,5-difluorophenyl)cyclopropyl)acetic acid (70);

3-(4-((5,6-difluoro-2,2-dimethyl-2,3-dihydrobenzofuran-7-yl)methoxy)-3,5-difluorophenyl)-2-methylpropanoic acid (71);

3-(4-((5,6-difluoro-2,2-dimethyl-2,3-dihydrobenzofuran-7-yl)methoxy)phenyl)-2-methylpropanoic acid (72);
3-(4-(((2,2-dimethyl-2,3-dihydrobenzofuran-7-yl)oxy)methyl)-3-fluorophenyl)-2-methylpropanoic acid (73);
3-(4-((6-fluoro-4H-benzo[d][1,3]dioxin-8-yl)methoxy)phenyl)-2-methylpropanoic acid (74);
3-(4-((5-fluoro-2,2-dimethyl-2,3-dihydrobenzofuran-7-yl)methoxy)-2-methylphenyl)propanoic acid (75);
3-(2-chloro-4-((5-fluoro-2,2-dimethyl-2,3-dihydrobenzofuran-7-yl)methoxy)phenyl)propanoic acid (76);
3-(2-fluoro-4-((5-fluoro-2,2-dimethyl-2,3-dihydrobenzofuran-7-yl)methoxy)phenyl)propanoic acid (77);
3-(2,6-difluoro-4-((5-fluoro-2,2-dimethyl-2,3-dihydrobenzofuran-7-yl)methoxy)phenyl)propanoic acid (78);
3-(4-((5-fluoro-2,2-dimethyl-2,3-dihydrobenzofuran-7-yl)methoxy)-2-methoxyphenyl)propanoic acid (79);
3-(4-((5-chloro-2,2-dimethyl-2,3-dihydrobenzofuran-7-yl)methoxy)-2-methylphenyl)propanoic acid (80);
3-(2-chloro-4-((5-chloro-2,2-dimethyl-2,3-dihydrobenzofuran-7-yl)methoxy)phenyl)-propanoic acid (81);
3-(4-((5-chloro-2,2-dimethyl-2,3-dihydrobenzofuran-7-yl)methoxy)-2-fluorophenyl)-propanoic acid (82);
3-(4-((5-chloro-2,2-dimethyl-2,3-dihydrobenzofuran-7-yl)methoxy)-2,6-difluorophenyl)propanoic acid (83);
3-(4-((5-chloro-2,2-dimethyl-2,3-dihydrobenzofuran-7-yl)methoxy)-2-methoxyphenyl)propanoic acid (84);
3-(2-bromo-4-((5-fluoro-2,2-dimethyl-2,3-dihydrobenzofuran-7-yl)methoxy)-5-methoxyphenyl)propanoic acid (85);
3-(2-bromo-4-((5-chloro-2,2-dimethyl-2,3-dihydrobenzofuran-7-yl)methoxy)-5-methoxyphenyl)propanoic acid (86);
2-((4-((5-fluoro-2,2-dimethyl-2,3-dihydrobenzofuran-7-yl)methoxy)phenyl)thio)-acetic acid (87);
2-((4-((5-chloro-2,2-dimethyl-2,3-dihydrobenzofuran-7-yl)methoxy)phenyl)thio)-acetic acid (88);
(E)-3-(2-ethyl-4-((5-fluoro-2,2-dimethyl-2,3-dihydrobenzofuran-7-yl)methoxy)phenyl)acrylic acid (89);
3-(4-((5-fluoro-2,2-dimethyl-2,3-dihydrobenzofuran-7-yl)methoxy)-2-(trifluoromethyl)phenyl)propanoic acid (90);
3-(4-((5-chloro-2,2-dimethyl-2,3-dihydrobenzofuran-7-yl)methoxy)-2-(trifluoromethyl)phenyl)propanoic acid (91);
(R)-3-(4-((5-fluoro-2,2-dimethyl-2,3-dihydrobenzofuran-7-yl)methoxy)phenyl)-2-methylpropanoic acid (94);
(S)-3-(4-((5-fluoro-2,2-dimethyl-2,3-dihydrobenzofuran-7-yl)methoxy)phenyl)-2-methylpropanoic acid (95);
3-(4-(((5-fluoro-2,2-dimethyl-2,3-dihydrobenzofuran-7-yl)methyl)amino)phenyl)-2-methylpropanoic acid (96);
3-(4-(5-fluoro-2,2-dimethyl-2,3-dihydrobenzofuran-7-carboxamido)phenyl)-2-methylpropanoic acid (97);
3-(3,5-difluoro-4-((5-fluoro-2,2-dimethyl-2,3-dihydrobenzofuran-7-yl)methoxy)phenyl)-2-ethoxypropanoic acid (98);
2-(4-(2-(5-fluoro-2,2-dimethyl-2,3-dihydrobenzofuran-7-yl)ethyl)phenoxy)acetic acid (99);
3-(5-((5-chloro-2,2-dimethyl-2,3-dihydrobenzofuran-7-yl)methoxy)-[1,1'-biphenyl]-2-yl)propanoic acid (100);
3-(5-((5-fluoro-2,2-dimethyl-2,3-dihydrobenzofuran-7-yl)methoxy)-[1,1'-biphenyl]-2-yl)propanoic acid (101);
3-(4-((5-chloro-2,2-dimethyl-2,3-dihydrobenzofuran-7-yl)methoxy)-5-fluoro-2-propylphenyl)propanoic acid (102);
3-(5-fluoro-4-((5-fluoro-2,2-dimethyl-2,3-dihydrobenzofuran-7-yl)methoxy)-2-propylphenyl)propanoic acid (103);
3-(4-((5-chloro-2,2-dimethyl-3-oxo-2,3-dihydrobenzofuran-7-yl)methoxy)-2-ethyl-3-fluorophenyl)propanoic acid (104);
3-(4-((5-chloro-2,2-dimethyl-3-oxo-2,3-dihydrobenzofuran-7-yl)methoxy)-2-propylphenyl)propanoic acid (105);
3-(4-((5-chloro-2,2-dimethyl-3-oxo-2,3-dihydrobenzofuran-7-yl)methoxy)-3-fluorophenyl)-2-methylpropanoic acid (106);
3-(3-fluoro-4-((5-fluoro-2,2-dimethyl-3-oxo-2,3-dihydrobenzofuran-7-yl)methoxy)phenyl)-2-methylpropanoic acid (107);
3-(4-((5-chloro-2,2-dimethyl-3-oxo-2,3-dihydrobenzofuran-7-yl)methoxy)-3-(trifluoromethyl)phenyl)-2-methylpropanoic acid (108);
3-(4-((5-chloro-3-hydroxy-2,2-dimethyl-2,3-dihydrobenzofuran-7-yl)methoxy)-3-fluorophenyl)-2-methylpropanoic acid (109);
3-(4-((5-bromo-2,2-dimethyl-2,3-dihydrobenzofuran-7-yl)methoxy)phenyl)-2-methylpropanoic acid (110);
3-(4-((5-(4-chlorophenyl)-2,2-dimethyl-2,3-dihydrobenzofuran-7-yl)methoxy)phenyl)-2-methylpropanoic acid (111);
3-(4-((5-(4-fluorophenyl)-2,2-dimethyl-2,3-dihydrobenzofuran-7-yl)methoxy)phenyl)-2-methylpropanoic acid (112);
3-(4-((5-(3-chlorophenyl)-2,2-dimethyl-2,3-dihydrobenzofuran-7-yl)methoxy)phenyl)-2-methylpropanoic acid (113);
3-(4-((5-(2-chlorophenyl)-2,2-dimethyl-2,3-dihydrobenzofuran-7-yl)methoxy)phenyl)-2-methylpropanoic acid (114);
3-(4-((5-(3-methoxyphenyl)-2,2-dimethyl-2,3-dihydrobenzofuran-7-yl)methoxy)phenyl)-2-methylpropanoic acid (115);
3-(4-((2,2-dimethyl-5-(3-(trifluoromethyl)phenyl)-2,3-dihydrobenzofuran-7-yl)methoxy)phenyl)-2-methylpropanoic acid (116);
3-(4-((5-chloro-2,2-dimethyl-2,3-dihydrobenzofuran-7-yl)methoxy)-3-((dimethylamino)methyl)phenyl)-2-methylpropanoic acid (117);
3-(4-((5-(diethylamino)-2,2-dimethyl-2,3-dihydrobenzofuran-7-yl)methoxy)phenyl)-2-methylpropanoic acid (118);
3-(4-((2,2-dimethyl-5-(1H-tetrazol-1-yl)-2,3-dihydrobenzofuran-7-yl)methoxy)phenyl)-2-methylpropanoic acid (119);
3-(4-((7-fluoro-2,2-dimethyl-2,3-dihydrobenzofuran-4-yl)methoxy)phenyl)-2-methylpropanoic acid (120);
3-(3,5-difluoro-4-((7-fluoro-2,2-dimethyl-2,3-dihydrobenzofuran-4-yl)methoxy)phenyl)-2-methylpropanoic acid (121);
2-(3,5-difluoro-4-((7-fluoro-2,2-dimethyl-2,3-dihydrobenzofuran-4-yl)methoxy)phenyl) cyclopropanecarboxylic acid (122);
3-(3,5-difluoro-4-((5-fluoro-2,2-dimethyl-2,3-dihydrobenzofuran-4-yl)methoxy)phenyl)-2-methylpropanbic acid (124);
3-(4-((5-fluoro-2,2-dimethyl-2,3-dihydrobenzofuran-4-yl)methoxy)phenyl)-2-methylpropanoic acid (125);
(R)-3-(3,5-difluoro-4-((5-fluoro-2,2-dimethyl-2,3-dihydrobenzofuran-4-yl)methoxy)phenyl)-2-methylpropanoic acid (126);

3-(4-((5-chloro-2,2-dimethyl-2,3-dihydrobenzofuran-7-yl)methoxy)-2-methoxyphenyl)-2-methylpropanoic acid (127);

2-(3,5-difluoro-4-((5-fluoro-2,2-dimethyl-2,3-dihydrobenzofuran-4-yl)methoxy)phenyl)cyclopropanecarboxylic acid (128);

3-(4-((5-chloro-2,2-dimethyl-2,3-dihydrobenzofuran-4-yl)methoxy)-3,5-difluorophenyl)-2-methylpropanoic acid (129);

3-(3,5-difluoro-4-((6-fluoro-2,2-dimethyl-2,3-dihydrobenzofuran-4-yl)methoxy)phenyl)-2-methylpropanoic acid (130);

3-(4-((5-chloro-2,2-dimethyl-2,3-dihydrobenzofuran-4-yl)methoxy)phenyl)-2-methylpropanoic acid (131);

2-(4-((5-chloro-2,2-dimethyl-2,3-dihydrobenzofuran-7-yl)methoxy)-3-methylphenoxy)acetic acid (132);

2-(4-((4-chloro-2,2-dimethyl-2,3-dihydrobenzofuran-7-yl)methoxy)-2-methylphenoxy)acetic acid (133);

2-(4-((5-chloro-2,2-dimethyl-2,3-dihydrobenzofuran-7-yl)methoxy)phenoxy)acetic acid (134);

3-(4-((5-chloro-2,2-dimethyl-2,3-dihydrobenzofuran-7-yl)methoxy)-3,5-difluorophenyl)butanoic acid (135);

3-(3,5-difluoro-4-((5-methoxy-2,2-dimethyl-2,3-dihydrobenzofuran-7-yl)methoxy)phenyl)-2-methylpropanoic acid (136);

3-(4-((5-methoxy-2,2-dimethyl-2,3-dihydrobenzofuran-7-yl)methoxy)phenyl)-2-methylpropanoic acid (137);

3-(4-((5-chloro-2,3,3-trimethyl-2,3-dihydrobenzofuran-7-yl)methoxy)-3,5-difluorophenyl)-2-methylpropanoic acid (138);

3-(4-((5-ethoxy-2,2-dimethyl-2,3-dihydrobenzofuran-7-yl)methoxy)-3,5-difluorophenyl)-2-methylpropanoic acid (139);

3-(4-((5-(benzyloxy)-2,2-dimethyl-2,3-dihydrobenzofuran-7-yl)methoxy)-3,5-difluorophenyl)-2-methylpropanoic acid (140);

6((5-fluoro-2,2-dimethyl-2,3-dihydrobenzofuran-7-yl)methoxy)-2-naphthoic acid (143);

3-(4-((5-fluoro-2,2-dimethyl-2,3-dihydrobenzofuran-7-yl)methoxy)-2-isopropoxyphenyl)propanoic acid (144);

3-(4-((5-chloro-2,2-dimethyl-2,3-dihydrobenzofuran-7-yl)methoxy)-2-isopropoxyphenyl)propanoic acid (145);

3-(4-((5-chloro-2,2-dimethyl-2,3-dihydrobenzofuran-7-yl)methoxy)-2-ethoxyphenyl)propanoic acid (146);

3-(2-ethoxy-4-((5-methoxy-2,2-dimethyl-2,3-dihydrobenzofuran-7-yl)methoxy)phenyl)propanoic acid (147);

3-(4-((5-chloro-2-methylbenzofuran-7-yl)methoxy)-2-ethylphenyl)propanoic acid (148);

3-(4-((5-chloro-2-methylbenzofuran-7-yl)methoxy)-3-fluorophenyl)-2-methylpropanoic acid (149);

3-(4-((5-fluoro-2,2-dimethyl-2,3-dihydrobenzofuran-7-yl)methoxy)naphthalen-1-yl)propanoic acid (150);

3-(2-((dimethylamino)methyl)-4-((5-fluoro-2,2-dimethyl-2,3-dihydrobenzofuran-7-yl)methoxy)phenyl)propanoic acid (151);

3-(4-((5-acetamido-2,2-dimethyl-2,3-dihydrobenzofuran-7-yl)methoxy)phenyl)-2-methylpropanoic acid (152);

3-(4-((2,2-dimethyl-5-(trifluoromethoxy)-2,3-dihydrobenzofuran-7-yl)methoxy)phenyl)-2-methylpropanoic acid (153);

3-(4-((5-fluoro-2,2-dimethyl-2,3-dihydrobenzofuran-7-yl)methoxy)-2-methylbenzofuran-7-yl)propanoic acid (154);

2-acetamidoethyl 3-(4-((5-chloro-2,2-dimethyl-2,3-dihydrobenzofuran-7-yl)methoxy)-3-(trifluoromethyl)phenyl)-2-methylpropanoate (155);

3-(4-(((5-chloro-2,2-dimethyl-2,3-dihydrobenzofuran-7-yl)methyl)amino)phenyl)propanoic acid (156);

3-(4-(((5-fluoro-2,2-dimethyl-2,3-dihydrobenzofuran-7-yl)methyl)amino)phenyl)propanoic acid (157);

3-(4-((5-chloro-2,2-dimethyl-3-oxo-2,3-dihydrobenzofuran-7-yl)methoxy)phenyl)-2-methylpropanoic acid (158);

3-(4-((5-chloro-3-hydroxy-2,2-dimethyl-2,3-dihydrobenzofuran-7-yl)methoxy)phenyl)-2-methylpropanoic acid (159);

2-(4-((5-fluoro-2,2-dimethyl-2,3-dihydrobenzofuran-7-yl)methoxy)phenyl)cyclopropanecarboxylic acid (160);

3-(4-((5-fluoro-2,2-dimethyl-2,3-dihydrobenzofuran-7-yl)methoxy)phenyl)propanoic acid (161);

2-(4-((5-fluoro-2,2-dimethyl-2,3-dihydrobenzofuran-7-yl)methoxy)phenyl)acetic acid (162);

3-(2-ethyl-4-((5-fluoro-2,2-dimethyl-2,3-dihydrobenzofuran-7-yl)methoxy)phenyl)propanoic acid (163);

3-(4-((5-fluoro-2,2-dimethyl-2,3-dihydrobenzofuran-7-yl)methoxy)-2-isopropylphenyl)propanoic acid (164);

3-(4-((5-fluoro-2,2-dimethyl-2,3-dihydrobenzofuran-7-yl)methoxy)-2-(trifluoromethoxy)phenyl)propanoic acid (165);

3-(4-((5-chloro-2,2-dimethyl-2,3-dihydrobenzofuran-7-yl)methoxy)-2-isopropylphenyl)propanoic acid (166);

3-(4-((5-chloro-2,2-dimethyl-2,3-dihydrobenzofuran-7-yl)methoxy)-2-ethylphenyl)propanoic acid (167);

3-(4-((5-chloro-2,2-dimethyl-2,3-dihydrobenzofuran-7-yl)methoxy)-2-(trifluoromethoxy)phenyl)propanoic acid (168);

3-(4-((2,2-dimethyl-2,3-dihydrobenzofuran-4-yl)methoxy)-2-ethylphenyl)propanoic acid (169);

(R)-3-(4-((5-chloro-2,2-dimethyl-2,3-dihydrobenzofuran-7-yl)methoxy)-3-fluorophenyl)-2-methylpropanoic acid (170);

(S)-3-(4-((5-chloro-2,2-dimethyl-2,3-dihydrobenzofuran-7-yl)methoxy)-3-fluorophenyl)-2-methylpropanoic acid (171);

(R)-3-(4-((5-chloro-2,2-dimethyl-2,3-dihydrobenzofuran-7-yl)methoxy)-3-(trifluoromethyl)phenyl)-2-methylpropanoic acid (172)

(S)-3-(4-((5-chloro-2,2-dimethyl-2,3-dihydrobenzofuran-7-yl)methoxy)-3-(trifluoromethypphenyl)-2-methylpropanoic acid (173);

3-(4-((3,3-dideuterio-5-fluoro-2,2-dimethyl-2,3-dihydrobenzofuran-7-yl)methoxy)phenyl)-2-methylpropanoic acid (174);

3-(4-((3,3-dideuterio-5-chloro-2,2-dimethyl-2,3-dihydrobenzofuran-7-yl)methoxy)-3-fluorophenyl)-2-methylpropanoic acid (175);

3-(4-((3,3-dideuterio-5-chloro-2,2-dimethyl-2,3-dihydrobenzofuran-7-yl)methoxy)-3-(trifluoromethyl)phenyl)-2-methylpropanoic acid (176);

3-(4-((5-chloro-3,3-dimethyl-2,3-dihydrobenzofuran-7-yl)methoxy)phenyl)-2-methylpropanoic acid (177);

3-(4-((5-chloro-3,3-dimethyl-2,3-dihydrobenzofuran-7-yl)methoxy)-3-fluorophenyl)-2-methylpropanoic acid (178);

3-(4-((2,2-dimethyl-2,3-dihydrobenzofuran-4-yl)methoxy)-2,3-dimethylphenyl)propanoic acid (179);

3-(3,5-difluoro-4-((2-methylbenzo[b]thiophen-7-yl)methoxy)phenyl)-2-methylpropanoic acid (180);

2-(5-((2-methylbenzo[b]thiophen-7-yl)methoxy)-2,3-dihydro-1H-inden-1-yl)acetic acid (181);

2-(6-((5-fluoro-2,2-dimethyl-2,3-dihydrobenzofuran-7-yl)methoxy)-1,2,3,4-tetrahydronaphthalen-1-yl)acetic acid (182);

2-(6-((5-chloro-2,2-dimethyl-2,3-dihydrobenzofuran-7-yl)methoxy)-1,2,3,4-tetrahydronaphthalen-1-yl)acetic acid (183);

3-(3-chloro-4-((5-fluoro-2,2-dimethyl-2,3-dihydrobenzofuran-7-yl)methoxy)phenyl)-2-methylpropanoic acid (184);

3-(4-((5-chloro-2,2-dimethyl-2,3-dihydrobenzofuran-7-yl)methoxy)phenyl)-3-methylbutanoic acid (185);

3-(4-((5-fluoro-2,2-dimethyl-2,3-dihydrobenzofuran-7-yl)methoxy)phenyl)-3-methylbutanoic acid (186);

3-methyl-3-(4-((2,2,5-trimethyl-2,3-dihydrobenzofuran-7-yl)methoxy)phenyl)butanoic acid (187);

3-(4-((5-chloro-3H-spiro[benzofuran-2,1'-cyclopentane]-7-yl)methoxy)phenyl)-2-methylpropanoic acid (188);

4-(4-((5-fluoro-2,2-dimethyl-2,3-dihydrobenzofuran-7-yl)methoxy)phenyl)butanoic acid (189);

4-(3,5-difluoro-4-((5-fluoro-2,2-dimethyl-2,3-dihydrobenzofuran-7-yl)methoxy)phenyl)butanoic acid (190);

3-(4-((5-fluoro-3H-spiro[benzofuran-2,1'-cyclopentane]-7-yl)methoxy)phenyl)-2-methylpropanoic acid (191);

2-(5-((5-fluoro-3H-spiro[benzofuran-2,1'-cyclopentane]-7-yl)methoxy)-2,3-dihydro-1H-inden-1-yl)acetic acid (192);

3-(4-((5-fluoro-3H-spiro[benzofuran-2,1'-cyclopentane]-7-yl)methoxy)phenyl)propanoic acid (193);

2-(4-((5-fluoro-3H-spiro[benzofuran-2,1'-cyclopentane]-7-yl)methoxy)phenyl)cyclopropanecarboxylic acid (194);

3-(4-((5-chloro-3H-spiro[benzofuran-2,1'-cyclopentane]-7-yl)methoxy)phenyl)propanoic acid (195);

4-(4-((2,2,5-trimethyl-2,3-dihydrobenzofuran-7-yl)methoxy)phenyl)butanoic acid (196);

4-(4-((5-chloro-2,2-dimethyl-2,3-dihydrobenzofuran-7-yl)methoxy)phenyl)butanoic acid (197);

4-(3,5-difluoro-4-((2,2,5-trimethyl-2,3-dihydrobenzofuran-7-yl)methoxy)phenyl)butanoic acid (198);

4-(4-((5-fluoro-2,2-dimethyl-2,3-dihydrobenzofuran-7-yl)methoxy)-3,5-difluorophenyl)butanoic acid (199);

4-(4-((5-fluoro-2,2-dimethyl-2,3-dihydrobenzofuran-7-yl)methoxy)phenyl)-2-methylbutanoic acid (200);

4-(4-((5-chloro-2,2-dimethyl-2,3-dihydrobenzofuran-7-yl)methoxy)phenyl)-2-methylbutanoic acid (201);

3-(4-((5-fluoro-2,2-dimethyl-2,3-dihydrobenzofuran-7-yl)methoxy)-3-methoxyphenyl)propanoic acid (202);

3-(4-((5-chloro-2,2-dimethyl-2,3-dihydrobenzofuran-7-yl)methoxy)-3-methoxyphenyl)propanoic acid (203);

3-(4-((5-chloro-2,2-dimethyl-2,3-dihydrobenzofuran-7-yl)methoxy)phenyl)propanoic acid (206);

2-(3-fluoro-4-((5-fluoro-2,2-dimethyl-2,3-dihydrobenzofuran-7-yl)methoxy)phenyl)cyclopropanecarboxylic acid (209);

2-(4-((5-chloro-2,2-dimethyl-2,3-dihydrobenzofuran-7-yl)methoxy)-3-fluorophenyl)cyclopropanecarboxylic acid (210);

4-(4-((5-fluoro-2,2-dimethyl-2,3-dihydrobenzofuran-7-yl)methoxy)phenyl)-3-methylbutanoic acid (211);

4-(4-((5-chloro-2,2-dimethyl-2,3-dihydrobenzofuran-7-yl)methoxy)phenyl)-3-methylbutanoic acid (212);

2-(3,5-difluoro-4-((5-fluoro-2,2-dimethyl-2,3-dihydrobenzofuran-7-yl)methoxy)benzyl)cyclopropanecarboxylic acid (213);

2-(4-((5-chloro-2,2-dimethyl-2,3-dihydrobenzofuran-7-yl)methoxy)-3,5-difluorobenzyl)cyclopropanecarboxylic acid (214);

3-(4-((2,2-dimethyl-5-phenyl-2,3-dihydrobenzofuran-7-yl)methoxy)phenyl)propanoic acid (215);

3-(2-fluoro-4-((5-fluoro-3H-spiro[benzofuran-2,1'-cyclopentane]-7-yl)methoxy)phenyl)propanoic acid (218);

3-(4-((5-fluoro-3H-spiro[benzofuran-2,1'-cyclopentane]-7-yl)methoxy)-2-methoxyphenyl)propanoic acid (219);

2-(4-((5-fluoro-2,2-dimethyl-2,3-dihydrobenzofuran-7-yl)methoxy)benzyl)cyclopropanecarboxylic acid (220);

2-(4-((5-chloro-2,2-dimethyl-2,3-dihydrobenzofuran-7-yl)methoxy)benzyl)cyclopropanecarboxylic acid (221);

3-(4-((5-chloro-3H-spiro[benzofuran-2,1'-cyclopentane]-7-yl)methoxy)-2-fluorophenyl)propanoic acid (222);

3-(4-((5-chloro-3H-spiro[benzofuran-2,1'-cyclopentane]-7-yl)methoxy)-2-methoxyphenyl)propanoic acid (223);

3-(2-chloro-4-((5-fluoro-3H-spiro[benzofuran-2,1'-cyclopentane]-7-yl)methoxy)phenyl)propanoic acid (224);

3-(2-chloro-4-((5-chloro-3H-spiro[benzofuran-2,1'-cyclopentane]-7-yl)methoxy)phenyl)propanoic acid (225);

3-(2,6-dichloro-4-((5-fluoro-2,2-dimethyl-2,3-dihydrobenzofuran-7-yl)methoxy)phenyl)propanoic acid (226);

3-(2,6-dichloro-4-((5-chloro-2,2-dimethyl-2,3-dihydrobenzofuran-7-yl)methoxy)phenyl)propanoic acid (227);

2-(2-(4-((5-fluoro-2,2-dimethyl-2,3-dihydrobenzofuran-7-yl)methoxy)phenyl)cyclopropyl)acetic acid (228);

2-(2-(4-((5-chloro-2,2-dimethyl-2,3-dihydrobenzofuran-7-yl)methoxy)phenyl)cyclopropyl)acetic acid (229);

2-(2-(4-((5-fluoro-3H-spiro[benzofuran-2,1'-cyclopentane]-7-yl)methoxy)phenyl)cyclopropyl)acetic acid (230);

2-(2-(4-((5-chloro-3H-spiro[benzofuran-2,1'-cyclopentane]-7-yl)methoxy)phenyl)cyclopropyl)acetic acid (231);

3-(2-ethyl-4-((5-fluoro-3H-spiro[benzofuran-2,1'-cyclopentane]-7-yl)methoxy)phenyl)propanoic acid (232);

3-(4-((5-fluoro-2,2-dimethyl-2,3-dihydrobenzofuran-7-yl)methoxy)-2,6-dimethylphenyl)propanoic acid (233);

3-(4-((5-chloro-2,2-dimethyl-2,3-dihydrobenzofuran-7-yl)methoxy)-2,6-dimethylphenyl)propanoic acid (234);

3-(4-((5-fluoro-2,2-dimethyl-2,3-dihydrobenzofuran-7-yl)methoxy)-2,5-dimethylphenyl)propanoic acid (235);

3-(4-((5-chloro-2,2-dimethyl-2,3-dihydrobenzofuran-7-yl)methoxy)-2,5-dimethylphenyl)propanoic acid (236);

3-(4-((5-fluoro-2,2-dimethyl-2,3-dihydrobenzofuran-7-yl)methoxy)-2,3-dimethylphenyl)propanoic acid (237);

3-(4-((5-chloro-2,2-dimethyl-2,3-dihydrobenzofuran-7-yl)methoxy)-2,3-dimethylphenyl)propanoic acid (238);

2-(2-(2-fluoro-4-((5-fluoro-2,2-dimethyl-2,3-dihydrobenzofuran-7-yl)methoxy)phenyl)cyclopropyl)acetic acid (239);

2-(2-(4-((5-chloro-2,2-dimethyl-2,3-dihydrobenzofuran-7-yl)methoxy)-2-fluorophenyl)cyclopropyl)acetic acid (240);

3-(4-((5-fluoro-2,2-dimethyl-2,3-dihydrobenzofuran-7-yl)methoxy)-2-propylphenyl)propanoic acid (241);

3-(4-((5-chloro-2,2-dimethyl-2,3-dihydrobenzofuran-7-yl)methoxy)-2-propylphenyl)propanoic acid (242);

3-(5-fluoro-4-((5-fluoro-2,2-dimethyl-2,3-dihydrobenzofuran-7-yl)methoxy)-2-methylphenyl)propanoic acid (243);

3-(4-((5-chloro-2,2-dimethyl-2,3-dihydrobenzofuran-7-yl)methoxy)-5-fluoro-2-methylphenyl)propanoic acid (244);

3-(2-ethyl-3-fluoro-4-((5-fluoro-2,2-dimethyl-2,3-dihydrobenzofuran-7-yl)methoxy)phenyl)propanoic acid (245);

3-(4-((5-chloro-2,2-dimethyl-2,3-dihydrobenzofuran-7-yl)methoxy)-2-ethyl-3-fluorophenyl)propanoic acid (246);

3-(4-((5-fluoro-2,2-dimethyl-2,3-dihydrobenzofuran-7-yl)methoxy)-5,6,7,8-tetrahydronaphthalen-1-yl)propanoic acid (247);

3-(4-((5-chloro-2,2-dimethyl-2,3-dihydrobenzofuran-7-yl)methoxy)-5,6,7,8-tetrahydronaphthalen-1-yl)propanoic acid (248);

3-(2-ethyl-5-fluoro-4-((5-fluoro-2,2-dimethyl-2,3-dihydrobenzofuran-7-yl)methoxy)phenyl)propanoic acid (249);

3-(4-((5-chloro-2,2-dimethyl-2,3-dihydrobenzofuran-7-yl)methoxy)-2-ethyl-5-fluorophenyl)propanoic acid (250);

3-(3-fluoro-4-((5-fluoro-2,2-dimethyl-2,3-dihydrobenzofuran-7-yl)methoxy)-2-propylphenyl)propanoic acid (251);

3-(4-((5-chloro-2,2-dimethyl-2,3-dihydrobenzofuran-7-yl)methoxy)-3-fluoro-2-propylphenyl)propanoic acid (252);

3-(3-fluoro-4-((5-fluoro-2,2-dimethyl-2,3-dihydrobenzofuran-7-yl)methoxy)-2-pentylphenyl)propanoic acid (253);

3-(4-((5-chloro-2,2-dimethyl-2,3-dihydrobenzofuran-7-yl)methoxy)-3-fluoro-2-pentylphenyl)propanoic acid (254);

3-(2-ethyl-3-fluoro-4-((5-fluoro-2,2-dimethyl-2,3-dihydrobenzofuran-7-yl)methoxy)phenyl)-2-methylpropanoic acid (255);

3-(4-((5-chloro-2,2-dimethyl-2,3-dihydrobenzofuran-7-yl)methoxy)-2-ethyl-3-fluorophenyl)-2-methylpropanoic acid (256);

3-(4-(dideuterio(5-fluoro-2,2-dimethyl-2,3-dihydrobenzofuran-7-yl)methoxy)-3-fluoro-2-ethylphenyl)propanoic acid (257);

3-(4-(dideuterio(5-fluoro-2,2-dimethyl-2,3-dihydrobenzofuran-7-yl)methoxy)-3-fluoro-2-propylphenyl)propanoic acid (258);

3-(4-(dideuterio(5-fluoro-2,2-dimethyl-2,3-dihydrobenzofuran-7-yl)methoxy)-3-fluorophenyl)-2-methylpropanoic acid (259);

3-(4-(dideuterio(5-fluoro-2,2-dimethyl-2,3-dihydrobenzofuran-7-yl)methoxy)-3-(trifluoromethyl)phenyl)-2-methylpropanoic acid (260);

3-(3-fluoro-4-((5-fluoro-2,2-dimethyl-2,3-dihydrobenzofuran-7-yl)methoxy)-2-isopentylphenyl)propanoic acid (261);

3-(4-((5-chloro-2,2-dimethyl-2,3-dihydrobenzofuran-7-yl)methoxy)-3-fluoro-2-isopentylphenyl)propanoic acid (262);

3-(4-(dideuterio(5-chloro-2,2-dimethyl-2,3-dihydrobenzofuran-7-yl)methoxy)-3-fluoro-2-ethylphenyl)propanoic acid (263);

3-(4-(dideuterio(5-chloro-2,2-dimethyl-2,3-dihydrobenzofuran-7-yl)methoxy)-3-fluoro-2-propylphenyl)propanoic acid (264);

3-(4-(dideuterio(5-chloro-2,2-dimethyl-2,3-dihydrobenzofuran-7-yl)methoxy)-3-fluorophenyl)-2-methylpropanoic acid (265);

3-(4-(dideuterio(5-chloro-2,2-dimethyl-2,3-dihydrobenzofuran-7-yl)methoxy)-3-(trifluoromethyl)phenyl)-2-methylpropanoic acid (266);

3-(2-butyl-3-fluoro-4-((5-fluoro-2,2-dimethyl-2,3-dihydrobenzofuran-7-yl)methoxy)phenyl)propanoic acid (267);

3-(2-butyl-4-((5-chloro-2,2-dimethyl-2,3-dihydrobenzofuran-7-yl)methoxy)-3-fluorophenyl)propanoic acid (268);

3-(4-((5-fluoro-2,2-dimethyl-2,3-dihydrobenzofuran-7-yl)methoxy)-3-(trifluoromethyl)phenyl)-2-methylpropanoic acid (269);

3-(4-((5-chloro-2,2-dimethyl-2,3-dihydrobenzofuran-7-yl)methoxy)-3-fluorophenyl)-2,2,3,3-tetradeuteriopropanoic acid (270);

3-(3-fluoro-4-((5-fluoro-2,2-dimethyl-2,3-dihydrobenzofuran-7-yl)methoxy)-2-propylphenyl)-2,2,3,3-tetradeuteriopropanoic acid (271);

3-(2-ethyl-3-fluoro-4-((5-fluoro-2,2-dimethyl-2,3-dihydrobenzofuran-7-yl)methoxy)phenyl)-2,2,3,3-tetradeuteriopropanoic acid (272);

3-(3-fluoro-4-((5-fluoro-2,2-dimethyl-2,3-dihydrobenzofuran-7-yl)methoxy)-2-methylphenyl)propanoic acid (273);

3-(4-((5-chloro-2,2-dimethyl-2,3-dihydrobenzofuran-7-yl)methoxy)-3-fluoro-2-methylphenyl)propanoic acid (274);

3-(3-ethyl-4-((5-fluoro-2,2-dimethyl-2,3-dihydrobenzofuran-7-yl)methoxy)phenyl)propanoic acid (275);

3-(4-((5-chloro-2,2-dimethyl-2,3-dihydrobenzofuran-7-yl)methoxy)-3-ethylphenyl)propanoic acid (276);

3-(3-ethyl-4-((5-fluoro-2,2-dimethyl-2,3-dihydrobenzofuran-7-yl)methoxy)phenyl)-2-methylpropanoic acid (277);

3-(4-((5-chloro-2,2-dimethyl-2,3-dihydrobenzofuran-7-yl)methoxy)-3-ethylphenyl)-2-methylpropanoic acid (278);

3-(2-((5-chloro-2,2-dimethyl-2,3-dihydrobenzofuran-7-yl)methoxy)phenyl)propanoic acid (279);

3-(3-((5-chloro-2,2-dimethyl-2,3-dihydrobenzofuran-7-yl)methoxy)phenyl)-2-methylpropanoic acid (280);

3-(4-((2,2-dimethyl-2,3-dihydrobenzofuran-7-yl)methoxy)phenyl)propanoic acid (281);

3-(4-((2,2-dimethyl-2,3-dihydrobenzofuran-7-yl)methoxy)phenyl)-2-methylpropanoic acid (282);

3-(4-((5-fluoro-2,2-dimethyl-2,3-dihydrobenzofuran-7-yl)methoxy)-2,3,5-trimethylphenyl)propanoic acid (283);

3-(4-((5-chloro-2,2-dimethyl-2,3-dihydrobenzofuran-7-yl)methoxy)-2,3,5-trimethylphenyl)propanoic acid (284);

3-(4-((5-fluoro-3H-spiro[benzofuran-2,1'-cyclopentan]-7-yl)methoxy)-2,3-dimethylphenyl)propanoic acid (285);

2-(5-((5-chloro-2-isopropoxybenzyl)oxy)-6-fluoro-2,3-dihydro-1H-inden-1-yl)acetic acid (286);

2-(5-((5-chloro-2-isopropoxybenzyl)oxy)-2,3-dihydro-1H-inden-1-yl)acetic acid (287);

2-(5-((2-isopropoxypyridin-3-yl)methoxy)-2,3-dihydro-1H-inden-1-yl)acetic acid (288);

3-(4-((1H-indazol-7-yl)methoxy)-3,5-difluorophenyl)-2-methylpropanoic acid (289);

3-(3,5-difluoro-4-((2-methylbenzo[d]oxazol-7-yl)methoxy)phenyl)-2-methylpropanoic acid (290);

2-(6-((5-fluoro-2,2-dimethyl-2,3-dihydrobenzofuran-7-yl)methoxy)benzofuran-3-yl)acetic acid (291);

2-(7-((5-fluoro-2,2-dimethyl-2,3-dihydrobenzofuran-7-yl)methoxy)-2-oxo-2H-chromen-4-yl)acetic acid (292);

3-(4-((5-fluoro-2,2-dimethyl-2,3-dihydrobenzofuran-7-yl)methoxy)phenyl)-N-hydroxy-2-methylpropanamide (293);

3-(4-((5-fluoro-2,2-dimethyl-2,3-dihydrobenzofuran-7-yl)methoxy)phenyl)-N-hydroxypropanamide (294);

3-(4-((5-chloro-2,2-dimethyl-2,3-dihydrobenzofuran-7-yl)methoxy)phenyl)-4-methylpentanoic acid (295);

3-(4-((6-chloro-2,2-dimethyl-2,3-dihydrobenzofuran-4-yl)methoxy)-2,3-dimethylphenyl)propanoic acid (296); and 3-(2-ethoxy-4-((5-fluoro-2,2-dimethyl-2,3-dihydrobenzofuran-7-yl)methoxy)phenyl)propanoic acid (297).

\* \* \* \* \*